US011857563B2

(12) United States Patent
Pernis et al.

(10) Patent No.: US 11,857,563 B2
(45) Date of Patent: Jan. 2, 2024

(54) INHIBITION OF EXPANSION AND FUNCTION OF PATHOGENIC AGE-ASSOCIATED B CELLS AND USE FOR THE PREVENTION AND TREATMENT OF AUTOIMMUNE DISEASE

(71) Applicant: New York Society for the Relief of the Ruptured and Crippled, maintaining the Hospital for Special Surgery, New York, NY (US)

(72) Inventors: Alessandra Pernis, Mountain Lakes, NJ (US); Michela Manni, New York, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 37 days.

(21) Appl. No.: 17/459,213

(22) Filed: Aug. 27, 2021

(65) Prior Publication Data

US 2021/0393670 A1 Dec. 23, 2021

Related U.S. Application Data

(63) Continuation of application No. 16/523,055, filed on Jul. 26, 2019, now Pat. No. 11,147,829, which is a continuation of application No. 15/833,398, filed on Dec. 6, 2017, now abandoned.

(60) Provisional application No. 62/512,803, filed on May 31, 2017, provisional application No. 62/487,645, filed on Apr. 20, 2017, provisional application No. 62/430,732, filed on Dec. 6, 2016.

(51) Int. Cl.
| | |
|---|---|
| C07H 21/02 | (2006.01) |
| A61K 31/7105 | (2006.01) |
| C07K 16/30 | (2006.01) |
| C12N 15/113 | (2010.01) |
| A61P 5/48 | (2006.01) |
| A61P 35/00 | (2006.01) |

(52) U.S. Cl.
CPC ............ *A61K 31/7105* (2013.01); *A61P 5/48* (2018.01); *A61P 35/00* (2018.01); *C07K 16/3061* (2013.01); *C12N 15/113* (2013.01); *C12N 2310/122* (2013.01); *C12N 2310/141* (2013.01); *C12N 2320/30* (2013.01)

(58) Field of Classification Search
CPC .................................................. C12N 15/113
See application file for complete search history.

(56) References Cited

U.S. PATENT DOCUMENTS

| | | | |
|---|---|---|---|
| 4,479,957 A | 10/1984 | Cullinan | |
| 8,785,433 B2 | 7/2014 | Knight | |
| 9,249,145 B2 | 2/2016 | Rodgers | |
| 9,409,886 B2 | 8/2016 | Bencsik | |
| 9,464,088 B2 | 10/2016 | Huang | |
| 9,637,492 B2 | 5/2017 | Ren | |
| 9,682,981 B2 | 6/2017 | Zhang | |
| 9,802,937 B2 | 10/2017 | Thormann | |
| 10,023,571 B2 | 7/2018 | Masse | |
| 2003/0166018 A1 | 9/2003 | Wabl et al. | |
| 2014/0037645 A1 | 2/2014 | Rubtsov et al. | |
| 2016/0003846 A1 | 1/2016 | Jessberger | |

FOREIGN PATENT DOCUMENTS

WO    WO 2014/122245    8/2014

OTHER PUBLICATIONS

Biswas et al., "IRF4 and its regulators: evolving insights into the pathogenesis of inflammatory arthritis?" *Immunological Reviews* Jan. 2010, 233(1):79-96.
Biswas et al., "Dual regulation of IRF4 function in T and B cells is required for the coordination of T-B cell interactions and the prevention of autoimmunity". *Journal of Experimental Medicine* Mar. 12, 2012, 209:581-596.
Buenrostro et al., "ATAC-seq: A Method for Assaying Chromatin Accessibility Genome-Wide". *Curr. Protoc. Mol. Biol.* Jan. 5, 2015, 109:21 29 21-29.
Buenrostro et al., "Single-cell chromatin accessibility reveals principles of regulatory variation". *Nature* Jul. 23, 2015, 523:486-490.
Cham et al., "Interferon regulatory factor 5 in the pathogenesis of systemic lupus erythematosus". *Clinical and Developmental Immunology* Sep. 12, 2012, 780456.
Chandrasekaran et al., "Regulation of Effector Treg Cells in Murine Lupus". *Arthritis and Rheumatology* Jun. 2016, 68(6):1454-1466.
Cohen-Solal and Diamond, "Lessons from an anti-DNA autoantibody". *Molecular Immunology* Jun. 2011, 48(11):1328-1331.
Deane et al., "Control of toll-like receptor 7 expression is essential to restrict autoimmunity and dendritic cell proliferation". *Immunity* Nov. 2007, 7(5):801-10.
Eames et al., "Interferon regulatory factor 5 in human autoimmunity and murine models of autoimmune disease". Translational research: Journal of Laboratory and Clinical Medicine 2016, 167(1):167-182. Accepted for publication Jun. 30, 2015.
Eisenberg, "Mechanisms of autoimmunity". Immunologic research Jun. 2003, 27(2-3):203-218.

(Continued)

*Primary Examiner* — Amy H Bowman
(74) *Attorney, Agent, or Firm* — LEASON ELLIS LLP

(57) ABSTRACT

This current invention provides methods and agents for preventing and treating autoimmune and lymphoproliferative disease by targeting pathogenic age-associated B cells as well as methods of detecting these pathogenic age-associated B cells as a method of diagnosing and predicting autoimmune disease and other lymphoproliferative and chronic inflammatory disorders.
The current invention also provides targets for drug development and basic research for autoimmune diseases and other lymphoproliferative and chronic inflammatory disorders.

2 Claims, 81 Drawing Sheets

Specification includes a Sequence Listing.

(56) References Cited

OTHER PUBLICATIONS

Fan et al., "Keap 1 facilitates p62-mediated ubiquitin aggregate clearance via autophagy". *Autophagy* Jul. 2010, 6(5):614-621.

Fang et al., "Unique contribution of IRF-S-Ikaros axis to the B-Cell IgG2a response". *Genes Immun.* Jul. 2012, 13:421-430.

Gupta et al., "Molecular Cloning of IBP, a SWAP-70 homologous GEF, which is highly expressed in the immune system". Human Immunology Apr. 2003, 64:389-401.

Hao et al, "A B-cell subset uniquely responsive to innate stimuli accumulates in aged mice". *Blood* Apr. 23, 2011, 118:1294-1304.

Jones et al. mTOR has distinct functions in generating versus sustaining humoral immunity. *J. Clin. Invest.* Nov. 2016, 126:4250-4261.

Kwon et al., "Analysis of interleukin-21-induced Prdrm 1 gene regulation reveals functional cooperation of STAT3 and IRF4 transcription factors". *Immunity* Dec. 18, 2009, 31:941-952.

Lazzari and Jefferies, "IRF5-mediated signaling and implications for SLE". Clin. Immunol. Jun. 10, 2014, 153:343-352.

Manni et al., "IRF4-Dependent and IRF4-Independent Pathways Contribute to DC Dysfunction in Lupus". *PloS one* Nov. 6, 2015, 10(11):e0141927.

Maynard et al., "Regulatory T cells expressing interleukin 10 develop from Foxp3+ and Foxp3-precursor cells in the absence of interleukin 10". Nature Immunology Aug. 12, 2007, 8(9):931-941.

Minnich et al., "Multifunctional role of the transcription factor Blimp-1 in coordinating plasma cell differentiation". Nature Immunology Jan. 18, 2016, 17:331-343.

Naradikian et al, "Cutting Edge: IL-4, IL-21, and IFN-gamma Interact To Govern T-bet and CD11C Expression in TLR-Activated B Cells". *Journal of Immunology* Jul. 2016a, 197(4):1023-1028.

Naradikian et al., "Age-associated B cells: key mediators of both protective and autoreactive humoral responses". Immunological Reviews Jan. 2016, 269(1):118-129.

Parish et al., "Chronic Viral infection promotes sustained Th1-derived immunoregulatory IL-10 Via BLIMP-1". *J. Clin. Invest.* Aug. 2014, 124(8):3455-3468.

Ripich et al., "SWEF Proteins Distinctly Control Maintenance and Differentiation of Hematopoietic Stem Cells". *PloS one* Aug. 25, 2016, 11(8):e0161060.

Rubtsova er al., "Age-Associated B Cells: A T-bet-Dependent Effector with Roles in Protective and Pathogenic Immunity". *Journal of Immunology* Sep. 1, 2015, 195(5):1933-1937.

Rubtsova et al., "B cells expressing the transcription factor T-bet drive lupus-like autoimmunity". *J Clin. Invest.* Apr. 2017, 127:1392-1404.

Rogatsky et al., "Epigenetics and the IRFs: a complex interplay in the control of immunity and autoimmunity". Autoimmunity 2014, 47:242-255. Published Online Nov. 11, 2013.

Sarra et al., "Interleukin-21 in Chronic inflammatory diseases". Biofactors Mar. 29, 2013,39:368-373.

Shi et al., "Transcriptional profiling of mouse B cell terminal differentiation defines a signature for antibody-secreting plasma cells". Nature Immunology Apr. 20, 2015, 16:663- 673.

Sun et al., "High-density genotyping of immune-related loci identifies new SLE risk variants in individuals with Asian ancestry". Nature Genetics Feb. 24, 2016, 48(3):323-330.

Tanaka et al., "SWAP-70-like adapter of T cells, an adapter protein that regulates early TCR-initiated signaling in Th2 lineage cells". *Immunity* Mar. 2003, 18:403-414.

Oka et al., Cooperation of DEF6 with Activated Rac in Regulating Cell Morphology*, J. Biol. Chem. Jan. 19, 2007, 282, pp. 2011-2018.

Marian et al., "Treatment targets in systemic lupus erythematosus: biology and clinical perspective", Arthritis Research & Therapy, Nov. 30, 2012, 14(Suppl 4)S3).

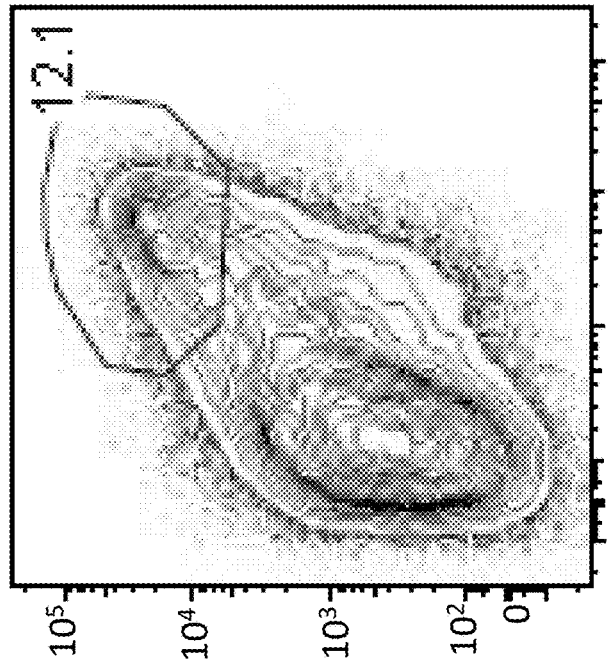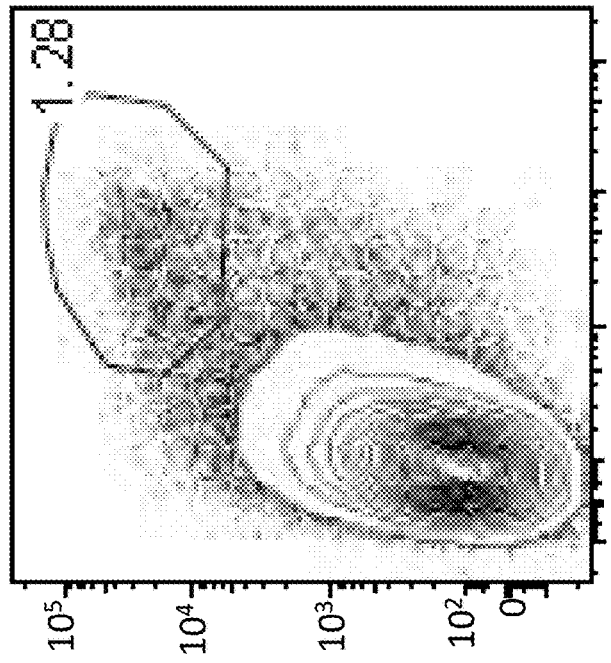
Figure 1A

Figure 1A (cont)
>23 weeks old
B220+CD19+
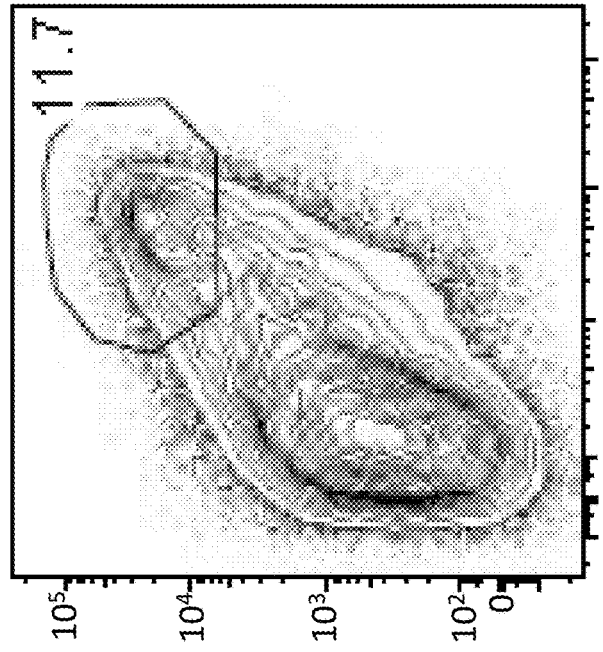
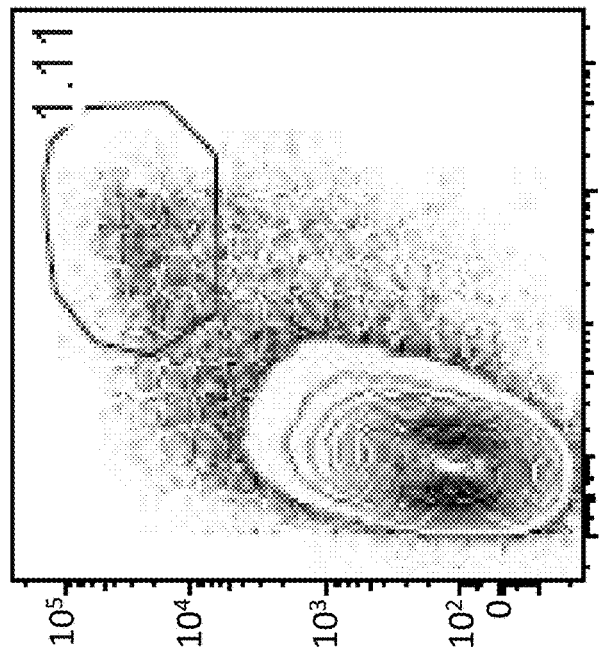

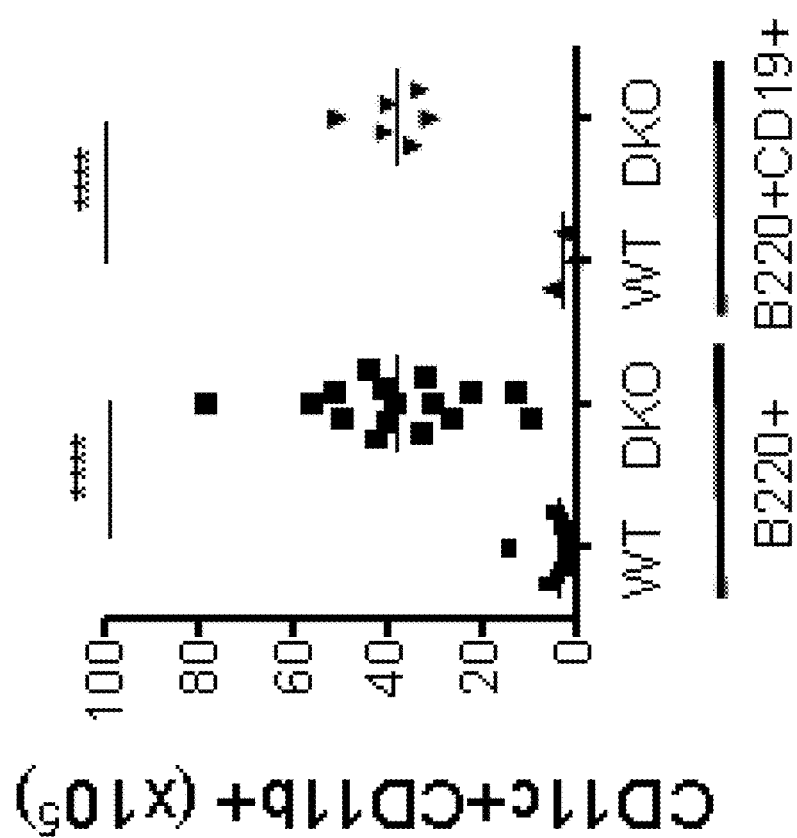
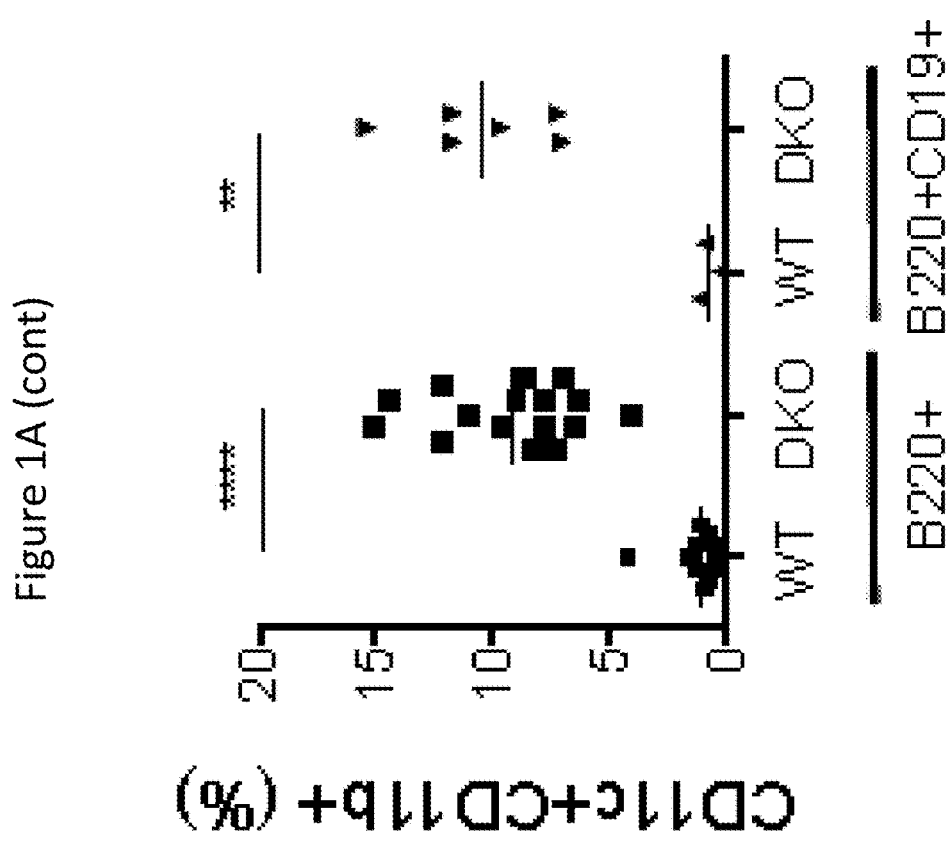
Figure 1A (cont)

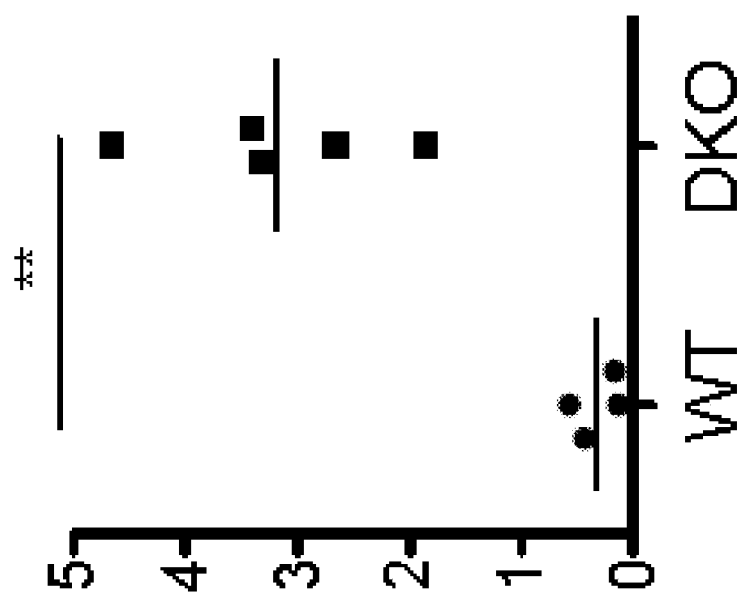
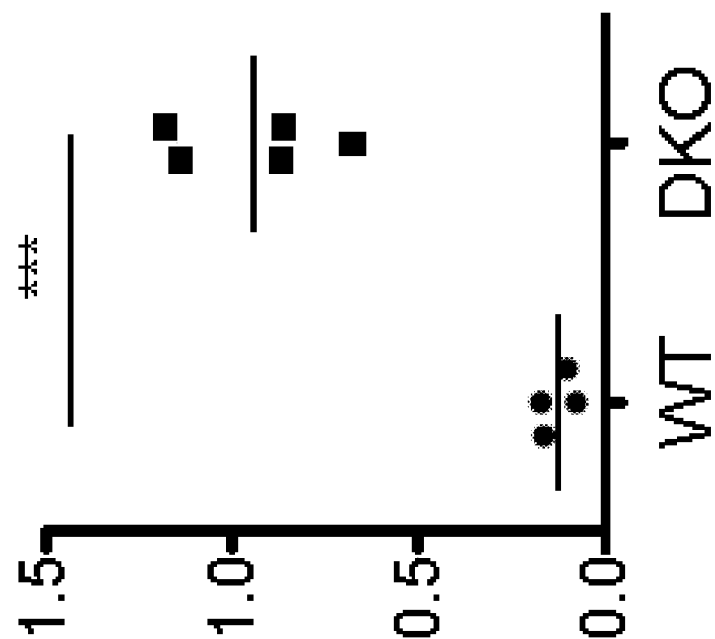
Figure 1C (cont)

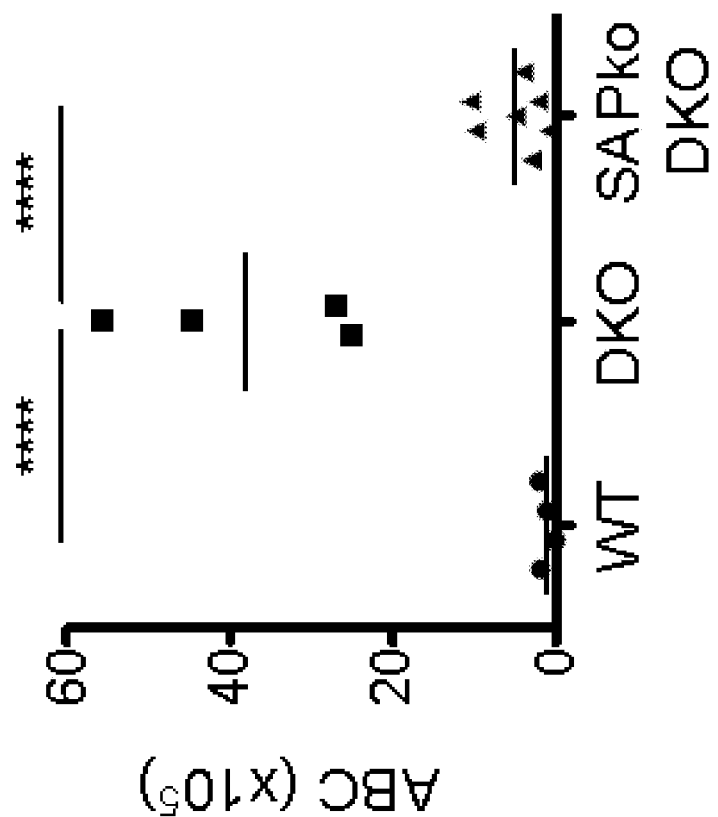
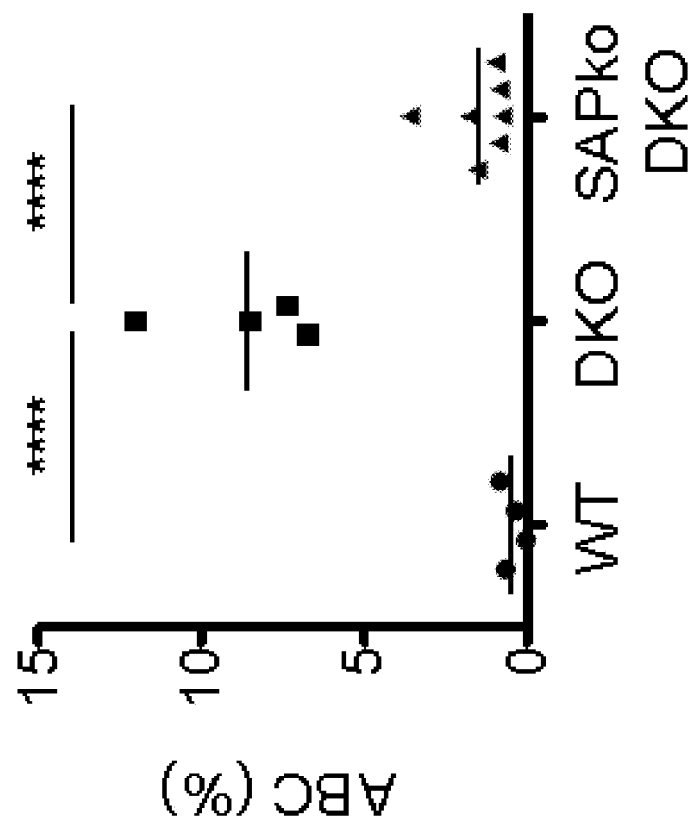
Figure 2D (cont)

Figure 6E
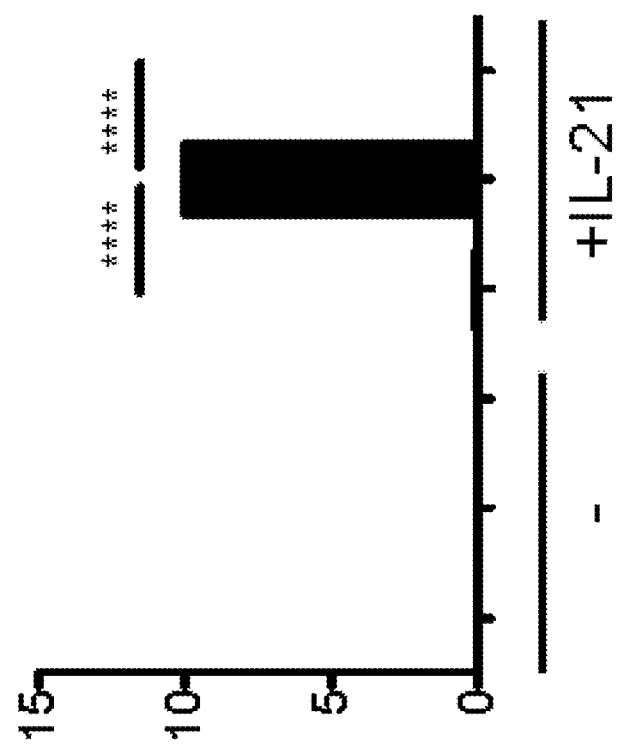
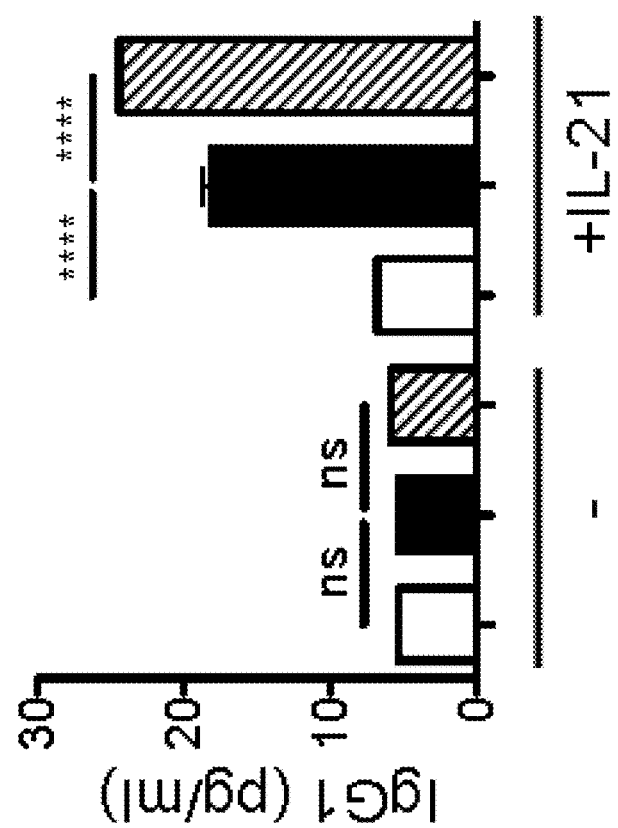

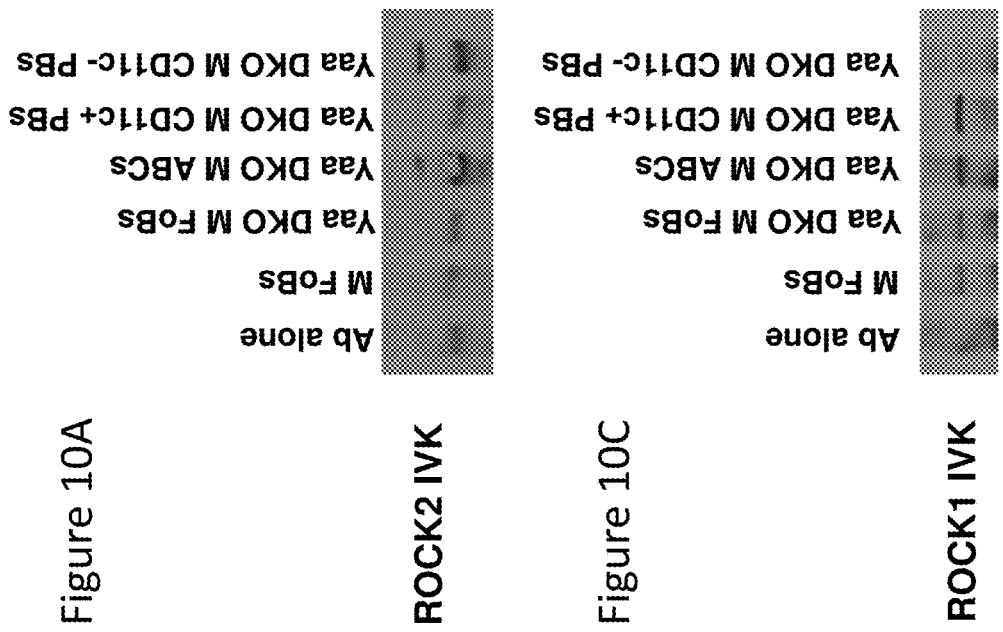

SEQUENCE LISTING

<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: synthetic primer

<400> SEQUENCE: 1
gcccacgtca aggagtattt cta                                           23

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
acacacttgg cggttccttc                                               20

<210> SEQ ID NO 3

```
<211> LENGTH: 22
<212> TYPE: DNA
<213> ORGANISM: Artificial Sequence
<220> FEATURE:
<223> OTHER INFORMATION: synthetic primer

<400> SEQUENCE: 3
gaggatacca ctcccaacag ac                                              22

<210> SEQ ID NO 4
<211> LENGTH: 22
<212> TYPE: DNA
<213> ORGANISM: Artificial Sequence
<220> FEATURE:
<223> OTHER INFORMATION: synthetic primer

<400> SEQUENCE: 4
aagtgcatca tcgttgttca ta                                              22

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
ccaagtgctg ccgtcatttt c                                               21

<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
ggctcgcagg gatgatttca a                                               21

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
ggatatctgg aggaactggc                                                 20

<210> SEQ ID NO 8
<211> LENGTH: 22
<212> TYPE: DNA
<213> ORGANISM: Artificial Sequence
<220> FEATURE:
<223> OTHER INFORMATION: synthetic primer

<400> SEQUENCE: 8
gcgccaagca ttcaatgagc tc                                              22

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
```
tgcagctctg tgaagtggtt                                            20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
agcgatggag aaagccatag                                            20

<210> SEQ ID NO 11
<211> LENGTH: 22
<212> TYPE: DNA
<213> ORGANISM: Artificial Sequence
<220> FEATURE:
<223> OTHER INFORMATION: synthetic primre

<400> SEQUENCE: 11
tccagatacg gtgctccctt ct                                         22

<210> SEQ ID NO 12
<211> LENGTH: 22
<212> TYPE: DNA
<213> ORGANISM: Artificial Sequence
<220> FEATURE:
<223> OTHER INFORMATION: synthetic primer

<400> SEQUENCE: 12
ccagagagct ttggagtggt tc                                         22

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
aattcattcc ggacgagaag                                            20

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
cgatcagctt gttctccaaa                                            20

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
agcagttggt gaccatgtcg                                            20

<210> SEQ ID NO 16
<211> LENGTH: 20
<212> TYPE: DNA

```
<213> ORGANISM: Artificial Sequence
<220> FEATURE:
<223> OTHER INFORMATION: syntthetic primre

<400> SEQUENCE: 16
tggagatctc ctgcttgagg                                                20

<210> SEQ ID NO 17
<211> LENGTH: 19
<212> TYPE: DNA
<213> ORGANISM: Artificial Sequence
<220> FEATURE:
<223> OTHER INFORMATION: synthetic primer

<400> SEQUENCE: 17
cgagaggtga ccttggaac                                                 19

<210> SEQ ID NO 18
<211> LENGTH: 28
<212> TYPE: DNA
<213> ORGANISM: Artificial Sequence
<220> FEATURE:
<223> OTHER INFORMATION: synthetic primer

<400> SEQUENCE: 18
agcttctctt tctccttata aaacattg                                       28

<210> SEQ ID NO 19
<211> LENGTH: 23
<212> TYPE: DNA
<213> ORGANISM: Artificial Sequence
<220> FEATURE:
<223> OTHER INFORMATION: synthetic primer

<400> SEQUENCE: 19
gcatcgaaag aatcacaact agg                                            23

<210> SEQ ID NO 20
<211> LENGTH: 21
<212> TYPE: DNA
<213> ORGANISM: Artificial Sequence
<220> FEATURE:
<223> OTHER INFORMATION: synthetic primer

<400> SEQUENCE: 20
agtagtcccc actgtctgac t                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
gtgagtccct ttagcaccag a                                              21

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
agcagtccct ttatgaacgg                                                20
```

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
gcttccatcc ctacacctaa g                                           21

<210> SEQ ID NO 24
<211> LENGTH: 20
<212> TYPE: DNA
<213> ORGANISM: Artificial Sequence
<220> FEATURE:
<223> OTHER INFORMATION: synthetic primer

<400> SEQUENCE: 24
agaacagctt ttgagcaccg                                             20

<210> SEQ ID NO 25
<211> LENGTH: 23
<212> TYPE: DNA
<213> ORGANISM: Artificial Sequence
<220> FEATURE:
<223> OTHER INFORMATION: synthetic primer

<400> SEQUENCE: 25
tggcttcaaa gtgactaaca gca                                         23

<210> SEQ ID NO 26
<211> LENGTH: 20
<212> TYPE: DNA
<213> ORGANISM: Artificial Sequence
<220> FEATURE:
<223> OTHER INFORMATION: synthetic primer

<400> SEQUENCE: 26
tgtaatgcct ggttgcctcc                                             20

<210> SEQ ID NO 27
<211> LENGTH: 21
<212> TYPE: DNA
<213> ORGANISM: Artificial Sequence
<220> FEATURE:
<223> OTHER INFORMATION: synthetic primer

<400> SEQUENCE: 27
gttcgggacc cacagtacat t                                           21

<210> SEQ ID NO 28
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 28
tgctgagtca cttttaaaga aaaaagaag agt                               33

<210> SEQ ID NO 29
<211> LENGTH: 100
<212> TYPE: DNA
<213> ORGANISM: Artificial Sequence
<220> FEATURE:

```
<223> OTHER INFORMATION: synthetic oligonucleotide

<400> SEQUENCE: 29
catagaaaat gttttcaaaa cccgcattcc gcttatgctg tctggtatct gaaatagatc        60
tgtcaggggg tcacatttta taagcaccac ttcgtgtttg                             100
```

INHIBITION OF EXPANSION AND FUNCTION OF PATHOGENIC AGE-ASSOCIATED B CELLS AND USE FOR THE PREVENTION AND TREATMENT OF AUTOIMMUNE DISEASE

CROSS REFERENCE TO RELATED APPLICATION

The present application is a continuation of U.S. application Ser. No. 16/523,055, filed Jul. 26, 2019, which is a continuation of U.S. application Ser. No. 15/833,398, filed Dec. 6, 2017, and claims priority to U.S. Patent Application Ser. No. 62/430,732 filed Dec. 6, 2016, U.S. Patent Application Ser. No. 62/487,645 filed Apr. 20, 2017, and U.S. Patent Application Ser. No. 62/512,803 filed May 31, 2017, all of which are hereby incorporated by reference in their entirety.

GOVERNMENT SUPPORT CLAUSE

This invention was made with government support under AR064883 and AR070146 awarded by NIH. The government has certain rights in the invention.

FIELD OF THE INVENTION

This invention relates to the field of preventing and treating autoimmune and lymphoproliferative disease by targeting pathogenic age-associated B cells as well as methods of detecting these pathogenic age-associated B cells as a method of diagnosing and predicting autoimmune disease and other lymphoproliferative and chronic inflammatory disorders.

The invention also provides targets for drug development and basic research for autoimmune diseases and other lymphoproliferative and chronic inflammatory disorders.

BACKGROUND OF THE INVENTION

Autoimmune diseases, such as systemic lupus erythematosus (SLE), also known as lupus, occur when the immune system of a vertebrate attacks the tissue of self rather than an infectious agent. Other autoimmune illnesses include rheumatoid arthritis, inflammatory bowel disease, and Type 1 diabetes. Autoimmune disorders can furthermore be associated with the development of lymphoproliferative disorders such as lymphomas.

While the cause of lupus and other autoimmune diseases is unknown, theories on their origin include genetics, environment, infections, and the defective failure to process the products of an immune response.

Precise regulation of the expansion and function of T and B cell subsets is critical for the prevention of autoimmune disorders like SLE, a disease which preferentially affects females (Eisenberg 2003; Cohen-Solal and Diamond 2011). Murine studies have recently uncovered the existence of a unique subset of B cells termed age/autoimmunity-associated B cells (ABCs) that preferentially expands in females with age. In addition to classical B cell markers like B220 and CD19, ABCs can also express markers such as CD11c and CD11b and are known to require T-bet for their generation. Formation of ABCs is promoted by TLR7/9 engagement and cytokines like IFNγ and IL-21. ABCs increase prematurely in murine models of lupus and can produce anti-chromatin antibodies. B cells with features similar to ABCs have also been detected in human autoimmune disorders including SLE. ABCs characteristically express T-bet and their generation depends on this transcription factor, hence, these cells are also known as CD11c+Tbet+ B cells (Naradikian et al. 2016a; Naradikian et al. 2016; Rubtsova et al. 2017). The molecular pathways that promote the expansion and pathogenic function of ABCs in autoimmune settings are largely unknown.

Multiple lines of evidence have implicated members of the Interferon Regulatory Factor (IRF) family of transcription factors in autoimmunity and lupus development. Amongst the nine IRF family members, IRF4 plays a fundamental and multifaceted role in the activation of both T and B cells (Rogatsky et al. 2014). In addition to IRF4, studies have demonstrated strong associations between IRF5 variants and human autoimmune disorders, particularly SLE (Cham et al. 2012; Lazzari and Jefferies 2014). It is also unknown whether IRF4 and IRF 5 play a role in the function of ABCs.

The SWEF family is a small family of proteins comprised of SWAP-70 and its homolog, DEF6 (Gupta et al. 2003; Tanaka et al. 2003; Ripich et al 2003). In addition to regulating T and B cell function by regulating the activity of the transcription factor IRF4 (Biswas et al. 2012; Manni et al. 2015), these proteins also control the cytoskeletal dynamics of T and B cells by regulating the activation of Rho GTPases (Biswas et al. 2010). The SWEF proteins play an important immunoregulatory role in vivo as evidenced by the finding that the simultaneous lack of DEF6 and SWAP-70 (in Doubleknockout=DKO mice) leads to the development of SLE in C57BL/6 mice, which, similarly to human SLE, preferentially affects females (Biswas et al. 2012). The development of autoimmunity in DKO mice is associated with dysregulation of both T and B cell compartments including expansion of $T_{FH}$ cells, increased IL-21 production, and enhanced formation of germinal centers, and plasma cells (Biswas et al. 2012). In further support of a role for this family of proteins in autoimmunity, the DEF6 locus has recently been identified as a genetic risk factor for human SLE (Sun et al. 2016).

There are currently very few methods of predicting whom will develop lupus or other autoimmune diseases and lymphoproliferative disorders, and there are no current therapies for treating SLE other than treatment of the symptoms, and no preventative therapy. Thus, there is a need in the art for new treatments and diagnostics for SLE, and other autoimmune and lymphoproliferative diseases.

SUMMARY OF THE INVENTION

The current invention is based on the discovery that age-associated B cells ("ABCs") expand and become pathogenic ("pathogenic ABCs") upon interaction of certain proteins. In particular, the aberrant expansion of ABCs depends on the transcription factor, interferon regulatory factor 5 ("IRF5"). Additionally, the aberrant expansion of ABCs is abolished or decreased by two proteins in the SWEF family, SWAP-70 and DEF6.

One embodiment of the current invention is a method of abolishing or decreasing pathogenic ABCs in a subject in need thereof by administering an effective amount of an agent that agonizes, activates or increases the expression and/or activity of SWAP-70 and DEF6.

A further embodiment of the current invention is a method of preventing and/or treating an autoimmune or lymphoproliferative disease by abolishing or decreasing pathogenic ABCs in a subject in need thereof by administering an effective amount of an agent that agonizes, activates or increases the expression and/or activity of SWAP-70 and DEF6.

Another embodiment of the current invention is a method of abolishing or decreasing pathogenic ABCs in a subject in need thereof by administering an effective amount of an agent that antagonizes, inhibits or reduces the expression and/or activity of IRF5.

A further embodiment of the current invention is a method of preventing and/or treating an autoimmune or lymphoproliferative disease by abolishing or decreasing pathogenic ABCs in a subject in need thereof by administering an effective amount of an agent that antagonizes, inhibits or decreases the expression and/or activity of IRF5.

Another embodiment of the current invention is a method of abolishing or decreasing pathogenic ABCs in a subject in need thereof by administering an effective amount of an agent that antagonizes, inhibits or reduces the expression of certain genes that are upregulated in pathogenic ABCs.

A further embodiment of the current invention is a method of preventing and/or treating an autoimmune or lymphoproliferative disease by abolishing or decreasing pathogenic ABCs in a subject in need thereof by administering an effective amount of an agent that antagonizes, inhibits or decreases the expression of certain genes that are upregulated in pathogenic ABCs.

A further embodiment of the current invention is a method of abolishing or decreasing pathogenic ABCs in a subject in need thereof by administering an effective amount of an agent that agonizes, activates or increases the number or expression of certain genes that are downregulated in pathogenic ABCs.

Yet a further embodiment of the current invention is a method of preventing and/or treating an autoimmune or lymphoproliferative disease by abolishing or decreasing pathogenic ABCs in a subject in need thereof by administering an effective amount of an agent that agonizes, activates or increases the number or expression of certain genes that are downregulated in pathogenic ABCs.

A further embodiment of the invention is a method of preventing and/or treating an autoimmune disease in a subject in need thereof by administering an effective amount of an agent that antagonizes or inhibits the ability of pathogenic ABCs to differentiate into plasma cells.

In some embodiments, the autoimmune disease is systemic lupus erythematosus, rheumatoid arthritis, type 1 diabetes, multiple sclerosis, myasthenia gravis, Graves disease, pernicious anemia, scleroderma, psoriasis, inflammatory bowel diseases, Hashimoto's disease, Addison's disease, and Sjögren's syndrome. In some embodiments, the lymphoproliferative disease is Hodgkin's lymphoma or non-Hodgkin's lymphoma.

A further embodiment of the current invention is a method of detecting pathogenic ABCs. The detection of pathogenic ABCs makes it possible to diagnose that a subject has an autoimmune or lymphoproliferative disease or predict that a subject will develop an autoimmune or lymphoproliferative disease. A method for detecting pathogenic ABCs comprises obtaining a sample from a subject and detecting the presence of pathogenic ABCs, wherein the pathogenic ABCs comprise B cells that express CD11c, as well as additional markers such as B220, CD86, MHCII and IgM, but downregulate CD5. The presence of the pathogenic ABCs can also be detected by detecting the expression of one or more genes as compared to a reference value of the expression of the same genes in ABCs that are not pathogenic or the same genes in other non-pathogenic B cells, such as follicular B cells.

The expression of the genes from the pathogenic ABCs from a subject with a suspected autoimmune or lymphoproliferative disease can be compared to a reference value of the expression of the same genes in non-pathogenic ABCs or other B cells from a healthy donor or control. The levels of expressed genes may be measured as absolute or relative. Absolute quantitation measure concentrations of specific RNA and requires a calibration curve. Relative quantification measures fold change differences of specific RNA in comparison to housekeeping genes. Relative quantification is usually adequate to investigate physiological changes in gene expression levels.

Once the pathogenic ABCs are detected, a further embodiment of the invention is abolishing or decreasing the pathogenic ABCs, by the methods set forth herein.

A further embodiment of the current invention is a method of evaluating or monitoring subjects with an autoimmune or lymphoproliferative disease for their response to treatment by the detection of pathogenic ABCs. A method for detecting pathogenic ABCs comprises obtaining a sample from a subject, isolating B cells and detecting the presence of pathogenic ABCs, wherein the pathogenic ABCs comprise B cells that express cell markers CD11c, and additional markers such as B220, CD86, MHC11 and IgM, but downregulate CD5. The presence of the pathogenic ABCs can also be detected by detecting the expression of one or more genes, as compared to the expression of the same genes in ABCs that are not pathogenic or the same genes in other B cells. In this method, the expression of the genes from the cells of the subject are compared before and after treatment.

The present invention also provides for methods and tools for drug design, testing of agents, and tools for basic research into the causes and etiology of pathogenic ABCs, and autoimmune or lymphoproliferative disease.

Thus, a further embodiment of the present invention is a method and/or assay for identifying a test agent for abolishing or decreasing pathogenic ABCs comprising contacting or incubating a test agent with a nucleotide comprising the gene for SWAP-70 or DEF6 which expresses a measurable phenotype, and measuring the phenotype before and after contact or incubation with the test agent, wherein if the expression of the measurable phenotype is increased after the contact or incubation with the test agent, the test agent is identified as an agent that can abolish or decrease pathogenic ABCs.

The measurable phenotype can be one that is native to the gene or one that is artificially linked, such as a reporter gene.

A further embodiment of the present invention is a method and/or assay for identifying a test agent for abolishing or decreasing pathogenic ABCs, comprising transforming a host cell with a gene construct comprising the gene for SWAP-70 or DEF6, detecting the expression of the gene in the host cell, contacting the test agent with the host cell, and detecting the expression of the gene from the host cell after contact with the test agent or compound, wherein if the expression of the gene is increased after contact with the test agent or compound, the test agent is identified as an agent that can abolish or decrease pathogenic ABCs.

One embodiment is a method and/or assay for identifying a test agent for abolishing or decreasing pathogenic ABCs, comprising contacting or incubating the test agent with IRF5, and detecting the presence of a complex between the test agent, wherein if a complex between the test agent and IRF5 is detected, the test agent is identified as an agent that can abolish or decrease pathogenic ABCs.

Another embodiment of the present invention is a method and/or assay for identifying a test agent for abolishing and/or decreasing pathogenic ABCs, comprising contacting or incubating the test agent with IRF5 and a known antibody of IRF5, and detecting the presence and quantity of unbound antibody, wherein the presence of the unbound antibody indicates that the test agent is binding to IRF5 and the test agent is identified as an agent that can abolish or decrease pathogenic ABCs.

A further embodiment of the present invention is a method and/or assay for identifying a test agent for abolishing or decreasing pathogenic ABCs comprising contacting or incubating a test agent to a nucleotide comprising the gene for IRF5, and determining if the test agent binds to the gene, wherein if the test agent binds to the nucleotide, the test agent is identified as an agent that can abolish or decrease pathogenic ABCs.

A further embodiment of the present invention is a method and/or assay for identifying a test agent for abolishing or decreasing pathogenic ABCs comprising contacting or incubating a test agent with a nucleotide comprising the gene for IRF5 which expresses a measurable phenotype, and measuring the phenotype before and after contact or incubation with the test agent, wherein if the expression of the measurable phenotype is decreased after the contact or incubation with the test agent, the test agent is identified as an agent that can abolish or decrease pathogenic ABCs.

The measurable phenotype can be one that is native to the gene or one that is artificially linked, such as a reporter gene.

One embodiment of the present invention is a method and/or assay for identifying a test agent for abolishing or decreasing pathogenic ABCs, comprising transforming a host cell with a gene construct comprising the gene for IRF5, detecting the expression of the gene in the host cell, contacting the test agent with the host cell, and detecting the expression of the gene from the host cell after contact with the test agent or compound, wherein if the expression of the gene is reduced or decreased after contact with the test agent or compound, the test agent is identified as an agent that can abolish or decrease pathogenic ABCs.

A further embodiment of the present invention is a method and/or assay for identifying a test agent for abolishing or decreasing pathogenic ABCs comprising contacting or incubating a test agent to a nucleotide comprising a gene that is upregulated in pathogenic ABCs, and determining if the test agent binds to the gene, wherein if the test agent binds to the nucleotide, the test agent is identified as an agent that can abolish or decrease pathogenic ABCs.

A further embodiment of the present invention is a method and/or assay for identifying a test agent for abolishing or decreasing pathogenic ABCs comprising contacting or incubating a test agent with a nucleotide comprising a gene that is upregulated in pathogenic ABCs which expresses a measurable phenotype, and measuring the phenotype before and after contact or incubation with the test agent, wherein if the expression of the measurable phenotype is decreased after the contact or incubation with the test agent, the test agent is identified as an agent that can abolish or decrease pathogenic ABCs.

The measurable phenotype can be one that is native to the gene or one that is artificially linked, such as a reporter gene.

A further embodiment of the present invention is a method and/or assay for identifying a test agent for abolishing or decreasing pathogenic ABCs, comprising transforming a host cell with a gene construct comprising a gene that is upregulated in pathogenic ABCs, detecting the expression of the gene in the host cell, contacting the test agent with the host cell, and detecting the expression of the gene from the host cell after contact with the test agent or compound, wherein if the expression of the gene is reduced or decreased after contact with the test agent or compound, the test agent is identified as an agent that can abolish or decrease pathogenic ABCs.

A further embodiment of the present invention is a method and/or assay for identifying a test agent for abolishing or decreasing pathogenic ABCs comprising contacting or incubating a test agent with a nucleotide comprising a gene that is downregulated in pathogenic ABCs which expresses a measurable phenotype, and measuring the phenotype before and after contact or incubation with the test agent, wherein if the expression of the measurable phenotype is increased after the contact or incubation with the test agent, the test agent is identified as an agent that can abolish or decrease pathogenic ABCs.

The measurable phenotype can be one that is native to the gene or one that is artificially linked, such as a reporter gene.

A further embodiment of the present invention is a method and/or assay for identifying a test agent for abolishing or decreasing pathogenic ABCs, comprising transforming a host cell with a gene construct comprising a gene that is downregulated in pathogenic ABCs, detecting the expression of the gene in the host cell, contacting the test agent with the host cell, and detecting the expression of the gene from the host cell after contact with the test agent or compound, wherein if the expression of the gene is increased after contact with the test agent or compound, the test agent is identified as an agent that can abolish or decrease pathogenic ABCs.

Any test agent identified by these methods and assays would be useful in preventing and/or treating an autoimmune or lymphoproliferative disease.

The present invention also includes kits.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

Certain abbreviations are used in the Figures and Brief Description of the Figures including: WT—wild type; FACS—flow cytometry analysis; and FoB cells—follicular B cells.

FIG. 1 shows the result showing the spontaneous expansion of ABCs in DKO mice. FIG. 1A is representative flow cytometric analysis (FACS) plots and graphs of ABC cells in the spleens from aging (greater than 23 weeks-old) wild type (WT) or DKO female mice. Graphs show frequencies and numbers of individual mice and mean value of 4-8 independent experiments (n=3-16). : $p \leq 0.01$, : $p \leq 0.0001$. (two-tailed Student t-test). FIG. 1G are graphs of the levels of anti-dsDNAIgG2c, anti-nRNP, and anti-Cardiolipin IgG antibodies in the supernatants of sorted ABC (CD11c+CD11b+B220+CD19+) and FoB (CD11c−CD11b−CD23+B220+CD19+) B cells stimulated in vitro±1 µg/ml imiquimod for 7 days as measured by ELISA (representative of 4 independent experiments). Mean±SEM is shown. \*: p≤0.001 (One-way ANOVA).

FIG. 2 shows the results that IL-21 regulates the generation of DKO ABCs in vitro and in vivo.

FIG. 3 shows the results showing differentially expressed genes in pathogenic ABCs.

FIG. 4 shows that the chromatin landscape of DKO ABCs is enriched in IRF and AP-1/BATF motifs.

FIG. 5 shows the results showing WT and DKO ABCs exhibit a distinctive transcriptional and chromatin profile.

FIG. 6 shows the results that IRF5 regulates the IL-21-mediated formation of DKO ABCs. FIG. 6E shows graphs of amount of IgG1 and IgG2c in the supernatants of cells stimulated±IL-21 7 days as analyzed by ELISA. Data are representative of 3 independent experiments. Mean±SEM is shown. ns: not significant, : p≤0.0001. (One-way ANOVA). FIG. 6O is a Western blot of 293T cells transiently transfected with various constructs as indicated. Immunoprecipitations were performed using an anti-HA antibody. Immunoprecipitates were analyzed by Western blotting using an anti-FLAG, T-bet or HA antibodies. Data are representative of 2 independent experiments with similar results.

FIG. 7 shows the results that monoallelic deletion of IRF5 abolishes accumulation of ABCs and lupus development in DKO mice.

FIG. 8 shows that a subset of CD11c+ DKO B cells upregulates PC markers.

FIG. 9 shows that DKO ABCs exhibit sex specific differences in autoantibody production.

FIG. 10 show the expression of Rho-kinase 1 and 2 in different populations of cells. FIG. 10A shows the indicated cells assayed with ROCK2 in vitro kinase assay. FIG. 10B shows the expression of phospho IRF4 in some of the same cells (plasmablasts) as assessed by Western blotting with a pIRF4 Antibody. FIG. 10C shows the same cells used in FIG. 10A assayed with a ROCK1 in vitro kinase assay.

DETAILED DESCRIPTION OF THE INVENTION

Definitions

Figure 1B:
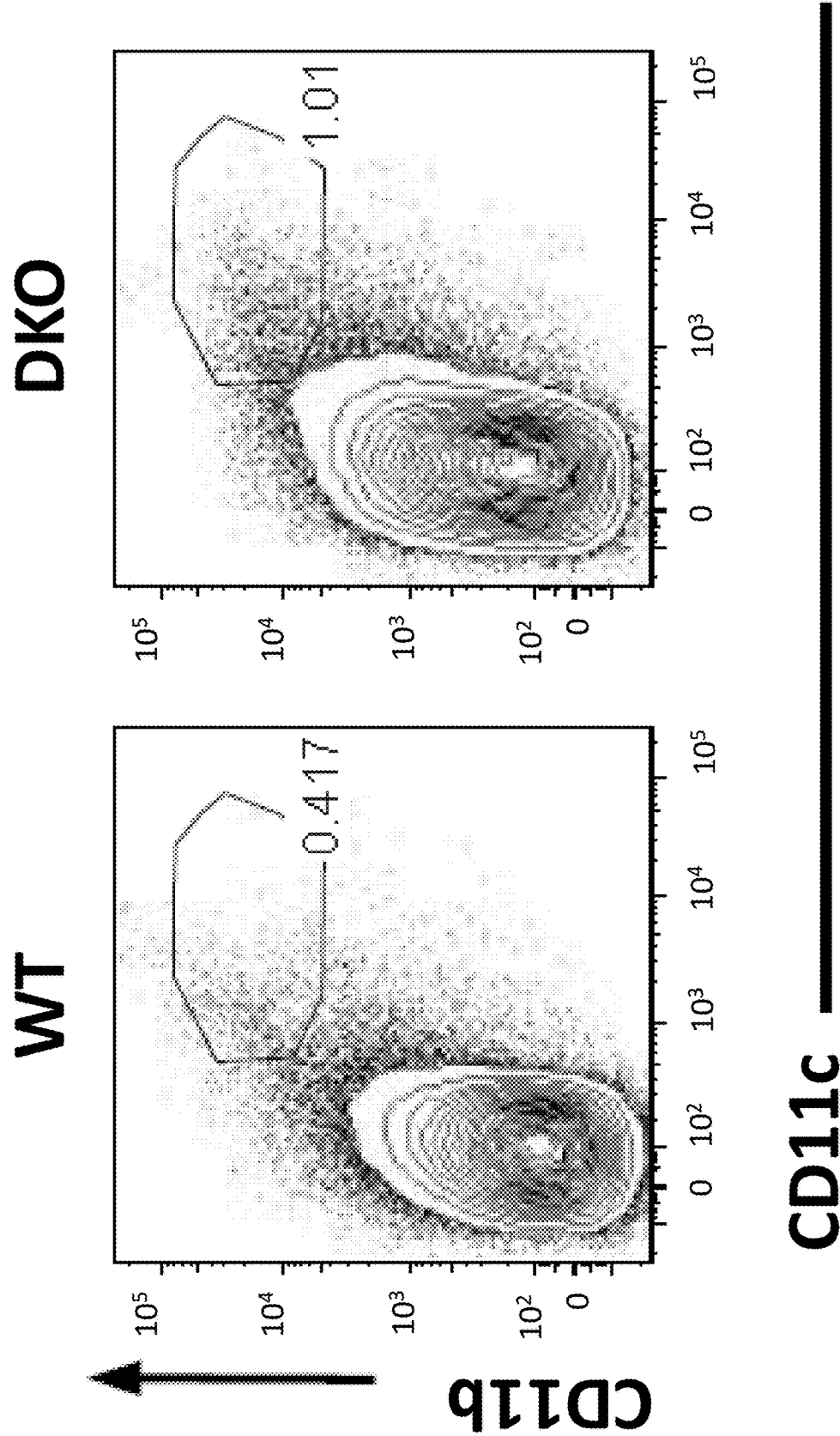
FIG. 1B is representative FACS plots and graphs for CD11b and CD11c expression after gating on B220+CD19+ cells in skin draining lymph nodes of WT, DKO, Def6ko (Def6$^{tr/tr}$), and SWAP70ko (Swap-70$^{-/-}$) mice (18-24 weeks old). Graphs show frequencies and numbers of cells in individual mice and mean value of 3 independent experiments (n=3-5). : $p \leq 0.01$. (One-way ANOVA).
Figure 1B:
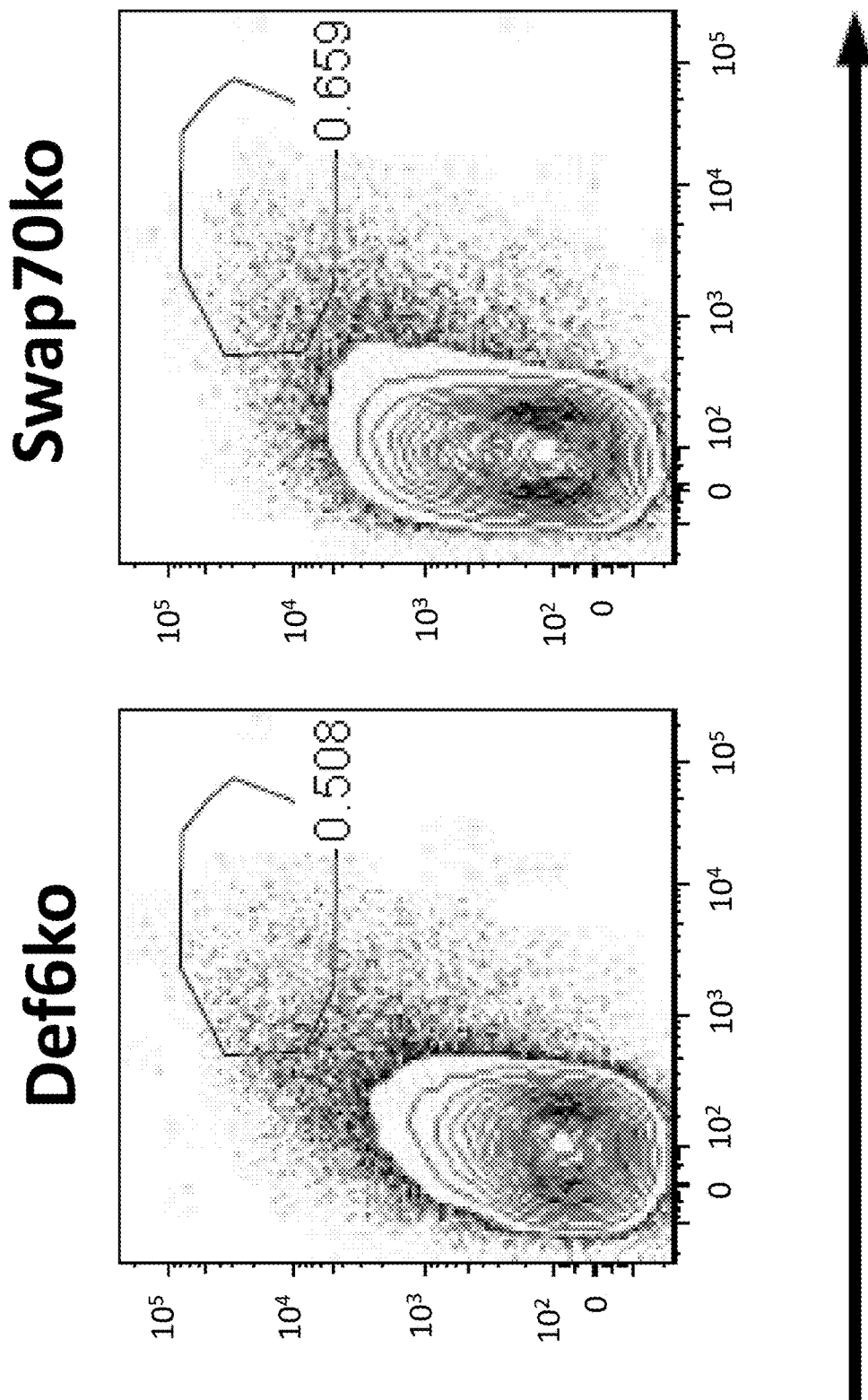
Figure 1B:
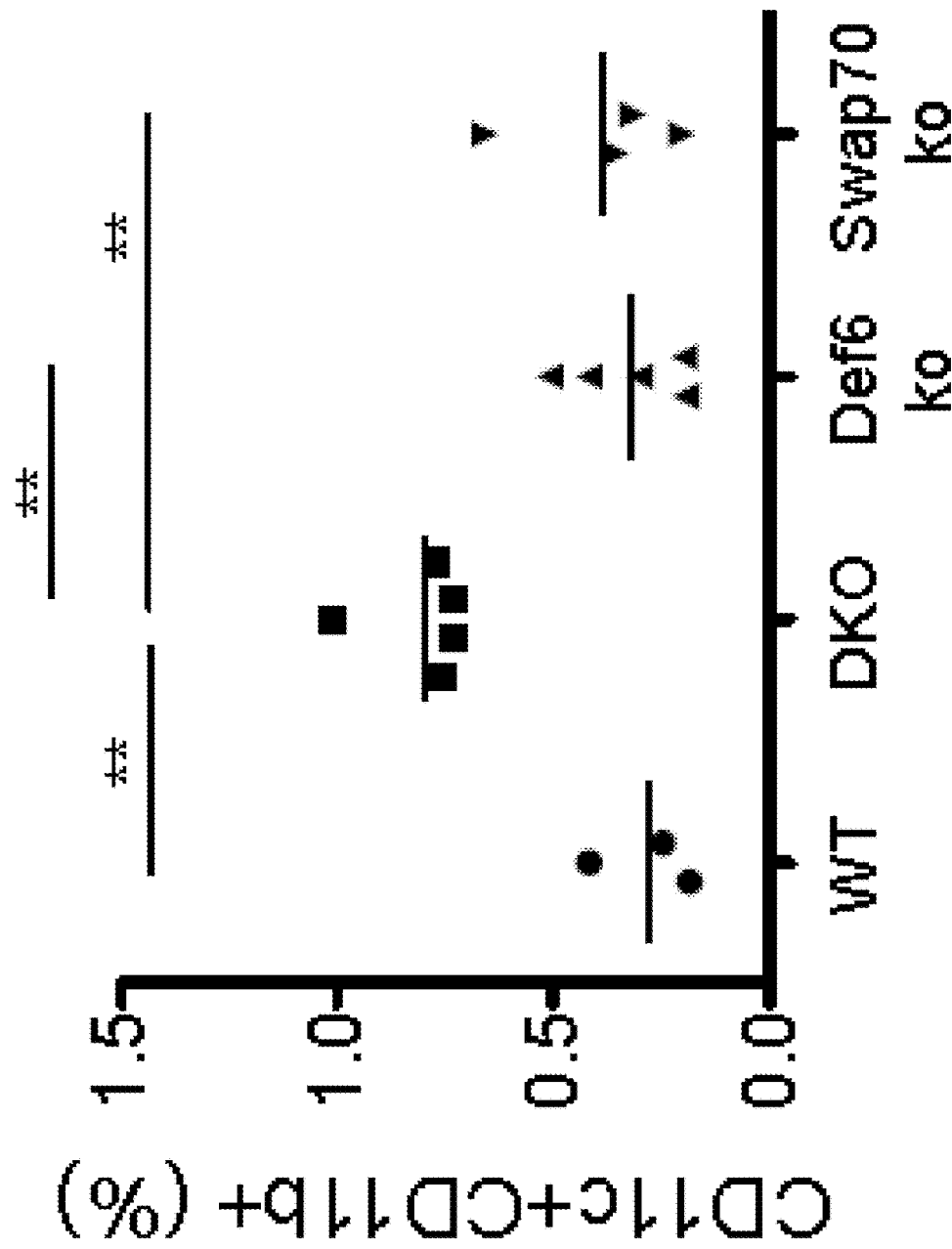

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The terms "pathogenic age-associated B cells", and "pathogenic ABCs" is used herein to denote the novel subset of B cells described herein that promote disease. The terms "DKO ABCs" and "autoimmune prone ABCs" also denote these cells.

The term "subject" as used in this application means an animal with an immune system such as avians and mammals. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is one suffering with an autoimmune or lymphoproliferative disease or suspected of suffering from an autoimmune or lymphoproliferative disease, such as systemic lupus erythematosus or lymphoma.

The term "detection", "detect", "detecting" and the like as used herein means as used herein means to discover the presence or existence of.

The terms "diagnosis", "diagnose", diagnosing" and the like as used herein means to determine what physical disease or illness a subject or patient has, in this case an autoimmune or lymphoproliferative disease.

The terms "identification", "identify", "identifying" and the like as used herein means to recognize a disease state or a clinical manifestation or severity of a disease state in a subject or patient. The term also is used in relation to test agents and their ability to have a particular action or efficacy.

The terms "prediction", "predict", "predicting" and the like as used herein means to tell in advance based upon special knowledge.

The term "reference value" as used herein means an amount or a quantity of a particular protein or nucleic acid in a sample from a healthy control or healthy donor.

The terms "healthy control", "healthy donor" and "HD" are used interchangeably in this application and are a human subject who is not suffering from systemic lupus erythematosus or any other autoimmune or lymphoproliferative disease.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The phrase "in need thereof" indicates a subject has an autoimmune or lymphoproliferative disease, is suspected of having an autoimmune or lymphoproliferative disease, or has risk factors for an autoimmune or lymphoproliferative disease.

The terms "expression profile" or "gene expression profile" refers to any description or measurement of one or more of the genes that are expressed by a cell, tissue, or organism under or in response to a particular condition. Expression profiles can identify genes that are upregulated, downregulated, or unaffected under particular conditions. Gene expression can be detected at the nucleic acid level or at the protein level. The expression profiling at the nucleic acid level can be accomplished using any available technology to measure gene transcript levels. For example, the method could employ in situ hybridization, Northern hybridization or hybridization to a nucleic acid microarray, such as an oligonucleotide microarray, or a cDNA microarray. Alternatively, the method could employ reverse transcriptase-polymerase chain reaction (RT-PCR) such as fluorescent dye-based quantitative real time PCR (TaqMan® PCR). In the Examples section provided below, nucleic acid expression profiles were obtained using Affymetrix GeneChip® oligonucleotide microarrays. The expression profiling at the protein level can be accomplished using any available technology to measure protein levels, e.g., using peptide-specific capture agent arrays.

The terms "gene", "gene transcript", and "transcript" are used somewhat interchangeable in the application. The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. "Transcript" or "gene transcript" is a sequence of RNA produced by transcription of a particular gene. Thus, the expression of the gene can be measured via the transcript.

The term "antisense DNA" is the non-coding strand complementary to the coding strand in double-stranded DNA.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid).

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form. The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoro-amidates, and carbamates) and with charged linkages (e.g., phosphorothioates, and phosphorodithioates). Polynucleotides may contain one or more additional covalently linked moieties, such as, for example, proteins (e.g., nucleases, toxins, antibodies, signal peptides, and poly-L-lysine), intercalators (e.g., acridine, and psoralen), chelators (e.g., metals, radioactive metals, iron, and oxidative metals), and alkylators. The polynucleotides may be derivatized by formation of a methyl or ethyl phosphotriester or an alkyl phosphoramidate linkage. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs. Furthermore, the polynucleotides herein may also be modified with a label capable of providing a detectable signal, either directly or indirectly. Exemplary labels include radioisotopes, fluorescent molecules, and biotin.

The term "polypeptide" as used herein means a compound of two or more amino acids linked by a peptide bond. "Polypeptide" is used herein interchangeably with the term "protein."

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Pathogenic Age-Associated B Cells, Their Regulation and Role in Autoimmune Disease Age-associated B cells (ABCs) are a B cell subset, which exhibits unique phenotypic and functional characteristics and can be regulated by T-bet. Although ABCs accumulate in autoimmune disorders, they can also accumulate in non-autoimmune subjects. Additionally, some ABCs produce autoantibodies, and some do not. A detailed understanding of the molecular pathways that promote their expansion and function in autoimmune settings is largely unknown. However, as shown herein, some ABCs are benign and some are pathogenic, causing autoimmune and lymphoproliferative diseases as well as chronic inflammatory disorders. The current invention is based upon the discovery of these pathogenic ABCs (i.e., ABCs that cause or are associated with disease) and the proteins that regulate their expansion, function and differentiation.

In particular, pathogenic ABCs express CD11c (Example 2). Using double knockout mice for SWAP70 and DEF6 (SWEF deficient) which develop a lupus-like syndrome, it was found that ABCs from these mice express many of the cell markers found in ABCs from wild type mice including CD86, MHCII and IgM. However, these cells downregulated CD5, which others reported that ABCs do express (see Rubtsova et al. 2015). Additionally, these pathogenic ABCs are detected at a much earlier age in the DKO mice than the benign ABCs found in wild type mice. These pathogenic ABCs also secrete anti-dsDNA IgG2c and other autoantibodies. See Example 2.

These pathogenic ABCs from the DKO mice exhibited an IL-21-dependent expansion with pro-inflammatory capabilities, produced autoantibodies, and as compared to ABCs from wild type non-autoimmune female mice, displayed a distinctive transcriptome marked by increased Ig transcription and diminished expression of a subset of myeloid-related programs. Chromatin accessibility profiles revealed a unique chromatin landscape in ABCs from DKO mice, which is enriched in open chromatin regions containing IRF, AP1/BATF, and T-bet binding motifs but depleted in regions containing motifs targeted by PU.1 and MAF. Furthermore, it is shown herein that in the absence of SWEF proteins, IL-21 stimulation of B cells leads to dysregulated IRF5 activity and that the generation of pathogenic ABCs and lupus development in DKO female mice does not occur. Thus, the generation of pathogenic ABCs is controlled at least in part by IRF5 and SWEF proteins. Taken together these studies uncover a new genetic pathway that controls the generation of pathogenic ABCs in autoimmunity as well as the distinction between these pathogenic ABCs and those that accumulate normally, benign ABCs. See Examples 3-8.

The genome-wide transcriptional profiling demonstrated that the SWEF proteins regulate several key processes that can impact the expansion and function of ABCs. In particular, the GSEA pathway analysis identified alterations in a number of pathways involved in the control of cellular proliferation, which can play a crucial role in the premature accumulation of ABCs in DKO mice. This analysis also revealed a marked ability of pathogenic ABCs to promote inflammation via the production of chemokines and cytokines. Thus, the contribution of ABCs to autoimmune pathophysiology is multifactorial and encompasses both production of autoantibodies especially of the pathogenic IgG2a/c isotype and the ability to promote inflammation via recruitment of inflammatory cells and production of pro-inflammatory cytokines. See Example 4.

The absence of SWEF proteins also resulted in increased binding of T-bet to several ABC specific peaks suggesting cooperativity between IRF5 and T-bet at least for some ABC specific regulatory regions. The notion that such cooperativity is at play was further reinforced by the decreased binding of T-bet to ABC-specific regions in the absence of IRF5 and by mutational analysis, which revealed an important role for the DNA binding domain of IRF5 in the optimal recruitment of T-bet to ABC-specific sites. See Example 7.

The enrichment in IRF motifs in DKO ABCs was mechanistically linked with an increase in the activity of IRF5 due to the lack of the inhibitory effects of the SWEF proteins. Coimmunoprecipitation experiments demonstrated that endogenous IRF5 can interact with both DEF6 and SWAP-70 supporting the idea that its activity can be inhibited by a heterodimer of the two SWEF proteins. Interaction of the SWEF proteins with IRF5 was mediated by the IRF Association Domain (IAD) of IRF5 in line with the known ability of this family to interact with the IAD of IRF4 and the presence of structural similarities between the IAD of IRF4 and that of IRF5. Indeed, the SWEF proteins do not interact with IRF2, which carries a distinct type of IAD. See Example 7.

The work described herein now implicates IRF5 downstream of IL-21 signaling thus positioning IRF5 as a common mediator of two key stimulatory pathways for ABC generation in autoimmune settings, IL21 and TLR7. The convergence of these two pathways onto IRF5 is likely to contribute to the dramatic effect observed upon monoallelic deletion of IRF5 on the development of disease in the model used herein (Example 8). Such strong gene dosage effects may be particular relevant for human SLE where IRF5 risk variants have been shown to result in alterations in IRF5 levels (Cham et al. 2012; Lazzari and Jefferies 2014).

In addition to enrichment for IRF and AP-1/BATF motifs, which could be observed irrespective of whether DKO ABCs were compared to DKO FoBs or to WT ABCs, comparison of the chromatin landscapes of wild type and DKO ABCs revealed that pathogenic ABCs also exhibited a marked loss of accessible chromatin regions containing PU.1, MAF, and C/EBP motifs. These epigenetic changes were associated with downregulation of MAF and MAFB expression but maintenance of PU.1 levels. Importantly, given the known repressive role of PU.1 on the quantity of antibody production and plasma cell differentiation, selective depletion of PU.1-bound peaks could also lessen the PU.1-mediated inhibitory effects and directly contribute to the increased levels of Ig transcription of DKO ABCs as well as enhance their ability to differentiate into plasma cells upon exposure to additional environmental stimuli. Thus, the presence of dysregulated IRF5 activity combined with the loss of PU.1-containing repressive complexes could represent a critical mechanism employed by autoimmune-prone ABCs to bypass critical checkpoints governing the transition of B cells into antibody secreting cells.

While most DKO ABCs express surface IgM, the ability of these cells to produce anti-dsDNA IgG2c upon stimulation suggests that they can undergo class switching and differentiate into PCs. Studies using Blimp1 reporter DKO mice have indeed demonstrated the presence of CD11c+ CD19loBlimp1hi cells in the spleens of DKO female mice (Example 9). These cells also express high levels of CD138 and IRF4 suggesting that they represent a population of ABCs that has differentiated toward PCs.

One of the most striking features of the autoimmune syndrome that develops in DKO mice is the finding that, as observed for human SLE, this disorder preferentially affects the female gender. Interestingly ABCs accumulate in both DKO female and male mice. Unlike pathogenic ABCs from DKO male mice, however, ABCs from DKO female mice readily secreted anti-dsDNA IgG2c antibodies upon TLR7 stimulation suggesting that the pathogenic potential of DKO ABCs differs in female and male mice. Remarkably, crossing DKO male mice to Yaa mice (which carry a duplication of TLR7 on the Y chromosome) leads to their ability to produce anti-dsDNA IgG2c upon stimulation (Example 10).

Taken together, these studies have led to the hypothesis that ABCs can undergo further differentiation into CD11c+ PCs and that the differentiation of ABCs into CD11c+ PCs is regulated by sex-specific mechanisms. By investigating the transcriptional and epigenetic profiles of CD11c+ PCs from DKO mice as compared to CD11c- PCs, and examining whether IRF4 cooperates with IRF5 in regulating the differentiation/function of CD11c+ PCs, it will be shown that the CD11c+ PC cells from DKO mice have a unique transcriptional and epigenetic profile and that IRF4 and IRF5 regulate the differentiation of the pathogenic ABCs to PCs (Example 11). The contribution of sex-specific pathways to the differentiation/function of CD11c+ PCs will also be investigated (Example 12). Since aberrant B cell and PC homeostasis is one of the hallmarks of SLE and several lymphoproliferative diseases, these studies will provide fundamental insights into the molecular features that characterize the PCs that expand in autoimmune and lymphoproliferative settings.

Thus the work reported herein shows that pathogenic ABC cells play a role in autoimmunity. Importantly these studies demonstrate that there is a subset of CD11c+ cells that uniquely relies on the cooperation of Tbet and IRF5 for their expansion and function. The genome-wide analysis set forth herein demonstrates that these cells exhibit a unique transcriptional profile that is associated with a distinctive chromatin landscape, especially when compared to non-pathogenic ABCs. Additionally, DEF6 and SWAP-70 regulate IRF5 activity thus controlling its accessibility to key target genes and its cooperativity with Tbet.

Furthermore, aberrancies and/or polymorphisms in IL-21, its receptor, or IRF5 have also been associated with several autoimmune disorders including rheumatoid arthritis and inflammatory bowel disease (Sarra et al. 2013; Eames et al. 2016). The dysregulation in the ability of the SWEF proteins to restrain IRF5 activity in response to IL-21 and, therefore, properly control ABC expansion and function, could also contribute to other autoimmune diseases.

Given that the ABCs are known to accumulate in non-autoimmune mice these studies also provide key information into the factors that regulate the expansion of these cells into pathogenic ABCs. The identification of these factors controlling the expansion and function of pathogenic ABC cells, which include DEF6, SWAP-70, IRF5, IL-21, and a number of genes, also provides a method to develop new therapeutic targets for therapeutic intervention for autoimmune, lymphoproliferative and aging-related diseases.

Inhibition of Interferon Regulatory Factor 5 (IRF5)

It has been discovered that the transcription factor, interferon regulatory factor 5, is necessary for ABCs to become pathogenic and cause autoimmune and lymphoproliferative disease. Thus, one embodiment of the current invention is a method of abolishing or reducing pathogenic ABCs in a subject in need thereof by administering a therapeutically effective amount of an agent that antagonizes, inhibits or reduces the expression and/or activity of IRF5. A further embodiment of the current invention is a method of preventing and/or treating an autoimmune or lymphoproliferative disease by abolishing or reducing pathogenic ABCs in a subject in need thereof by administering a therapeutically effective amount of an agent that antagonizes, inhibits or reduces the expression and/or activity of IRF5. Methods for reducing expression of a protein are also well known in the art. Reduction of IRF5 expression may be at the transcriptional, translational or post-translational level.

IRF5 as used herein includes human IRF5, which is encoded by the human IRF5 gene located at chromosome 7q32 (OMIM ID 607218). IRF5 is a member of the IRF family; it is a transcription factor that possesses a helix-turn-helix DNA-binding motif and mediates virus- and interferon (IFN)-induced signaling pathways. It is appreciated that several isoforms/transcriptional variants of IRF5 are known. Preferably, the inhibitor of IRF5 inhibits at least the expression or activity of any human IRF5 variant. It is also well known that IRF5 is polymorphic, and a large number of polymorphisms, including SNPs are known. Thus, in an embodiment, the inhibitor of IRF5 also inhibits expression or activity of naturally-occurring variants of human IRF5 in which one or more of the amino acid residues have been replaced with another amino acid.

One agent for inhibition of IRF5 is a small molecule.

Additional inhibitors of IRF5 expression and activity include IRF5-specific RNAi, IRF5-specific short RNA, IRF5-specific antisense (e.g., IRF5-specific morpholinos) and triplet-forming oligonucleotides, and IRF5-specific ribozymes.

Short RNA molecules include short interfering RNA (siRNA), small temporal RNAs (stRNAs), short hairpin RNA (shRNA), and micro-RNAs (miRNAs). Short interfering RNAs silence genes through an mRNA degradation pathway, while stRNAs and miRNAs are approximately 21 or 22 nt RNAs that are processed from endogenously encoded hairpin-structured precursors, and function to silence genes via translational repression. See, e.g., McManus et al. (2002). *RNA* 8(6):842-50; Morris et al. (2004). *Science* 305(5688):1289-92; He and Hannon. (2004). *Nat. Rev. Genet.* 5(7):522-31. IRF5 siRNA are commercially available, for example, as On-target SMMRT pool reagents from Dharmacon, USA (catalogue No. L-011706-00-0005), and from Santa Cruz Biotechnology, USA (catalogue No. sc-72044).

"RNA interference, or RNAi" a form of post-transcriptional gene silencing ("PTGS"), describes effects that result from the introduction of double-stranded RNA into cells (reviewed in Fire. (1999). *Trends Genet.* 15:358-363; Sharp. (1999) *Genes Dev.* 13:139-141; Hunter. (1999). *Curr. Biol.* 9:R440-R442; Baulcombe. (1999). *Curr. Biol.* 9:R599-R601; Vaucheret et al. (1998). *Plant J.* 16:651-659). The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. (2001). *Nature* 411:494-498). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of IRF5, siRNAs to the gene encoding IRF5 can be specifically designed using computer programs. Illustrative nucleotide sequences encoding the amino acid sequences of these components are readily available.

Software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siR-NAext/."

Alternatively, double-stranded (ds) RNA is a powerful way of interfering with gene expression in a range of organisms that has recently been shown to be successful in mammals (Wianny and Zernicka-Goetz. (2002), *Nat. Cell. Biol.* 2:70-75). Double stranded RNA corresponding to the sequences of a IRF5 polynucleotides can be introduced into or expressed in cells of a candidate organism to interfere with IRF5 activity.

MicroRNA can also be used to inhibit IRF5. MicroRNAs are small non-coding RNAs averaging 22 nucleotides that regulate the expression of their target mRNA transcripts by binding. Binding of microRNAs to their targets is specified by complementary base pairing between positions 2-8 of the microRNA and the target 3' untranslated region (3' UTR), an mRNA component that influences translation, stability and localization. Additionally, this microRNA can also be modified for increasing other desirable properties, such as increased stability, decreased degradation in the body, and increased cellular uptake.

Ribozymes are RNA molecules capable of cleaving targeted RNA or DNA. Examples of ribozymes are described in, for example, U.S. Pat. Nos. 5,180,818; 5,168,053; 5,149,796; 5,116,742; 5,093,246; and 4,987,071, all incorporated herein by reference. Ribozymes specific for IRF5 can be designed by reference to the IRF5 cDNA sequence.

A further approach is to express anti-sense constructs directed against the polynucleotides of IRF5 to inhibit gene function and to abolish or decrease pathogenic ABCs.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. By binding to the target nucleic acid, antisense oligonucleotides can inhibit the function of the target nucleic acid. Typically, antisense oligonucleotides are 15 to 35 bases in length. However, it is appreciated that it may be desirable to use oligonucleotides with lengths outside this range, for example 10, 11, 12, 13, or 14 bases, or 36, 37, 38, 39 or 40 bases. Thus, with knowledge of the IRF5 cDNA sequence, polynucleotide inhibitors of IRF5 expression can be produced using methods well known in the art.

The antisense molecules may be expressed from any suitable genetic construct and delivered to the subject. Typically, the genetic construct which expresses the antisense molecule comprises at least a portion of the IRF5 cDNA or gene operatively linked to a promoter which can express the antisense molecule in the cell. Preferably, the genetic construct is adapted for delivery to a human cell.

Other agents would include antibodies to the components of IRF5. Such antibodies are commercially available or can be produced by methods known in the art.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies and humanized antibodies are particularly useful in the present invention.

Antibody fragments that have specific binding affinity for a target of interest can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

It is also well known that IRF5 is polymorphic, and a large number of polymorphisms, including SNPs are known. Thus, in an embodiment, the inhibitor of IRF5 also inhibits at least one function or activity of naturally-occurring variants of human IRF5 in which one or more of the amino acid residues have been replaced with another amino acid.

It is also appreciated that the IRF5 inhibitor may be one that inhibits at least one function or activity of an orthologue of IRF5 in another species, for example IRF5 from a horse, dog, pig, cow, sheep, rat, mouse, guinea pig or a primate. It will be appreciated, that when the inhibitor is administered to a particular individual, the inhibitor is one that modulates at least one function or activity of IRF5 from the same species as that individual. Thus, when the patient is a human patient, the inhibitor inhibits at least one function or activity of human IRF5, and so on.

Methods and routes of administering polynucleotide inhibitors, such as siRNA molecules, antisense molecules and ribozymes, to a patient, are well known in the art and described in more detail below. It is appreciated that polynucleotide inhibitors of IRF5 may be administered directly, or may be administered in the form of a polynucleotide that encodes the inhibitor. Thus, as used herein, unless the context demands otherwise, by administering to the individual an inhibitor of IRF5 which is a polynucleotide, includes the meanings of administering the inhibitor directly, or administering a polynucleotide that encodes the inhibitor, typically in the form of a vector.

In a further embodiment, the inhibitor may be a dominant-negative mutant of IRF5. As well as those mentioned above, the dominant-negative mutant may have a mutated or deleted DNA binding domain (DBD). Specific examples of mutations that have dominant-negative effect include a mutation at Alanine at position 68, especially when substituted with Proline, which results in complete loss of DNA binding activity (Yang et al. (2009). *Plos One* v4(5):e5500). Suitable methods, routes and compositions for preparing polypeptide inhibitors of IRF5 and nucleic acid molecules that encode them and administering them to a patient are known in the art and described below, and include viral vectors such as adenoviral vectors.

Agonizing, Activating or Increasing SWEF Proteins

As discussed above, the current invention is based upon the discovery that reducing the aberrant expansion of pathogenic ABCs depend on two SWEF proteins, SWAP70 and DEF6. Thus, increasing the expression and/or activity of these proteins can reduce or abolish pathogenic ABCs. Methods for increasing expression and/or activity of a protein are also well known in the art. Increasing SWEF expression may be at the transcriptional, translational or post-translational level.

Thus, a further embodiment of the current invention is a method of abolishing or reducing pathogenic ABCs in a subject in need thereof by administering a therapeutically effective amount of an agent that agonizes, activates or increases the expression and/or activity of SWAP-70 and/or DEF6. Such agents that can be used in this method include but are not limited to agents for increasing the expression of the gene encoding SWAP-70 and/or DEF6 and include nucleic acids which encode the SWAP-70 and/or DEF6 proteins, or the entire SWAP-70 and/or DEF6 gene, or a nucleic acid that is substantially homologous to the SWAP-70 and/or DEF6 genes, or a variant, mutant, fragment, homologue or derivative of the SWAP-70 and/or DEF6 genes that produces a protein that maintains or increases their function.

The gene or a nucleic acid which encodes the SWAP-70 and/or DEF6 proteins, or a nucleic acid that is substantially homologous to the SWAP-70 and/or DEF6 genes, or a variant, mutant, fragment, homologue or derivative of the SWAP-70 and/or DEF6 genes that produce proteins with maintained or increased function can also be used in the methods of the invention.

The sequences of human SWAP-70 and DEF6 are available on the National Center for Biotechnology Database and can be used to manufacture variants, mutants, fragments, homologues and derivatives which maintain or have increased function.

DNA or other nucleic acids such as mRNA can also be used in the method.

While it would be understood that any agent or agents that increase or upregulate the expression of SWAP-70 and/or DEF6, would also most likely increase SWAP-70 and/or DEF6 proteins, alternatively, an agent or agents that directly increase or promote the activation, amount and/or activity of the proteins can be used in the methods.

Alternatively, administering the proteins can be used in the methods. This includes the administration of a polypeptide, or a variant thereof having at least 90% sequence identity with the SWAP 70 and/or DEF6 polypeptides.

In an embodiment, the variant of the polypeptide has at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, with the sequence of the polypeptide of which it is a variant. Thus, preferably, the variant of the polypeptide has at least 91%, 92%, 93%, 94%, 95%, 96%, 97%, 98% or 99% sequence identity with the sequence of the SWAP70 and/or DEF6 polypeptide. Such variants may be made, for example, using the methods of recombinant DNA technology, protein engineering and site-directed mutagenesis, which are well known in the art, and discussed in more detail below.

The percent sequence identity between two polypeptides may be determined using suitable computer programs.

Polypeptides, may be prepared using an in vivo or in vitro expression system. Preferably, an expression system is used that provides the polypeptides in a form that is suitable for pharmaceutical use, and such expression systems are known to the skilled person. As is clear to the skilled person, polypeptides of the invention suitable for pharmaceutical use can be prepared using techniques for peptide synthesis.

A nucleic acid molecule encoding, for example, the proteins or variants thereof, may be used to transform a host cell or host organism for expression of the desired polypeptide. Suitable hosts and host cells are known in the art and may be any suitable fungal, prokaryotic or eukaryotic cell or cell line or organism, for example: bacterial strains, including gram-negative strains such as *Escherichia coli* and gram-positive strains such as *Bacillus subtilis* or of *Bacillus brevis*; yeast cells, including *Saccharomyces cerevisiae*; or *Schizosaccharomyces pombe*; amphibian cells such as *Xenopus oocytes*; insect-derived cells, such SF9, Sf21, Schneider and Kc cells; plant cells, for example tobacco plants; or mammalian cells or cell lines, CHO-cells, BHK-cells (for example BHK-21 cells) and human cells or cell lines such as HeLa, as well as all other hosts or host cells that are known and can be used for the expression and production of polypeptides.

The polypeptides or variants thereof, may be made by chemical synthesis, again using methods well known in the art for many years. In certain embodiments, polypeptides for administration to a patient may be in the form of a fusion molecule in which the polypeptide is attached to a fusion partner to form a fusion protein. Many different types of fusion partners are known in the art. One skilled in the art can select a suitable fusion partner according to the intended use of the fusion protein. Examples of fusion partners include polymers, polypeptides, lipophilic moieties, and succinyl groups. Certain useful protein fusion partners include serum albumin and an antibody Fc domain, and certain useful polymer fusion partners include, but are not limited to, polyethylene glycol, including polyethylene glycols having branched and/or linear chains. In certain embodiments, the polypeptide may be PEGylated, or may comprise a fusion protein with an Fc fragment.

In an embodiment, the polypeptide may be fused to or may comprise additional amino acids in a sequence that facilitates entry into cells (i.e. a cell-penetrating peptide). Thus, for example, the SWAP70, DEF6 or variant thereof or a polypeptide may further comprise the sequence of a cell-penetrating peptide (also known as a protein transduction domain) that facilitates entry into cells. As is well known in the art, cell-penetrating peptides are generally short peptides of up to 30 residues having a net positive charge and act in a receptor-independent and energy-independent manner.

Additionally or alternatively, the polypeptide may be fused to or may comprise additional amino acids in a sequence that facilitates entry into the nucleus (i.e., a nuclear localization sequence (NLS), aka nuclear localization domain (NLD)). Thus, for example, the SWAP70 or DEF6 protein or variant thereof may further comprise the sequence of an NLS that facilitates entry into the nucleus. NLS includes any polypeptide sequence that, when fused to a target polypeptide, is capable of targeting it to the nucleus. Typically, the NLS is one that is not under any external regulation (e.g. calcineurin regulation) but which permanently translocates a target polypeptide to the nucleus.

It is appreciated that the sequence of the cell-penetrating peptide and/or the NLS may be adjacent to the sequence of the protein or variant, or these sequences may be separated by one or more amino acids residues, such as glycine residues, acting as a spacer.

Therapeutic proteins produced as an Fc-chimera are known in the art. For example, Etanercept, the extracellular domain of TNFR2 combined with an Fc fragment, is a therapeutic polypeptide used to treat autoimmune diseases, such as rheumatoid arthritis.

In certain embodiments, the fusion partner may be a polymer, for example, polyethylene glycol (PEG). PEG may comprise branched and/or linear chains. In certain embodiments, a fusion partner comprises a chemically-derivatised polypeptide having at least one PEG moiety attached.

The fusion partner may be attached, either covalently or non-covalently, to the amino-terminus or the carboxy-terminus of the polypeptide. The attachment may also occur at a location within the polypeptide other than the amino-terminus or the carboxy-terminus, for example, through an amino acid side chain (such as, for example, the side chain of cysteine, lysine, histidine, serine, or threonine).

Modulating Genes that Upregulated and Downregulated in Pathogenic ABCs

As shown herein, certain genes are upregulated and/or enriched in pathogenic ABCs and some are downregulated.

Thus, one embodiment of the current invention is a method of abolishing or reducing pathogenic ABCs in a subject in need thereof by administering a therapeutically effective amount of an agent that antagonizes, inhibits or reduces the expression and/or activity of certain upregulated genes. A further embodiment of the current invention is a method of preventing and/or treating an autoimmune or lymphoproliferative disease by abolishing or reducing pathogenic ABCs in a subject in need thereof by administering an therapeutically effective amount of an agent that antagonizes, inhibits or reduces the expression and/or activity of certain upregulated genes.

In particular, 111 genes listed in Table 1 were upregulated in pathogenic or DKO ABCs as compared to WT ABCs. One or more of these upregulated genes would be a target for reduction of expression in order to reduce or abolish pathogenic ABCs.

More specifically, the methods of the invention include the inhibition of one or more genes including but not limited to: Cxcl9, Cxcl10, Ccl4, Ccl5, Ccl8, Il1r2, Li2rb2, Il18r1, Il18rap, Csf1, Tbx21, Itgax, Itgam, Ctla4, Sema3d, Sema4c, Bmp6, Itga8, Cc122, Tnsfsf4, Cxcr3, Ccr1, Plxnd1, Itgb1, Ifnγ, Il6, Runx, MyoG, NF-kB, stat5, Hbp1, Srebf1, Zbtb32, Nfil3, IL-12a, CD28, CD9, FcRL5, CD30/CD30L, c-kit, CD15, CD244, CD68, Lmo7, Tnip3, Msc, Mist1, Id2, Insm1, TNFa, Thsd7a, IL-13/IL-13Ra1, IL-4, IL-5, and NDNF.

Other genes whose expression and/or activity are upregulated in pathogenic ABCs as compared to benign ABCs include but are not limited to Stat5, Hbp1, Srebf1, Zbtb32, LifR, AP1 family members and Batf family members. These genes would also be considered targets for reduction of expression in order to reduce or abolish pathogenic ABCs.

Most specifically, one or more genes related to higher immunoglobulin production including but not limited to Nfil3, Jun, and IL-9/IL-9R, would be targets for reduction of expression in order to reduce or abolish pathogenic ABCs.

The inhibition of these genes can be accomplished by any method known in the art including but not limited to the ones described above for decreasing expression of the gene that encodes IRF5, including but not limited to small molecules, RNAi, short RNA, antisense (e.g., morpholinos) and triplet-forming oligonucleotides, and ribozymes.

A further embodiment of the current invention is a method of abolishing or reducing pathogenic ABCs in a subject in need thereof by administering a therapeutically effective amount of an agent that agonizes, activates or increases the number, expression and/or activity of certain downregulated genes. A further embodiment of the current invention is a method of preventing and/or treating an autoimmune or lymphoproliferative disease by abolishing or reducing pathogenic ABCs in a subject in need thereof by administering a therapeutically effective amount of an agent that agonizes, activates or increases the number, expression and/or activity of certain downregulated genes. This could be accomplished by introducing a nucleic acid encoding the gene or a portion into the subject as described above for increasing SWEF proteins.

In particular, the genes listed in Table 2 were downregulated in pathogenic or DKO ABCs as compared to WT ABCs. One or more of these downregulated genes would be a target for an increase of expression in order to reduce or abolish pathogenic ABCs. More specifically, genes that are downregulated in pathogenic ABCs include but are not limited to MafA, MafB, c-maf, Mertk, Cebp, Rora, Bcl6, Pxk, Smad1, Emp2, Pouf2f2, PU.1, Rel, Foxj3, Hand1, Cebp, Rora, Prdm1, Spic, and Pparg. More specifically, one or more genes related to myeloid-related genes including but not limited to AHR and PPARGc1a would be targets for an increase of expression in order to reduce or abolish pathogenic ABCs.

TABLE 1

Genes Upregulated in Pathogenic (DKO) ABCs

| Genes | Genes | Genes | Genes |
|---|---|---|---|
| Gm9825 | Nfil3 | Socs1 | Slc25a19 |
| Gdpd3 | Igkv8-21 | Serpina3f | 9330175E14Rik |
| Hmga1-rs1 | Igkv3-10 | Ighv1-61 | C920025E04Rik |
| Gm4841 | Igkv4-80 | Gm16710 | Glo1 |
| Thsd7a | Gm10505 | Tmem176b | Gatsl3 |
| H2-T10 | Igkv17-121 | Cplx2 | Fgl2 |
| Adm | Ighv14-3 | Trp73 | Gas7 |
| Ighe | Igkv4-68 | Tmem176a | Egr2 |
| Ndnf | Hspg2 | Slc30a4 | Il2ra |
| Igkv5-45 | Il12a | Ndrg1 | Zbtb32 |
| Lifr | Ighv5-16 | Jun | Csf1 |
| Ighv1-84 | Igkv6-20 | Camkk1 | Igkv16-104 |
| Igkv3-2 | Ighv3-6 | Iigp1 | Fscn1 |
| Ighg1 | Sox5 | Nostrin | Tmem231 |
| Dnah8 | Ighv9-2 | Lrrk2 | H2-T24 |
| Ighv5-2 | Il9r | Il4i1 | Gnb4 |
| Igkv17-127 | Gramd2 | Eml5 | Lipc |
| Tagap1 | Ffar2 | H2-Q6 | Havcr1 |
| Ighv1-85 | Slc22a15 | Prr5l | Akap5 |
| Zfp365 | Igkv6-25 | Csf2rb2 | Mical3_1 |
| Tnip3 | Igkv13-84 | Nlrc3 | Hipk2 |
| Wdfy1 | Plcg1 | Plscr1 | Lmo7 |
| Igkv6-14 | Gadd45g | Pdcd1lg2 | Pmepa1 |
| Pard3b | Wee1 | Ermard | |
| Aox4 | Lamp3 | Osm | |
| Igkv4-74 | Nrp2 | Ighv1-52 | |
| Igkv14-126 | Gm2619 | Rec8 | |
| Igkv3-5 | Myo3b | Igkv11-125 | |
| Ighv9-1 | Chst7 | Trio | |

TABLE 2

Genes Downregulated in Pathogenic (DKO) ABCs

| Genes | Genes | Genes | Genes | Genes | Genes |
|---|---|---|---|---|---|
| Rnaset2b | Dnase1l3 | Slc37a2 | Dennd2d | Pld3 | Calcrl |
| Rap2a | Gclm | Kcnk6 | Nr4a1 | Ighv5-9 | Itga2 |
| Hpcal1 | Tns3 | Myo10 | Slc35f6 | Igkv6-13 | Gpm6b |
| 4632428N05Rik | P2rx4 | Dram2 | Cr2_1 | Plekhg3 | Smad1 |
| Mcfd2 | Cfp | Tmem206 | Esr1 | Rnf149 | Rtp4 |
| Rnps1 | 8430419L09Rik | Nagk | Igkv1-132 | Gna12 | Arl4d |
| Spred1 | Adrb2 | Lidlr | Arhgap18 | Rasgef1b | Tmem51 |
| Fam105a | Il6ra | Mid1 | Erlin2 | Megf8 | S100a4 |
| Zfp36l2 | Lpin1 | Arhgap19 | Stard8 | Dip2c | Hmga1 |
| Asah2 | Por | Glul | Megf9 | Plcl1 | Il13ra1 |
| Akr1b10 | Wwp1 | Lag3 | Abcc5 | Blvra | Hsd11b1 |
| Il6st | Dmxl2 | Slc29a1 | Rab11fip5 | Swap70 | Itsn1 |
| Cebpb | Galnt7 | Arrb2 | Marveld1 | Fam149a | Cmtm3 |
| Arrdc3 | Ubtd1 | Ppap2a | Pik3cb | Ifnlr1 | Osbpl1a |
| Cyb5a | Cttn | Asah1 | Pcyox1 | Bmf | Lpar5 |
| P4ha1 | Etv5 | Hexa | Nfix | Lmbrd2 | Efnb1 |
| Leprot | Hip1 | Comt | Ece1 | Alpl | Pira2 |
| Slc7a7 | Ets2 | Tlr4 | Paqr4 | Lcp2 | Pvrl4 |
| Apobec2 | Gm4951 | Ifih1 | Fam26f | Clec7a_1 | Cdld1 |
| Mpp6 | Eno3 | Cd63 | RP23-458B6.6 | Mcoln2 | Skp2 |
| Hes1 | Gna15 | Emr1 | Slc46a1 | 1190002N15Rik | Abcb4 |
| Slc43a2 | St3gal4 | Nucb2 | Fhod1 | Mllt4 | Gstm1 |
| Hs6st1 | Csf2ra | Rab6b | Rbpms | Slc48a1 | Mpeg1 |
| Ccdc88b | Lgals3bp | Slc8b1 | Tlr3 | Tcn2 | Smagp |
| Lgmn | Sh2d1b2 | Fez2 | Spon1 | Slc15a2 | Ftl1 |
| Plin2 | Man1c1 | Dfna5 | Gab2 | Kcnk13 | Slc1a3 |

TABLE 2-continued

| Genes | Genes | Genes | Genes | Genes | Genes |
|---|---|---|---|---|---|
| Tenm4 | Nxpe4 | Plxna1 | Tmem65 | Gm13994 | Mgst1 |
| Hist1h1c | Kif13a | Pla2g7 | Nxpe5 | Ppm1h | Sgk1 |
| Rab20 | C5ar2 | Rnf150 | Rgl1 | Ms4a7 | C3 |
| Basp1 | Lipa | A4galt | Angptl4 | Abcg3 | B430306N03Rik |
| Prkra | Dnajb13 | 1700025G04Rik | E330020D12Rik | Crisp3 | Lst1 |
| Pkp4 | Sema4c | Rab32 | Nfam1 | Fcgrt | Ckb |
| Itfg3 | Ppap2b | Gsr | Aoah | Acer3 | Ctnnd1 |
| Rasa4 | Syt15 | Aph1b | Marcks | Tyrobp | Slamf8 |
| Gsto1 | Vamp5 | Asph | Ninj1 | Cadm1 | Tbc1d4 |
| Map4k3 | Ms4a6d | P2rx7 | Parp12 | Sirpa | Mcoln3 |
| Arhgap39 | Hist1h2bc | Akr1c13 | Pla2g15 | Slc9a9 | Epb4.1l1 |
| Igsf8 | Acot11 | Lima1 | Galc | Btnl6 | Pla2g4a |
| Sh3bgrl2 | Fads1 | Myo9a | Fcgr4 | Smox | Gas6 |
| Id2 | Rnase4 | Klk1 | Scamp1 | Ccl5 | Dram1 |
| Slc12a2 | 4931406C07Rik | Cyp27a1 | Hpgds | Lyz2 | Ifitm2 |
| Slc16a7 | Myof | Idh1 | Tmem141 | Osgin1 | Ggt5 |
| Pde2a | Fam102b | Cln8 | Crim1 | Lpcat2 | Camk1 |
| Plxnb2 | Gbp8 | Mitf | Mical2 | Ppt2 | Avpi1 |
| Lrp8 | Ighv1-7 | Tmem26 | Tppp | Ccnd1 | Cd200r4 |
| Tle1 | Car2 | Ctsl | Abcb1a | Sdc3 | Scn1b |
| Dhrs3 | Rsad2 | Slc39a8 | Fam213b | Ctsb | Cd51 |
| Cd36 | Dse | Scarb1 | Anpep | Serpinb6a | Bmpr2 |
| Cyb5r1 | Hsd3b7 | Fabp4 | Pstpip2 | Il11ra1 | Asb2 |
| Cpq | Mt1 | Fblim1 | Ctsd | Igha | Lrrc25 |
| Kdelc2 | Tbc1d8 | Cmtm4 | Metrnl | Cxcl9 | Ctsf |
| Mgat4b | Plod1 | Dab2ip | Cd200r1 | Pald1 | Frmd4a |
| Rragd | Slc12a7 | Hnrnpll | Ptafr | Lrp12 | Ptgs1 |
| 1830077J02Rik | Cd68 | Abca9 | Slc8a1 | Cd244 | Adam23 |
| Timp2 | Anxa3 | Npl | Dlg2 | Hk3 | Sirpb1b |
| Arsg | Def6 | Fcer1g | Itga9 | Il18 | Tbxas1 |
| Tspan15 | Tifab | Actn1 | Tlr13 | Snx24 | B3galnt1 |
| Creg1 | Tmem86a | Gpr35 | Fcgr1 | Dock4 | Havcr2 |
| Parvb | Sepp1 | Tlr8 | Cdc42ep2 | Arhgap32 | Sash1 |
| Rgs10 | Tnfrsf1a | Fcgr3 | Fpr1 | Pla2g2d | C1qa |
| Il18bp | Trim47 | Sall2 | Pdgfc | Cd302 | Ltbr |
| Sema6d | Stk39 | Lair1 | C6 | Lrp5 | C1qc |
| Siglech | Ppfia4 | Clec4a3 | Tgfbi | AF251705 | Trf |
| Tnfrsf21 | Ubd | Lilra5 | Dmpk | Fgd4 | Dock5 |
| Cnksr3 | Tbc1d2b | Slc4a1 | Clec4a1 | Nr1h3 | Pdgfb |
| Soga1 | Sirpb1a | Acot1 | Itgad | Agap1 | Epb4.1l3 |
| Gdpd1 | Dock7 | Amz1 | Kcnj2 | Aatk | Kcna2 |
| Ifitm3 | Rua | Clec12a | Itgb5 | Hba-a1 | Rab3il1 |
| Ccl6 | Fmnl2 | Raver2 | Mafb | Acp2 | Alas2 |
| AI607873 | 6430548M08Rik | Adamdec1 | Jup | Gtf2ird1 | Pygl |
| Cebpa | Cttnbp2nl | Iqgap2 | Aif1 | Pak1 | Pparg |
| Nuak1 | Pigz | F11r | Adrbk2 | Wdfy3 | Mrc1 |
| Matn2 | Ttyh2 | Lrp1 | Abcd2 | Siglece | Cmklr1 |
| Ifi204 | Nptxr | Fzd7 | Igsf6 | Clec1b | Hba-a2 |
| Adap2 | Dgat2 | Csf3r | Sqrdl | Pid1 | Pdlim4 |
| Tgm2 | Spic | Slc16a10 | Snta1 | Scamp5 | Fyb |
| Large | Rin2 | Unc5a | Rims3 | Oaf | Klrk1 |
| Adam22 | Tns1 | Hap1 | Ear2 | Tjp1 | Maf |
| Enpp4 | Klra2 | Slc22a23 | Tfec | C1qb | Tsku |
| Tcf7l2 | Serpinb9b | Vnn3 | Adrb1 | Ptgis | |
| Slc7a8 | Ptprm | Pilrb2 | Clec4n | Ccl24 | |
| Cd4 | Cela1 | Cd300e | 1810011H11Rik | Nfasc | |
| Hfe | Slc11a1 | Hmox1 | Apobr | A530099J19Rik | |
| Dgki | Kcnj10 | Rnf144b | Cmbl | | |
| Trpm2 | Dysf | Axl | Mrap | | |
| Aph1c | Nos1 | Igf1 | Hs3st2 | | |
| Hbb-bs | Apoc1 | Slco2b1 | Nav1_1 | | |
| Ccdc148 | Gm5150 | Treml4 | Gpd1 | | |
| Nlrp3 | Frmd4b | Fkbp9 | Slc40a1 | | |
| Clec4a2 | Gfra2 | Slc16a9 | Gsta4 | | |
| Tgm1 | Ccr3 | Pilrb1 | Enpp2 | | |
| Hebp1 | Kcnj16 | Vcam1 | Slc45a3 | | |
| Hbb-bt | Hpgd | Gzma | B4galt4 | | |
| Tspan4 | Gm13710 | Pilra | Akr1b7 | | |
| Cystm1 | Lrp4 | St6galnac2 | Agmo | | |
| Kctd12b | Ptplad2 | Abcc3 | Tspan9 | | |
| Sulf2 | Cd14 | Galnt3 | RP24-247B20.1 | | |
| Paqr9 | Mpzl1 | Gm4980 | Kitl | | |
| Mertk | Sort1 | Cd300ld | Apol7c | | |
| Prkar1b | Slc7a2 | Hcar2 | Lphn3 | | |
| Nid2 | Csf1r | Fcna | Sdc2 | | |
| Tnfaip2 | Stab2 | Emr4 | Glis3 | | |

TABLE 2-continued

Genes Downregulated in Pathogenic (DKO) ABCs

| Genes | Genes | Genes | Genes | Genes | Genes |
|---|---|---|---|---|---|
| Mras | Vwf | Epor | Gpr141 | | |
| Erbb2 | Clec4b1 | Pcolce2 | Cd163 | | |
| Tmem37 | Cd300a | Vstm4 | Rps13 | | |
| Tnfrsf11a | Crip2 | Dlc1 | Col14a1 | | |

Administration of Agents

When the SWAP-70, DEF6, or IRF5 inhibitor, or inhibitor or activator of a misregulated gene, is a nucleic acid such as DNA, RNA, interfering RNA or microRNA, methods for delivery include receptor mediated endocytosis where the nucleic acid is coupled to a targeting molecule that can bind to a specific cell surface receptor, inducing endocytosis and transfer of the nucleic acid into cells. Coupling is normally achieved by covalently linking poly-lysine to the receptor molecule and then arranging for (reversible) binding of the negatively charged DNA or RNA to the positively charged poly-lysine component. Another approach utilizes the transferrin receptor or folate receptor which is expressed in many cell types. When producing the microRNA for this method of administration, the microRNA could be manufactured to have a guide strand which is identical to the microRNA of interest and a passenger strand that is modified and linked to a molecule for increasing cellular uptake Another method to administer the nucleic acid to the proper tissue is direct injection/particle bombardment, where the nucleic acid is be injected directly with a syringe and needle into a specific tissue, such as muscle.

An alternative direct injection approach uses particle bombardment ('gene gun') techniques: nucleic acid is coated on to metal pellets and fired from a special gun into cells. Successful gene transfer into a number of different tissues has been obtained using this approach. Such direct injection techniques are simple and comparatively safe.

Another method for delivery of nucleic acid to the proper tissue or cell is by using adeno-associated viruses (AAV). Nucleic acid is delivered in these viral vectors is continually expressed, replacing the expression of the DNA or RNA that is not expressed in the subject. Also, AAV have different serotypes allowing for tissue-specific delivery due to the natural tropism toward different organs of each individual AAV serotype as well as the different cellular receptors with which each AAV serotype interacts. The use of tissue-specific promoters for expression allows for further specificity in addition to the AAV serotype.

Other mammalian virus vectors that can be used to deliver the DNA or RNA include oncoretroviral vectors, adenovirus vectors, Herpes simplex virus vectors, and lentiviruses.

Liposomes are spherical vesicles composed of synthetic lipid bilayers which mimic the structure of biological membranes. The nucleic acid to be transferred is packaged in vitro with the liposomes and used directly for transferring the nucleic acid to a suitable target tissue in vivo. The lipid coating allows the nucleic acid to survive in vivo, bind to cells and be endocytosed into the cells. Cationic liposomes (where the positive charge on liposomes stabilize binding of negatively charged DNA), have are one type of liposome.

The nucleic acid can also be administered with a lipid to increase cellular uptake. The nucleic acid may be administered in combination with a cationic lipid, including but not limited to, lipofectin, DOTMA, DOPE, and DOTAP.

Other lipid or liposomal formulations including nanoparticles and methods of administration have been described as for example in U.S. Patent Publication 20030203865, 2002/0150626, 2003/0032615, and 2004/0048787. Methods used for forming particles are also disclosed in U.S. Pat. Nos. 5,844,107, 5,877,302, 6,008,336, 6,077,835, 5,972,901, 6,200,801, and 5,972,900.

The polypeptide or nucleic acid molecule for administration to the patient may be formulated as a nanoparticle. Nanoparticles are a colloidal carrier system that has been shown to improve the efficacy of an encapsulated drug by prolonging the serum half-life. Polyalkylcyanoacrylates (PACAs) nanoparticles are a polymer colloidal drug delivery system that is in clinical development (described, for example, by Stella et al. (2000) J. Pharm. Sci., 89: 1452-1464; Brigger et al. (2001) Int. J. Pharm 214: 37-42; Calvo et al. (2001) Pharm. Res. 18: 1157-1166; and Li et al. (2001) Biol. Pharm. Bull. 24: 662-665). Biodegradable poly(hydroxyl acids), such as the copolymers of poly(lactic acid) (PLA) and poly(lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier has the ability to be freeze-dried and reconstituted in solution without aggregation; (iv) that the carrier be biodegradable; (v) that the carrier system be of small size; and (vi) that the carrier enhances the particles persistence. Nanoparticles may be synthesized using virtually any biodegradable shell known in the art. In one embodiment, a polymer, such as poly(lactic-acid) (PLA) or poly(lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charged nucleic acids. Nanoparticles may also be modified with polyethylene glycol (PEG), which also increases the half-life and stability of the particles in circulation. Alternatively, the COOH group may be converted to an N-hydroxysuccinimide (NHS) ester for covalent conjugation to amine-modified compounds.

Other protein modifications to stabilize a polypeptide, for example to prevent degradation, as are well known in the art may also be employed. Specific amino acids may be modified to reduce cleavage of the polypeptide in vivo. Typically, N- or C-terminal regions are modified to reduce protease activity on the polypeptide. A stabilizing modification is any modification capable of stabilizing a protein, enhancing the in vitro half life of a protein, enhancing circulatory half life of a protein and/or reducing proteolytic degradation of a protein. For example, polypeptides may be linked to the serum albumin or a derivative of albumin. Methods for linking polypeptides to albumin or albumin derivatives are well known in the art.

It is appreciated that the compounds for administration to a patient, for example as described above, will normally be formulated as a pharmaceutical composition, i.e. together with a pharmaceutically acceptable carrier, diluent or excipient.

The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Preferred methods of administration include oral; mucosal, such as nasal, sublingual, vaginal, buccal, or rectal; parenteral, such as subcutaneous, intravenous, bolus injection, intramuscular, or intraarterial; or transdermal administration to a subject. Most preferred method of administration are parenteral and oral.

These administrations can be performed using methods standard in the art. Oral delivery can be performed by complexing a therapeutic composition of the present invention to a carrier capable of withstanding degradation by digestive enzymes in the gut of an animal. Examples of such carriers, include plastic capsules or tablets, such as those known in the art. One method of local administration is by direct injection. Administration of a composition locally within the area of a target cell refers to injecting the composition centimeters and preferably, millimeters from the target cell or tissue. The inhibitor may be provided in any suitable form, including without limitation, a tablet, a powder, an effervescent tablet, an effervescent powder, a capsule, a liquid, a suspension, a granule or a syrup.

Alternatively, a further embodiment of the invention provides methods of ex vivo cell therapy, wherein a population of pathogenic ABCs is obtained from the subject, contacted, incubated or treated with one of the agents disclosed herein for abolishing or decreasing pathogenic ABCs, and then administered back to the subject in need thereof.

Obtaining the pathogenic ABCs from the subject would be the same as set forth below for detection of pathogenic ABCs. Administration of the ex vivo treated cells of the present invention can be effected using any suitable route of introduction, such as intravenous, intraperitoneal, intra-gastrointestinal track, subcutaneous, transcutaneous, intramuscular, intracutaneous, intrathecal, epidural, and rectal. According to presently preferred embodiments, the ex vivo treated cells of the present invention may be introduced to the individual using intravenous and/or intraperitoneal administration.

Also within the scope of the present disclosure are multiple administrations (e.g., doses) of the agents and/or populations of cells. In some embodiments, the agents and/or populations of cells are administered to the subject once. In some embodiments, agents and/or populations of cells are administered to the subject more than once (e.g., at least 2, 3, 4, 5, or more times). In some embodiments, the agents and/or populations of cells are administered to the subject at a regular interval, e.g., every six months.

Detection of Pathogenic ABCs

It has also been discovered that pathogenic ABCs, those ABCs that would be found in subjects with or predicted to develop an autoimmune or lymphoproliferative disease, would have different gene expression profile than ABCs which are not pathogenic as well as other B cells. The expansion and/or function of ABCs that are pathogenic are inhibited by the SWEF proteins and depend upon IRF5 and other IRFs and these cells differentially express certain genes, including but not limited to, Cxcl9, Cxcl10, Ccl4, Ccl5, Ccl8, Il1r2, Li2rb2, Il18r1, Il18rap, Csf1, Tbx21, Itgax, Itgam, Ctla4, Sema3d, Sema4c, Bmp6, Itga8, Ccl22, Tnsfsf4, Cxcr3, Ccr1, Plxnd1, Itgb1, Ifnγ, Il6, AP1 family members like Jun, Batf family members, PU.1 and other Ets family members like SpiC, Runx, MyoG, NF-kB, Stat5, Hbp1, Srebf1 and 2, Zbtb32, Nfil3, LifR, Bcl6, Pxk, Smad1, Emp2, Pouf2f2, Rel, Foxj3, Hand1, MafA, MafB, c-Maf, Cebp, Rora, Prdm1, Mertk, Axl, Pparg, CD28, CD9, FcRL5, CD36, CD30/CD30L, c-kit, CD15, CD244, CD68, LXRa, AHR, LDLR, Lmo7, Tnip3, Ppargc1a, Msc, and Mist1.

Most methods start with obtaining a sample of biological tissue or fluid that contains peripheral blood cells from the subject and extracting, isolating and/or purifying B cells from the tissue or fluid.

Preferred biological tissues include, but are not limited to, epidermal, whole blood, and plasma. The biological tissue obtained from a lymph node or spleen biopsy.

Preferred fluids include, but are not limited to, plasma, saliva, and urine.

The isolated B cells can be stimulated with an agent including but not limited to IL21, TLR7 and combinations thereof.

After stimulation nucleic acid is extracted, isolated and purified from the cells by methods known in the art.

If required, a nucleic acid sample having the gene sequence(s) are prepared using known techniques. For example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, mRNA or other nucleic acids are analyzed by methods known to those of skill in the art. The nucleic acid sequence corresponding to a gene can be any length, with the understanding that longer sequences are more specific. Preferably a nucleic acid corresponding to a gene is at least 20 nucleotides in length. Preferred ranges are from 20 to 100 nucleotides in length, with from 30 to 60 nucleotides being more preferred, and from 40 to 50 being most preferred.

In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces, such as sonication, or by cleaving the nucleic acid using restriction endonucleases, or any other methods known in the art. However, in most cases, the natural degradation that occurs during archiving results in "short" oligonucleotides. In general, the methods and assays of the invention can be done on oligonucleotides as short as 20-100 base pairs, with from 20 to 50 being preferred, and between 40 and 50, including 44, 45, 46, 47, 48 and 49 being the most preferred.

A preferred method of the invention is performing gene expression profiling of the sample. Gene expression profiling refers to examining expression of one or more RNAs in a cell, preferably mRNA. Often at least or up to 10, 100, 100, 10,000 or more different mRNAs are examined in a single experiment.

In a preferred method and assay of the invention, the gene expression of the mRNA or other nucleic acid obtained from the B cells from the subject is compared to the reference gene expression of B cells from a healthy donor. In some cases, these cells are ABCs from a healthy donor, i.e., one without an autoimmune or lymphoproliferative disease. In some cases, the cells are other B cells from a healthy donor.

When the gene expression of the B cells from the subject is being compared to ABCs from a healthy donor or control, a finding of at least one of the following genes being expressed at a higher or greater level than the expression in the healthy donor or control would indicate the B cells from the subject are pathogenic ABCs: Stat5, Hbp1, Sreb1, Zbtb32, Jun, Nfil3, LifR, and AP1-Batf. The expression of any of the genes listed in Table 1 at a higher or greater level than the expression in the healthy donor or control would indicate the B cells from the subject are pathogenic ABCs When the gene expression of the B cells from the subject is being compared to ABCs from a healthy donor or control, a finding of at least one of the following genes being expressed at a lower level or less than the expression in the healthy donor or control would indicate the B cells from the subject are pathogenic ABCs: MafA, MafB, c-maf, Mertk, Cebp, Rora, PU.1, Mertk, MafB, Spic, Pparg, Ppargc1a, and Prdm1. The expression of any of the genes listed in Table 2 at a lower or lesser level than the expression in the healthy donor or control would indicate the B cells from the subject are pathogenic ABCs.

When the gene expression of the B cells from the subject is being compared to other B cells a healthy donor or control, a finding of at least one of the following genes being expressed at a higher or greater level than the expression in the healthy donor or control would indicate the B cells from the subject are pathogenic ABCs: Cxcl9, Cxcl10, Ccl4, Ccl5, Ccl8, Il1r2, Li2rb2, Il18r1, Il18rap, Csf1, Tbx21, Itgax, Itgam, Ctla4, Sema3d, Sema4c, Bmp6, Itga8, Ccl22, Tnsfsf4, Cxcr3, Ccr1, Plxnd1, Itgb1, Ifnγ, Il6, AP1, Batf, Runx, MyoG, NF-kB, IL-9/IL-9R, IL13/IL-13Ra1, and IL-4.

When the gene expression of the B cells from the subject is being compared to other B cells from a healthy donor or control, a finding of at least one of the following genes being expressed at a lower or lesser level than the expression in the healthy donor or control would indicate the B cells from the subject are pathogenic ABCs: Bcl6, Pxk, Smad1, Emp2, Pouf2f2, PU.1, Rel, Foxj3, and Hand1.

When a method of detecting pathogenic ABCs is used to monitor response to treatment in a subject, the gene expression from B cells of the subject after treatment can be compared to the gene expression from B cells from the subject before treatment. The gene expression from the B cells of the subject can also be compared to the reference gene expression of the B cells from a healthy donor or control.

Typically expression is compared to expression of a consistently expressed housekeeping gene transcript, the relative expression determined, and then the expression of the subject is compared to the reference expression of the healthy control:

Methods for examining gene expression, are often hybridization based, and include, Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

Alternatively, the level of protein product of the genes can be measured from a protein sample from the biological tissue or fluid using methods described below.

For a general description of these techniques, see also Sambrook et al. 1989; Kriegler 1990; and Ausebel et al. 1990.

The preferred method for the detection of the transcripts is the use of arrays or microarrays or RNA-sequencing or nanostring.

These terms are used interchangeably and refer to any ordered arrangement on a surface or substrate of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, cDNA, PCR products, and proteins.

Microarrays, RNA-sequencing and nanostring are useful for simultaneously detecting the presence, absence and quantity of a plurality of different target molecules in a sample. The presence and quantity, or absence, of the probe's target molecule in a sample may be readily determined by analyzing whether and how much of a target has bound to a probe at a particular location on the surface or substrate.

In a preferred embodiment, arrays used in the present invention are "addressable arrays" where each different probe is associated with a particular "address."

The arrays used in the present invention are preferable nucleic acid arrays that comprise a plurality of nucleic acid probes immobilized on a surface or substrate. The different nucleic acid probes are complementary to, and therefore can hybridize to, different target nucleic acid molecules in a sample. Thus, each probe can be used to simultaneously detect the presence and quantity of a plurality of different genes, e.g., the presence and abundance of different mRNA molecules, or of nucleic acid molecules derived therefrom (for example, cDNA or cRNA).

The arrays are preferably reproducible, allowing multiple copies of a given array to be produced and the results from each easily compared to one another. Preferably microarrays are small, and made from materials that are stable under binding conditions. A given binding site or unique set of binding sites in the microarray will specifically bind to the target. It will be appreciated that when cDNA complementary to the RNA of a cell is made and hybridized to a microarray under suitable conditions, the level or degree of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding a nucleic acid product of the gene) that is not transcribed in the cell will have little or no signal, while a gene for which mRNA is highly prevalent will have a relatively strong signal.

By way of example, GeneChip® (Affymetrix, Santa Clara, CA), generates data for the assessment of gene expression profiles and other biological assays. Oligonucleotide expression arrays simultaneously and quantitatively "interrogate" thousands of mRNA transcripts. Each transcript can be represented on a probe array by multiple probe pairs to differentiate among closely related members of gene families. Each probe contains millions of copies of a specific oligonucleotide probe, permitting the accurate and sensitive detection of even low-intensity mRNA hybridization patterns. After hybridization data is captured, using a scanner or optical detection systems, software can be used to automatically calculate the intensity values for each probe cell. Probe cell intensities can be used to calculate an average intensity for each gene, which correlates with mRNA abundance levels. Expression data can be quickly sorted based on any analysis parameter and displayed in a variety of graphical formats for any selected subset of genes.

Further examples of microarrays that can be used in the assays and methods of the invention are microarrays synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591.

Other exemplary arrays that are useful for use in the invention include, but are not limited to, Sentrix® Array or Sentrix® BeadChip Array available from Illumina®, Inc. (San Diego, Calif.) or others including beads in wells such as those described in U.S. Pat. Nos. 6,266,459; 6,355,431; 6,770,441; and 6,859,570. Arrays that have particle on the surface can also be used and include those described in U.S. Pat. Nos. 6,489,606; 7,106,513; 7,126,755; and 7,164,533.

An array of beads in a fluid format, such as a fluid stream of a flow cytometer or similar device, can also be used in methods for the invention. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

A spotted microarray can also be used in a method of the invention. An exemplary spotted microarray is a CodeLink™ Array available from Amersham Biosciences.

Another microarray that is useful in the invention is one that is manufactured using inkjet printing methods such as SurePrint™ Technology available from Agilent Technologies. Other microarrays that can be used in the invention include, without limitation, those described in U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751.

DASL can be used for quantitative measurements of RNA target sequences as well as for DNA target sequences. DASL is described, for example, in Fan et al. 2004.

Additional techniques for rapid gene sequencing and analysis of gene expression include, SAGE (serial analysis of gene expression). For SAGE, a short sequence tag (typically about 10-14 bp) contains sufficient information to uniquely identify a transcript. These sequence tags can be linked together to form long serial molecules that can be cloned and sequenced. Quantitation of the number of times a particular tag is observed proves the expression level of the corresponding transcript (see, e.g., Velculescu et al. 1995; Velculescu et al. 1997; and de Waard et al. 1999).

Screening and diagnostic method of the current invention may involve the amplification of the target loci. A preferred method for target amplification of nucleic acid sequences is using polymerases, in particular polymerase chain reaction (PCR). PCR or other polymerase-driven amplification methods obtain millions of copies of the relevant nucleic acid sequences which then can be used as substrates for probes or sequenced or used in other assays.

Kits

It is contemplated that all of the assays disclosed herein can be in kit form for use by a health care provider and/or a diagnostic laboratory.

Assays for the detection and quantitation of one or more of the genes can be incorporated into kits. Such kits would include probes for one or more of the genes, reagents for isolating and purifying ABCs and other B cells and nucleic acids from biological tissue or bodily fluid, reagents for performing assays on the isolated and purified nucleic acid, instructions for use, and reference values or the means for obtaining reference values in a control sample for the included genes.

A preferred embodiment of these kits would have the probes attached to a solid state. A most preferred embodiment would have the probes in a microarray format wherein nucleic acid probes for one or more of the genes differentially regulated in pathogenic ABCs would be in an ordered arrangement on a surface or substrate.

Drug Screening Assays and Research Tools

All of the biomarkers disclosed herein can be used as the basis for drug screening assays and research tools.

In one embodiment, IRF5, SWAP-70, and DEF6 polypeptides and proteins can be used in drug screening assays, free in solution, or affixed to a solid support. All of these forms can be used in binding assays to determine if agents being tested form complexes with the peptides, proteins or fragments, or if the agent being tested interferes with the formation of a complex between the peptide or protein and a known ligand.

High throughput screening can also be used to screen for therapeutic agents. Small peptides or molecules can be synthesized and bound to a surface and contacted with the polypeptides, and washed. The bound peptide is visualized and detected by methods known in the art.

Antibodies to the polypeptides can also be used in competitive drug screening assays. The antibodies compete with the agent being tested for binding to the polypeptides. The antibodies can be used to find agents that have antigenic determinants on the polypeptides, which in turn can be used to develop monoclonal antibodies that target the active sites of the polypeptides.

The invention also provides for polypeptides to be used for rational drug design where structural analogs of biologically active polypeptides can be designed. Such analogs would interfere with the polypeptide in vivo, such as by non-productive binding to target. In this approach the three-dimensional structure of the protein is determined by any method known in the art including but not limited to x-ray crystallography, and computer modeling. Information can also be obtained using the structure of homologous proteins or target-specific antibodies.

Using these techniques, agents can be designed which act as inhibitors or antagonists of the polypeptides, or act as decoys, binding to target molecules non-productively and blocking binding of the active polypeptide, or which act as agonists.

A further embodiment of the present invention is gene constructs comprising the genes that encode IRF5, SWAP-70, and Def6 and any of the differentially expressed genes described herein, and a vector. These gene construct can be used for testing of therapeutic agents as well as basic research. These gene constructs can also be used to transform host cells can be transformed by methods known in the art.

The resulting transformed cells can be used for testing for therapeutic agents as well as basic research.

EXAMPLES

The present invention may be better understood by reference to the following non-limiting examples, which are presented in order to more fully illustrate the preferred embodiments of the invention. They should in no way be construed to limit the broad scope of the invention.

Example 1

Materials and Methods

Mice

C57BL/6, CD21-Cre and CD11c-Cre were obtained from Jackson Laboratory. DEF6 deficient ($Def6^{tr/tr}$) mice were generated by Lexicon Pharmaceuticals, Inc. using a gene trapping strategy as previously described (Biswas et al. 2012). Swap-70 deficient mice ($Swap-70^{-/-}$) were generated by R. Jessberger as previously described (Biswas et al. 2012). $Def6^{tr/tr}$ $Swap-70^{-/-}$ (DKO) mice were generated by crossing $Def6^{tr/tr}$ (Def6ko) mice with $Swap-70^{-/-}$ (Swap70ko) mice that had been backcrossed onto C57BL/6 background for greater than 10 generations (Biswas et al. 2012).

$SAP^{-/-}$ mice were obtained from Taconic and crossed to DKO mice to obtain SAP-/- DKO mice. $IL21^{-/-}$ mice on mixed strain background were obtained from the Mutant Mouse Regional Resource Centers (Lexicon strain ID 011723-UCD), and then backcrossed into a C57BL/6 background for greater than 10 generations and then crossed with DKO mice to obtain $IL21^{-/-}$ DKO mice.

CD11c CreIRF4$^{fl/fl}$ DKO mice were generated as previously described (Manni et al. 2015).

IRF5$^{fl/fl}$ mice, which do not carry the Dock2 mutation, were originally obtained from Paula Pitha-Rowe (Johns Hopkins University, MD) (Fang et al. 2012). CD21-Cre mice were crossed with IRF5$^{fl/fl}$ mice to produce CD21-Cre IRF5$^{fl/fl}$ mice. These mice were further crossed with DKO mice expressing either CD21Cre or CD11cCre to produce IRF5$^{fl/fl}$ DKO, CD21-Cre IRF5$^{fl/-}$ DKO, CD11cCre IRF$^{fl/-}$ DKO, and IRF5$^{fl/-}$ DKO mice.

BLIMP-YFP-10BiT double reporter mice have been described previously (Parish et al 2014; Maynard et al. 2007) and were crossed with DKO mice to generate BLIMP-YFP-10BiT DKO mice as described in Chandrasekaran et al. 2016.

Yaa-DKO male mice were obtained by crossing DKO male mice with Yaa mice which carry a duplication of TLR7 on the Y chromosome (Deane et al. 2007).

All mice used in the experiments were kept under specific pathogen-free conditions. The experimental protocols were approved by the Institutional Animal Care and Use Committee of the Hospital for Special Surgery and WCMC/MSKCC.

Antibodies and Flow Cytometry

The following monoclonal antibodies to mouse proteins were used for multiparameter flow cytometry: CD11c (N418), CD11b (M1/70), CD19 (6D5), B220 (RA3-6B2), T-bet (4B10), CD4 (RM4-5), CD21/CD35 (7E9), CD23 (B3B4), CD86 (GL-1), MHCII (AF6-120.1), IgG1 (RMG1-1) and IgG2a (RMG2a-62) were obtained from Biolegend. Antibodies to CD43 (S7), CD138 (281-2), GL-7 and Fas (Jo2) were obtained from BD. Antibodies to Ki-67 (SolA15), IgD (11-26), IgM (II/41), CD93 (AA4.1), CD5 (53-7.3), PDCA-1 (eBio927), PD1 (J43) and Foxp3 (FJK-16s) were obtained from Ebioscience.

For staining of CXCR5 (2G8; BD), cells were incubated in dark at room temperature for 25 minutes.

For intracellular staining, cells were fixed after surface staining at 4° C. with the Foxp3 Staining Buffer Set (eBioscience) following the manufacturer instruction.

For active caspase-3 staining, cells were stained using the CaspGLOW Active Caspase-3 Staining kit (BioVision) following the manufacturer instructions. For viability analysis, cells were stained with 0.5 μg of propidium iodide/samples prior to acquisition. Data were acquired on FACS Canto (Becton Dickinson) and analyzed with FlowJo (TreeStar) software.

Cell Sorting and B Cell Differentiation

Single-cell suspensions from pooled spleens and lymph nodes were pre-enriched for B cells with B220 microbeads (Miltenyi Biotec) following the manufacturer instructions. B cells were stained with CD11c (N418), CD11b (M1/70), CD19 (6D5), B220 (RA3-6B2) and CD23 (B3B4) and were sorted on FACS Aria (Becton Dickinson).

B Cell Differentiation

Single-cell suspensions from pooled spleens were enriched for B cells with biotinylated anti-CD23 (BD Bioscience) and streptavidin microbeads (Miltenyi Biotec) following the manufacturer instructions. CD23+ B cells were cultured in RPMI 1640 medium (Corning) supplemented with 10% FBS (Atlanta Biologicals), 100 U/ml Penicillin (Corning), 100 mg/ml Streptomycin (Corning), 1× Non-Essential Amino Acids (Corning), 2 mM L-Glutamine (Corning), 25 mM Hepes and 50 µM β-Mercaptoethanol, and stimulated with 5 µg/ml F(ab')2 anti-mouse IgM (αIgM; Jackson ImmunoResearch Laboratories), 5 µg/ml Ultra-LEAF purified anti-mouse CD40 (Biolegend), in presence or absence of 50 ng/ml IL-21 (Peprotech), 1 µg/ml imiquimod (Invivogen), 10 ng/ml IL-4 (Peprotech) or 20 ng/ml IFN-γ (Peprotech). For proliferation assays, CD23+B cells were labelled with 2.5 µM CFSE or Cell trace violet (Invitrogen) for 1 minute at room temperature prior stimulation.

Real-Time RT-PCR

Total RNA was isolated from cells using RNeasy Plus Mini kit (Qiagen). cDNAs were prepared using the iScript cDNA synthesis kit (Biorad). and analyzed for the expression of the gene of interest by real-time PCR using the iTaq Universal SYBR Green Supermix (Biorad). Gene expression was calculated using the ΔΔCt method and normalized to Cyclophilin a Lifr and Jun primers were obtained from Qiagen.

```
ccl5 forward
                                       (SEQ ID NO: 1)
5'-GCCCACGTCAAGGAGTATTTCTA-3';

ccl5 reverse
                                       (SEQ ID NO: 2)
5'-ACACACTTGGCGGTTCCTTC-3';

il6 forward
                                       (SEQ ID NO: 3)
5'-GAGGATACCACTCCCAACAGAC-3';

il6 reverse
                                       (SEQ ID NO: 4)
5'-AAGTGCATCATCGTTGTTCATA-3';

cxcl10 forward
                                       (SEQ ID NO: 5)
5'-CCAAGTGCTGCCGTCATTTTC-3';

cxcl10 reverse
                                       (SEQ ID NO: 6)
5'-GGCTCGCAGGGATGATTTCAA-3';

ifnγ forward
                                       (SEQ ID NO: 7)
5'-GGATATCTGGAGGAACTGGC-3';

Ifnγ reverse
                                       (SEQ ID NO: 8)
5'-GCGCCAAGCATTCAATGAGCTC-3';

spi1 forward
                                       (SEQ ID NO: 9)
5'-TGCAGCTCTGTGAAGTGGTT-3';

spi1 reverse
                                      (SEQ ID NO: 10)
5'-AGCGATGGAGAAAGCCATAG-3';

zbtb32 forward
                                      (SEQ ID NO: 11)
5'-TCCAGATACGGTGCTCCCTTCT-3';

zbtb32 reverse
                                      (SEQ ID NO: 12)
5'-CCAGAGAGCTTTGGAGTGGTTC-3';

Nfil3 forward
                                      (SEQ ID NO: 13)
5'-AATTCATTCCGGACGAGAAG-3';

Nfil3 reverse
                                      (SEQ ID NO: 14)
5'-CGATCAGCTTGTTCTCCAAA-3';

Maf forward
                                      (SEQ ID NO: 15)
5'-AGCAGTTGGTGACCATGTCG-3';

maf reverse
                                      (SEQ ID NO: 16)
5'-TGGAGATCTCCTGCTTGAGG-3';

axl forward
                                      (SEQ ID NO: 17)
5'-CGAGAGGTGACCTTGGAAC-3';
```

DNA Constructs

Expression plasmids for untagged and HA-tagged DEF6 were generated as described previously (Biswas et al. 2012). The full-length wild type human SWAP-70 expression plasmid (pIRES2-EGFP-HA-SWAP70) was constructed by cloning the entire coding region of the human Swap-70 cDNA, fused in frame with a hemagglutinin (HA) epitope coding sequence at its 5' end, into the pIRES2-EGFP bicistronic expression vector (Clonetech). Various deletion mutants of human SWAP-70 were generated by PCR using appropriate primers. The full-length wild type human IRF5 expression construct in pcDNA3 was a kind gift of Dr. Inez Rogatsky. Full length human IRF5 (variant 5) and T-bet expression constructs were purchased from Genescript. Expression plasmids for Flag-tagged IRF5 (variant 5) and its various deletion mutants were constructed in p3XFLAG-CMV-10 expression vector (Sigma) using IRF5 construct (Genescript) as a template. Expression plasmid for untagged T-bet was generated in pIRES2-EGFP bicistronic expression vector (Clonetech) using T-bet expression construct (Genescript) as a PCR template.

Western Blotting and Immunoprecipitation

Nuclear and cytoplasmic extracts were prepared with NEPER Nuclear and Cytoplasmic Extraction Reagents (Pierce), as previously described (Biswas et al. 2012). For expression analysis cell extracts were analyzed by Western blotting with anti-STAT3 (BD Bioscience), anti-pSTAT3 (Y705) (Cell Signaling), anti-IRF5(Cell Signaling) or anti-HDAC1 (Cell Signaling) antibodies. For protein-protein interactionstudies, cell extracts were immunoprecipitated with an anti-IRF5 (Cell Signaling), or anti-HA (3F10; Roche Applied Science) antibodies. The immunoprecipitates were resolved by 8% SDS-PAGE, transferred to a nitrocellulose membrane, and then immunoblotting with either an anti-SWAP-70 antibody (Santa Cruz Biotechnology, Inc.), anti-DEF6 antiserum (Gupta et al. 2003) or anti-HA antibody (Roche Applied Science).

ChIP Assays

CD23+ B cells were purified and stimulated in vitro for 48 hours. After harvesting, the cells were cross-linked with formaldehyde, and chromatin extracts were prepared using the truChIP Chromatin Shearing Reagent Kit (Covaris) according to manufacturer instructions. The DNA-protein complexes were immunoprecipitated with an anti-IRF5 (Abcam, ab21689) or anti-T-bet (Santa Cruz; sc-21749X) specific antibody or a control antibody. After cross-linking was reversed and proteins were digested, the DNA was purified from the immunoprecipitates as well as from input extracts, and then analyzed by quantitative PCR using the following primers within the ABC-specific ATAC-seq peaks (murine):

```
Il6 TSS (Forward):
                                        (SEQ ID NO: 18)
5'-AGCTTCTCTTTCTCCTTATAAAACATTG-3';

Il6 TSS (Reverse);
                                        (SEQ ID NO: 19)
5'-GCATCGAAAGAATCACAACTAGG-3';

Cxcl10 Cluster (Forward):
                                        (SEQ ID NO: 20)
5'-AGTAGTCCCCACTGTCTGACT-3';

Cxcl10 Cluster (Reverse):
                                        (SEQ ID NO: 21)
5'-GTGAGTCCCTTTAGCACCAGA-3';

Zeb2 Exon8 (Forward):
                                        (SEQ ID NO: 22)
5'-AGCAGTCCCTTTATGAACGG-3';

Zeb2 Exon8 (Reverse):
                                        (SEQ ID NO: 23)
5'-GCTTCCATCCCTACACCTAAG-3';

Jun (Forward):
                                        (SEQ ID NO: 24)
5'-AGAACAGCTTTTGAGCACCG-3';

Jun (Reverse):
                                        (SEQ ID NO: 25)
5'-TGGCTTCAAAGTGACTAACAGCA-3';

IgG2c (Forward):
                                        (SEQ ID NO: 26)
5'-TGTAATGCCTGGTTGCCTCC-3';

IgG2c (Reverse)
                                        (SEQ ID NO: 27)
5'-GTTCGGGACCCACAGTACATT-3.
```

ONP Assays

ONP assays were conducted as previously described (Biswas et al. 2010). Briefly, nuclear extracts were pre-cleared with streptavidin-agarose beads and then incubated with trimerized biotinylated double-stranded oligonucleotide containing potential IRF binding site within the ATAC-seq peak at the IL-6 TSS (5'-TGCTGAGTCACTTT-TAAAGAAAAAAAGAAGAGT-3') (SEQ ID NO: 28) or the CXCL10 Cl (5'-CATAGAAAATGTTTT-CAAAACCCGCATTCCGCTTATGCTGTCTGGTATCT-GAAATAGATCTGTCAGGGGGTCACATTT-TATAAGCACCACTTCGTGTTTG-3') (SEQ ID NO: 29). Proteins bound to the biotin-labeled DNA were collected by streptavidin-agarose beads, separated by 8% SDS-PAGE, and analyzed by Western blotting using anti-mouse IRF5 Ab (Cell signaling), anti-human IRF5 Ab (Santa Cruz SC-390364) or an anti-T-bet Ab (Santa Cruz; sc-21749).

Cytokines ELISA

IL-6 and CXCL10 in culture supernatants were measured using the mouse ELISA Max Standard Set (Biolegend) and the mouse Quantikine ELISA kit (R&D Systems) respectively.

Anti-ds DNA ELISA and ANA

For anti-dsDNA ELISA, plates were coated with 100 μg/ml salmon sperm DNA (Invitrogen AM9680) at 37° C. overnight and blocked in 2% BSA in PBS, at room temperature for 2 hours. For anti-cardiolipin ELISA Immulon 2HB plates (ThermoFisher) were coated with 75 μg/ml of cardiolipin dissolved in 100% ethanol at room temperature overnight. Sera were diluted 1:200 and incubated on coated plates at room temperature for 2 hours. Plates were then incubated with horseradish peroxidase-labelled goat anti-mouse IgG, IgG1 or IgG2 Fc antibody for 1 hour (eBioscience). Anti-ssDNA and anti-nRNP IgG ELISAs were obtained from Alpha Diagnostic International. $OD_{450}$ was measured on a microplate reader. ANAs were detected on Hep-2 slides (MBL international) at a 1:200 dilution using Alexa Flour 488-conjugated anti-mouse IgG (Jackson ImmunoResearch). Fluorescent intensity was semi-quantitated by following the guidelines established by the Center for Disease Control, Atlanta, Georgia Histology and Immunofluorescence Staining Tissue specimens were fixed in 10% neutral buffered formalin and embedded in paraffin. Tissue sections were stained with periodic acid schiff (PAS) and analyzed by light microscopy. The nephritis scoring system was adapted from the International Society of Nephrology/Renal Pathology Society (ISN/RPS) classification of human lupus nephritis. At least 40 glomeruli per mouse were evaluated. The final score accounted for morphological pattern (mesangial, capillary, membranous) and for the percentage of involved glomeruli. Immunofluorescence analysis on frozen kidney sections was performed by staining with FITC-labeled goat anti-mouse IgG (Jackson ImmunoResearch Laboratories) and specimens were analyzed with a LSM 510 laser scanning confocal microscope (Carl Zeiss, Inc.). Images were captured by Q capture software. Five representative glomeruli per mouse were chosen and mean fluorescence intensity (MFI) was calculated using ImageJ software.

RNA Seq Analysis

Total RNA was isolated using RNeasy Plus Mini kit (Qiagen). SMARTSeq v3 Ultra Low Input RNA Kit (Clontech) followed by Nextera library preparation were used to prepare Illumina-compatible sequencing libraries. Quality of all RNA and library preparations were evaluated with BioAnalyser 2100 (Agilent). Sequencing libraries were pair-end sequenced by the Weill Cornell Epigenomics Core using HiSeq2500 at the depth of ~30-50 million fragments per sample. Sequencing performance was evaluated using FASTQC. 50-bp paired reads were mapped to mouse genome (mm10, build 38.75, 41,128 genes and 87,108 transcripts) with CLC Bio Genomic Workbench 7.5 software (Qiagen).

Duplicated reads with more than 5 copies were discarded. Read count tables were created using unique exon read counts and the differential expression was analyzed using EDGER (Bioconductor). Genes with the expression levels less than 1 cpm in at least three conditions were considered non-expressing and removed from further analysis. A negative binomial generalized log-linear model was fit to read counts for each gene. A likelihood ratio tests with the null hypothesis that the pairwise contrasts of the coefficients are equal to zero was used to evaluate the significance of differences in expression between analyzed groups. Benjamini-Hochberg false discovery rate (FDR) procedure was used to correct for multiple testing. Genes with a FDR-corrected p-value>0.01 and less than 2 fold change were filtered out. Genes that passed the filtering were considered to be differentially expressed. Gene Set Enrichment Analysis was performed using the difference of log-transformed count per million (cpm) for contrasted conditions as a ranking metric. Molecular Signatures DataBase v 5.2 (Broad Institute) was used as source of gene sets with defined functional relevance. Gene sets ranging between 15 and 1000 genes were included into analysis. Nominal p values were FDR corrected and gene sets with FDR<0.05 were used to create GSEA enrichment plot. To define the groups of potentially co-regulated genes, unsupervised hierarchical clustering analysis of log-transformed expression values (cpm) in R was performed. The distances between genes were calculated as (1−Pearson correlation). The Euclidean distance was used to determine the distances between samples. Ward.D2 methods was used to performs clustering. The expression values were z-transformed and visualized using heatmaps.

ATAC-seq, Peak Calling and Annotation

The nuclei of sorted WT and DKO ABC or DKO Follicular B cells were prepared by incubation of cells with nuclear preparation buffer (0.30 M sucrose, 10 mM Tris, pH 7.5, 60 mM KCl, 15 mM NaCl, 5 mM MgCl2, 0.1 mM EGTA, 0.1% NP40, 0.15 mM spermine, 0.5 mM spermidine and 2 mM 6AA) (Minnich et al. 2016). Libraries were prepared as described previously (Buenrosto et al. 2015). Paired-end 50 bp sequences were generated from samples on an Illumina HiSeq2500. The makeTagDirectory was used followed by findPeaks command from HOMER version 4.7.2 to identify peaks of ATAC-seq. A false discovery rate (FDR) threshold of 0.001 was used for all data sets. The following HOMER command was used: cmd=findPeaks <sample tag directory>-style factor or histone-o<output file>-i<input tag directory>. The total number of mapped reads in each sample was normalized to ten million mapped reads. Peak-associated genes were defined based on the closest genes to these genomic regions using RefSeq coordinates of genes. The annotatePeaks command from HOMER was used to calculate ATAC-seq tag densities from different experiments and to create heatmaps of tag densities. Sequencing data were visualized by preparing custom tracks for the UCSC Genome browser.

Motif Enrichment Analysis

De novo transcription factor motif analysis was performed with motif finder program findMotifsGenome from HOMER package, on given ATAC-seq peaks. Peak sequences were compared to random genomic fragments of the same size and normalized G+C content to identify motifs enriched in the targeted sequences.

Statistics

P values were calculated with unpaired two-tailed Student's t-test for two-group comparisons and by one-way ANOVA followed by Bonferroni's multiple comparisons test for multi-group comparisons. For statistical analysis of ANA intensity score the non-parametric Mann-Whitney test was used. P values of <0.05 were considered significant. Ns: not significant, *: $p \leq 0.05$, : $p \leq 0.01$ *: $p \leq 0.001$***: $p \leq 0.0001$. Statistical analysis was performed with Graphpad Prism 5.

Example 2

Female DKO Mice Have Premature Expansion of Pathogenic ABCs, which is Dependent on the Absence of Both SWEF Proteins and Contribute to Lupus The finding that ABCs expand in autoimmune mouse strains coupled with the spontaneous development of autoimmunity in DKO mice prompted the investigation as to whether this B cell subset accumulates prematurely in these mice. The mice and methods described in Example 1 were used.

As compared to wild type mice, DKO female mice demonstrated a marked increase in the frequencies and numbers of splenic B cells expressing CD11c and CD11b (FIG. 1A). This increase could be observed by gating either on B220 alone or on both B220 and CD19 (FIG. 1A). Expansion of CD11c+CD11b+ B cells was primarily observed in spleens and, only minimally, in lymph nodes (FIG. 1B). Further staining for PDCA-1 confirmed that accumulation of these cells was not due to an increase in plasmacytoid dendritic cells (results not shown).

Figure 1C:
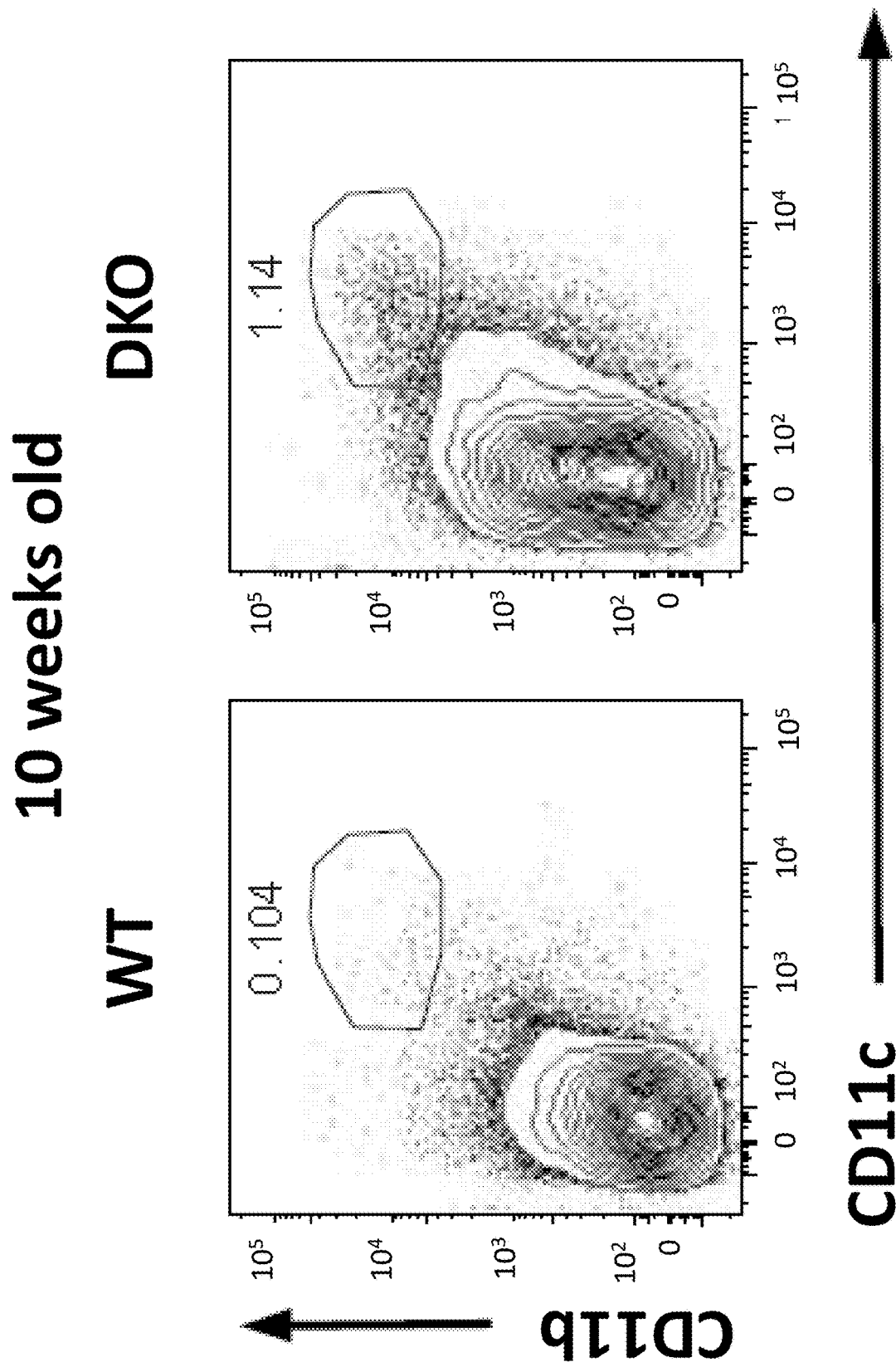
FIG. 1C is representative FACS plots and graphs for CD11b and CD11c expression after gating on B220+CD19+ cells in the spleens of 10 weeks old WT and DKO female mice. Graphs show frequencies and numbers of individual mice and mean value of 2 independent experiments (n=4-5). \: p≤0.01; \*: p≤0.001. (two-tailed Student-t test).

While ABCs in wild type female mice are normally detected after 12 months of age, ABCs in DKO female mice started appearing by 10 weeks of age (FIG. 1C), were readily observed by 18 weeks of age (FIG. 1D), and comprised up to 15% of splenic B cells in older (>23 weeks) mice (FIG. 1A).

Since B cells express both DEF6 and SWAP-70, it was also examined whether lack of either DEF6 alone or SWAP-70 alone was sufficient to promote the accumulation of ABCs in vivo (FIG. 1B). While a small increase in the frequencies of these cells could be observed in the spleens of female mice lacking only DEF6 or only SWAP-70, their abundance did not reach the levels observed in DKO female mice (FIG. 1B). The premature expansion of CD11c+ CD11b+ B cells observed in DKO mice was thus dependent on the concomitant absence of DEF6 and SWAP-70, thus, both SWEF proteins control the accumulation of these cells in vivo.

Figure 1D:
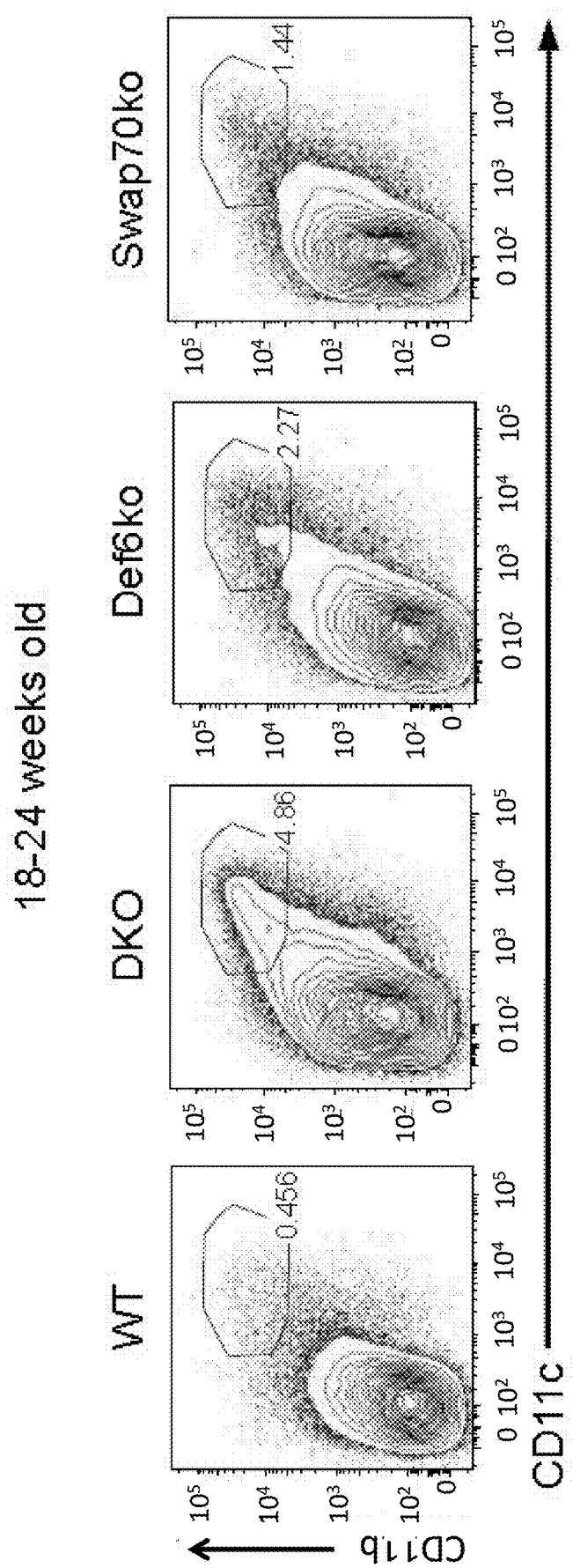
FIG. 1D is representative FACS plots and graphs for CD11c and CD11b expression gated on B220+CD19+ cells in the spleens of WT, DKO, Def6ko and Swap70ko female mice (18-24 weeks old). Graphs show frequencies and numbers for individual mice and mean values from 3 independent experiments (n=3-5). \**: p≤0.0001 (One-way ANOVA).
Figure 1D:
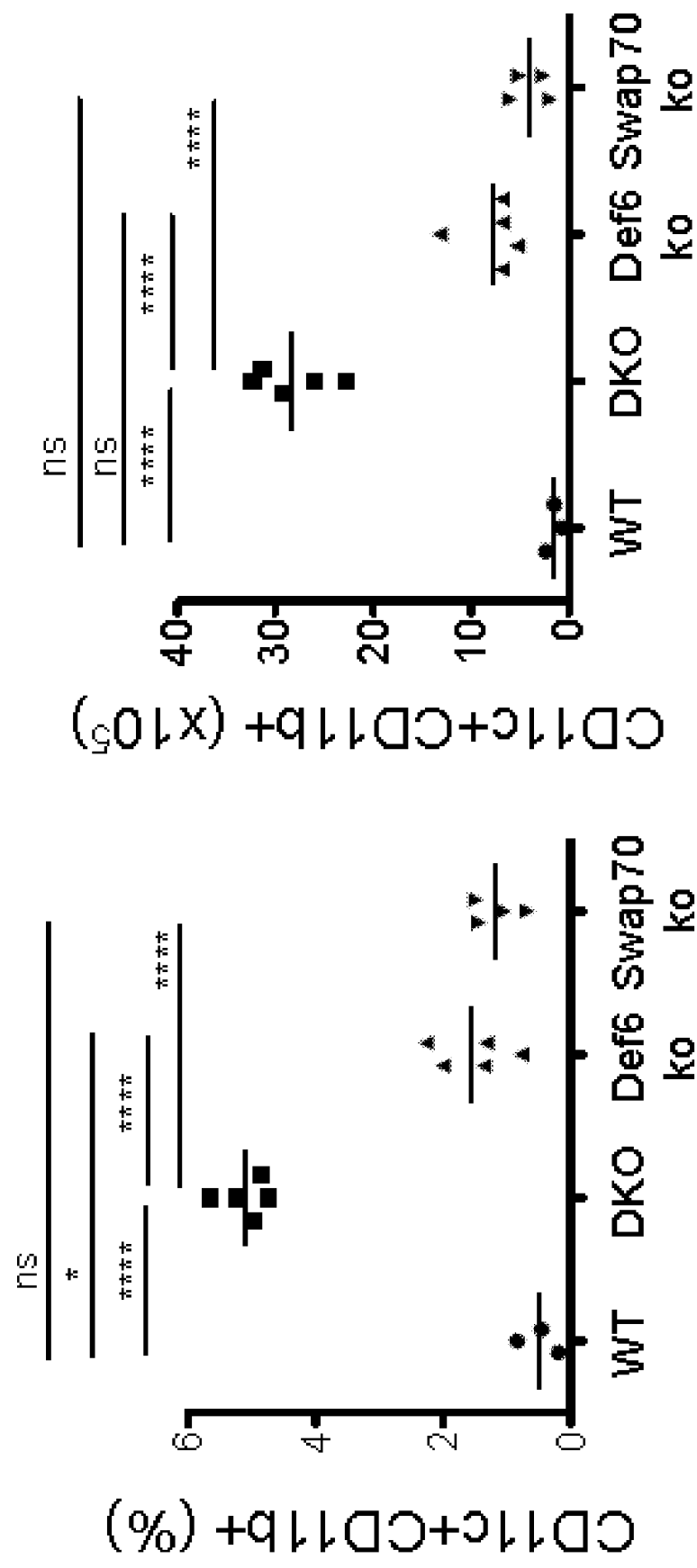
Figure 1E:
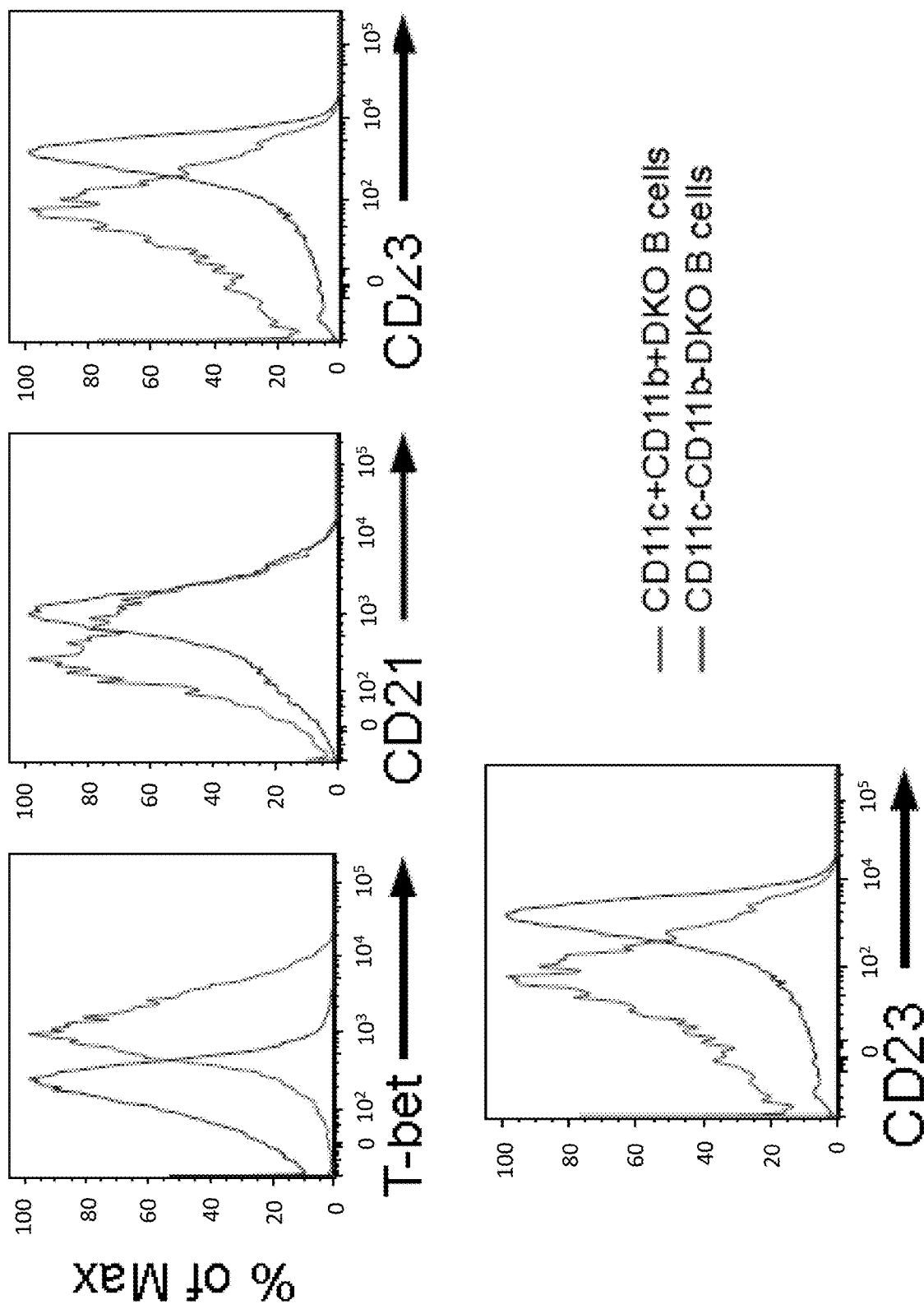
FIG. 1E are histograms that show relative expression (percentage) of the indicated marker on CD11c+ CD11b+B220+CD19+ and CD11c−CD11b−B220+CD19+ cells in the spleens of DKO female mice (greater than 18 weeks old). Data are representative of least 2 independent experiments (n=4-11).
Figure 1E:
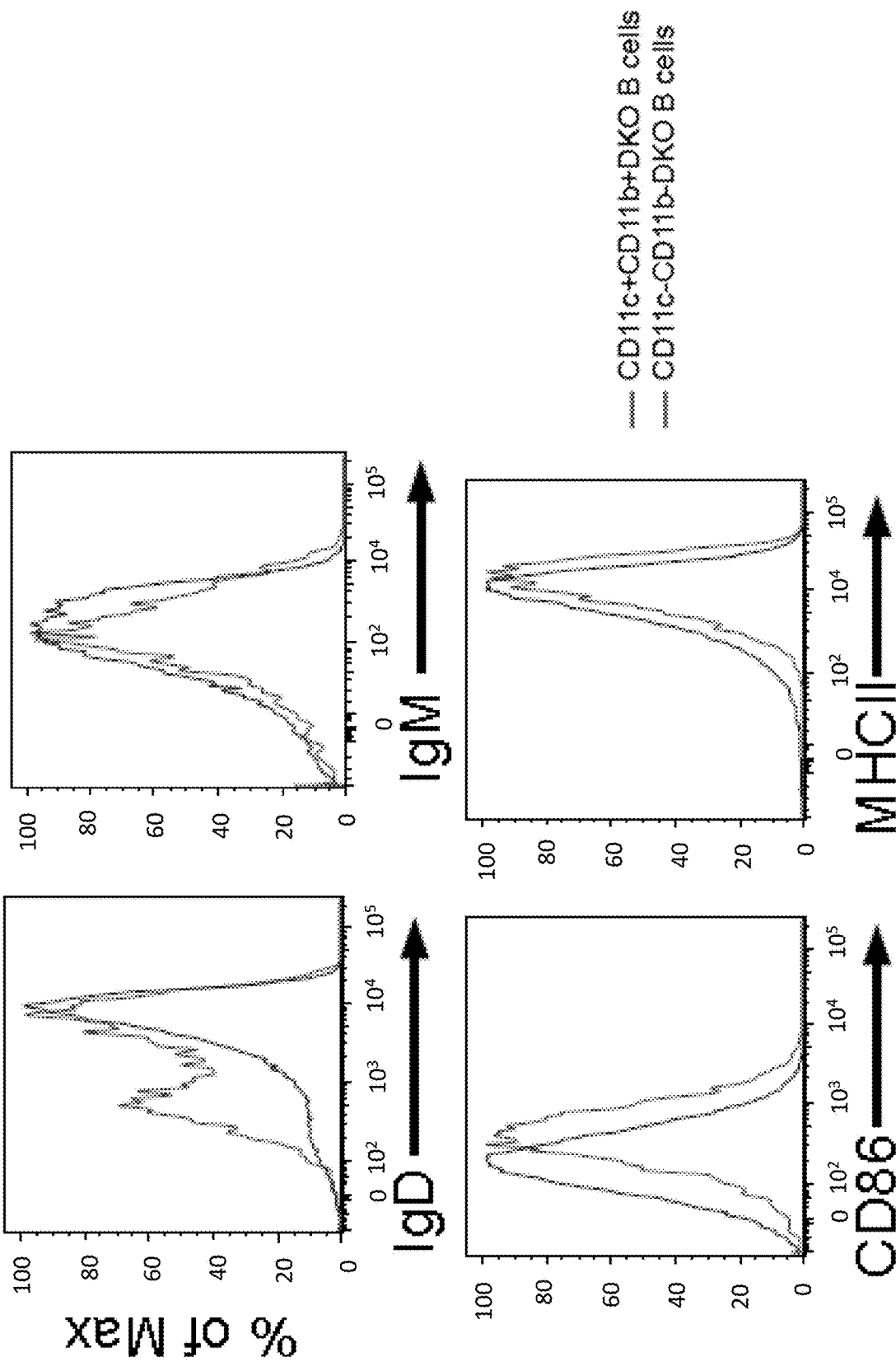
Figure 1E:
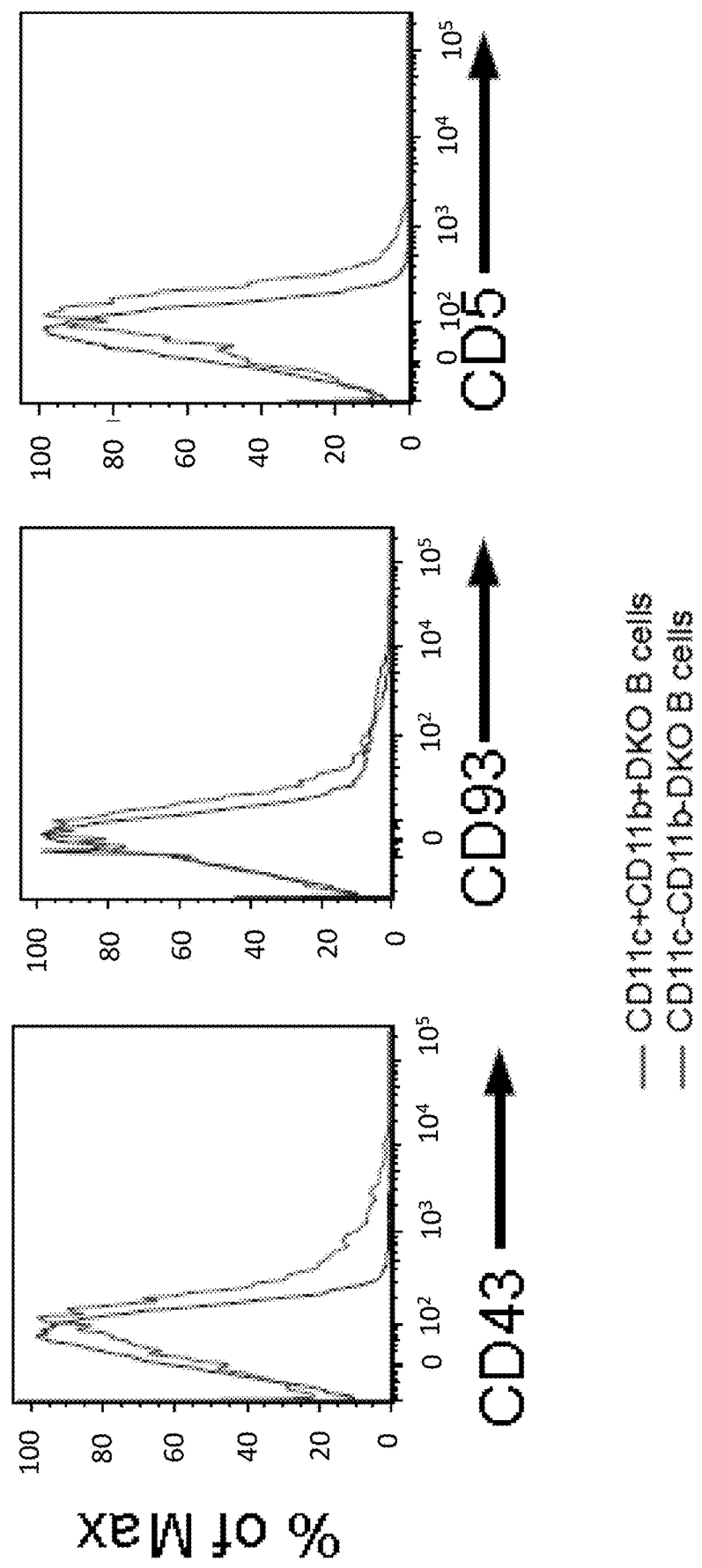
Figure 1F:
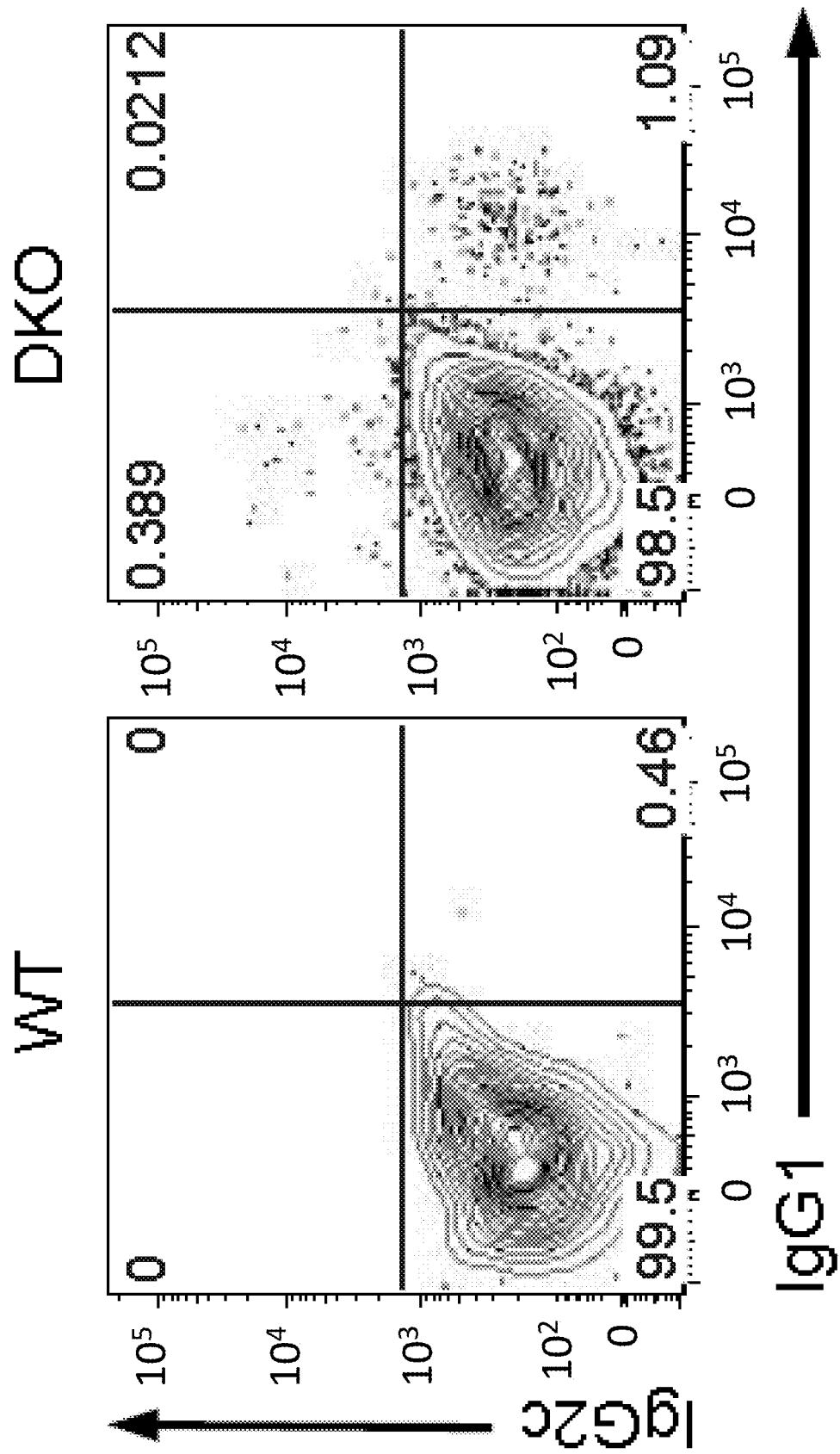
FIG. 1F is representative FACS plots and graphs for IgG1 and IgG2c expression on B220+CD19+ CD11c+CD11b+ cells. Graphs show frequencies and numbers for individual mice and mean values from 16 independent experiments (n=17-30). \: p≤0.01, \*: p≤0.001, \: p≤0.0001. (two-tailed Student-t test).
Figure 1F:
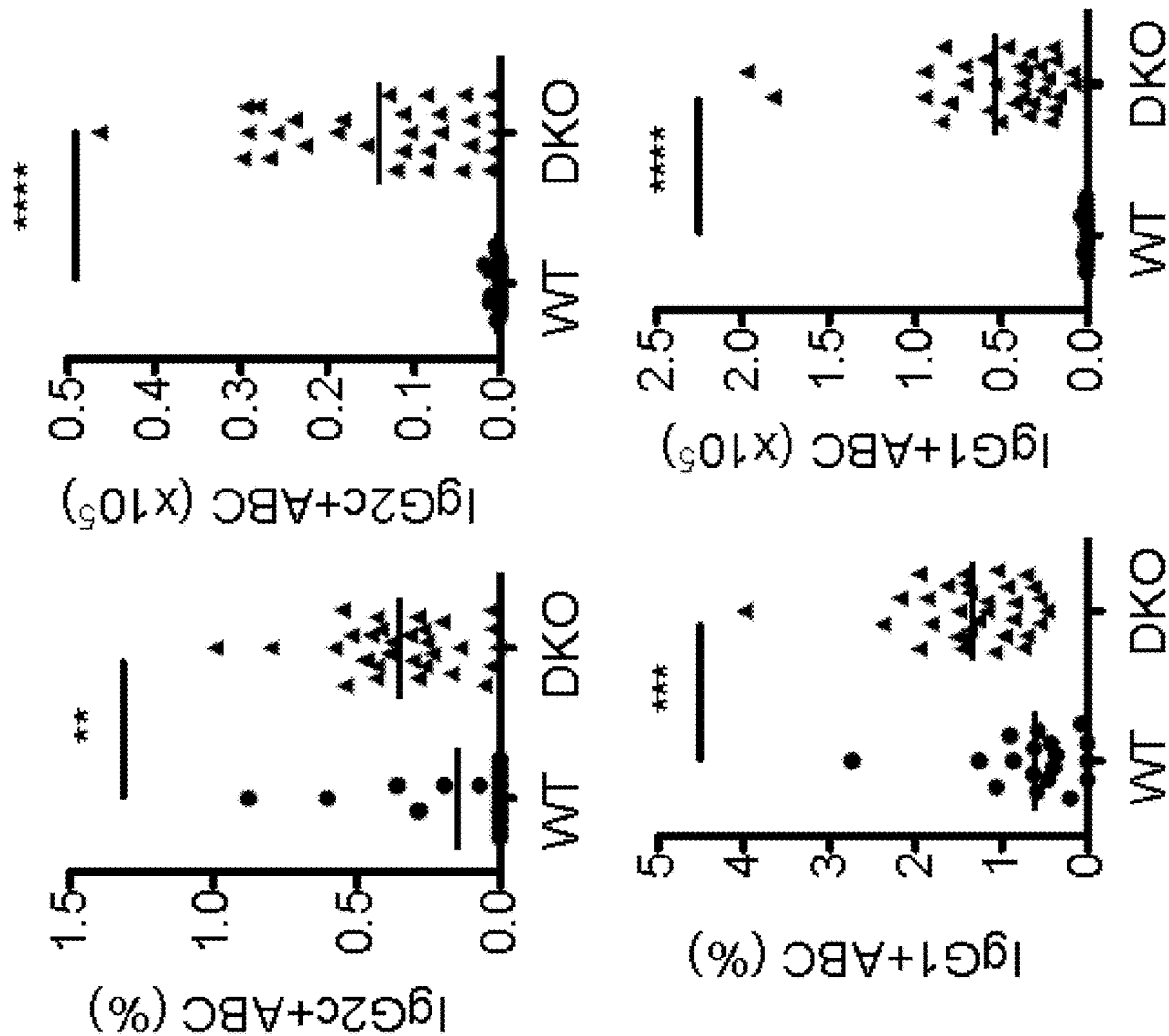

To further characterize the CD11c+CD11b+ B cells that accumulated in DKO female mice, the expression of several markers whose presence or absence defines ABCs was examined (FIG. 1E). As expected, the expression of Tbet, a major regulator of ABC generation, was significantly higher in CD11c+CD11b+ DKO B cells as compared to CD11c− CD11b− DKO B cells and corresponded to a marked expansion of CD11c+T-bet+ B cells in DKO female mice. Moreover, CD11c+CD11b+ DKO B cells downregulated the expression of CD21 and CD23 and expressed high levels of CD86, MHCII, and IgM (FIG. 1D). CD11c+CD11b+ DKO B cells did not express CD5, CD43, or CD93 (FIG. 1D). While most CD11c+CD11b+ DKO B cells expressed sIgM, a small number of these cells had undergone class-switching and expressed IgG1 and IgG2c (FIG. 1F).

In order to investigate whether ABCs contribute to the development of lupus in DKO female mice, their ability to produce autoantibodies was investigated. CD11c+CD11b+ B cells from DKO mice were FACS-sorted and cultured in vitro in the presence or absence of the TLR7 agonist, imiquimod (FIG. 1G). ABCs, but not Follicular B cells (FoB) from DKO mice secreted anti-dsDNA IgG2c (FIG. 1G). No anti-dsDNA IgG1 production was instead observed under these stimulatory conditions (not shown). TLR7 stimulation of DKO ABCs also resulted in the production of anti-nRNP and anti-cardiolipin IgG antibodies (FIG. 1G). DKO ABCs can thus directly contribute to the autoimmune syndrome in DKO mice by producing autoantibodies and are thus denoted as "pathogenic ABCs".

Example 3

IL-21 Regulates the Generation of ABCs in DKO Mice In Vitro and In Vivo

Figure 2A:
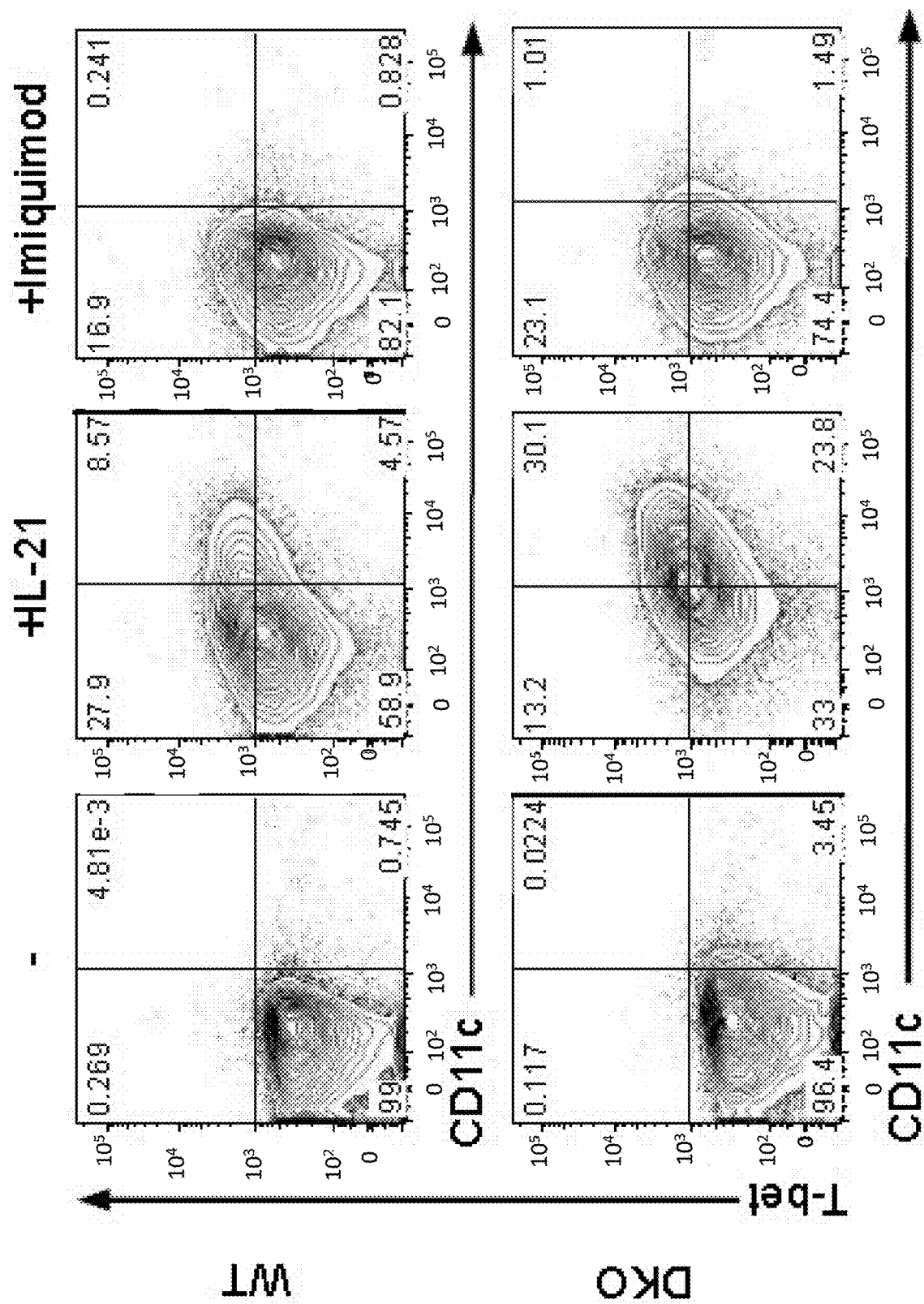
FIG. 2A is representative FACS plots and graph of the generation of ABCs (CD11c+T-bet+B220+) from cultures of CD23+ B cells purified from WT and DKO female mice (8-10 weeks of age) stimulated with αIgM and αCD40, alone or with IL-21 or imiquimod for 3 days. Graph shows frequencies of cells in mice as combined results of 5 independent experiments. Mean±SEM is shown. \**: p≤0.0001. (One-way ANOVA).
Figure 2A:
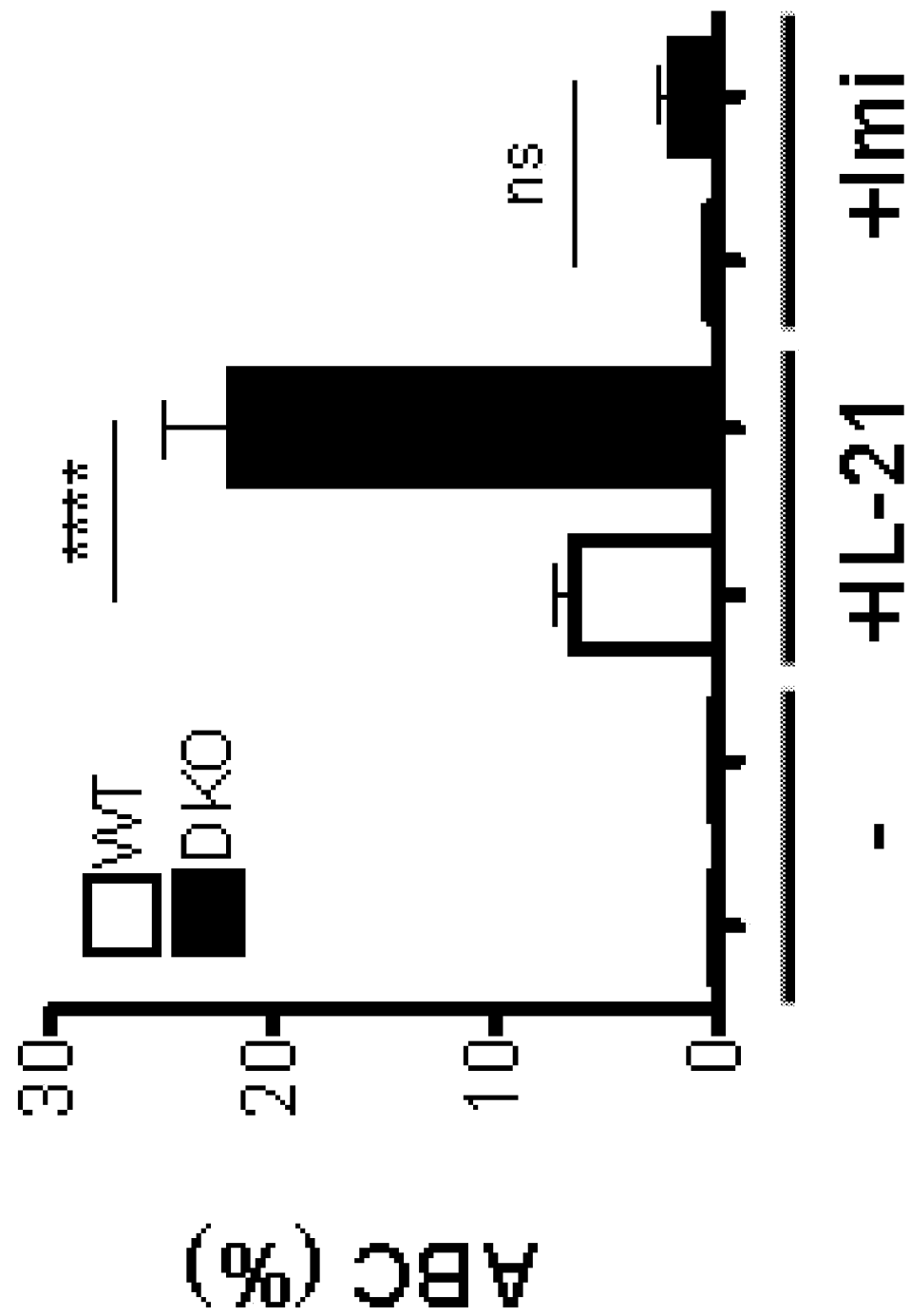
Figure 2B:
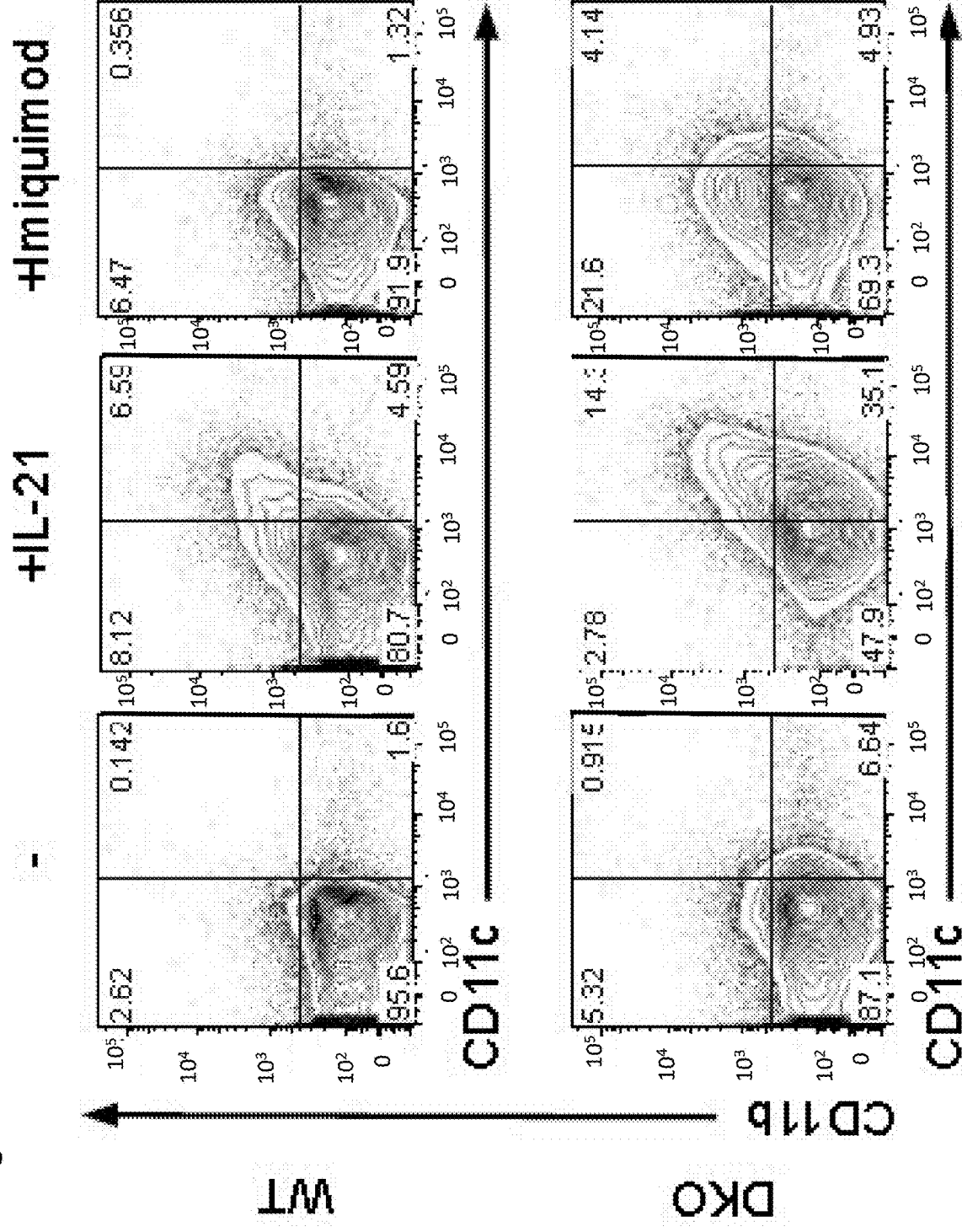
FIG. 2B is representative FACs plots and graph of generation of ABCs (CD11c+CD11b+B220+) B cells from cultures of CD23+ B cells purified from WT and DKO female mice (8-10 weeks of age) stimulated with αIgM and αCD40 (5 µg/ml), alone or with IL-21 or imiquimod. Graph shows frequencies of cells in mice as combined results of 5 independent experiments. \*: p≤0.001. (One-way ANOVA).
Figure 2B:
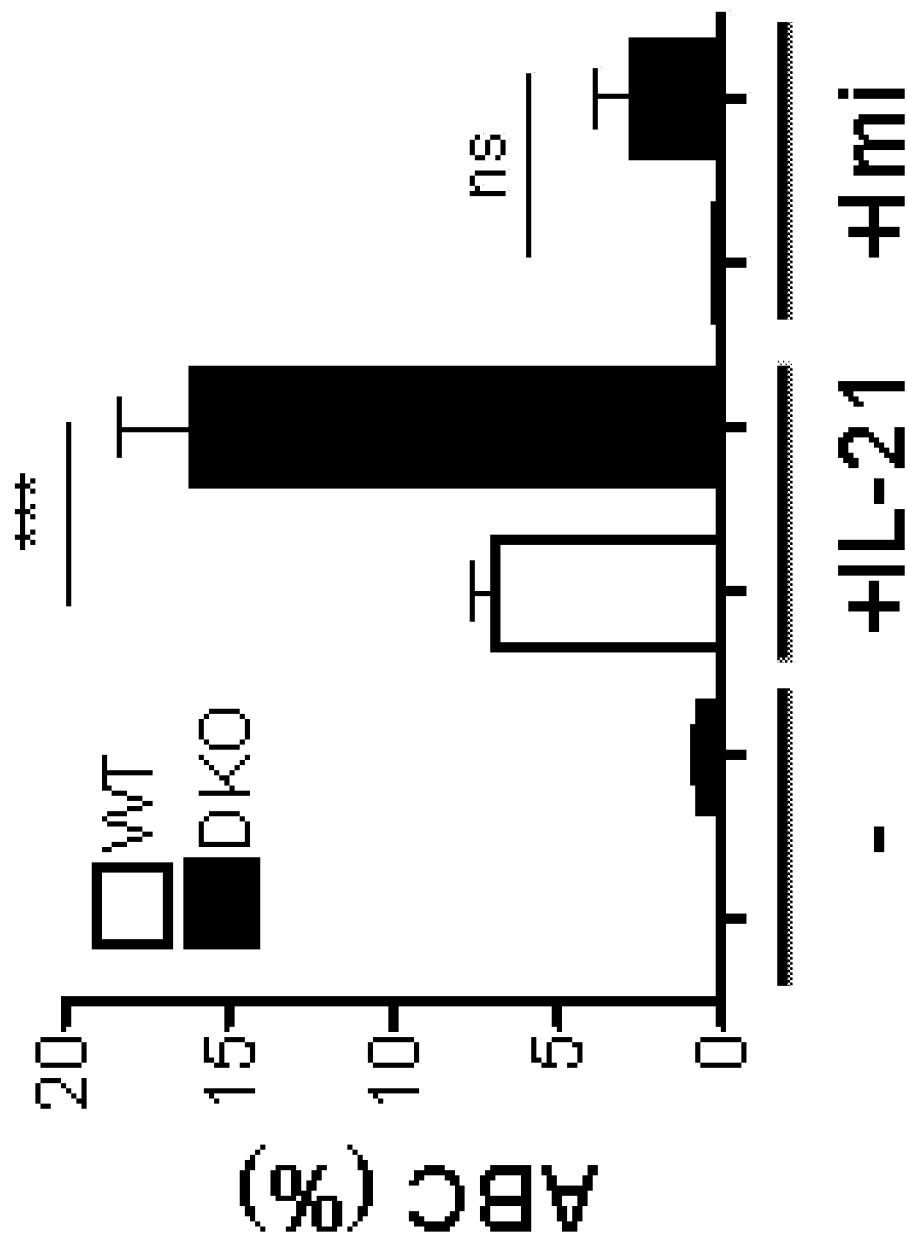

In addition to TLRs, T cells can also promote the generation of ABCs by providing contact-dependent signals and cytokines like IL-21 (Naradikian et al. 2016). An in vitro system to directly investigate the ability of these signals to drive the formation of ABCs from B cells purified from 8 week-old wild type or DKO female mice (Example 1) was set up (FIG. 2A). Culturing wild type or DKO B cells with αIgM (5 µ/ml) and αCD40 (5 µg/ml), either alone or with imiquimod, (1 µg/ml) did not result in the formation of CD11c+CD11b+ B cells. However, the addition of IL-21 (50 ng/ml) led to a significantly greater population of CD11c+ CD11b+ cells in cultures of DKO than wild type B cells (FIG. 2A). A population of CD11c+CD11b− B cells could also be observed in these DKO cultures (FIG. 2A). Similar results were obtained by using either CD11c and T-bet or CD11c and CD11b as markers (FIGS. 2A and 2B). In line with previous reports (Naradkian et al. 2016a), stimulation of wild type and DKO B cells with either IL-4 or IFNγ alone did not result in the formation of CD11c+T-bet+ B cells and addition of IL-4 inhibited the IL-21-mediated formation of these cells in both wild type and DKO cultures (results not shown). DKO B cells therefore exhibited an increased ability to generate ABCs in vitro in response to IL-21 stimulation.

Figure 2C:
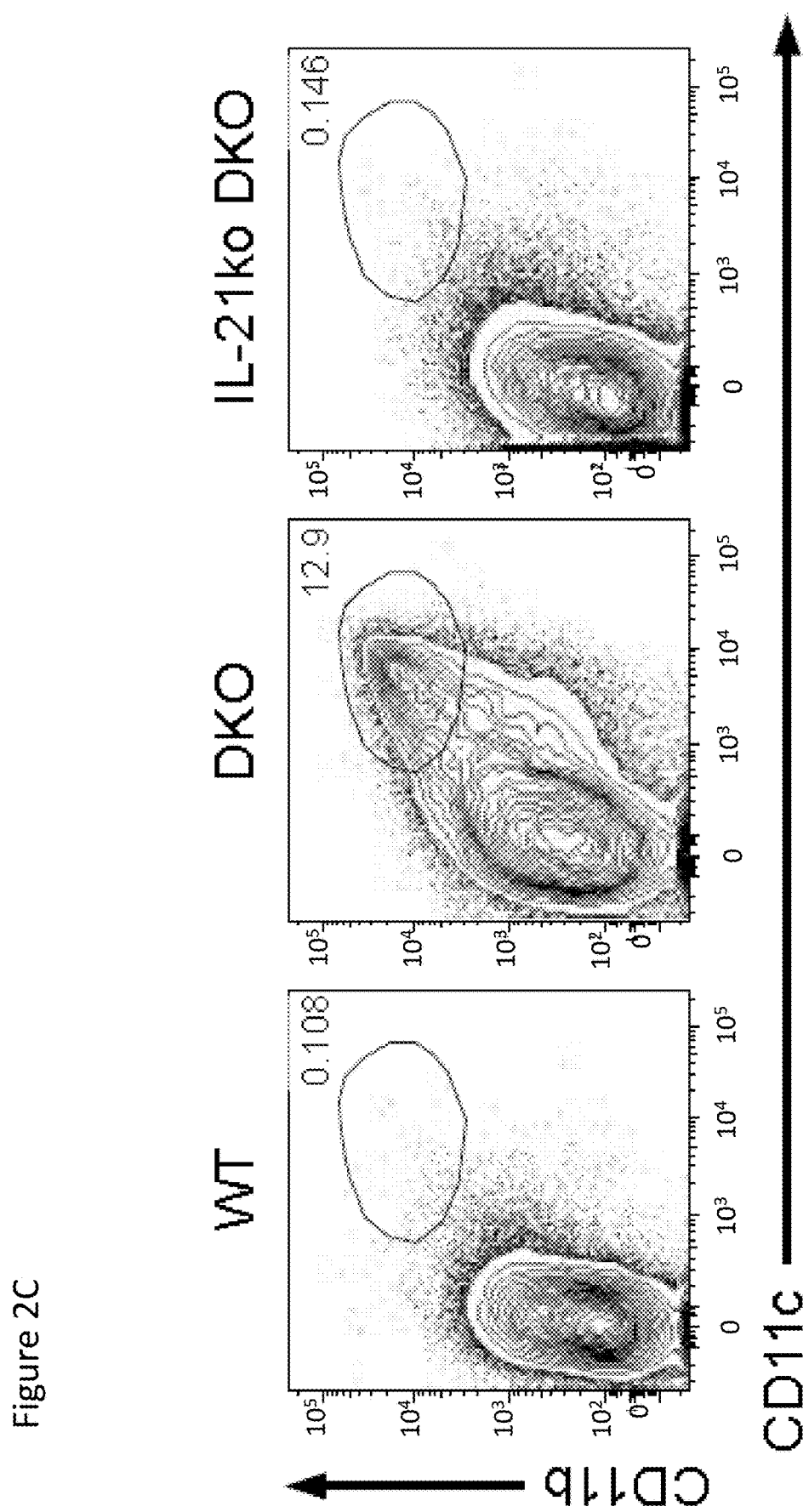
FIG. 2C is representative FACS plots and graphs of ABCs in the spleens from aging (greater than 24 weeks-old) wild type, DKO, or IL-21ko DKO female mice for CD11c and CD11b expression gated on B220+ cells. Graphs show the frequencies and numbers of CD11c+CD11b+ cells of individual mice gated as indicated as well as the mean value of at least 4 independent experiments (n=5-8) \*: p≤0.001, \: p≤0.0001 (One-way ANOVA).
Figure 2C:
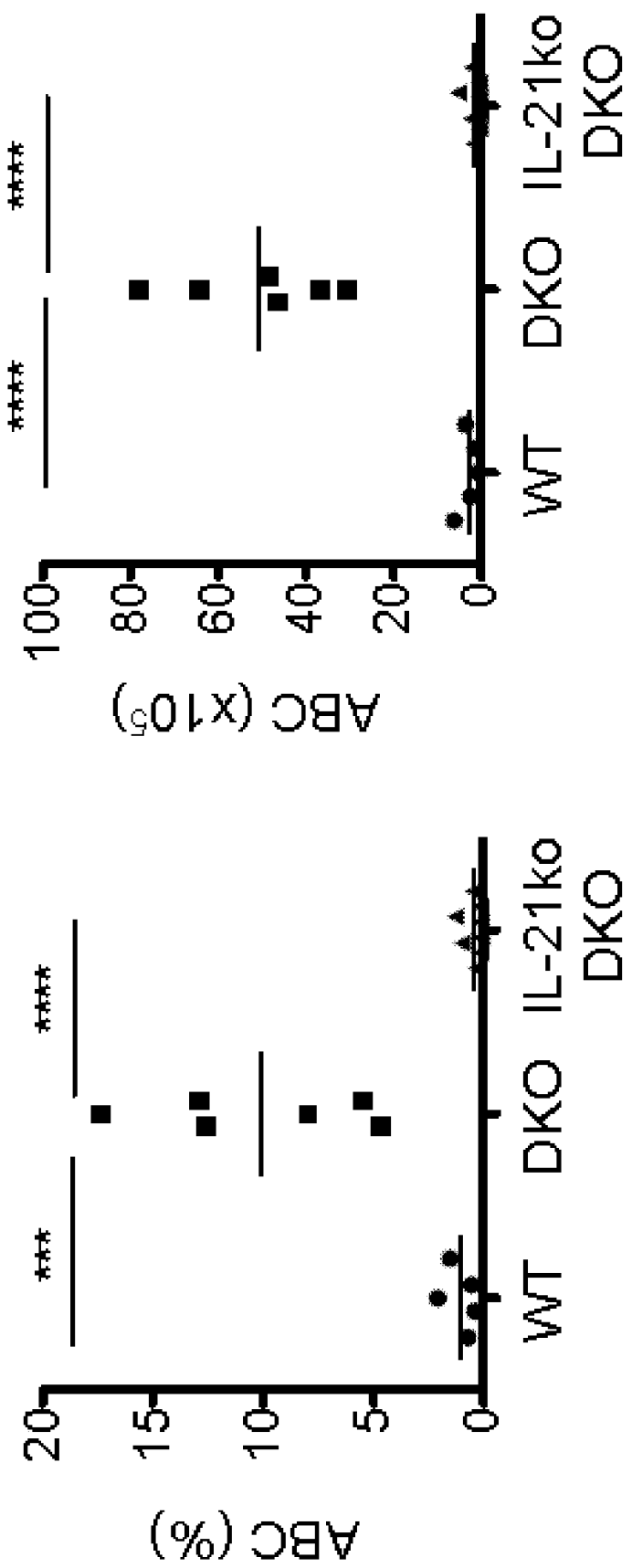
Figure 2D:
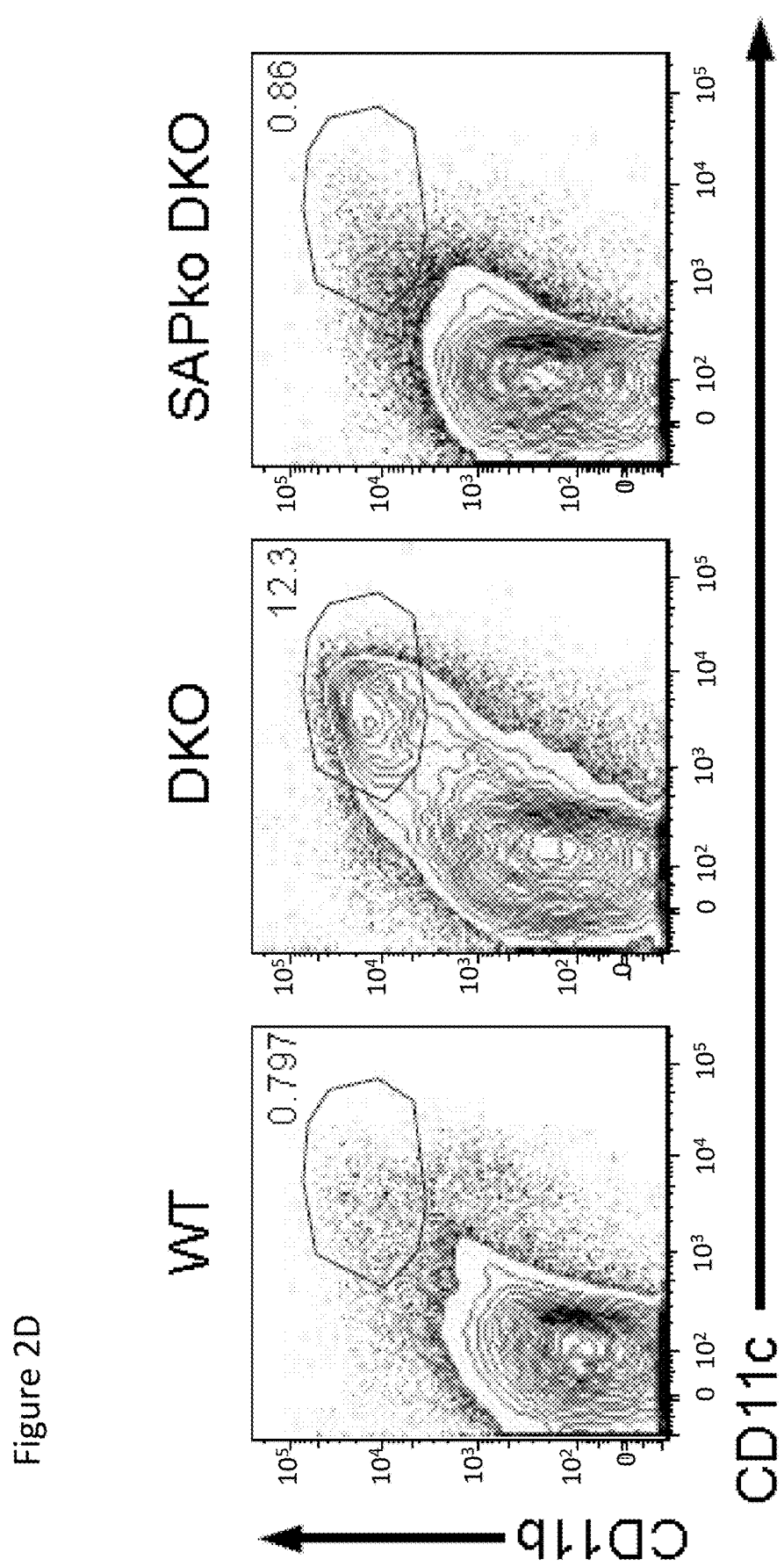
FIG. 2D shows representative FACS plots and graphs of ABCs in the spleens from aging (greater than 24 weeks-old) wild type, DKO, or SAPko DKO female mice for CD11c and CD11b (left panels) expression gated on B220+ cells. Graphs show the frequencies and numbers of CD11c+CD11b+ cells of individual mice gated as indicated as well as the mean value of at least 4 independent experiments (n=4-7). \: p≤0.0001.
Figure 2D:
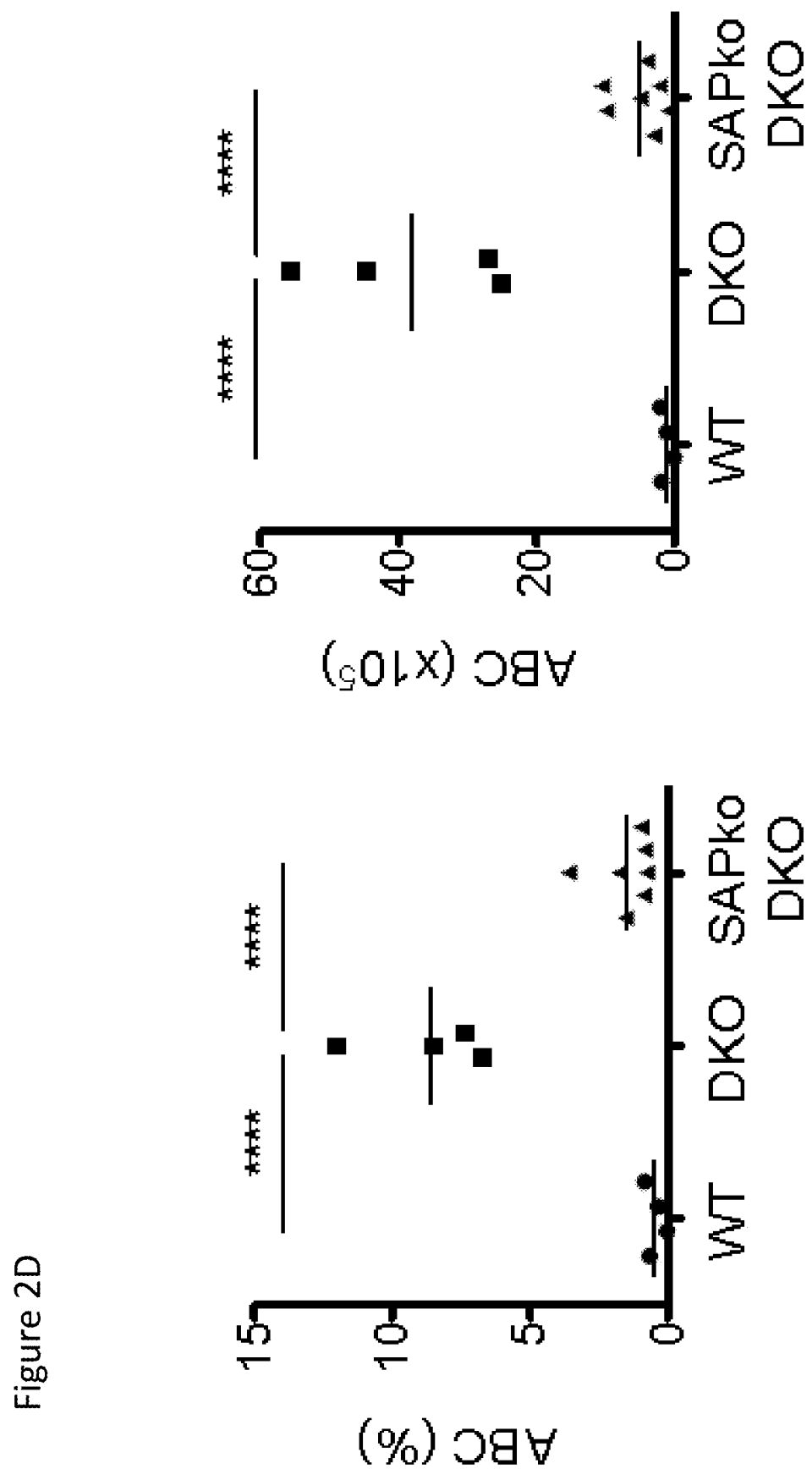
Figure 2E:
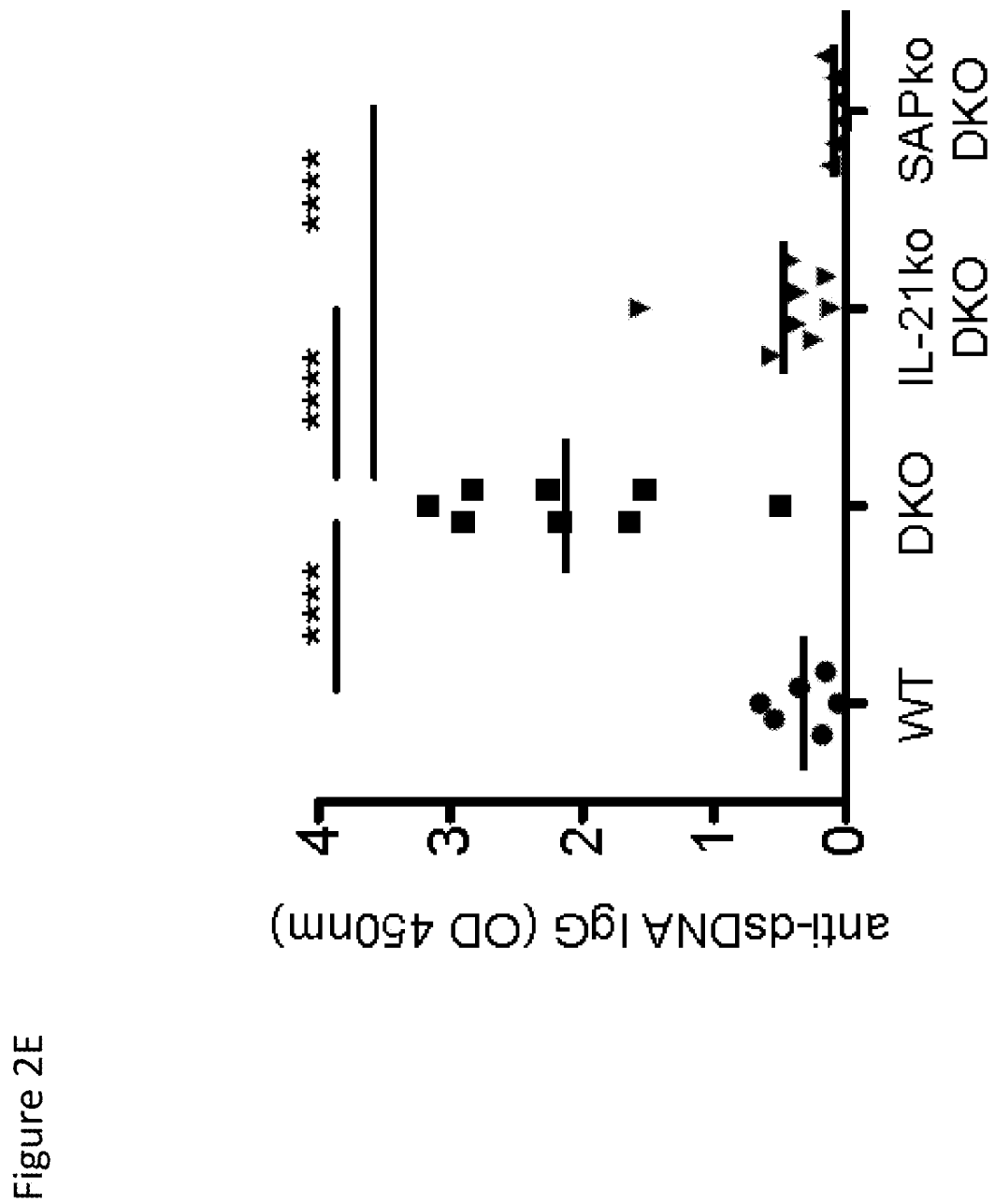
FIG. 2E show graphs of amount of IgG anti-ds DNA from serum from the indicated mice as assayed by ELISA. Graphs show data of individual mice and mean value of 4 independent experiments (n=6-8). \**: p≤0.0001.
Figure 2F:
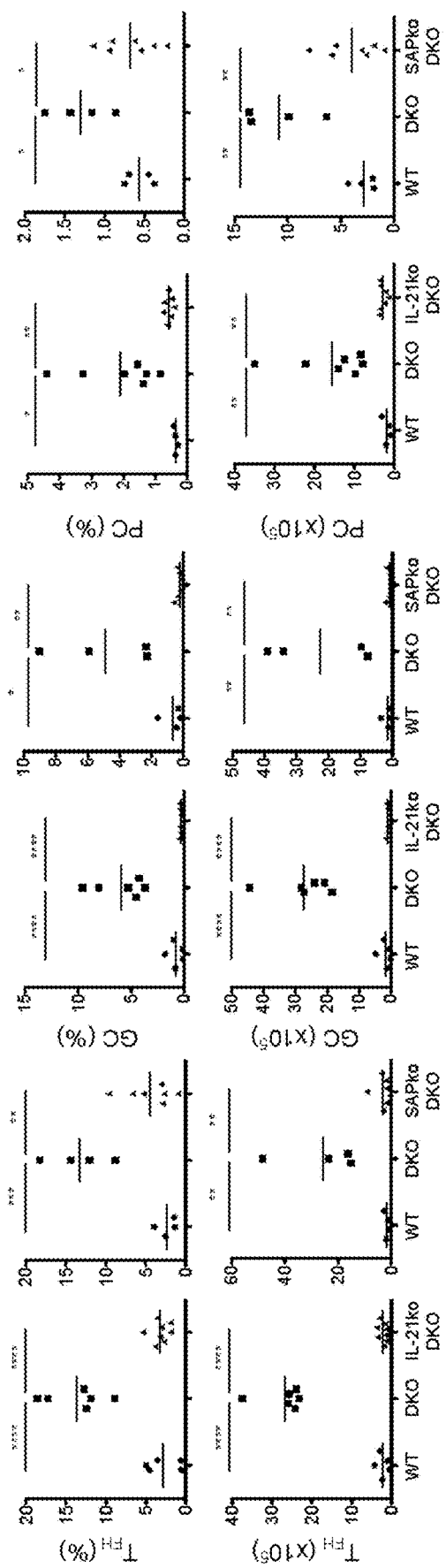
FIG. 2F are graphs showing the quantification (both in percentages and absolute numbers) of $T_{FH}$ (CD4+ CXCR5+PD1+Foxp3−), germinal center (GC) B cells (B220+FAS+GL-7+), and $B220^{int}CD138+$ plasma cells (PC) in spleens of WT, DKO, IL-21ko DKO or SAPko DKO female mice (>24 weeks old). Graphs show percentages and numbers of specific cells types in individual mice per genotype (n=4-8). \*: p≤0.05; \: p≤0.01; \*: p≤0.001. \****: p≤0.0001. (One-way ANOVA).

To further evaluate the importance of IL-21 in the aberrant expansion of ABCs observed in DKO mice, DKO female mice that also lack IL-21 (IL-21ko DKO) were generated. Accumulation of CD11c+CD11b+ B cells was completely abrogated in these mice as compared to age-matched female DKO mice (FIG. 2C). DKO mice lacking IL-21 also failed to accumulate $T_{FH}$ cells, germinal center (GC) B cells, and plasma cells, and failed to produce anti-dsDNA autoantibodies (FIGS. 2E and 2F).

To determine whether, in addition to IL-21 production, direct T-B interactions were also necessary for the expansion of DKO ABCs in vivo, their presence in DKO mice that lack SAP (SLAM-associated protein) was examined. SAP is required to mediate sustained interactions between T and B cells (Fang et al. 2012). As shown in FIG. 2D, the concomitant absence of SAP in DKO mice (SAPko DKO) resulted in diminished accumulation of pathogenic ABCs. This was again accompanied by profound reductions in $T_{FH}$ cells, GC B cells, plasma cells and markedly lower anti-dsDNA autoantibody titers (FIGS. 2E and 2F). Thus, the aberrant expansion of pathogenic ABCs observed in DKO mice is dependent on IL-21 and cognate T-B cell interactions, signals that also control the development of lupus.

Example 4

Figure 3A:
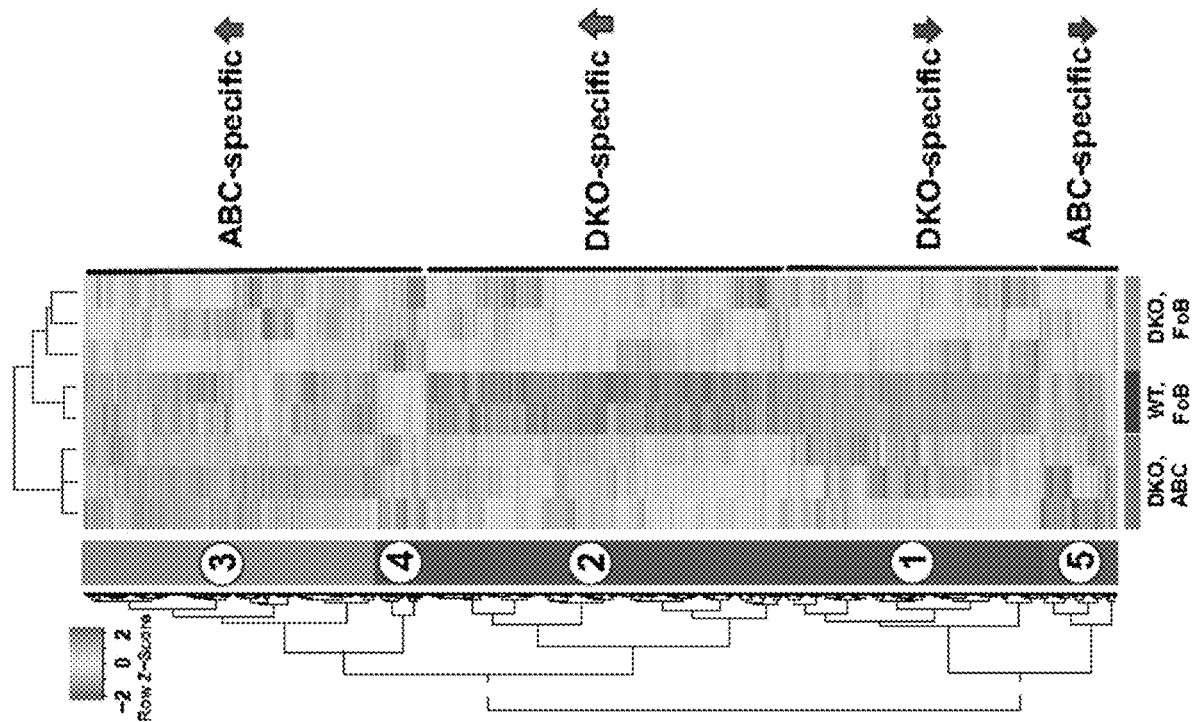
FIG. 3A shows the hierarchical clustering of log-transformed counts per million (cpm) for differentially expressed genes identified by RNAseq analysis from FACS sorted ABC (B220+CD19+CD11c+CD11b+) from DKO female mice or FoB (B220+CD19+CD11c−CD11b−CD23+) cells from WT and DKO female mice (greater than 20 weeks old) (n=2 WT, 3 DKO/group).

The SWEF Proteins Regulate the Proliferation and Proinflammatory Capacity of ABCs B cells were sorted based on the levels of expression of CD11c and CD11b and RNA-Seq employed as described in Example 1 to compare the transcriptome of CD11c+CD11b+ (ABC) DKO B cells to that of CD11c−CD11b− (FoB) B cells obtained from either wild type or DKO mice. A total of 3049 genes were differentially expressed amongst the three different subsets (FIG. 3A). A set of genes (cluster 2, DKO-specific up) was upregulated or downregulated (cluster 1, DKO-specific down) in DKO B cells irrespective of the expression of CD11c and CD11b suggesting that the lack of SWEF proteins altered the expression of these genes in B cells independently of their differentiation state (FIG. 3A).

Figure 3B:
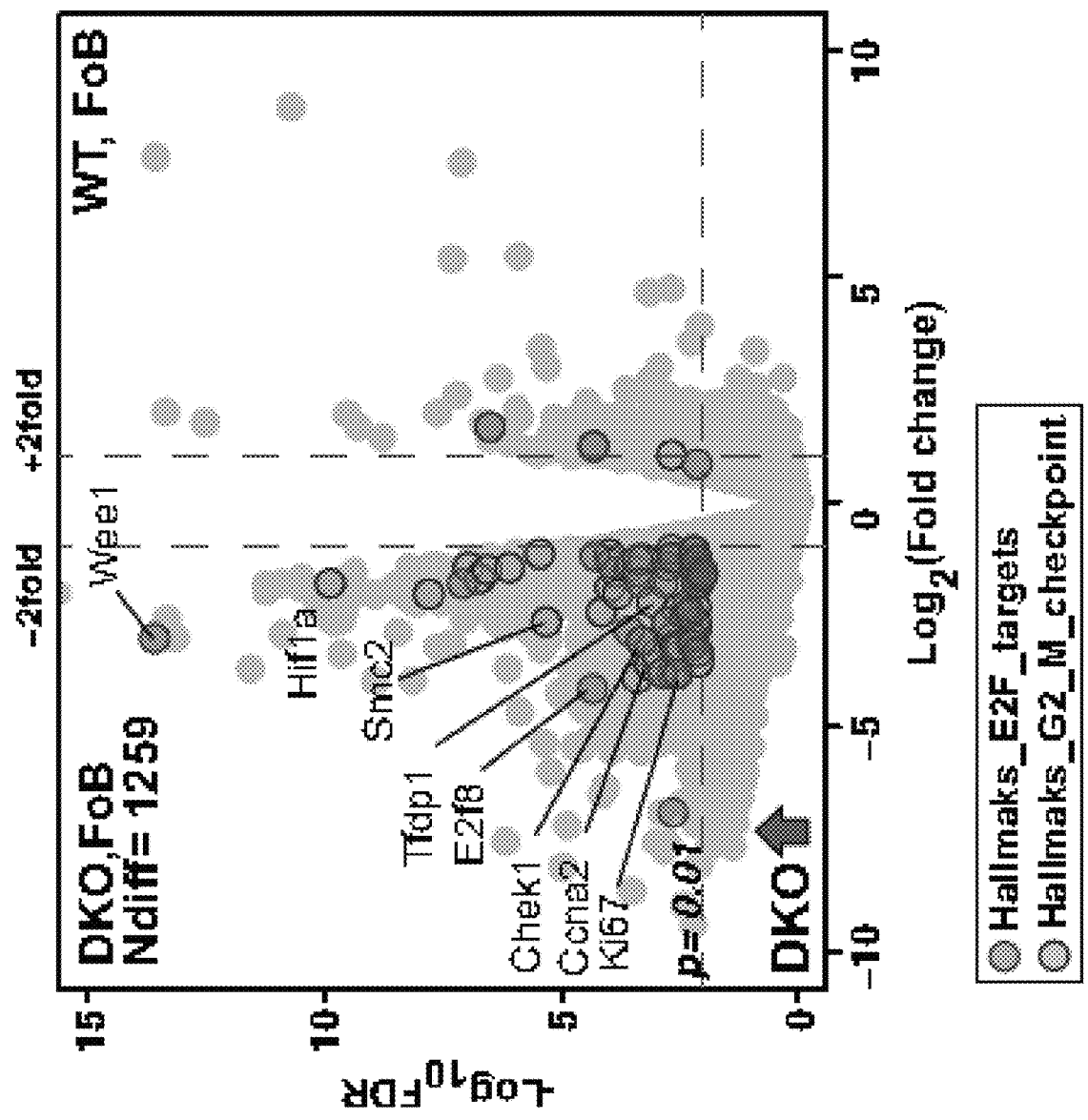
FIG. 3B is a volcano plot of differentially expressed genes in FoB wild type and FoB DKO mice. Colors indicate differentially expressed genes (P value<0.01, Fold change>2) belonging to selected GSEA Hallmark pathways as indicated.

To gain insights into the critical processes controlled by the SWEF proteins in B cells, the transcriptional profile of FoBs from wild type mice was first compared to that of FoBs from DKO mice. Based on gene set enrichment analysis (GSEA) (FIG. 3B) lack of the SWEF proteins affected the control of B cell proliferation, potentially, via E2F family of transcription factors and regulators of the G2/M checkpoint such as Wee1 and Chek1.

Figure 3C:
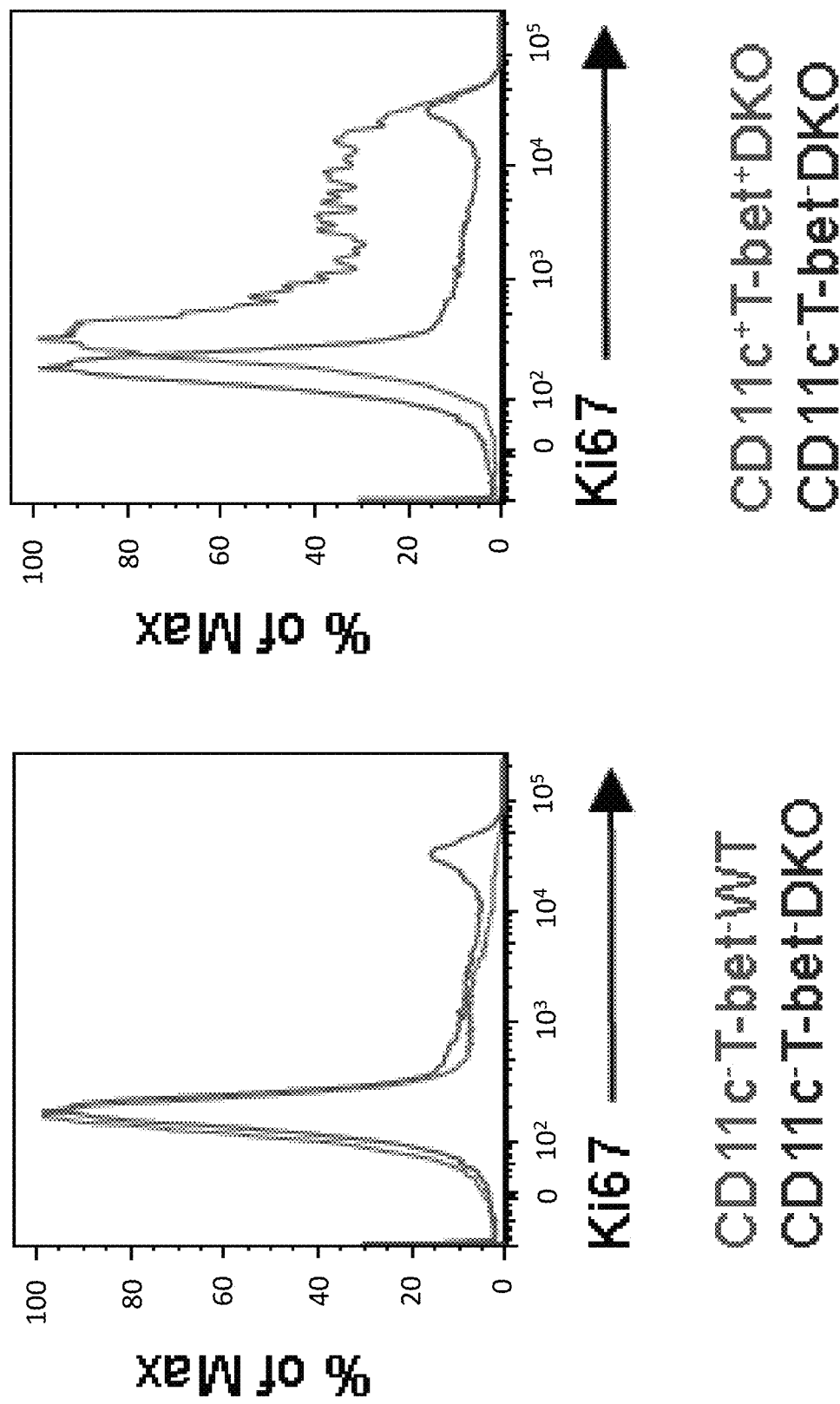
FIG. 3C shows the results of flow cytometry analysis showing the proliferation of CD11c−T-bet−B220+ cells in the spleens of WT and DKO female mice (>23 weeks old, left panel) or of CD11c−T25 bet−B220+ cells and CD11c+T-bet+B220+ (ABCs) in the spleens of DKO female mice (>23 weeks old) as assessed by Ki67 staining and flow cytometry. Shown is a representative histogram of 4 and 5 independent experiments, respectively (n=5 and 6 mice/group, respectively).

To extend and confirm these observations, the proliferative capabilities of B cells in wild type and DKO mice were assessed by staining for Ki67. As compared to wild type B cells, CD11c−Tbet− DKO B cells contained a small population of highly proliferative cells (FIG. 3C). Strikingly, CD11c+Tbet+ DKO B cells proliferated even more robustly than CD11c−Tbet− DKO B cells (FIG. 3C).

Figure 3D:
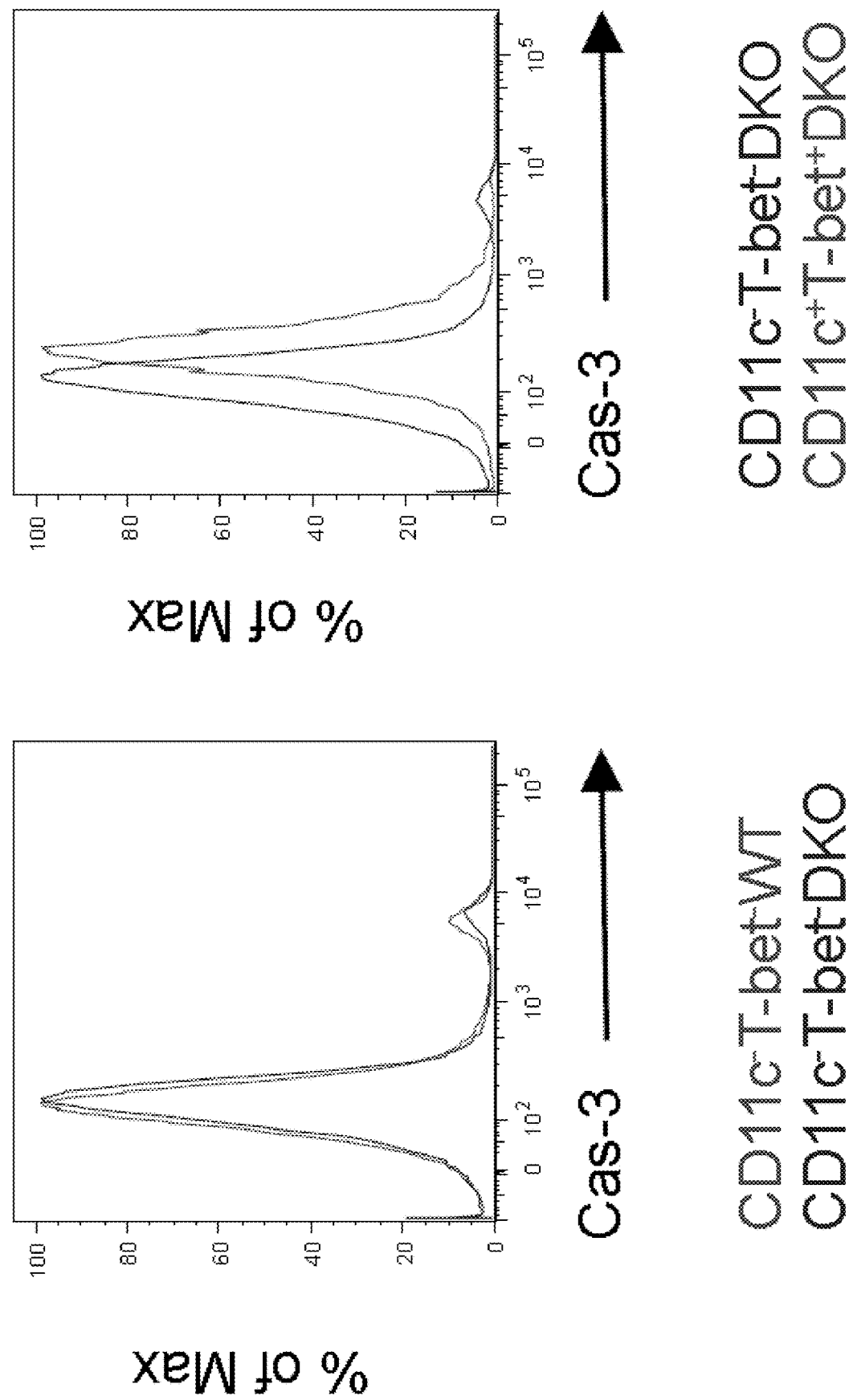
FIG. 3D are graphs showing the apoptotic rate as measured by caspase 3 cleavage in CD11c−T-bet−B220+ B cells in WT and DKO mice or in CD11c−T-bet− B cells and CD11c+ T-bet+ (ABC) B cells in DKO mice. Shown is a representative histogram. All data are representative of 3 independent experiments. (n=4 mice).
Figure 3E:
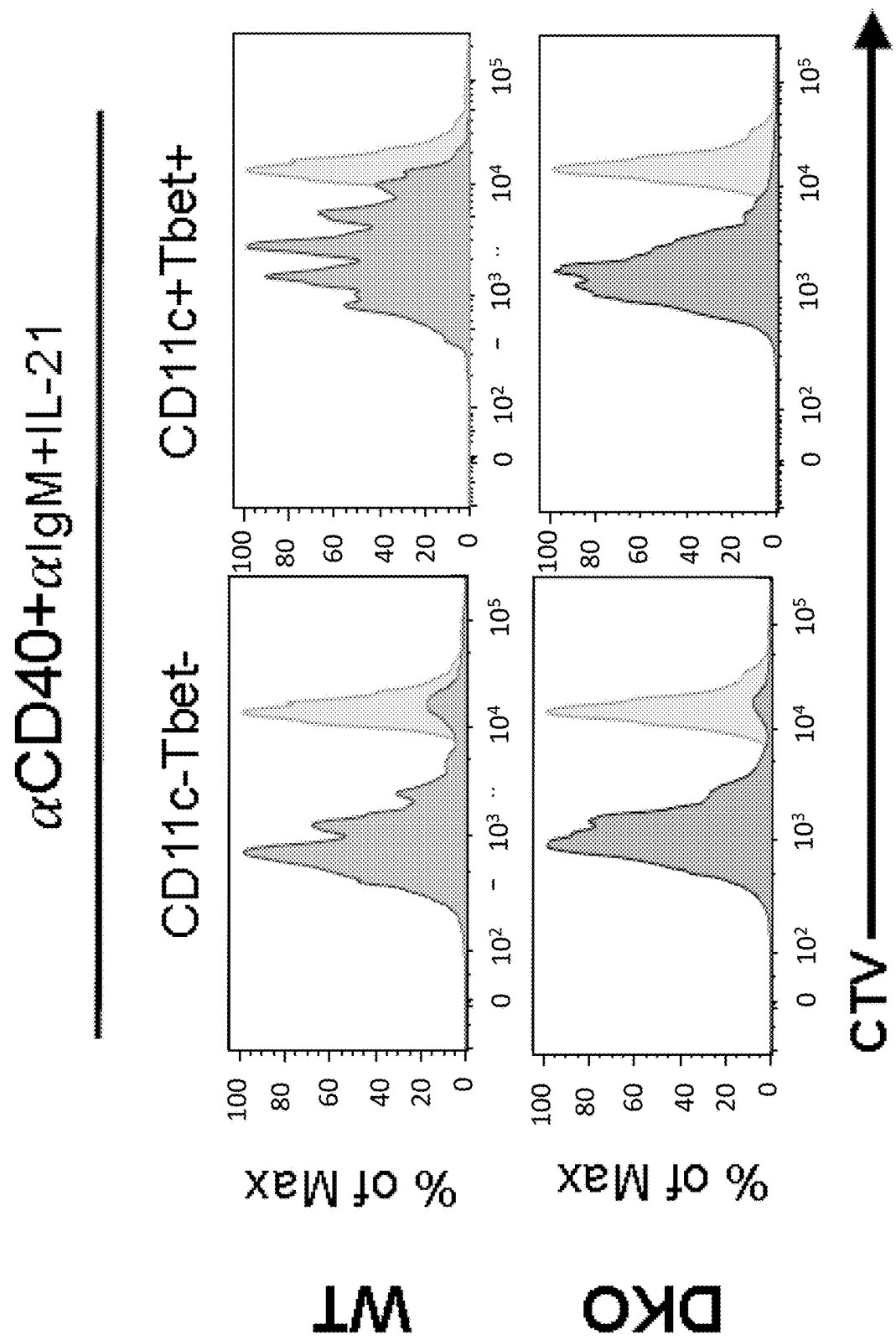
FIG. 3E is a representative histogram of 5 independent experiments (n=5) showing the results of the proliferation of CD11c−T-bet−B220+ cells and ABCs (CD11c+T-bet+B220+) assessed by evaluating dilution of cell trace violet by flow cytometry.
Figure 3F:
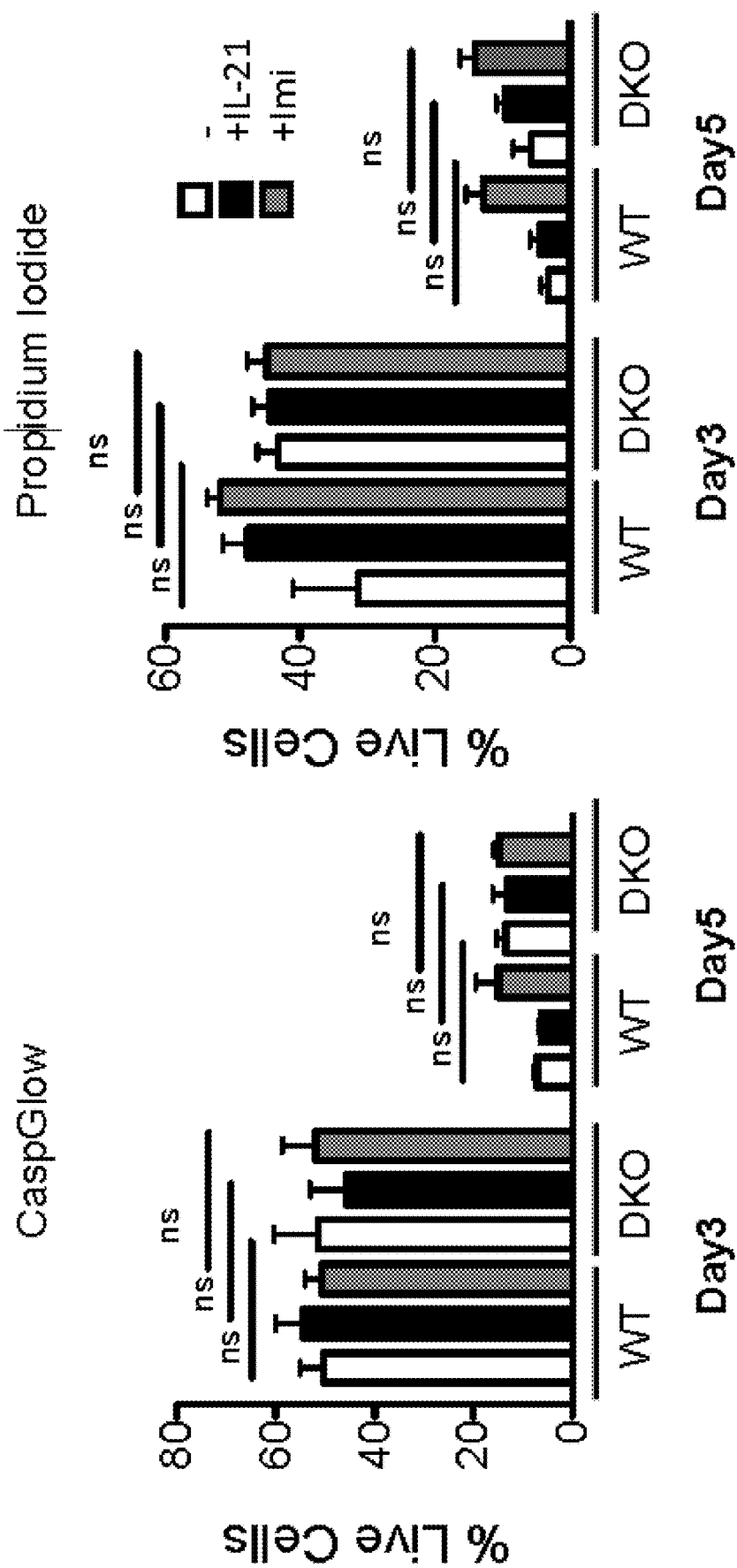
FIG. 3F are graphs of cell viability of CD23+ B cells purified from WT and DKO female mice (6-9 weeks old) and stimulated with αIgM and αCD40, alone or with IL-21 or imiquimod for 3 or 5 days assessed by staining with CaspGlow orcpropidium iodide as indicated.

No differences in apoptotic rates were instead observed between wild type and DKO B cells (FIG. 3D). In vitro experiments wherein CD23+ B cells were purified from wild type and DKO female mice (6-9 weeks old), labeled with CFSE and cultured with αIgM (5 μg/ml), αCD40 (5 μg/ml), and IL-21 (50 ng/ml) for 3 days, demonstrated that DKO ABCs proliferated to a greater extent than WT ABCs upon stimulation with IL-21 (FIG. 3E). In line with the in vivo findings, WT and DKO B cells exhibited similar survival rates in vitro as assessed by either PI staining or Caspase 3 cleavage at different times after stimulation with αIgM (5 μg/ml), αCD40 (5 μg/ml), IL-21c (50 ng/ml) or imiquimod (1 μg/ml) for 3 or 5 days (FIG. 3F). Thus, SWEF proteins regulate the proliferation of B cells, and play a particularly important role in restraining the capacity of pathogenic ABCs to proliferate in response to IL-21.

Figure 3G:
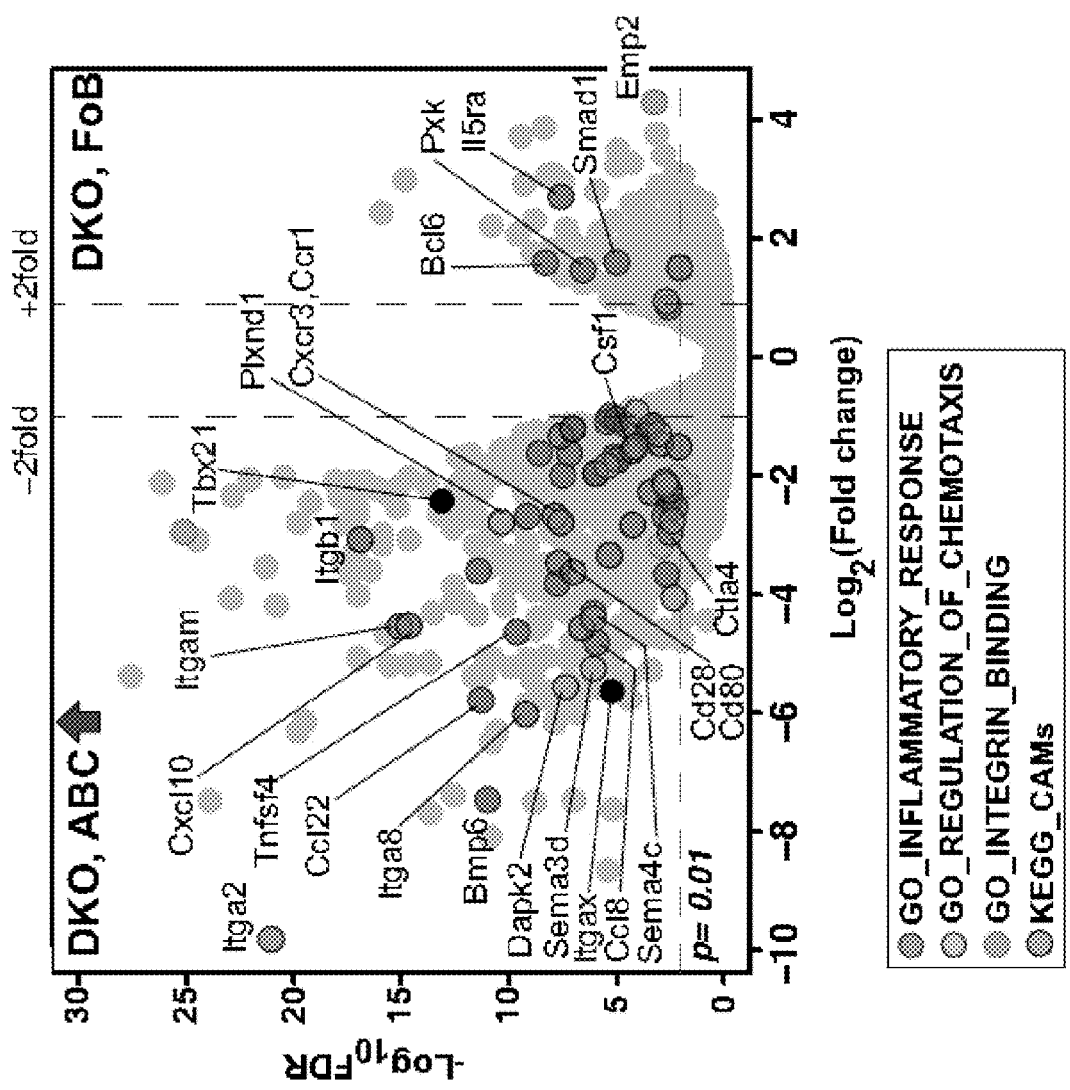
FIG. 3G is a volcano plot comparing gene expression in FoB (CD11c−CD11b−CD23+B220+ CD19+) and ABC (CD11c+CD11b+B220+CD19+) cells sorted from DKO female mice (>20 weeks old). Colors indicate differentially expressed genes (P value<0.01, Fold change>2, DKOFoB/DKO ABC) belonging to selected GSEA pathways as indicated.

In addition to clusters 1 and 2 that were differentially expressed in all DKO B cells, the transcriptomic analysis also uncovered additional clusters of genes (clusters 3 and 5), which were specifically upregulated in CD11c+CD11b+ DKO B cells as compared to CD11c−CD11b− B cells obtained from either wild type or DKO mice (FIGS. 3A and 3G). As expected, DKO ABCs expressed higher levels of T-bet (Tbx21), CD11c (Itgax) and CD11b (Itgam), which were used for ABC isolation, as compared to FoBs (FIG. 3G).

Figure 3H:
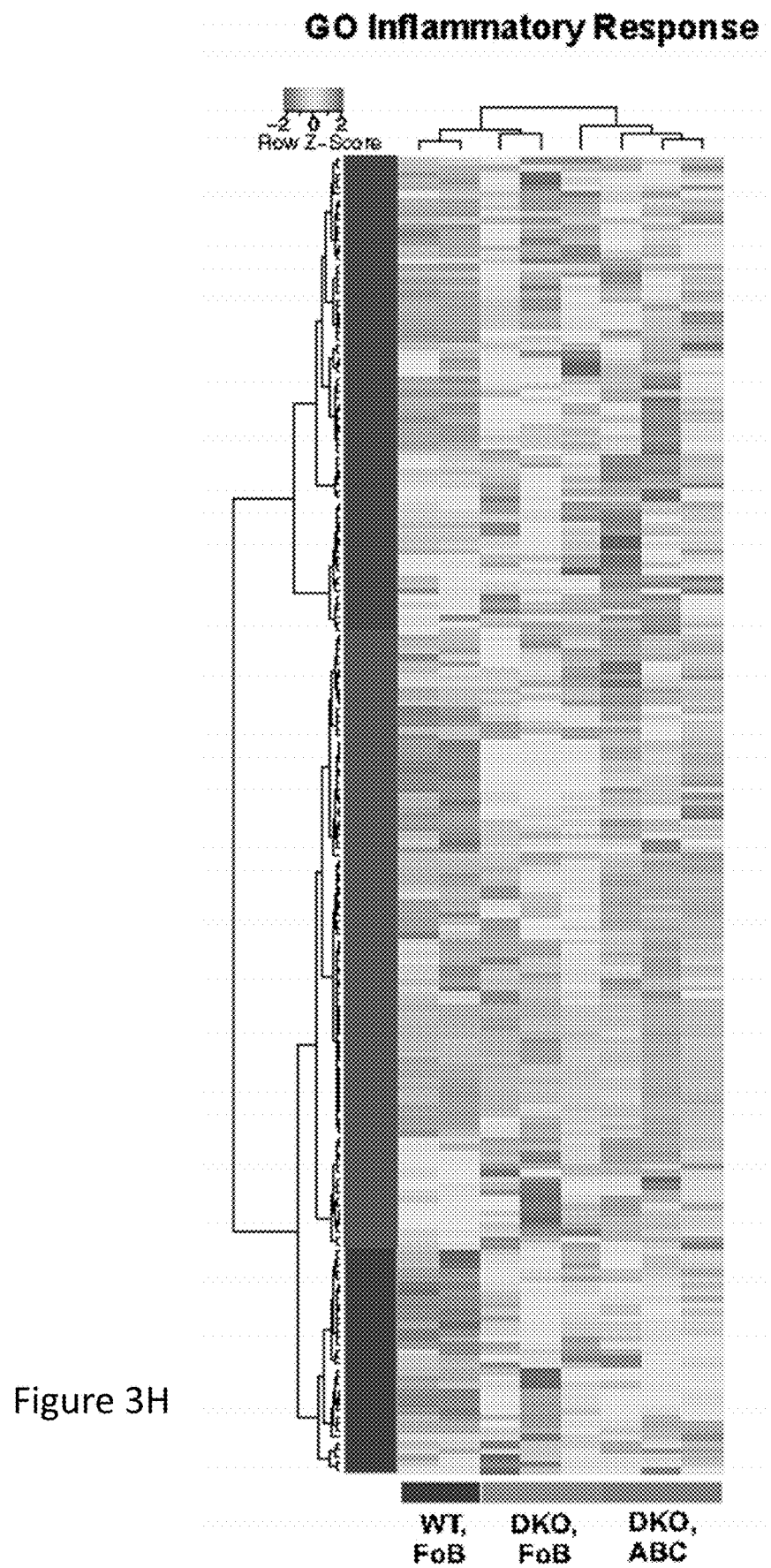
FIG. 3H shows hierarchical clustering of log-transform counts per million (cpm) for genes that belong to the GO_inflammatory_response gene set (MsigDB) identified by RNA-Seq analysis of RNA from FACS sorted FoB (B220+CD19+CD11c−CD11b−CD23+) and ABC (B220+CD19+CD11c+CD11b+) cells from DKO female mice (n=3).
Figure 3I:
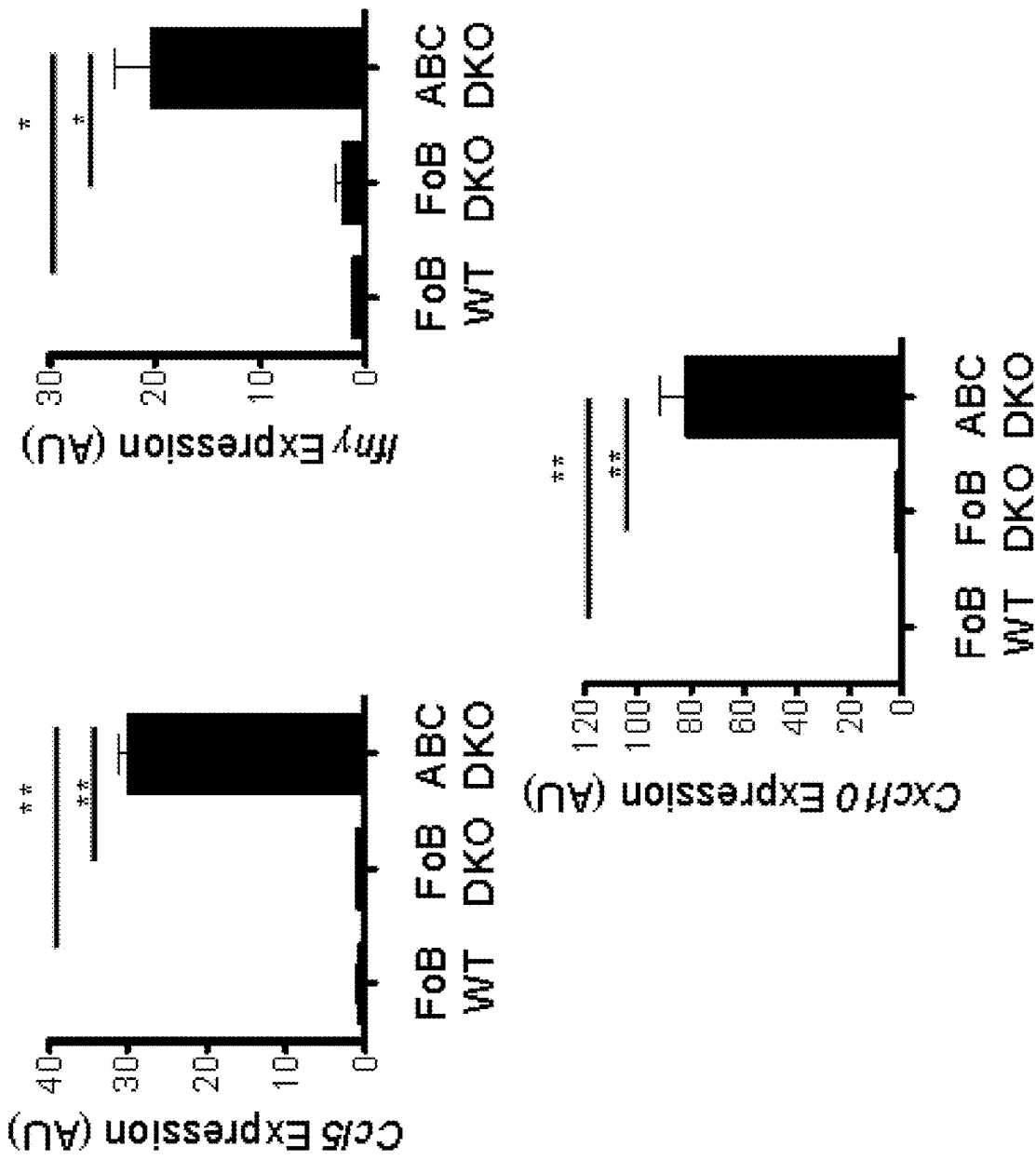
FIG. 3I are graphs that show the results of qPCR analysis of the expression of Ccl5, Ifnγ, and Cxcl10 mRNA in sorted FoB (B220+CD19+CD11c−CD11b− CD23+) cells from WT and DKO female mice and ABC (B220+CD19+CD11c+CD11b+) cells from DKO female mice as indicated. The data were normalized relative to ppia mRNA expression. Data are representative of 2 (Ccl5) or 3 (Ifnγ and Cxcl10) independent experiments.
Figure 3J:
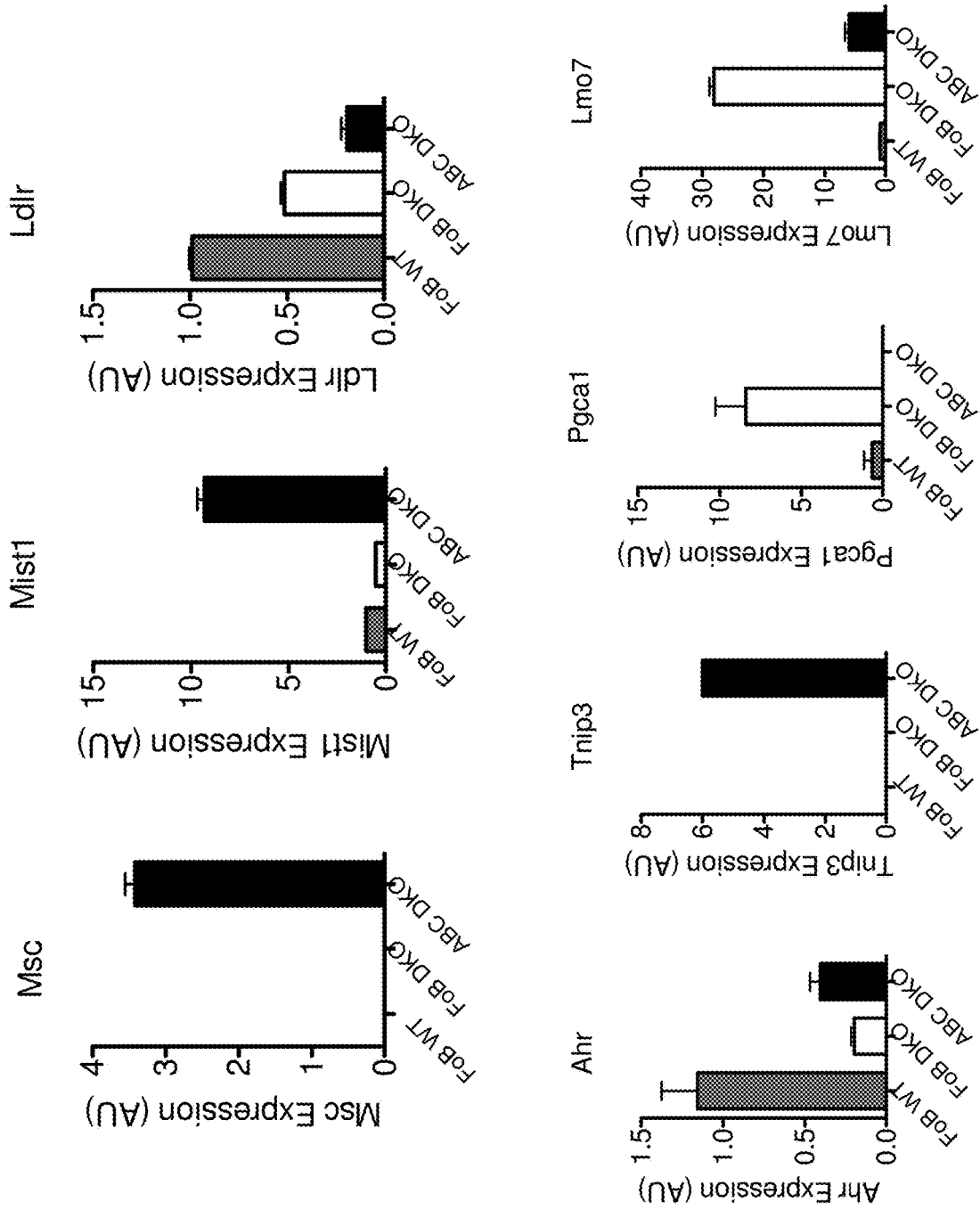
FIG. 3J are graphs of qPCR analysis of the expression of the indicated mRNA (gene) in FACS sorted FoB (B220+CD19+CD11c− CD11b−CD23+) cells from WT and DKO female mice and ABC (B220+CD19+CD11c+CD11b+) cells from DKO female mice. The data were normalized relative to ppia mRNA expression.
Figure 3K:
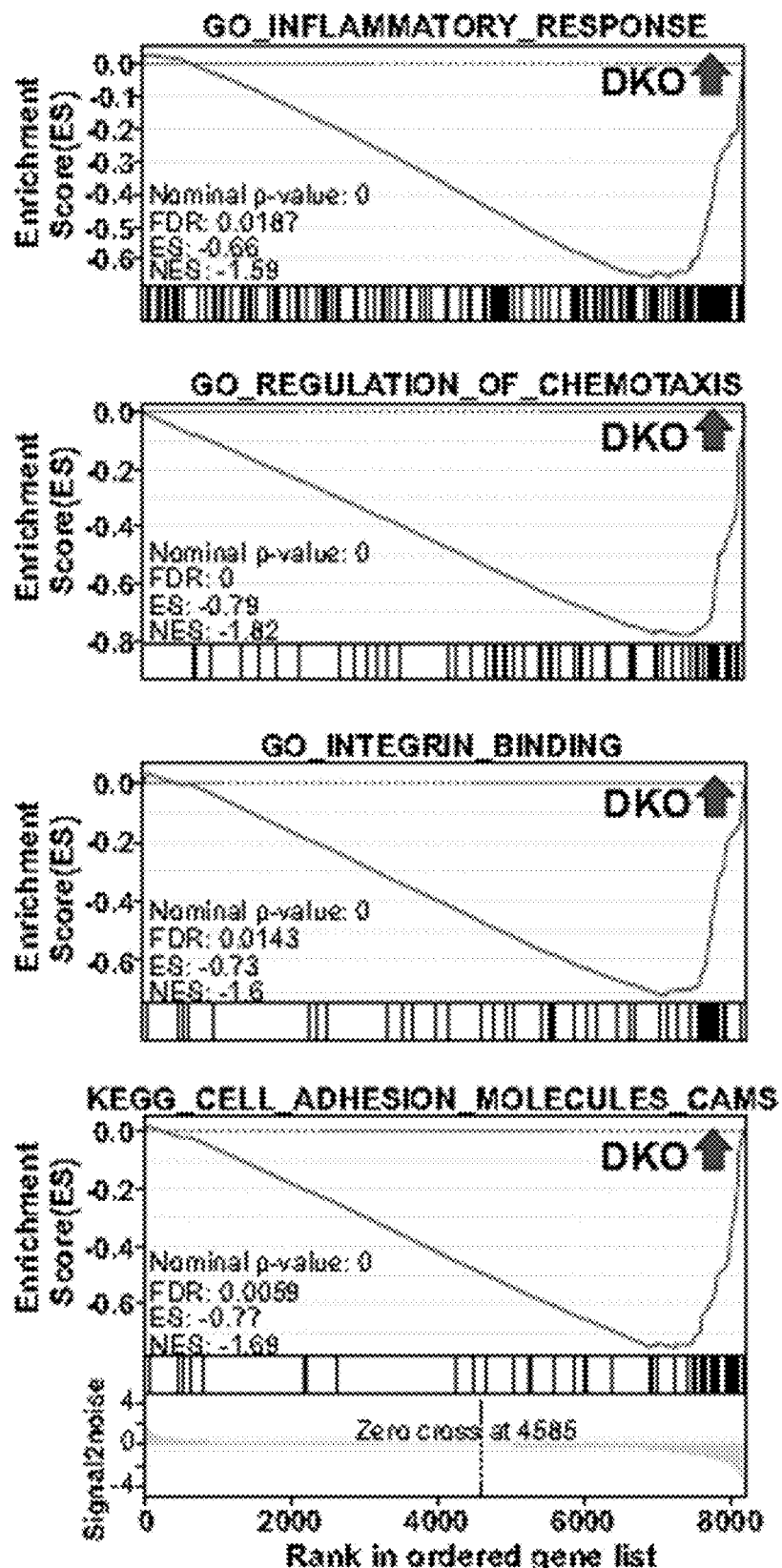
FIG. 3K shows selected GSEA pathways analysis of DKO FoB compared to DKO ABC cells.

GSEA was used to gain insights into the pathways that were uniquely upregulated in DKO ABC cells. Notably the top enriched sets (FDR, q<0.05) included several gene sets enriched in transcripts controlling chemotaxis, integrin binding, cell adhesion, and inflammation (FIGS. 3H and 3J). Prominent amongst the upregulated genes were a number of chemokines (e.g. Cxcl9, Cxcl10, Ccl4, Ccl5, Ccl8), cytokine receptors (Il1r2, Il12rb2, Il18r1, and Il18rap) and cytokines including Csf1 (FIGS. 3G and 3K), some of which were further validated by qPCR in FoB and ABC populations sorted from WT and DKO female mice (FIGS. 3I and 3J). Thus, as compared to FoBs, the ABCs from DKO female mice were endowed with proinflammatory capabilities and unique migratory and adhesive attributes. In addition to promoting the proliferation of pathogenic ABC cells, the lack of SWEF proteins altered their migratory/adhesive attributes and endowed them with enhanced proinflammatory functions.

Example 5

The Chromatin Landscape of DKO ABC Cells is Enriched with IRF and AP-1/BATF Motifs as Compared to FoB Celle The distinctive transcriptional program of DKO ABC cells suggested that these cells might exhibit a unique chromatin landscape. To directly address this possibility, ATAC-seq (assay for transposase-accessible chromatin using sequencing), which enables the identification of accessible regions of chromatin even in small number of cells as described in Example 1 and Buenrostro et al. 2015 was employed.

Figure 4A:
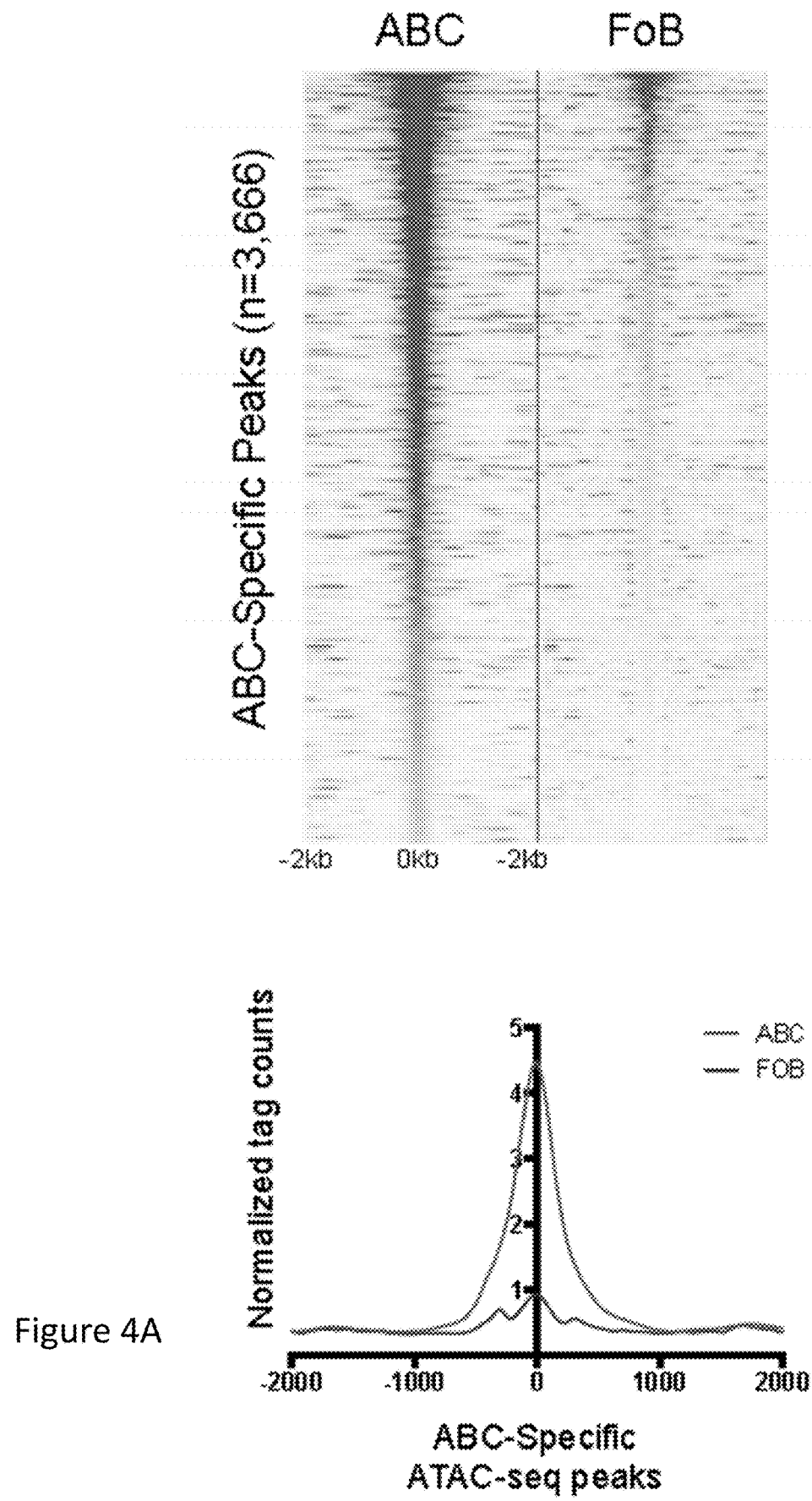
FIG. 4A shows the normalized ATAC-seq tag density distributions for 4 kb window centered at the summit of ABC-specific peaks (n=3,666, top panel) and average distribution of ATAC-seq normalized tag densities (bottom). (n=2/group).
Figure 4B:
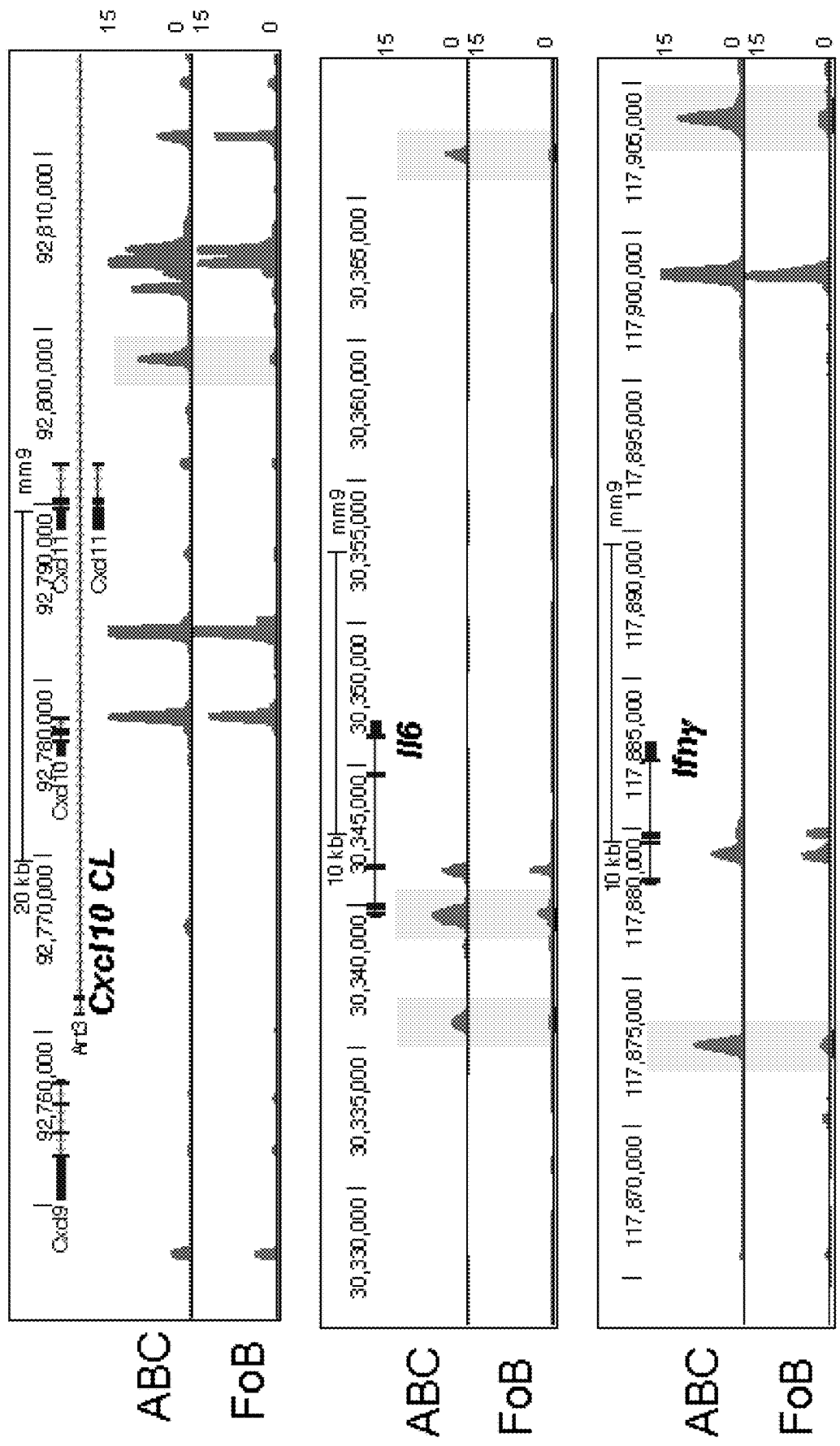
FIG. 4B are representative UCSC Genome Browser tracks displaying ATAC-seq normalized tag densities at representative genomic regions Cxcl10 cluster, Il6, and IFNγ genes. Highlighted are ABC-specific ATAC-seq peaks.

ATAC-seq signals from sorted CD11c+CD11b+ DKO cells were compared to those from sorted CD11c−CD11b− cells from the same mice. The focus of the analysis was on regions with higher signals and 3,666 ABC-specific peaks that satisfied those criteria were identified (FIG. 4A). The ABC specific peaks were primarily found in intergenic (45%) and intronic (50%) regions and only rarely in promoters. Loci which were differentially accessible in ABCs as compared to CD11c–CD11b– cells included a number of proinflammatory cytokines like IFNγ and IL-6 and other ABC-specific targets like the CXCL10 cluster of genes (FIG. 4B). Consistent with the results of the transcriptomic analysis, ABC-specific peaks were positively associated with transcriptionally active genes in ABC DKO cells as compared to FoB DKO cells and pathway analysis showed that many of the differentially expressed ATAC-seq associated genes were involved in locomotion and cellular adhesion (Table 5 and FIG. 4D).

Figure 4C:
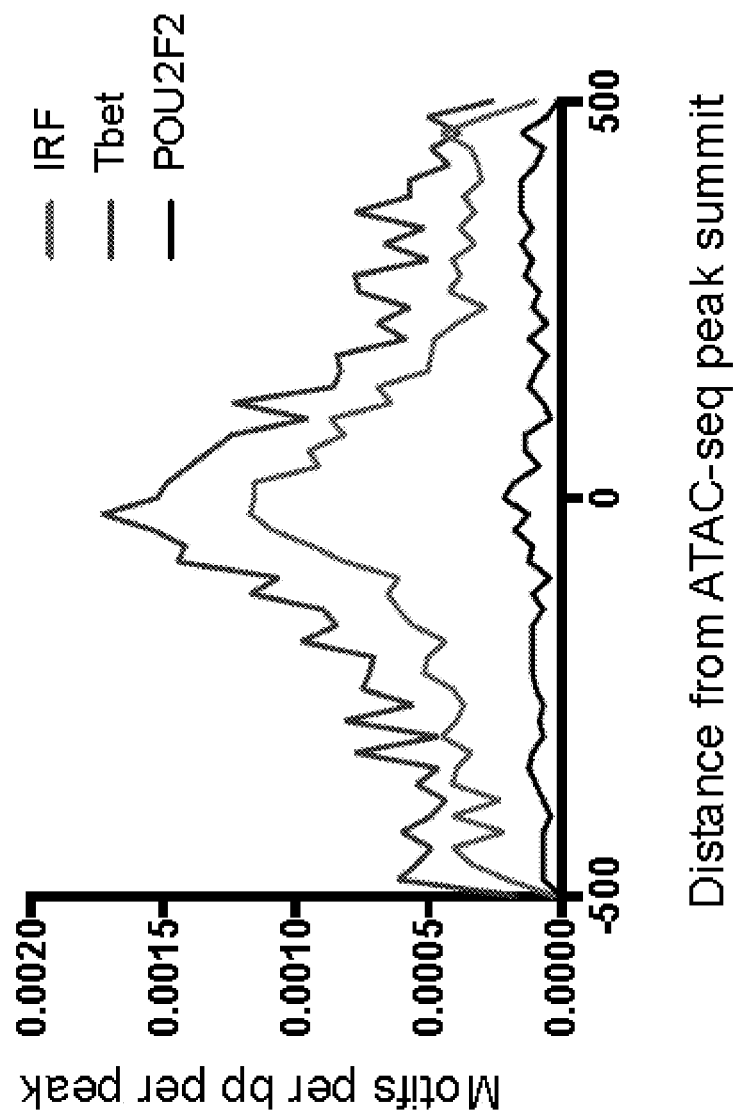
FIG. 4C is graph of motif density distribution relative to the peak summit for IRF, T-bet and POU2F2 motifs in ABC-specific ATAC-seq peaks.
Figure 4D:
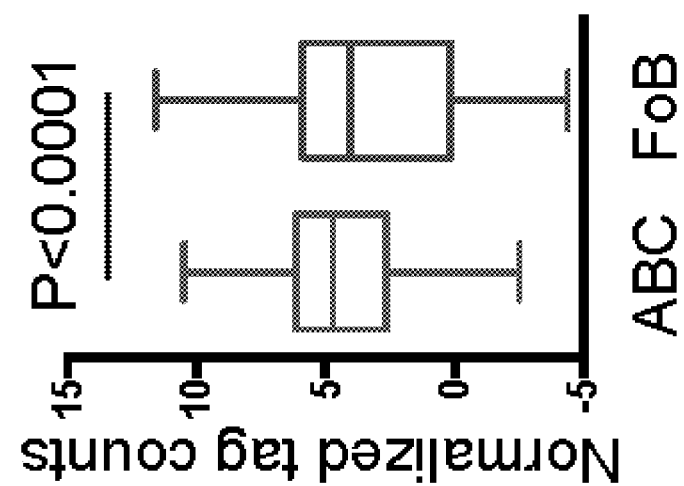
FIG. 4D is a graph of normalized tag counts for ABC and FOB expression (RNAseq) of total ABC-specific peaks associated genes (n=2,482) from three independent experiments (n=3) normalized tag counts.

To gain insights into the molecular mechanisms responsible for the distinctive chromatin profile of DKO ABCs, the transcription factor motifs enriched in ABC specific peaks were determined (Tables 3 and 4). ABC-specific accessible loci displayed enrichment in AP-1/BATF, IRF, and T-bet binding motifs (Table 3). Interestingly, the ABC specific peaks exhibited substantial positional bias in the distribution of IRF and T-bet binding motifs, which coincided with the peak summit (FIG. 4C). This pattern contrasted with that observed in FoB-specific peaks, which exhibited enrichment in motifs for a distinct set of transcription factors including POU2F2 (Tables 3 and 4, FIG. 4C). Thus, DKO ABCs, ABCs that aberrantly expand in this autoimmune setting, i.e., pathogenic ABCs, exhibited a unique chromatin landscape, which, in addition to T-bet motifs, is enriched in IRF and AP-1/BATF motifs and correlates with a distinctive transcriptional profile.

TABLE 3

Best Match for Motifs in DKO ABC-Specific Peaks

| Best Match | P-value |
|---|---|
| AP1-BATF | 1e–116 |
| IRF | 1e–107 |
| T-bet | 1e–102 |
| PU.1 | 1e–73 |
| RUNX | 1e–72 |
| MyoG | 1e–45 |
| NF-κB | 1e–28 |

TABLE 4

Best Match for Motifs for DKO FoB-Specific Peaks

| Best Match | P-value |
|---|---|
| POU2F2 | 1e–81 |
| E2A-PU.1 | 1e–41 |
| REL | 1e–14 |
| Foxj3 | 1e–14 |
| Hand1 | 1e–12 |

TABLE 5

Functionally Enriched Gene Ontology (GO) Categories of Genes associated with ABC-Specific Peaks of ATAC-seq (n = 487).

| Description | P-value | FDR q-value |
|---|---|---|
| GO_IMMUNE_SYSTEM PROCESS | 4.17E–27 | 1.85E–23 |
| GO_POSTIVE_REGULATION_OF_ RESPONSE_TO_ STIMULUS | 1.02E–22 | 2.25E–19 |

TABLE 5-continued

Functionally Enriched Gene Ontology (GO) Categories of Genes associated with ABC-Specific Peaks of ATAC-seq (n = 487).

| Description | P-value | FDR q-value |
|---|---|---|
| GO_LOCOMOTION | 3.04E–21 | 4.28E–18 |
| GO_CELLULAR_ RESPONSE_TO_ORGANIC_SUBSTANCE | 3.86E–21 | 4.28E–18 |
| GO_BIOLOGICAL_ADHESION | 1.40E–20 | 1.25E–17 |

Example 6

Distinctive Transcriptional and Epigenomic Programs of Autoimmune Prone DKO ABCs as Compared to Non-Autoimmune ABCs To gain insights into the programs that are specifically dysregulated in pathogenic, autoimmune-prone DKO ABCs as compared to the ABCs that slowly accumulate in non-autoimmune WT female mice, CD11c+CD11b+ B cells from older WT female mice were sorted and compared their transcriptional profiles to those of CD11c+CD11b+ B cells derived from DKO female mice.

Figure 5A:
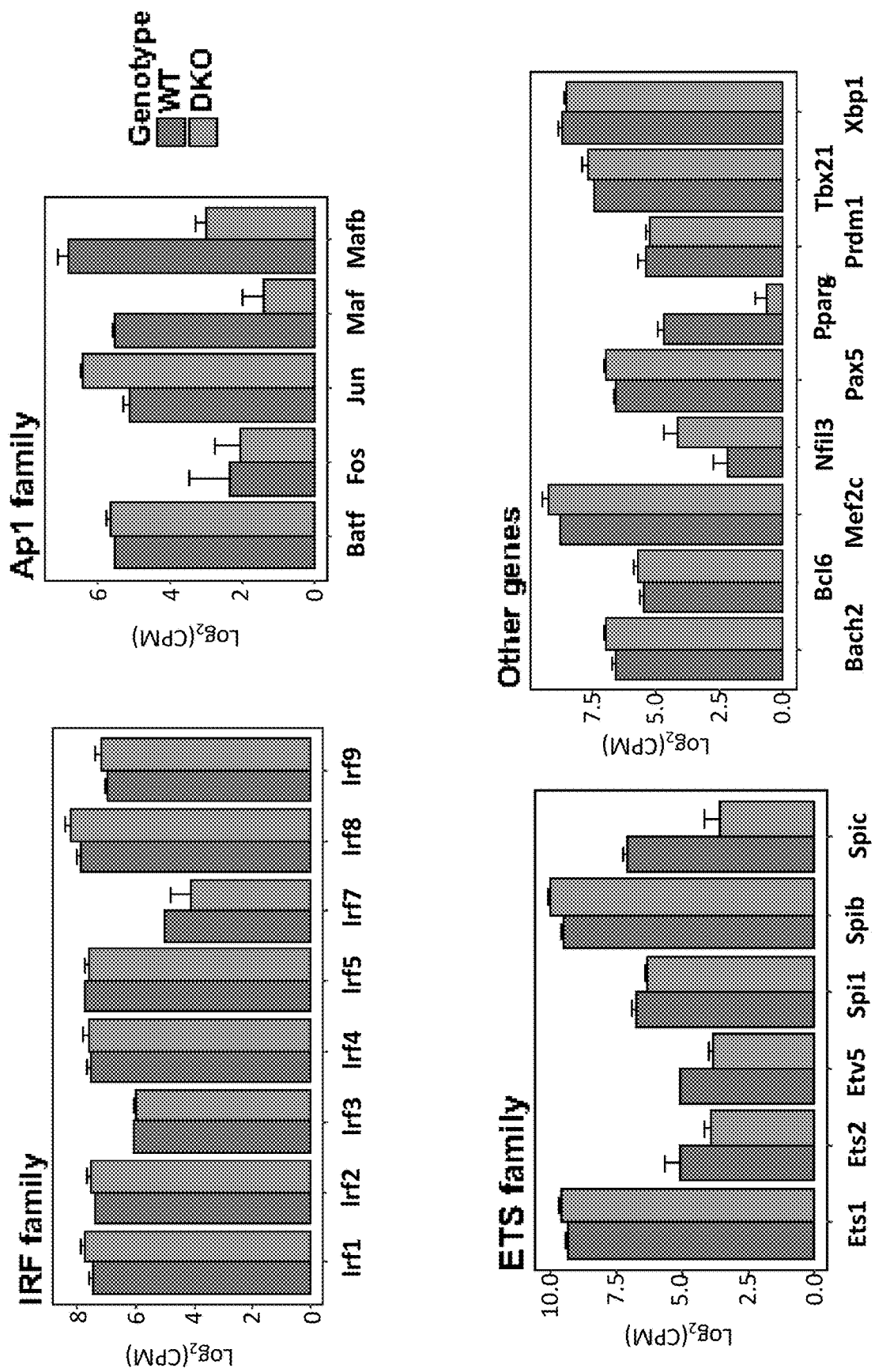
FIG. 5A is a graph of the expression of selected transcription factors transcripts in WT and DKO ABC cells as identified by RNA-seq analysis.
Figure 5B:
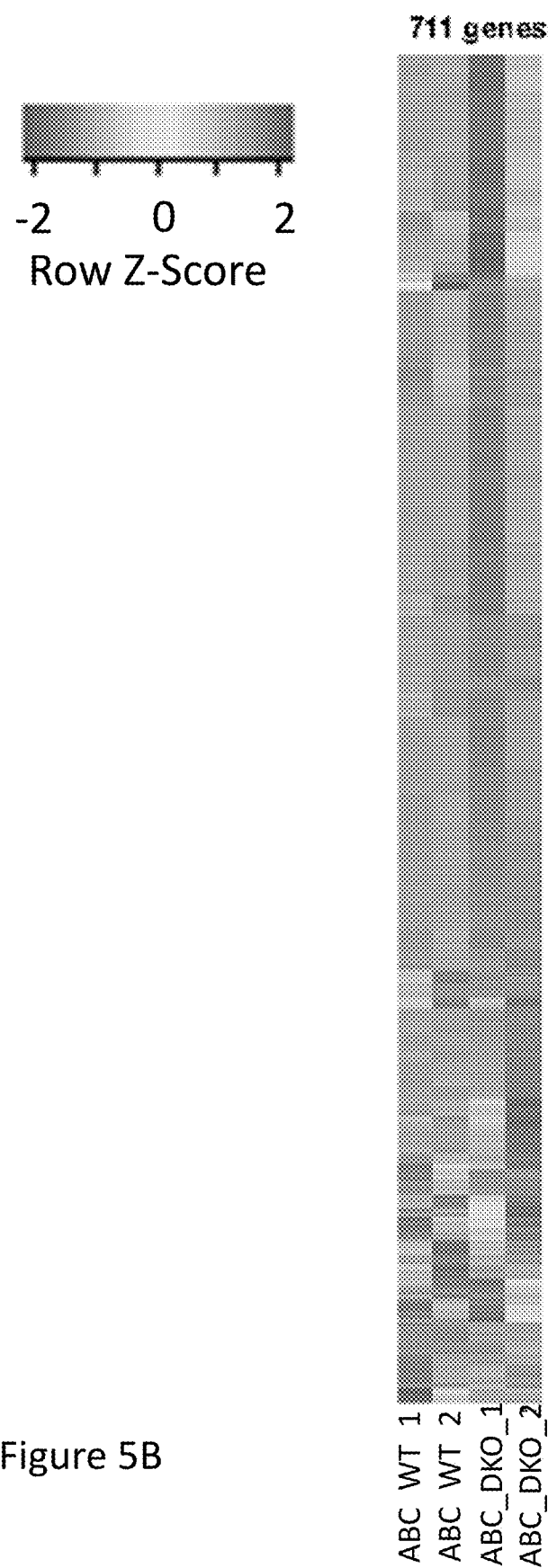
FIG. 5B shows the hierarchical clustering of log-transformed counts per million (cpm) for differentially expressed genes identified by RNAseq analysis of RNA from FACS sorted ABC (B220+CD19+CD11c+CD11b+) cells from WT and DKO female mice (>20 weeks old). (n=2/group).
Figure 5C:
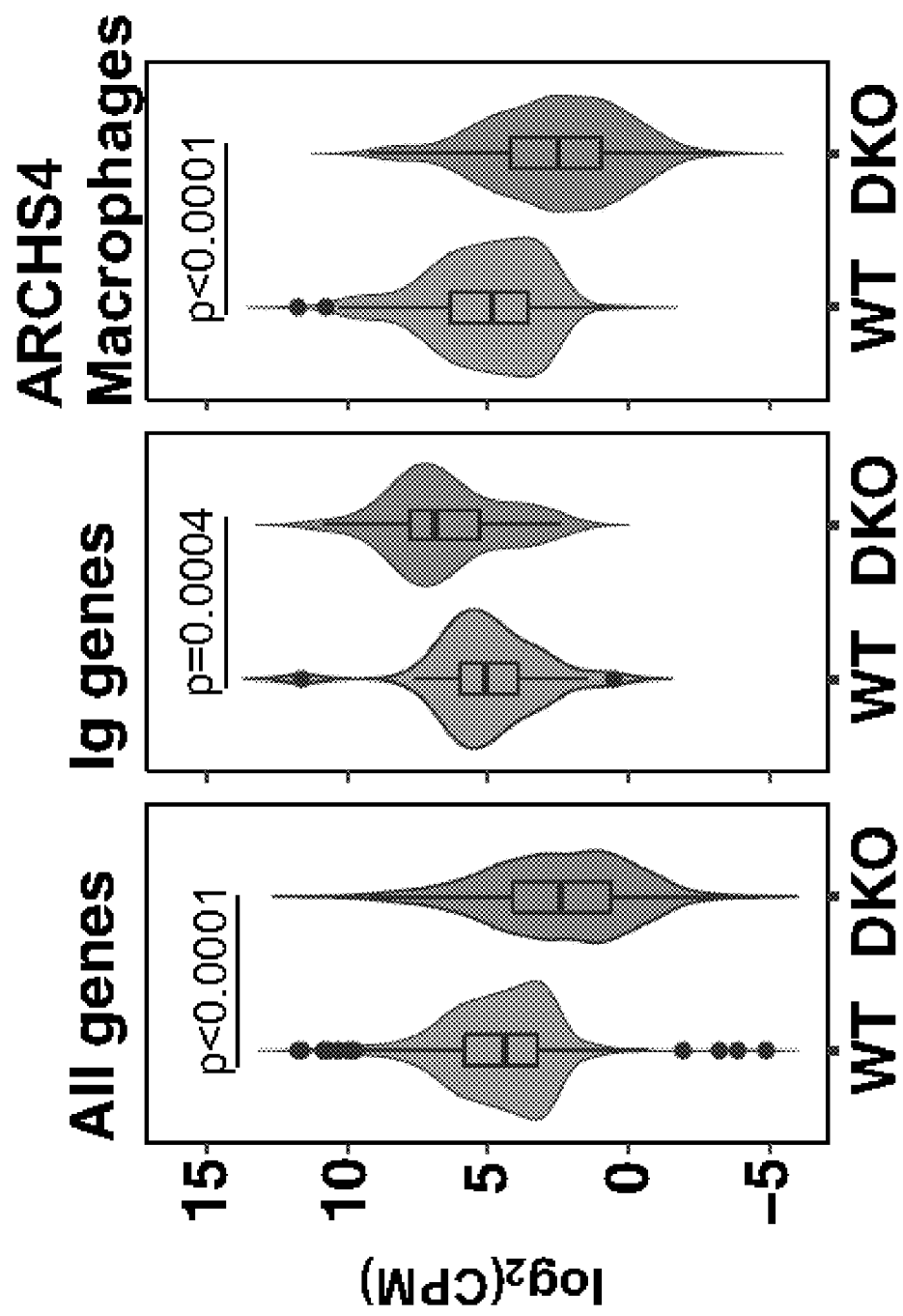
FIG. 5C shows violin plot analysis of all genes, Ig genes and ARCHS4 Macrophage genes in WT and DKO.

WT and DKO ABCs expressed similar levels of T-bet (Tbx21) (FIG. 5A). A total of 711 genes were differentially expressed between the two populations, of which 111 genes were upregulated in DKO ABCs as compared to WT ABCs and 600 genes were downregulated (Tables 1 and 2 and FIG. 5B). Notably, ABCs from DKO mice expressed higher levels of immunoglobulin gene transcripts than ABCs derived from WT mice but downregulated a subset of myeloid-related transcripts (FIGS. 5B and 5C). The increased levels of immunoglobulin gene transcripts displayed by the DKO ABCs were not associated with changes in the expression of key regulators of plasma cell differentiation like IRF4, IRF8, Bcl6 or Blimp1 (FIG. 5A) suggesting that the differences between WT and DKO ABCs were not due to the presence of contaminating plasmablasts within the DKO ABC population.

Figure 5D:
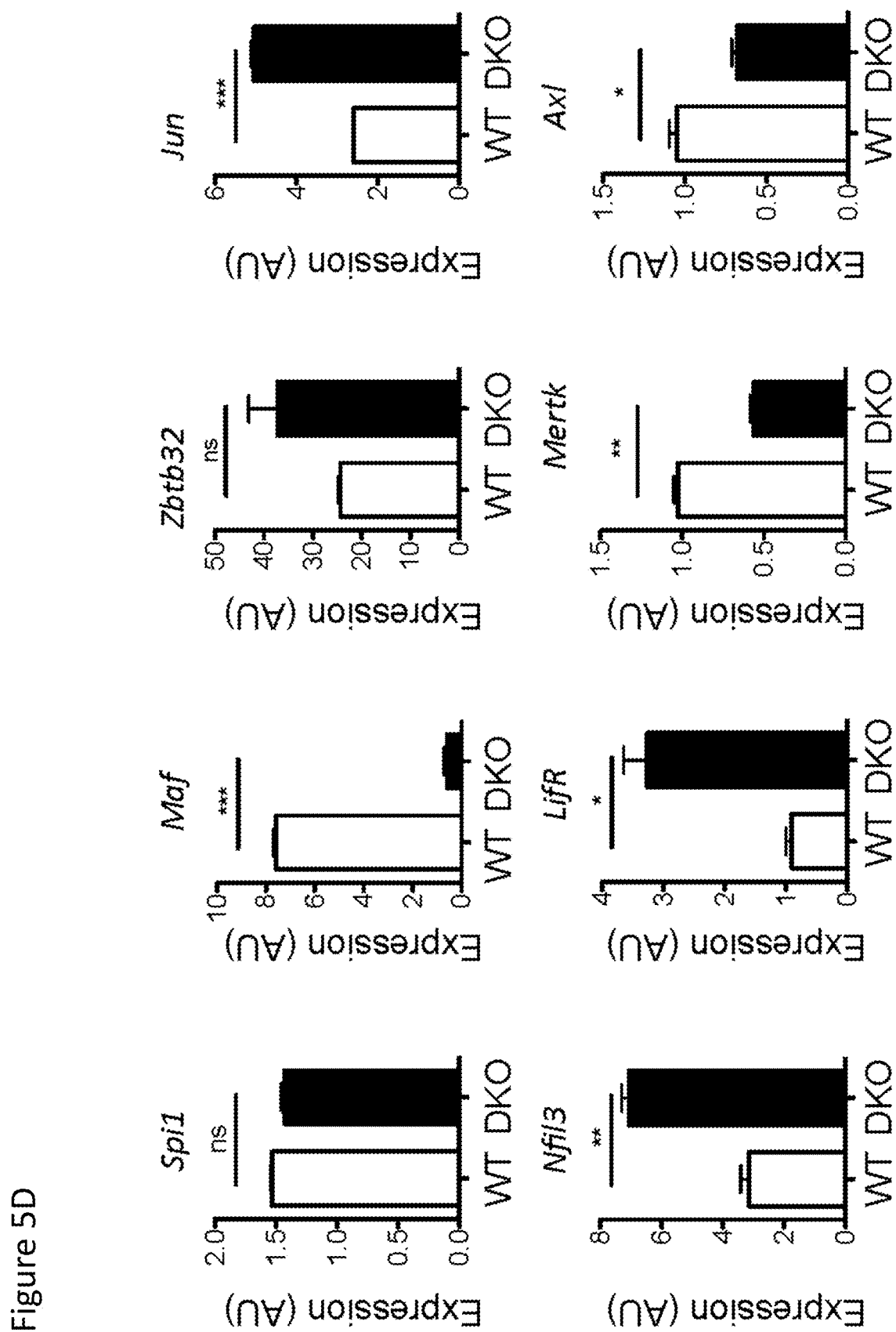
FIG. 5D are graphs of the results of qPCR analysis of the expression of representative genes in sorted ABC (B220+CD19+CD11c+CD11b+) cells from WT and DKO female mice as indicated. The data were normalized relative to ppia mRNA expression. Data are representative of 2 independent experiments. ns: not significant, *: p≤0.05, : p≤0.01 *: p≤0.001.
Figure 5E:
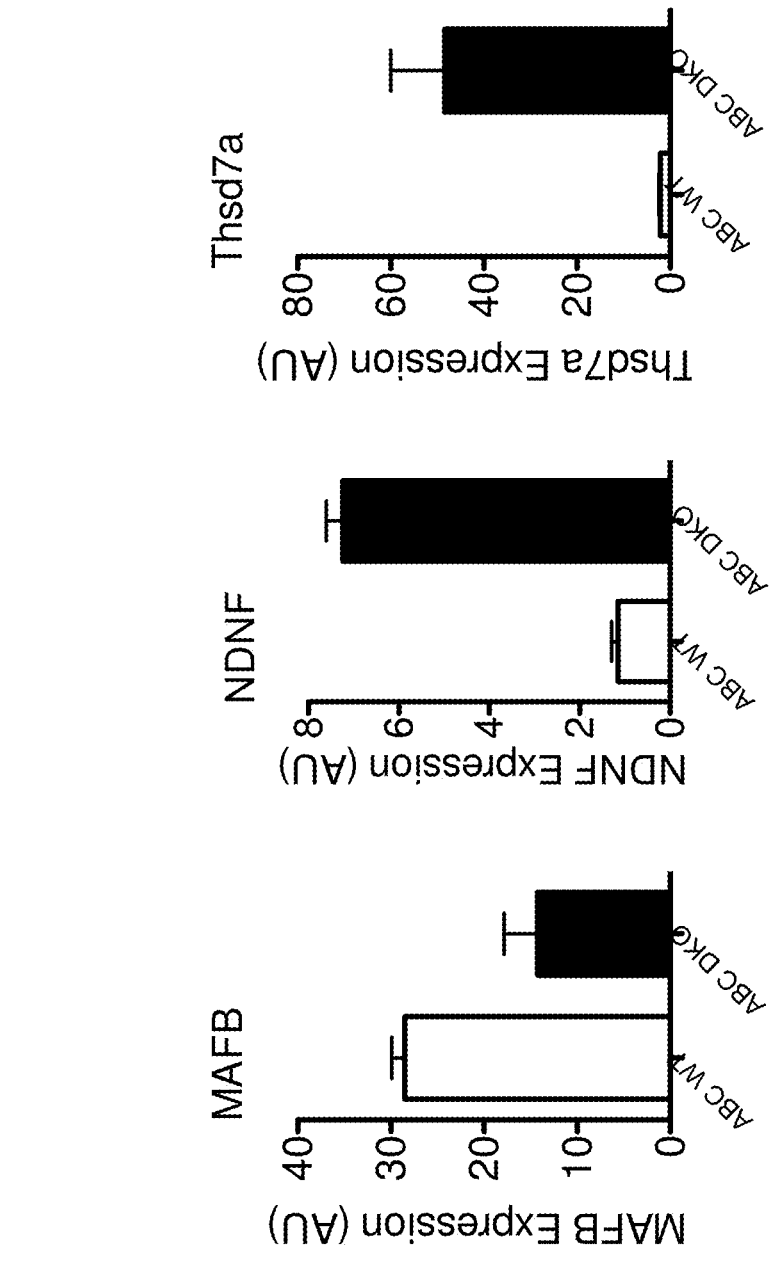
FIG. 5E are graphs of qPCR expression analysis of the indicated genes in FACS sorted ABC (B220+CD19+CD11c+CD11b+) cells from WT and DKO female mice (>24 weeks). The data were normalized relative to ppia mRNA expression.

DKO ABCs, however, exhibited selective changes in the expression of other transcription factors including upregulation of Jun and NFIL-3 and downregulation of c-maf, MafB, and PPAR-γ while levels of PU.1 were similar to those of WT ABCs (FIG. 5A). Differential expression of selected targets, which included key regulators of apoptotic cell engulfment like Mertk and Axl, was further confirmed by qPCR (FIG. 5D). Thus, the ABCs that accumulate in autoimmune-prone DKO female mice were endowed with a higher immunoglobulin producing capacity than WT ABCs but downregulate some of the myeloid related features that can be associated with this B cell subset. Also as shown by qPCR, MAFB, NDNF and Thsd7a were differentially expressed between wild type ABCs and DKO ABCs (FIG. 5E).

Figure 5F:
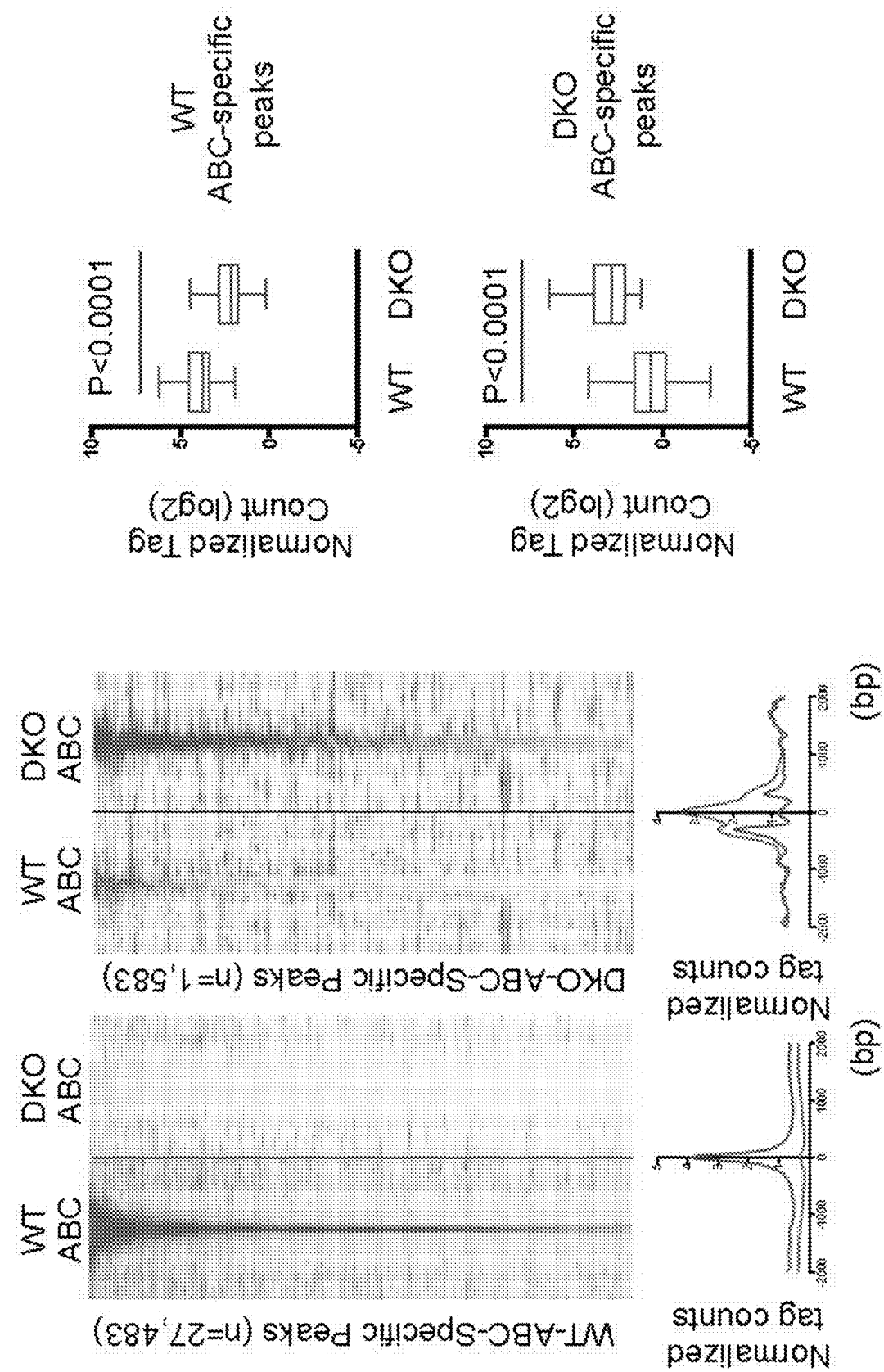
FIG. 5F show normalized ATAC-seq tag density distributions for 4 kb window centered at the summit of WT-specific (right, n=27,483) or DKO-specific (left, n=1583) peaks and average distribution of ATAC-seq normalized tag densities (bottom). (n=2/group). Histograms show expression (RNAseq) of total ABC-specific peaks associated genes in WT and DKO from three independent experiments (n=2-3). The graphs show the quantitated results.
Figure 5G:
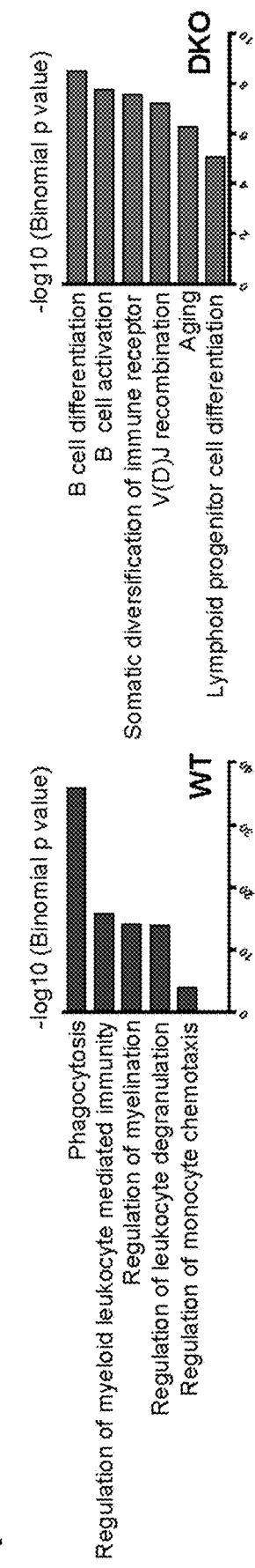
FIG. 5G are graphs of functionally enriched Gene Ontology (GO) categories of WT-specific and DKO-specific peaks of ATAC-seq.

To investigate the differences in the chromatin landscape of WT and DKO ABCs that might accompany these distinct transcriptional profiles, ATAC-seq signals from sorted WT ABCs were compared to those of DKO ABCs. 27,483 WT ABC-specific peaks and 1,583 DKO-ABC specific peaks (FIG. 5F) were identified. Most of the WT or DKO ABC-specific peaks were primarily found in intergenic and intronic regions and only rarely in promoters, with 44% being intergenic and 46% being intronic regions in the WT-ABC specific peaks (n=27,483) and 51% being intergenic and 43% being intronic regions of DK-ABC specific peaks (n=1,583). DKO ABC-specific accessible loci again displayed enrichment in IRF, AP-1/BATF, and T-bet binding motifs (Table 6). In contrast, the pattern associated with WT ABC-specific peaks was associated with enrichment in PU.1, MAF, and C/EBP binding motifs (Table 7). These results were consistent with the downregulation of MAF and MAF-B observed in DKO ABCs and were reflected in differences in the accessibility of the MAF and MAF-B loci in the ATAC-seq (results not shown). In line with the results of the transcriptomic analysis and supporting the idea that the differential chromatin accessibility between WT and DKO ABCs is functionally important, gene ontology (GO) categories of genes associated with WT-specific or DKO-specific peaks of ATAC-seq indicated that WT ABC-specific peaks were positively associated with transcriptional programs regulating phagocytosis and other myeloid-related functions while DKO ABC-specific peaks were enriched in processes linked to B cell differentiation, activation and Ig regulation (FIG. 5G).

Thus, in comparison to the ABCs that slowly accumulate in WT mice with age, i.e., non-pathogenic ABCs, the chromatin landscape of pathogenic autoimmune-prone ABCs was characterized by dual abnormalities whereby enrichment in IRF and AP-1/BATF motifs was coupled with depletion of PU.1- and MAF-bound regulatory regions.

TABLE 6

Best Matches to Motifs in DKO ABC-Specific ATAC-seq Peaks

| Best Match | P-value |
|---|---|
| IRF | 1e−81 |
| AP1-BATF | 1e−29 |
| STAT5 | 1e−28 |
| Hbp1 | 1e−27 |
| SREBF1 | 1e−25 |
| Tbet | 1e−24 |

TABLE 7

Best Matches to Motifs in WT ABC-Specific ATAC-seq Peaks

| Best Match | P-value |
|---|---|
| PU.1 | 1e−1151 |
| MafA | 1e−165 |
| CEBP | 1e−109 |
| RORA | 1e−107 |
| PRDM1 | 1e−84 |
| PU.1-RF | 1e−68 |

Example 7

Expansion of ABCs Depends Upon IRF5

While ABC generation is known to be dependent on Tbet (Rubtsova et al. 2015; Naradikian et al. 2016), the role of the IRFs in the formation and function of ABCs is unknown. Given that the SWEF proteins can regulate the activity of IRF4 (Biswas et al. 2012; Manni et al. 2015), an analysis of whether the aberrant expansion of ABCs in DKO mice might depend on this transcription factor was performed, using CD11c-Cre IRF4fl/flDKO mice (Manni et al. 2015.) However, it was determined that deleting IRF4 in CD11c+ expressing cells did not affect the accumulation of ABCs (results not shown) or any of the autoimmune parameters that characterize the development of lupus in DKO mice (Manni et al. 2015). Thus, the dysregulated expansion of ABCs in DKO mice does not rely on IRF4.

Given the high degree of homology amongst IRF DNA binding domains the possibility that another IRF may regulate the aberrant generation of DKO ABCs was investigated. The focus was on IRF5 given its ability to regulate the production of IgG2a/c, proinflammatory mediators like IL-6 and the strong association with SLE (Cham et al. 2012; Lazzari and Jefferies 2014). To facilitate these studies, DKO mice completely lacking IRF5 in B cells (CD21Cre-IRF5$^{fl/-}$ DKO) were generated and then assessed the ability of B cells from these mice to generate ABCs in vitro. Expression of IRF5 was similar in WT and DKO B cells and was absent in B cells from CD21Cre-IRF5$^{fl/-}$ DKO mice (results not shown).

Figure 6A:
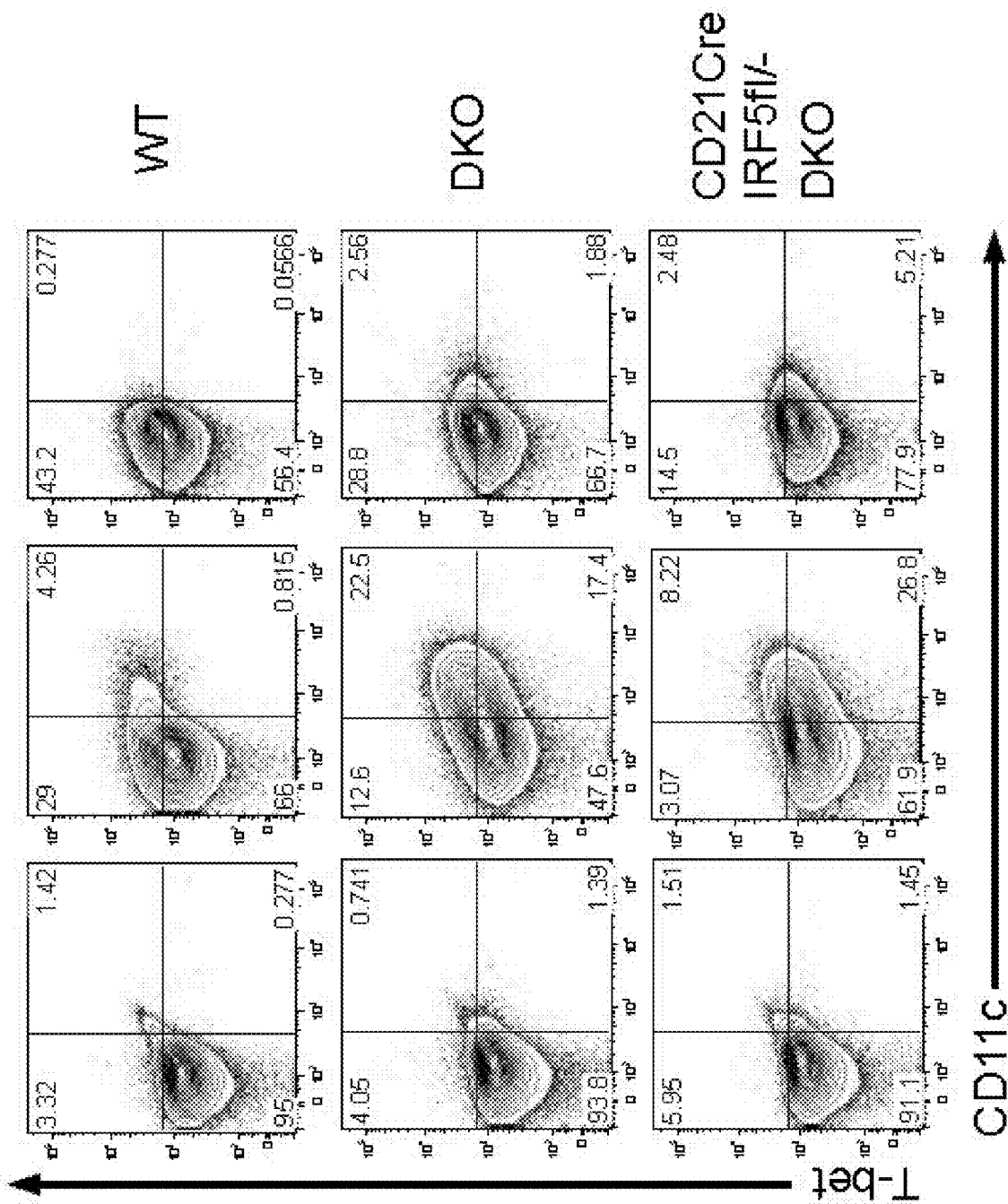
FIG. 6A is representative FACS plots of purified wild type, DKO and CD21Cre IRF5$^{fl/-}$-DKO (8-10 weeks of age) CD23+B cells were treated with a combination of αCD40, αIgM, IL-21 and/or imiquimod. CD11c+Tbet+Bcells in each culture condition were assayed by FACS at day 3. Representative FACS plot of 6 independent experiments is shown.
Figure 6B:
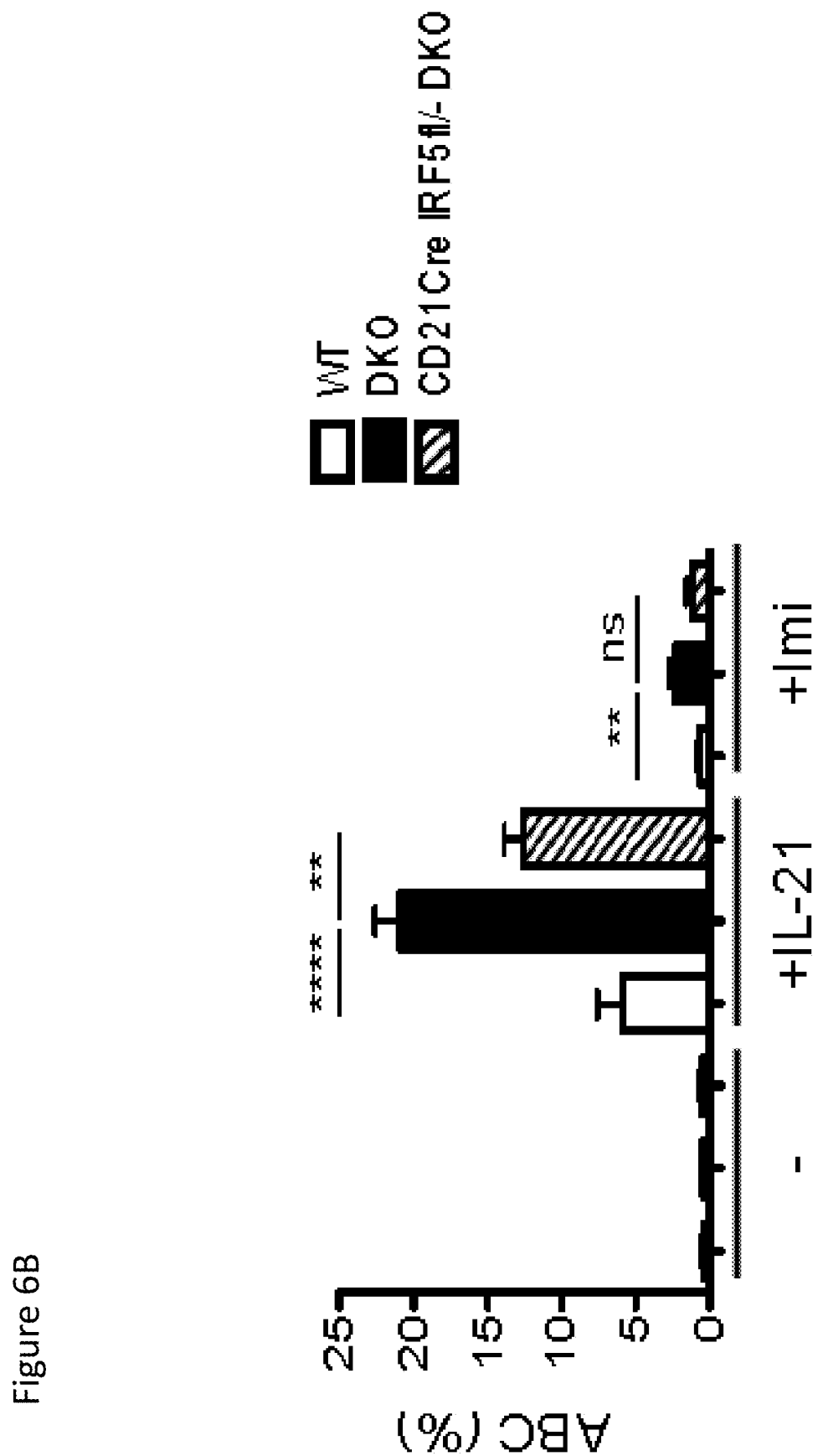
FIG. 6B shows the graphical results of percentage of ABCs from the FAC analysis in FIG. 6A (n=6). Mean±SEM is shown. : p≤0.01, *: p≤0.001. (One-way ANOVA).
Figure 6C:
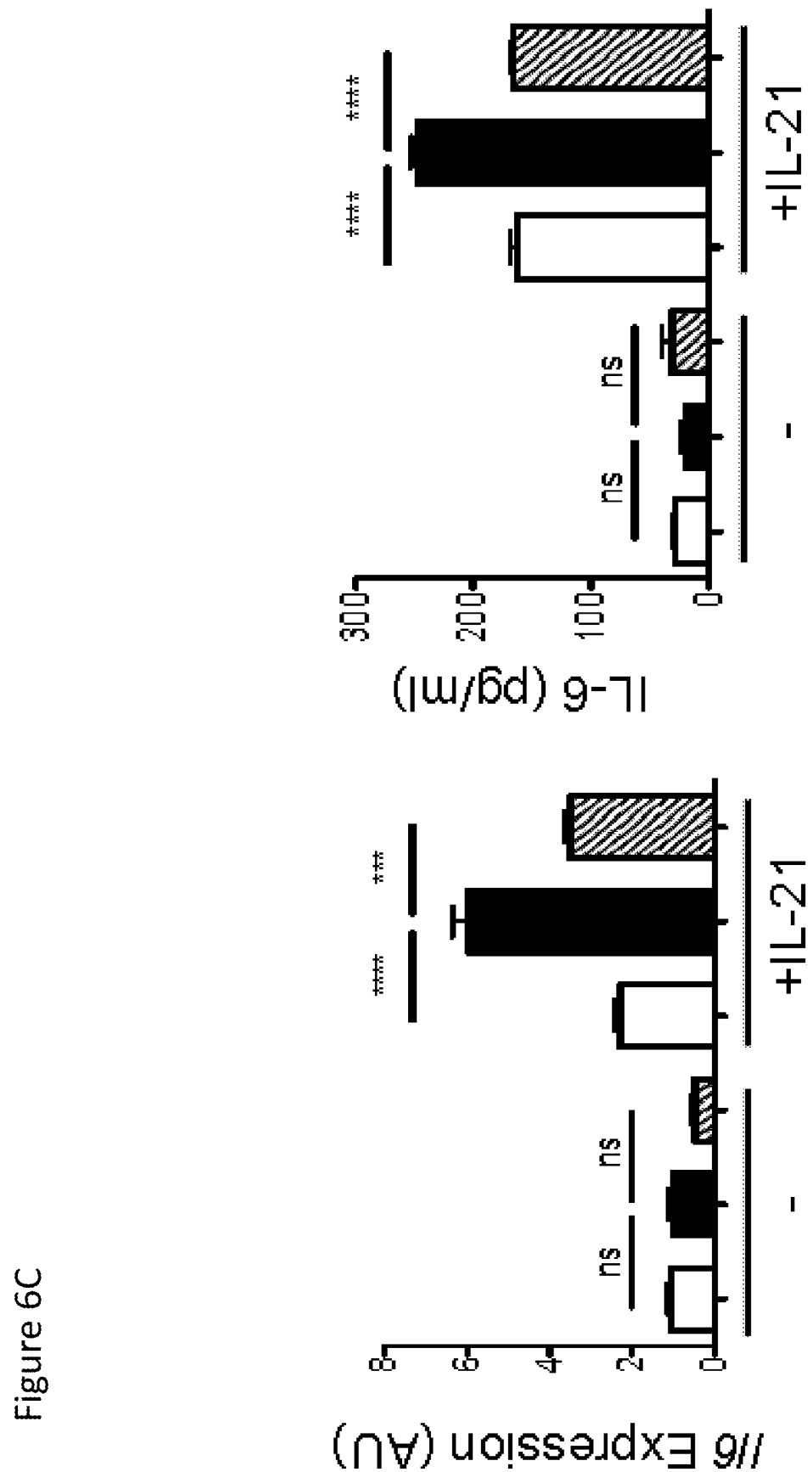
FIG. 6C shows graphs of the analysis of the expression and production of IL-6 in cultures of cells stimulated±IL-21 as assessed by qPCR and ELISA. qPCR data were normalized relative to ppia mRNA expression. Data are representative of 3 independent experiments. Mean±SEM is shown. ns: not significant, *: p≤0.001, : p≤0.0001. (One-way ANOVA).
Figure 6D:
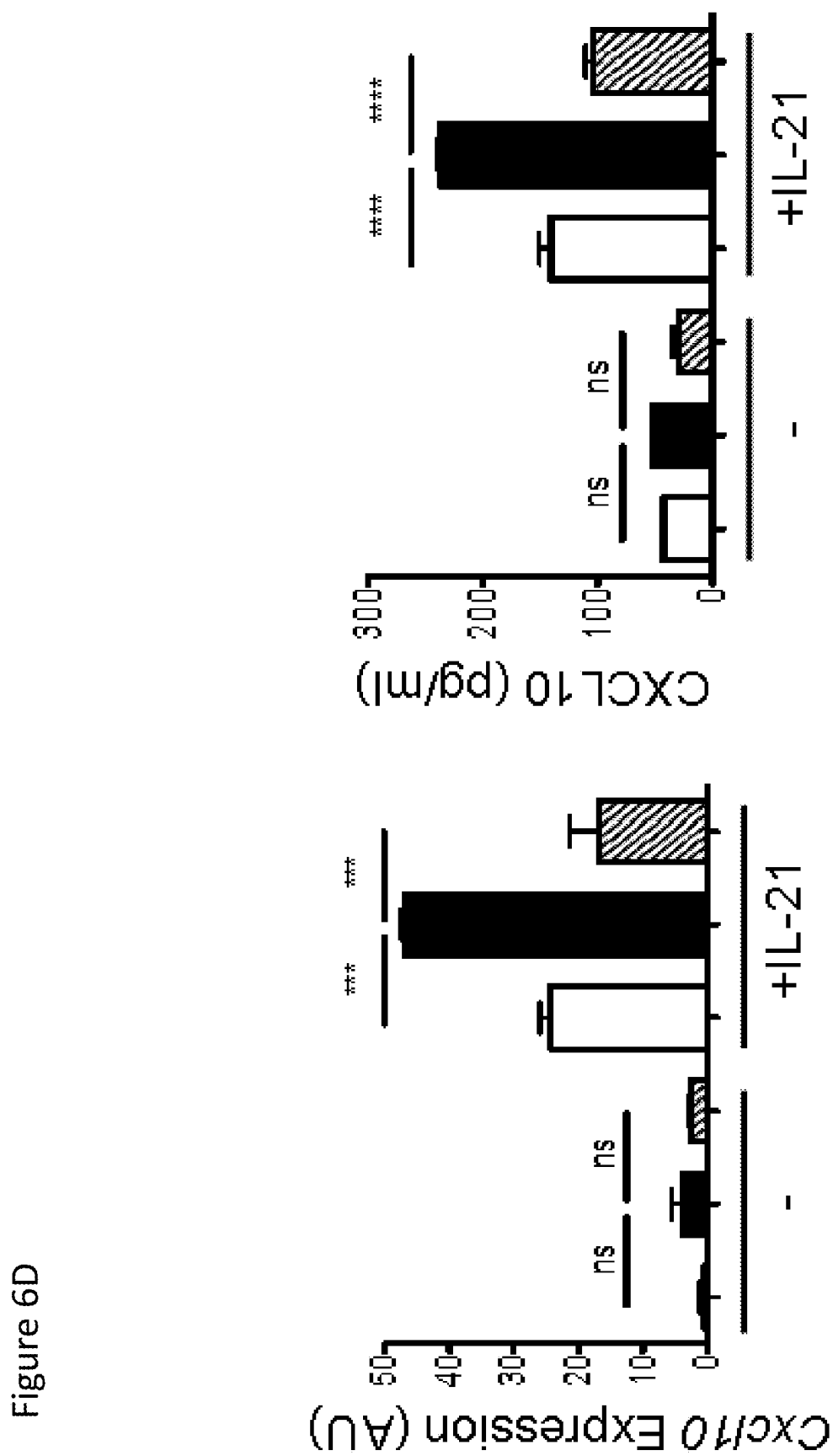
FIG. 6D shows graphs of the analysis of the expression and production of Cxcl10 in cultures of cells stimulated with and without IL-21 as assessed by qPCR (left panel) and ELISA (right panel). qPCR data were normalized relative to ppia mRNA expression. Data are representative of 3 independent experiments. Mean±SEM is shown. ns: not significant, *: p≤0.001, **: p≤0.0001. (One-way ANOVA).
Figure 6F:
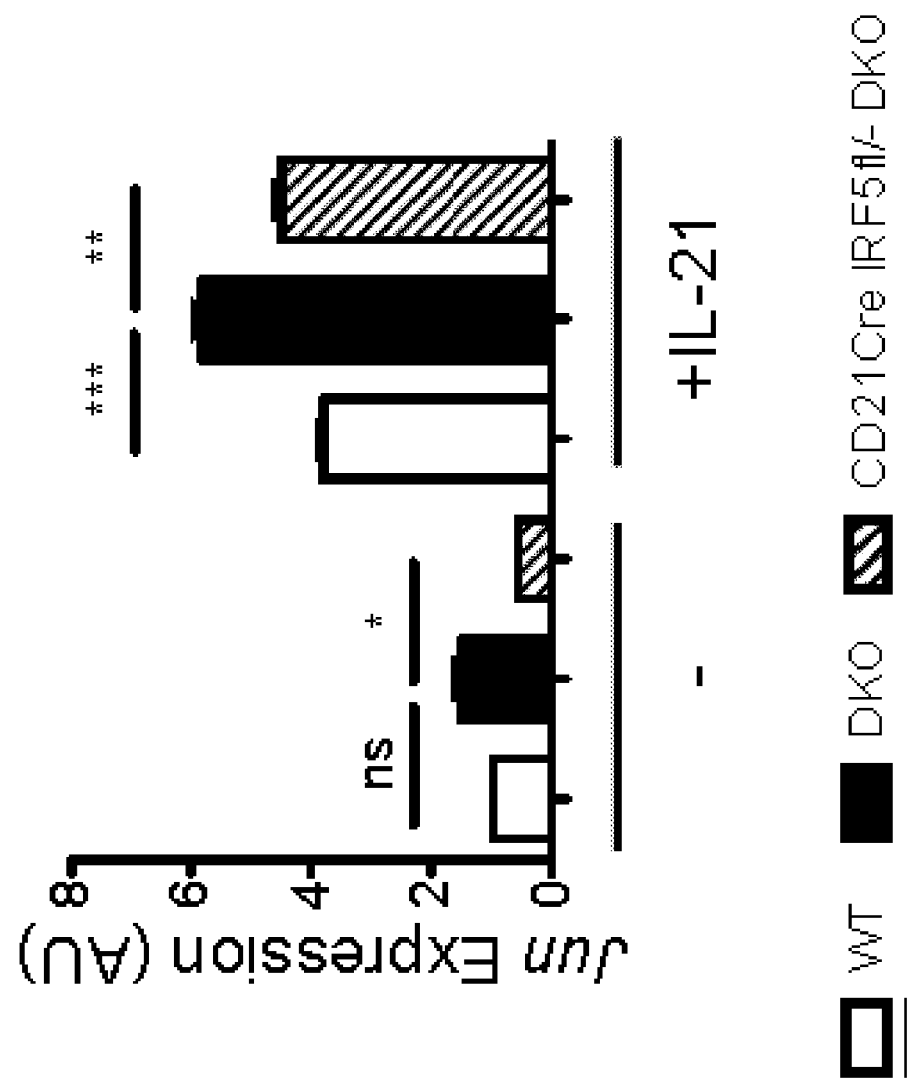
FIG. 6F shows the results of qPCR analysis of the expression of Jun in cultures of cells stimulated±IL-21. Data were normalized relative to ppia mRNA expression. Data are representative of 2 independent experiments. Mean±SEM is shown. : p≤0.01 *: p≤0.001; : p≤0.0001.

Lack of IRF5 markedly diminished the ability of DKO B cells to generate ABCs in cultures supplemented with IL-21 (FIGS. 6A and 6B). The increased ability of DKO B cells to produce IL-6 and CXCL10 upon IL-21 stimulation was also decreased by the absence of IRF5 (FIGS. 6C and 6D). Deleting IRF5 in DKO B cells also profoundly decreased the IL-21-mediated production of IgG2c, but not that of IgG1 (FIG. 6E). Expression of Jun was also dysregulated in DKO B cells in an IL-21- and IRF-5-dependent manner (FIG. 6F). Thus, the IL-21 driven abnormalities in ABC generation and function exhibited by DKO B cells are dependent on the presence of IRF5.

Figure 6G:
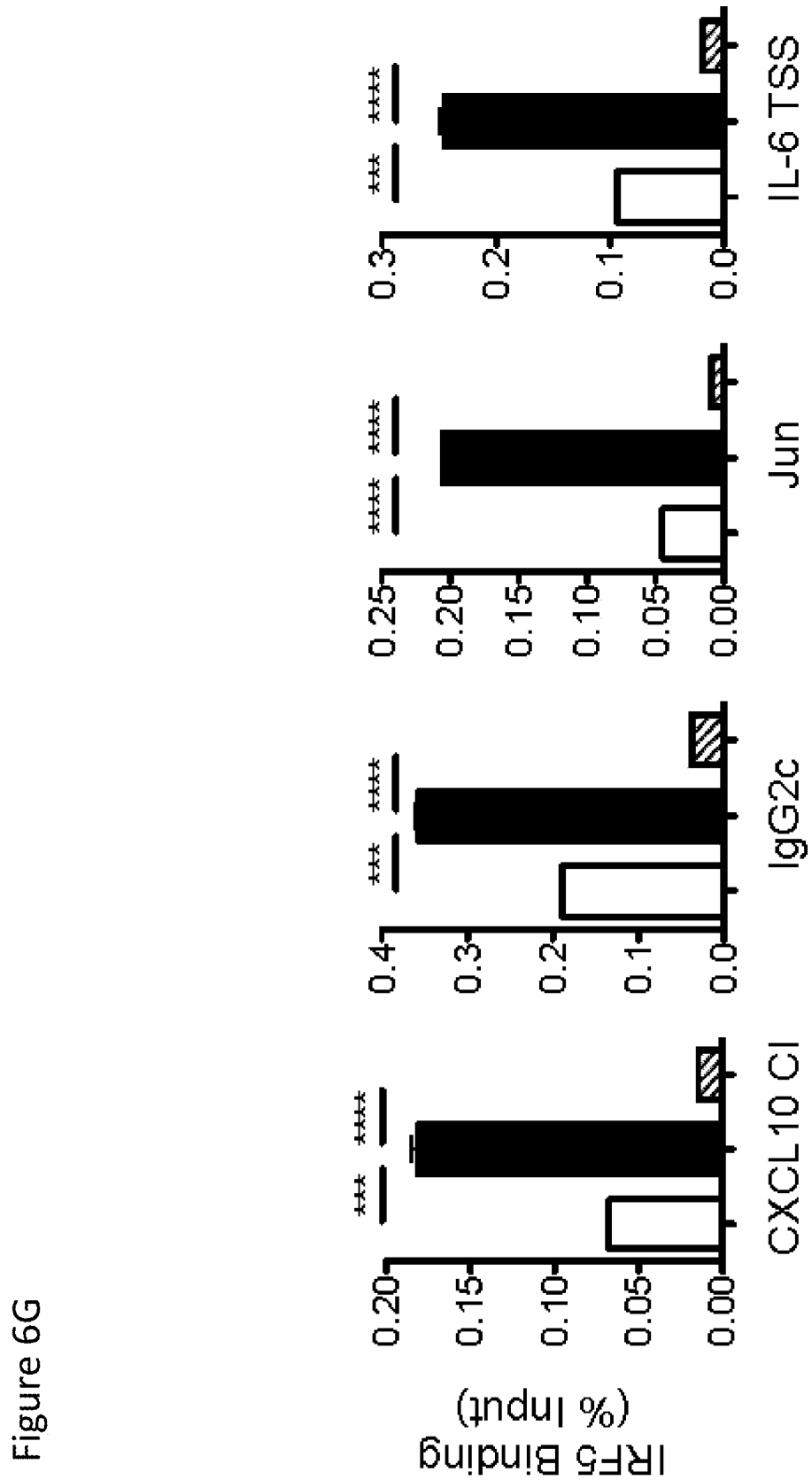
FIG. 6G are graphs of the results of ChIP assays performed with an IRF5 antibody on cells stimulated with IL-21 for 2 days. Immunoprecipitated DNA was analyzed by qPCR using primers within the ABC-specific ATAC-seq peaks at the CXCL10 cluster (Cl), IgG2c, Jun, and the IL-6 TSS. Data are representative of 4 (IL-6 TSS and CXCL10 Cl) or 2 (IgG2c and Jun) independent experiments. Mean±SEM is shown. *: p≤0.001; ****: p≤0.0001. (One-way ANOVA).
Figure 6H:
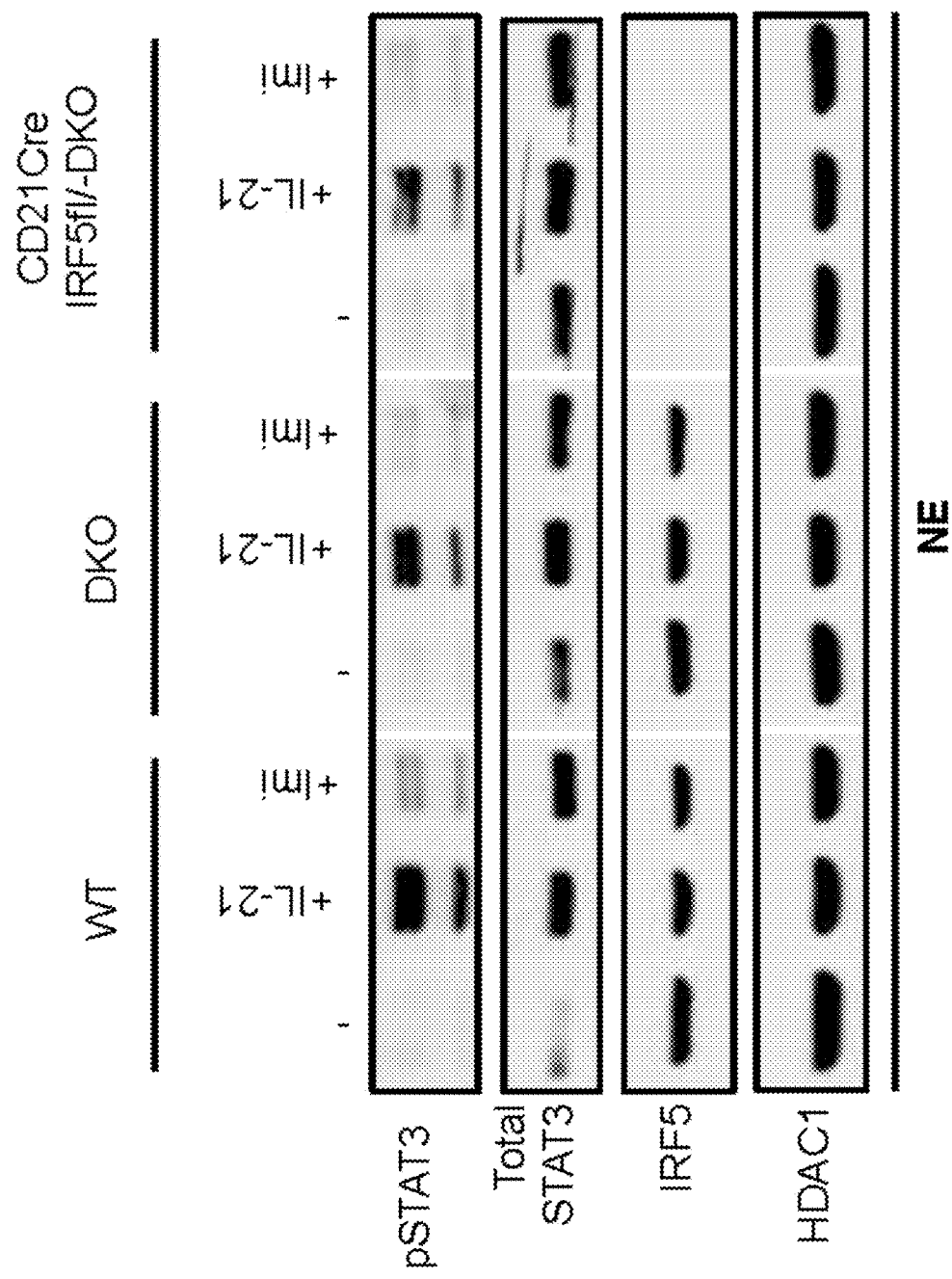
FIG. 6H is a Western blot of nuclear extracts prepared from CD23+ B cells purified from WT, DKO and CD21Cre IRF5$^{fl/-}$ DKO female mice (8-10 weeks of age) stimulated with αIgM (5 μg/ml), αCD40 (5 μg/ml), IL-21 (50 ng/ml) or imiquimod (1 μg/ml) for 3 days. Extracts were analyzed by Western blotting with pSTAT3, STAT3, IRF5, and HDAC1 antibodies. Data are representative of 2 independent experiments.

Given that the ATAC-seq analysis had revealed an enrichment of IRF binding sites in ABC specific peaks located at the Il6 TSS, the Cxcl10 cluster, the IgG2c region, and Jun, ChIP-assays were performed to assess the binding of IRF5 to these regulatory regions. As compared to wild type B cells, DKO B cells exhibited enhanced binding of IRF5 to these sites upon IL-21 stimulation despite exhibiting similar levels of Stat3 phosphorylation and IRF5 nuclear translocation (FIGS. 6G and 6H). Minimal IRF5 binding was observed in IRF5-deleted DKO B cells or when cells were stimulated in the absence of IL-21 supporting the specificity of the findings (FIG. 6G).

Figure 6I:
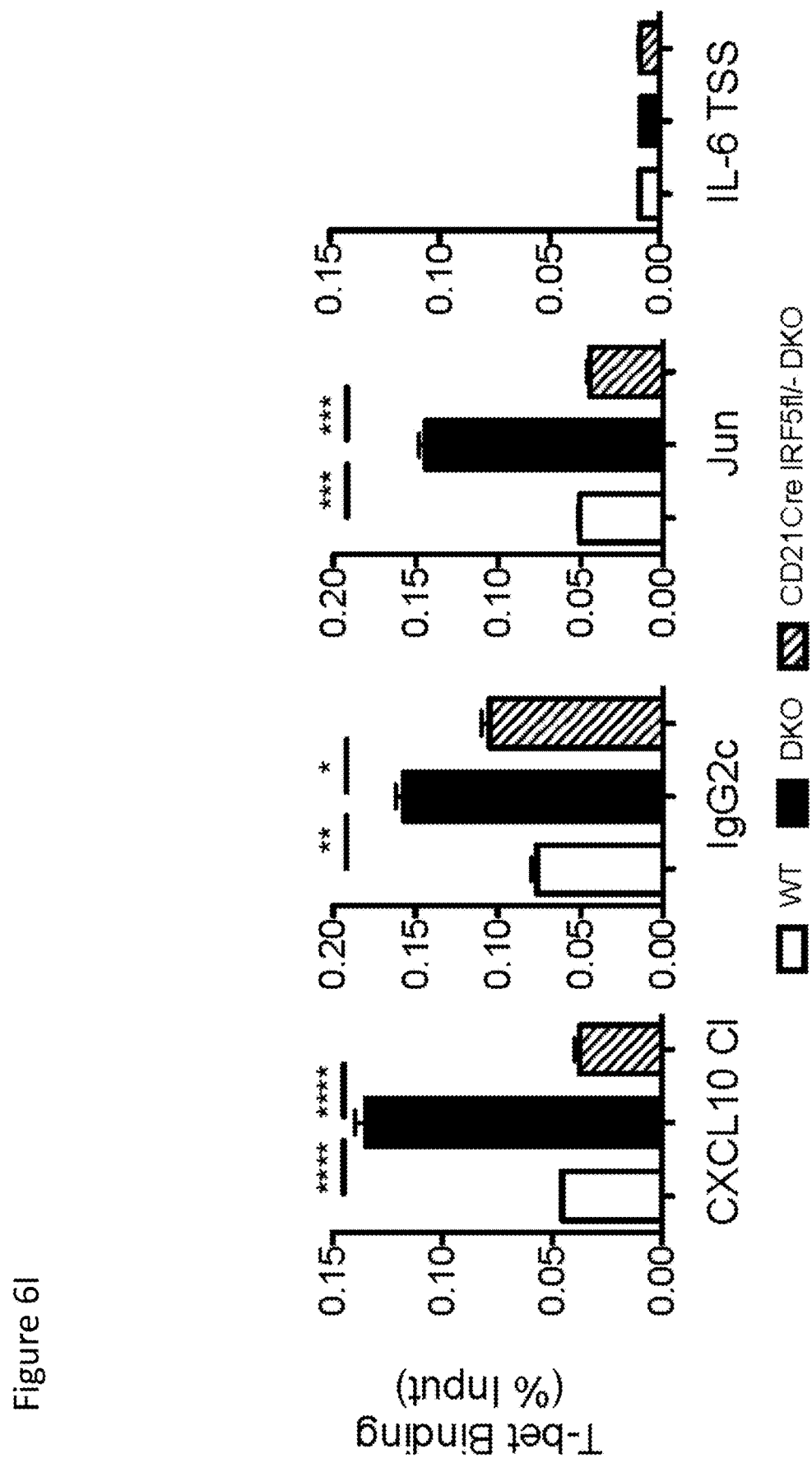
FIG. 6I are graphs of the results of a ChIP assay performed with a T-bet antibody. Data are representative of 4 (IL-6 TSS and CXCL10 Cl) or 2 (IgG2c and Jun) independent experiments. Mean±SEM is shown. *: p≤0.05, : p≤0.01 *: p≤0.001; ****: p≤0.0001.
Figure 6J:
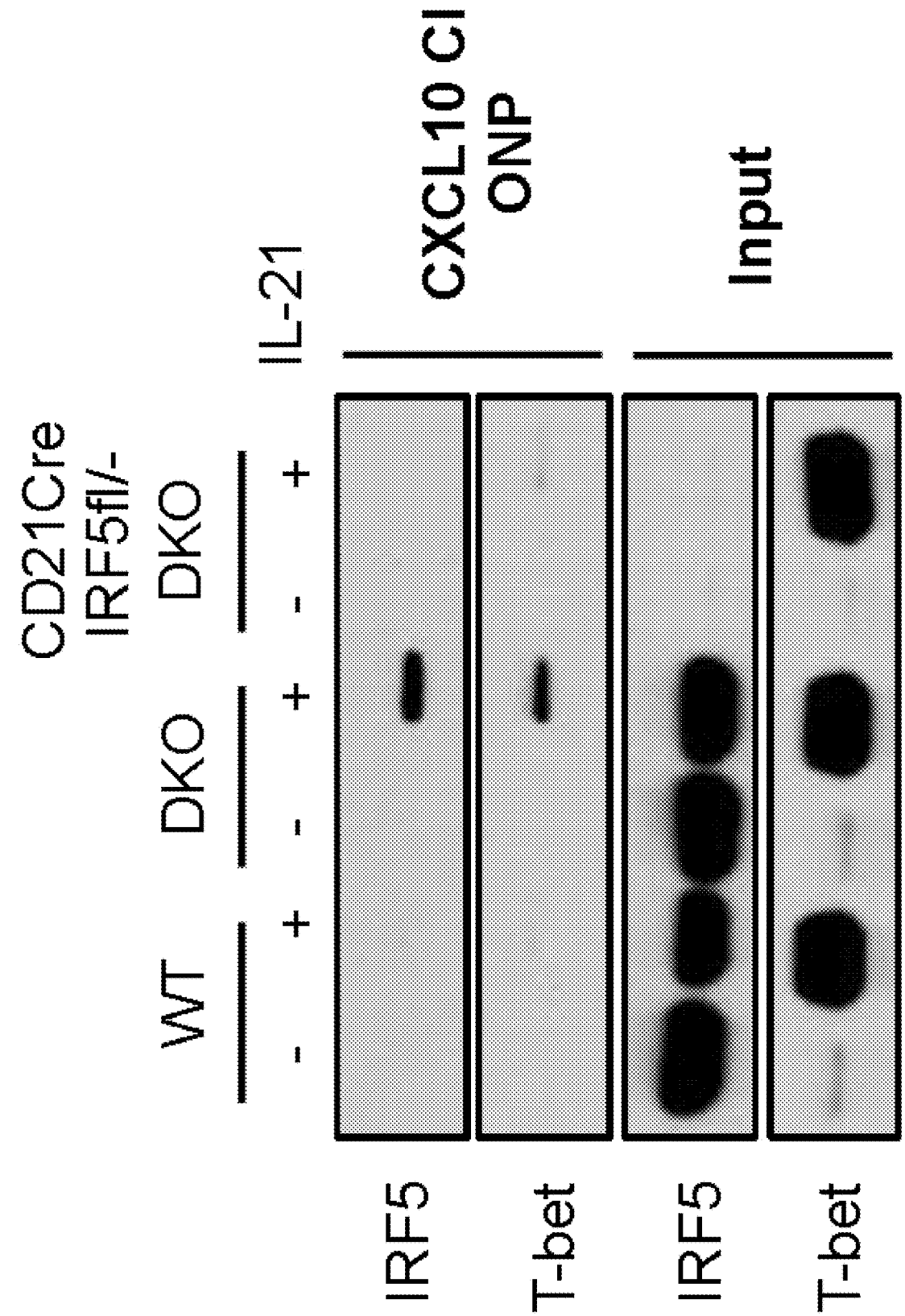
FIG. 6J show Western Blots of nuclear extracts prepared from cells stimulated with and without IL-21 for 2 days and subjected to ONP assay with a biotinylated oligonucleotide from the CXCL10 Cl. Precipitated proteins were analyzed by Western blotting with an IRF5 and T-bet antibody as indicated. Data are representative of 2 independent experiments.
Figure 6K:
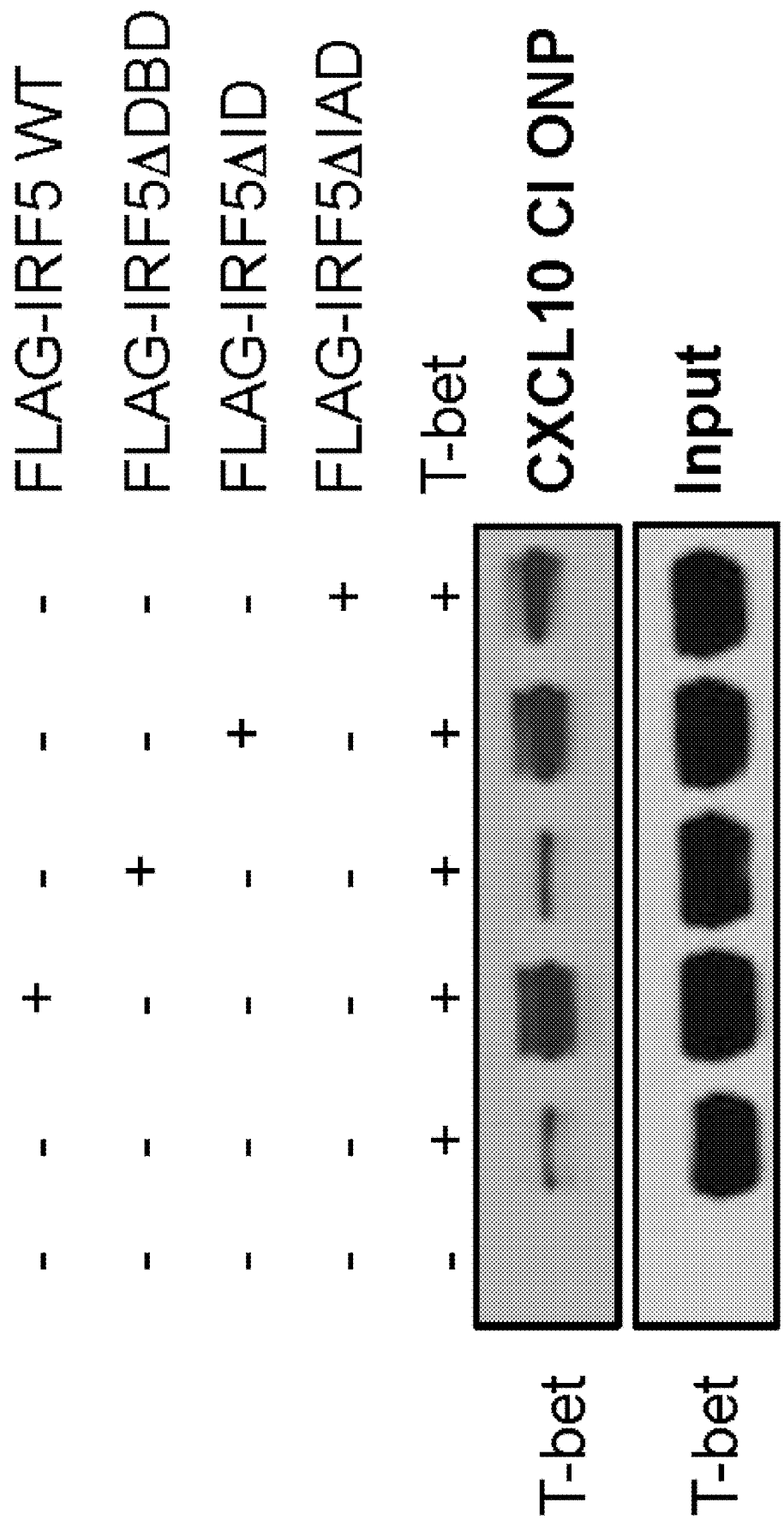
FIG. 6K shows Western Blots of nuclear extracts from 293T cells transiently transfected as indicated and subjected to ONP assay with a biotinylated oligonucleotide from the CXCL10 Cl or IL-6 TSS. Precipitated proteins were analyzed by Western blotting with an IRF5 or T-bet antibody. Data are representative of 2 independent experiments.

To evaluate whether ABC-specific peaks bound by IRF5 could also be targeted by T-bet, ChIP-assays with a T-bet antibody were performed (FIG. 6I). DKO B cells exhibited increased binding of T-bet to the ABC-specific region at the CXCL10 cluster, the IgG2c peak, and Jun but not to the IL-6 TSS or the negative control, a site in Zeb2 gene previously shown not to bind T-bet (Dominguez et al. 2015). Notably, IRF5 deletion in DKO B cells resulted in decreased binding of T-bet to the CXCL10 cluster, the IgG2c peak, and Jun. Further corroboration that IL-21 stimulation of DKO B cells leads to an aberrant ability of IRF5 and T-bet to target the CXCL10 cluster was obtained by performing oligonucleotide precipitation assays (ONPs). As observed with the ChIP assays, the presence of IRF5 was necessary for the ability of T-bet to bind to the CXCL10 cluster while no binding of T-bet to the IL-6 TSS could be detected (FIG. 6J). Co-transfection of T-bet with IRF5 coupled with a mutational analysis further confirmed that optimal recruitment of T-bet to the CXCL10 cluster requires DNA binding by IRF5 (FIG. 6K) Taken together these findings support a model whereby, in the absence of SWEF proteins, IL-21 stimulation leads to an increased ability of IRF5 to target ABC-specific peaks. Targeting of these regions by IRF5 subsequently enables strong recruitment of T-bet to a subset of these sites.

Figure 6L:
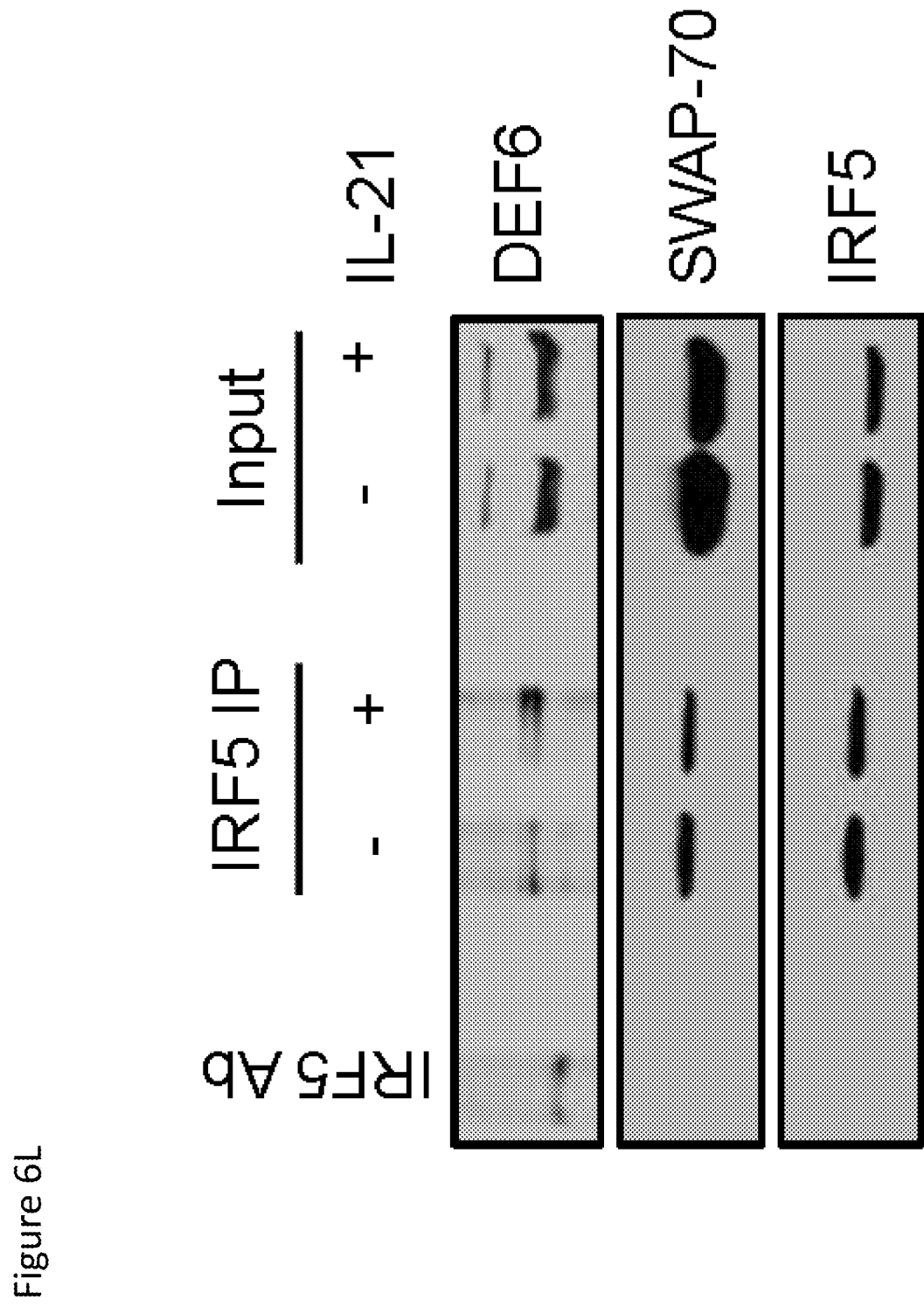
FIG. 6L is a Western blot of IRF5/SWEF proteins coimmunoprecipitation from nuclear extracts from cells stimulated with or without IL-21 for 2 days. Immunoprecipitation was performed with an IRF5 antibody and probed with a DEF6, SWAP-70 or IRF5 antibody as indicated. Data are representative of 2 independent experiments.
Figure 6M:
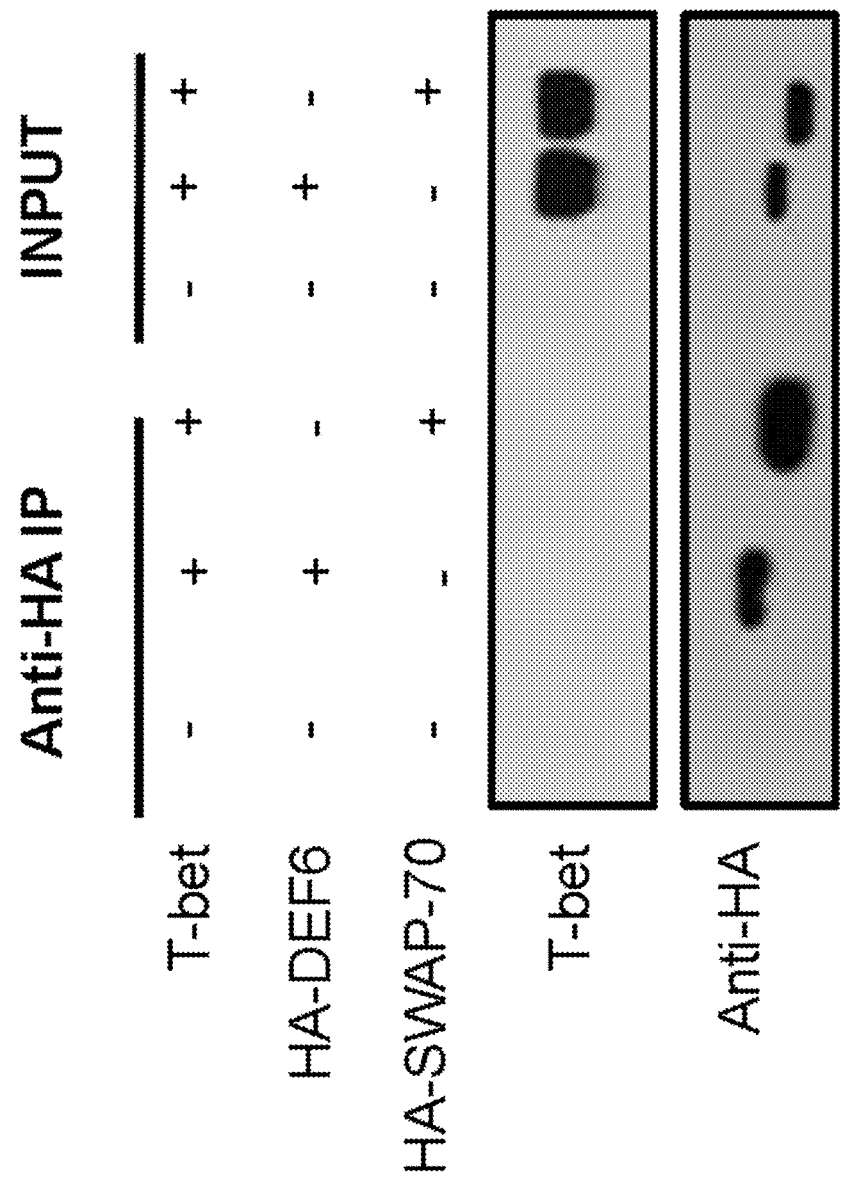
FIG. 6M is a Western blot of nuclear extracts of 293T cells transiently transfected with various constructs as indicated. Immunoprecipitations were performed using an anti-HA antibody. Immunoprecipitates were analyzed by Western blotting using HA antibodies. Data are representative of 2 independent experiments with similar results.
Figure 6N:
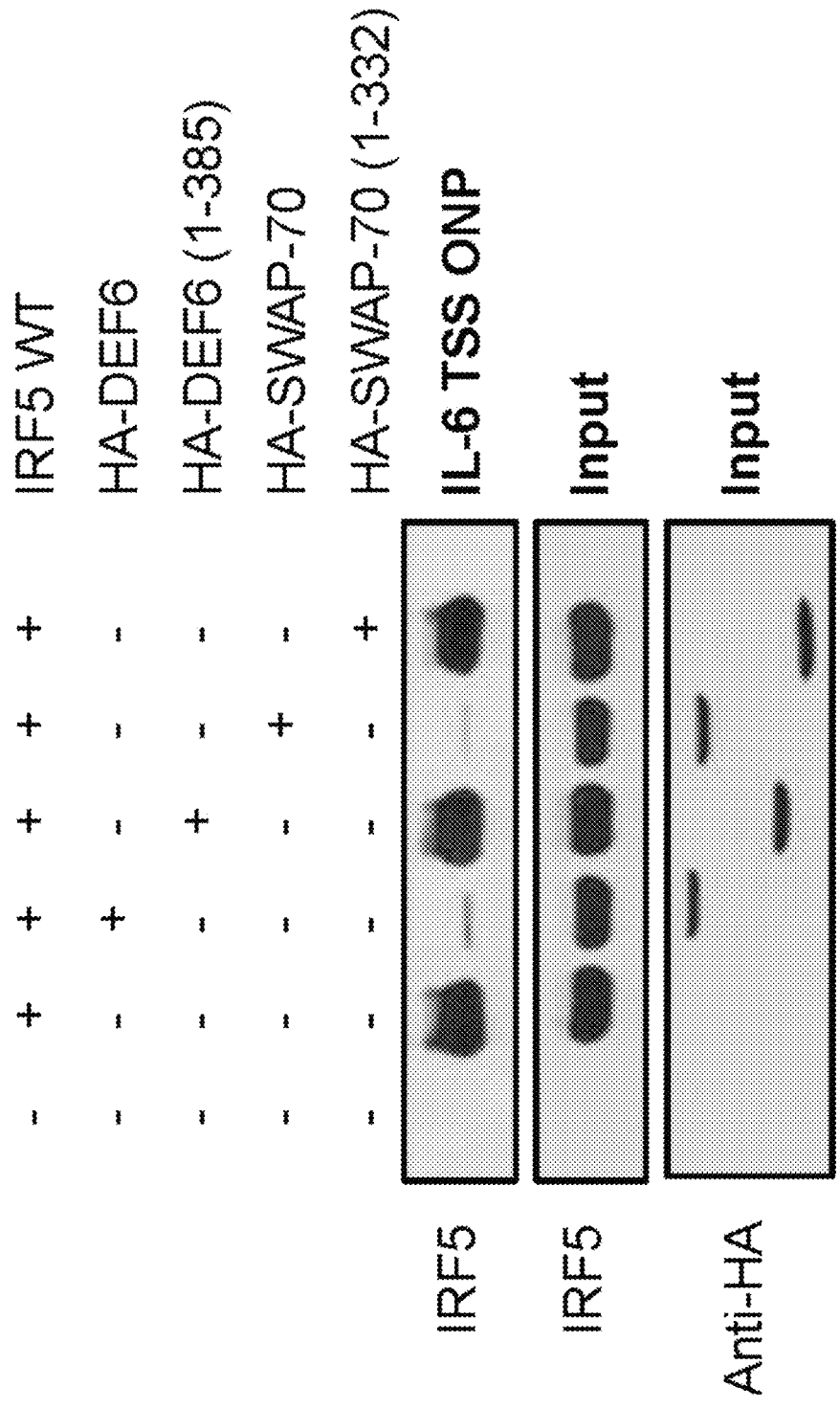
FIG. 6N is a Western blot of nuclear extracts of 293T cells subjected to ONP assay with a biotinylated oligonucleotide from the IL-6 TSS. Precipitated proteins were analyzed by Western blotting with an IRF5 antibody. Data are representative of 2 independent experiments.
Figure 60:
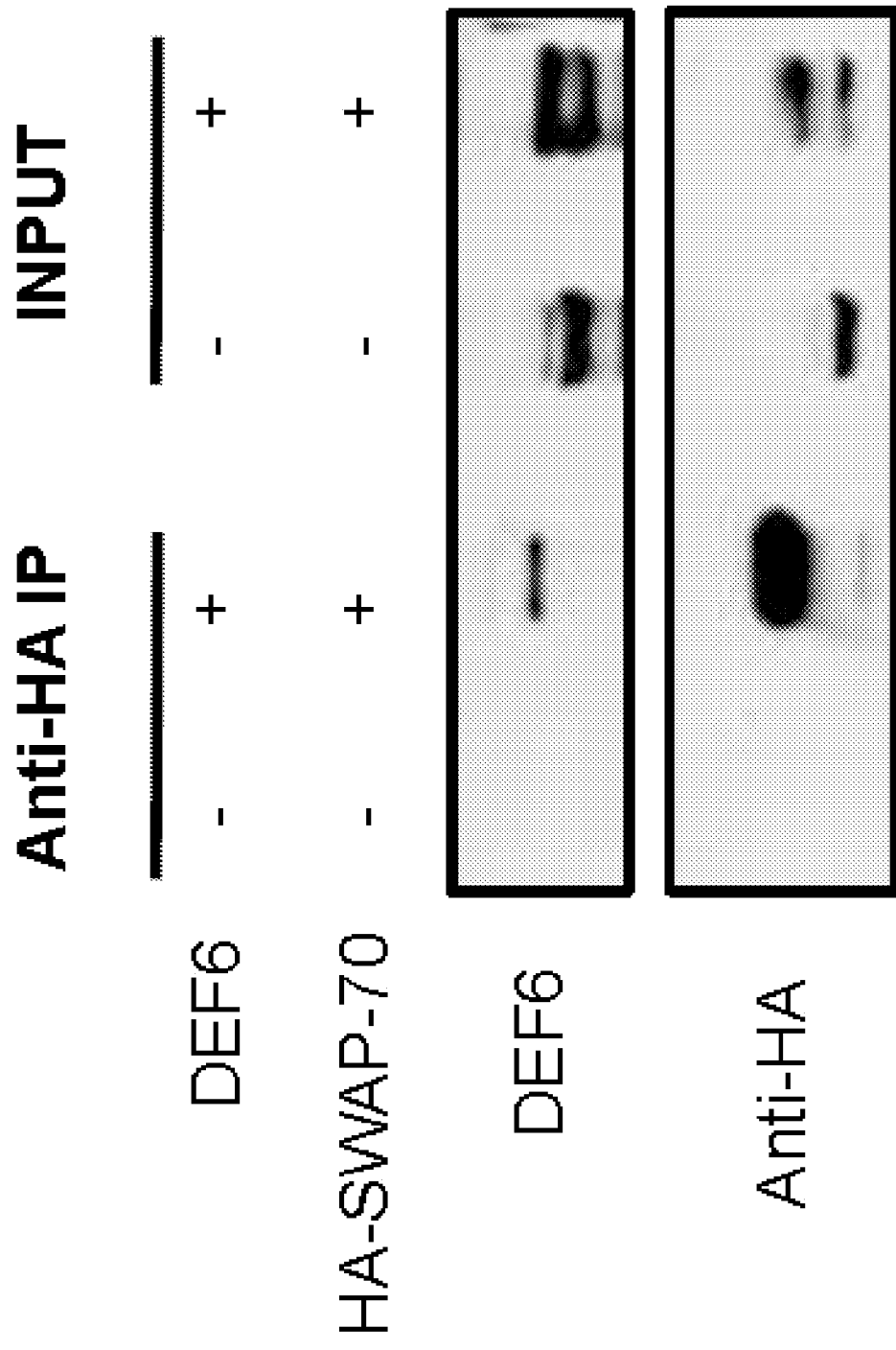

To delineate the mechanisms by which the lack of SWEF proteins results in enhanced IRF5 activity, the possibility that they can directly interact with IRF5 and thus restrain its activity was investigated. As shown in FIG. 6L, coimmunoprecipitation experiments indeed revealed that endogenous IRF5 in B cells interacts with both DEF6 and SWAP-70. A mutational analysis furthermore revealed that the association of IRF5 with either DEF6 or SWAP-70 maps to the C-terminal portion of the SWEF proteins, which contains their IRF-interacting region, and requires the IAD (IRF Association Domain) of IRF5, a domain within IRFs known to mediate protein-protein interaction (results not shown). No interaction of either DEF6 or SWAP-70 with T-bet could instead be detected (FIG. 6M). Co-transfections of IRF5 with DEF6 or SWAP-70 followed by ONP assays demonstrated that the full-length SWEF proteins, but not mutants of these molecules which are unable to interact with IRF5, interfere with the ability of IRF5 to bind to the IL-6 TSS (FIG. 6N). Since DEF6 and SWAP-70 can heterodimerize (FIG. 6O), these results show that interaction of IRF5 with a SWEF heterodimer can directly regulate IRF5 activity and thus indirectly alter the recruitment of T-bet to selected target genes.

Example 8

Figure 7A:
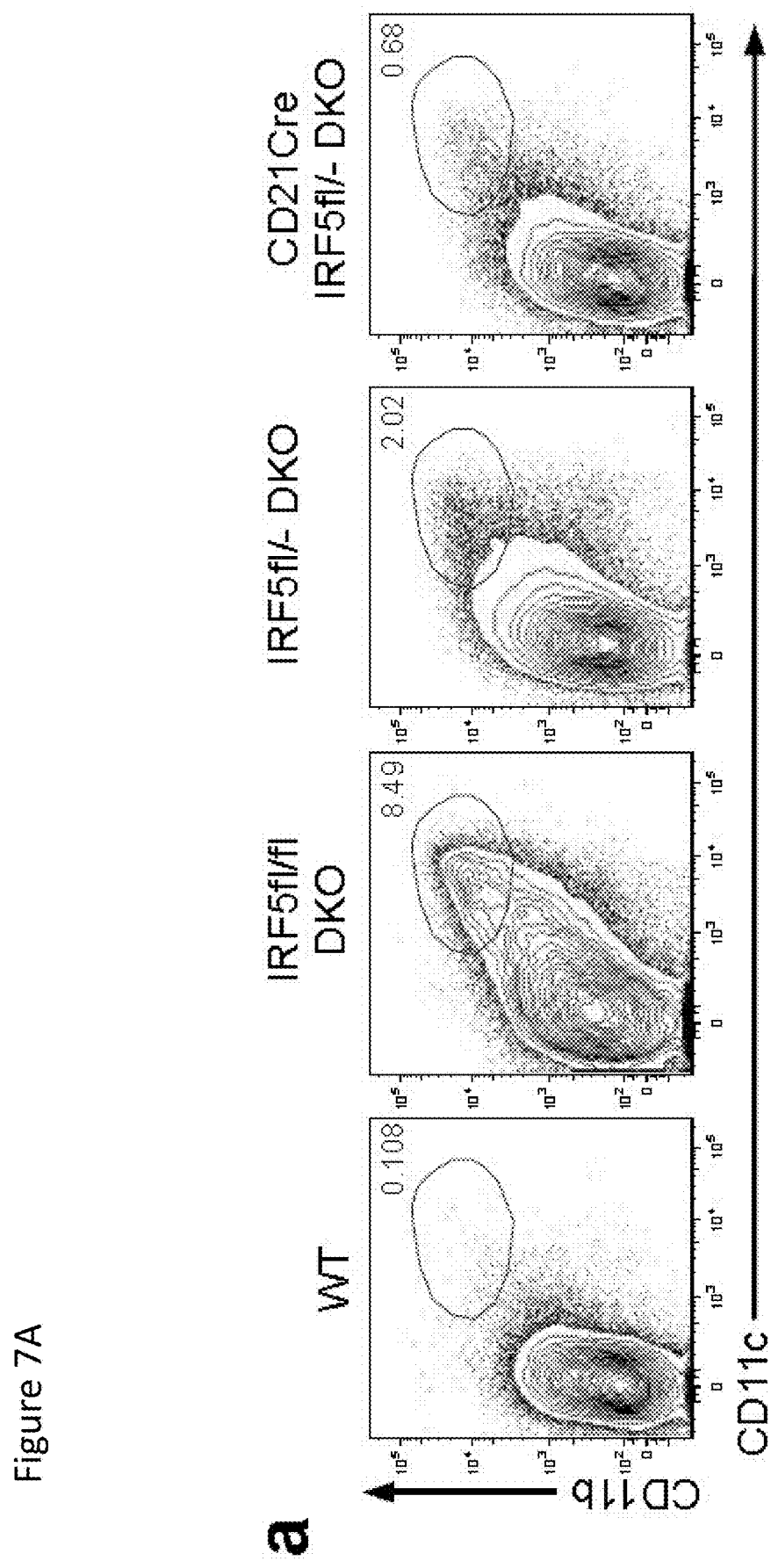
FIG. 7A shows representative FACS plots of CD11c and CD11b expression in CD11c+CD11b+ B cells in the spleens of WT, IRF5$^{fl/fl}$ DKO, IRF5$^{fl/-}$ DKO and CD21Cre IRF5$^{fl/-}$ DKO female mice (>20 weeks-old).
Figure 7B:
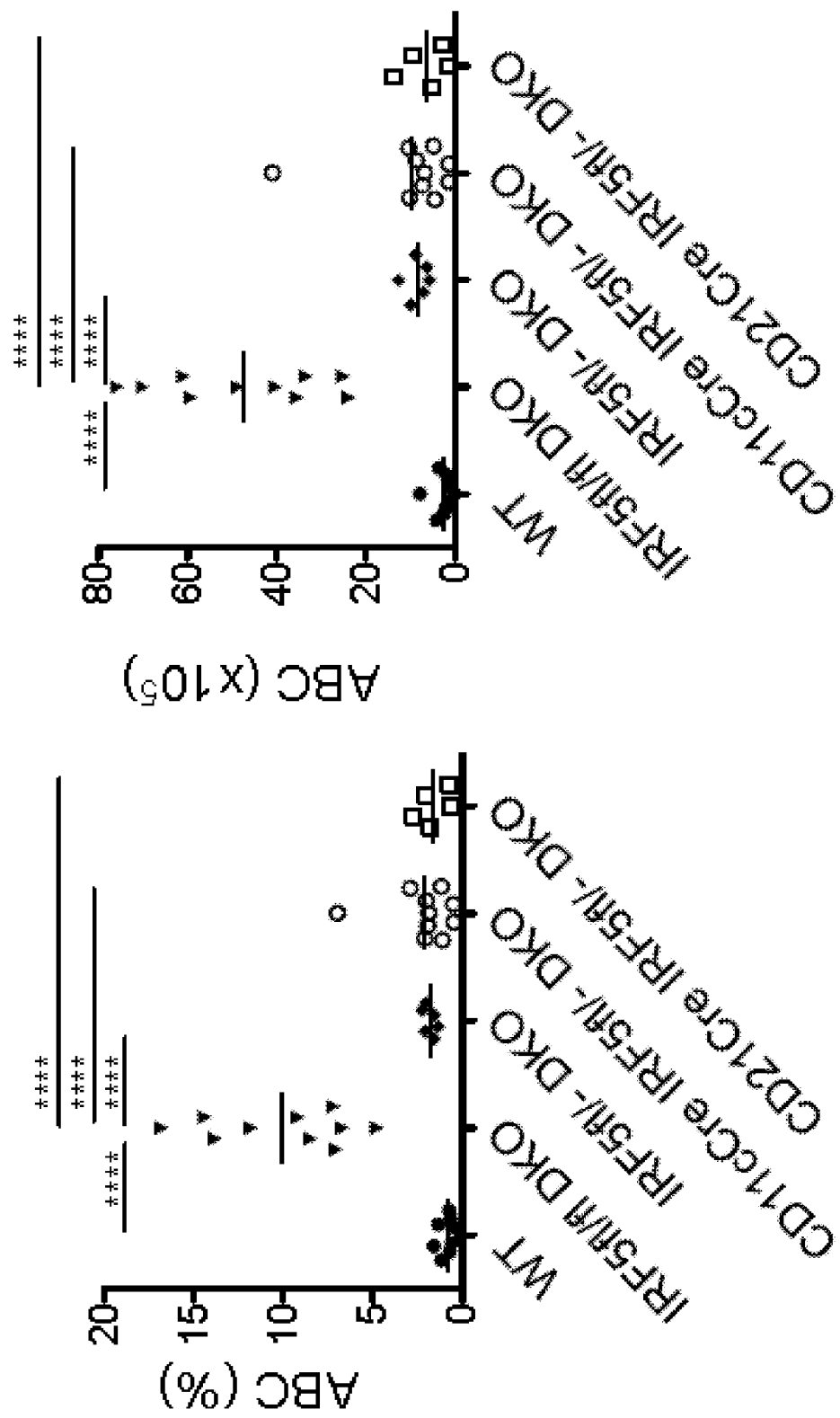
FIG. 7B are graphs of the percentage and absolute numbers of ABCs (CD11c+CD11b+B220+) in mice of the indicated genotypes. (n=5-10 mice). **: p≤0.0001. (One-way ANOVA).
Figure 7C:
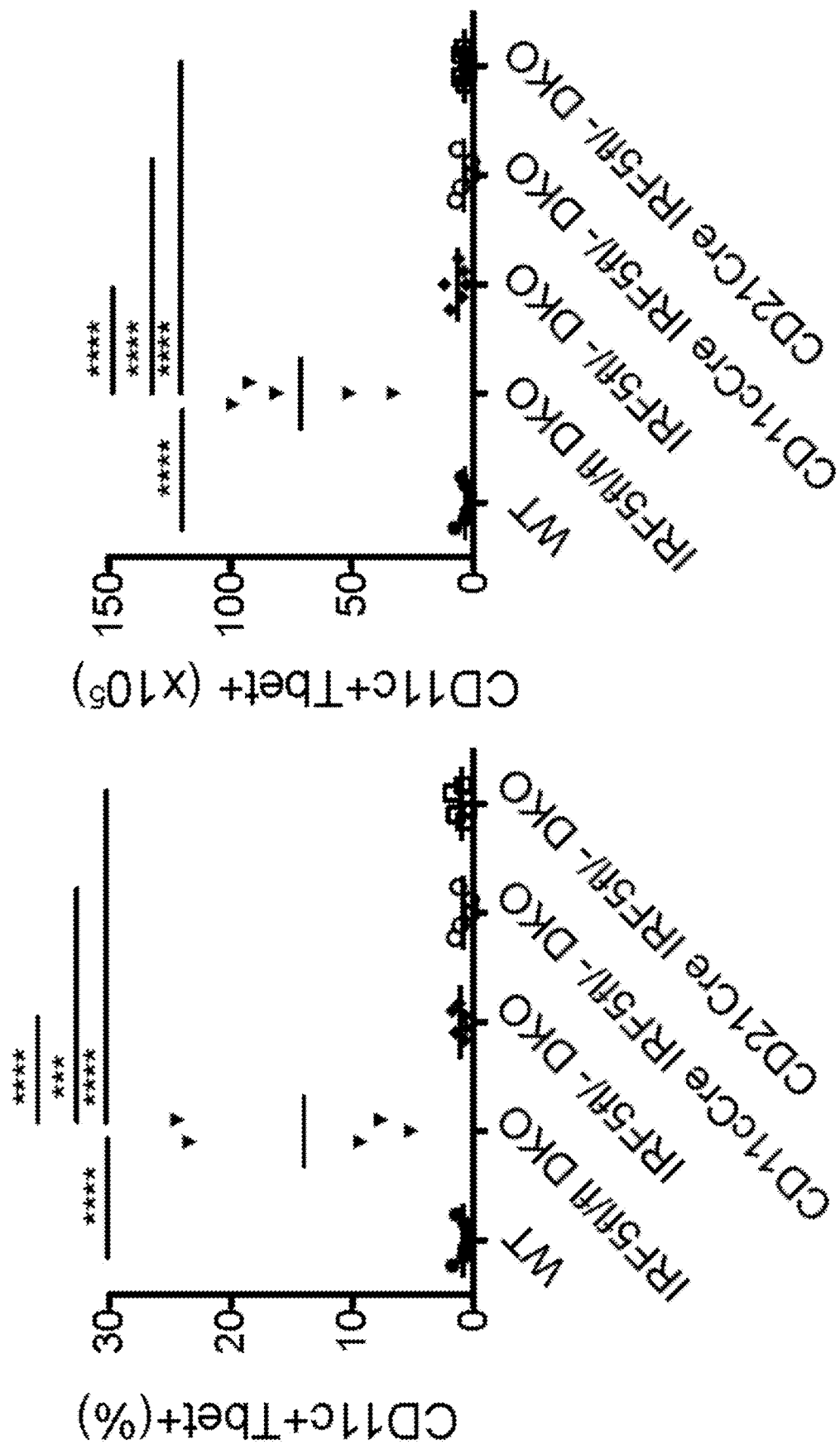
FIG. 7C are graphs of percentages and absolute numbers of B220+CD19+CD11c+Tbet+ B cells in the spleens of WT, IRF5$^{fl/fl}$ DKO, IRF5$^{fl/-}$ DKO, CD11cCre IRF5$^{fl/-}$ DKO and CD21Cre IRF5$^{fl/-}$ DKO female mice (>20 weeks-old). Graphs show percentages and numbers in individual mice (n=5-7). *: p≤0.001; **: p≤0.0001. (One-way ANOVA).
Figure 7D:
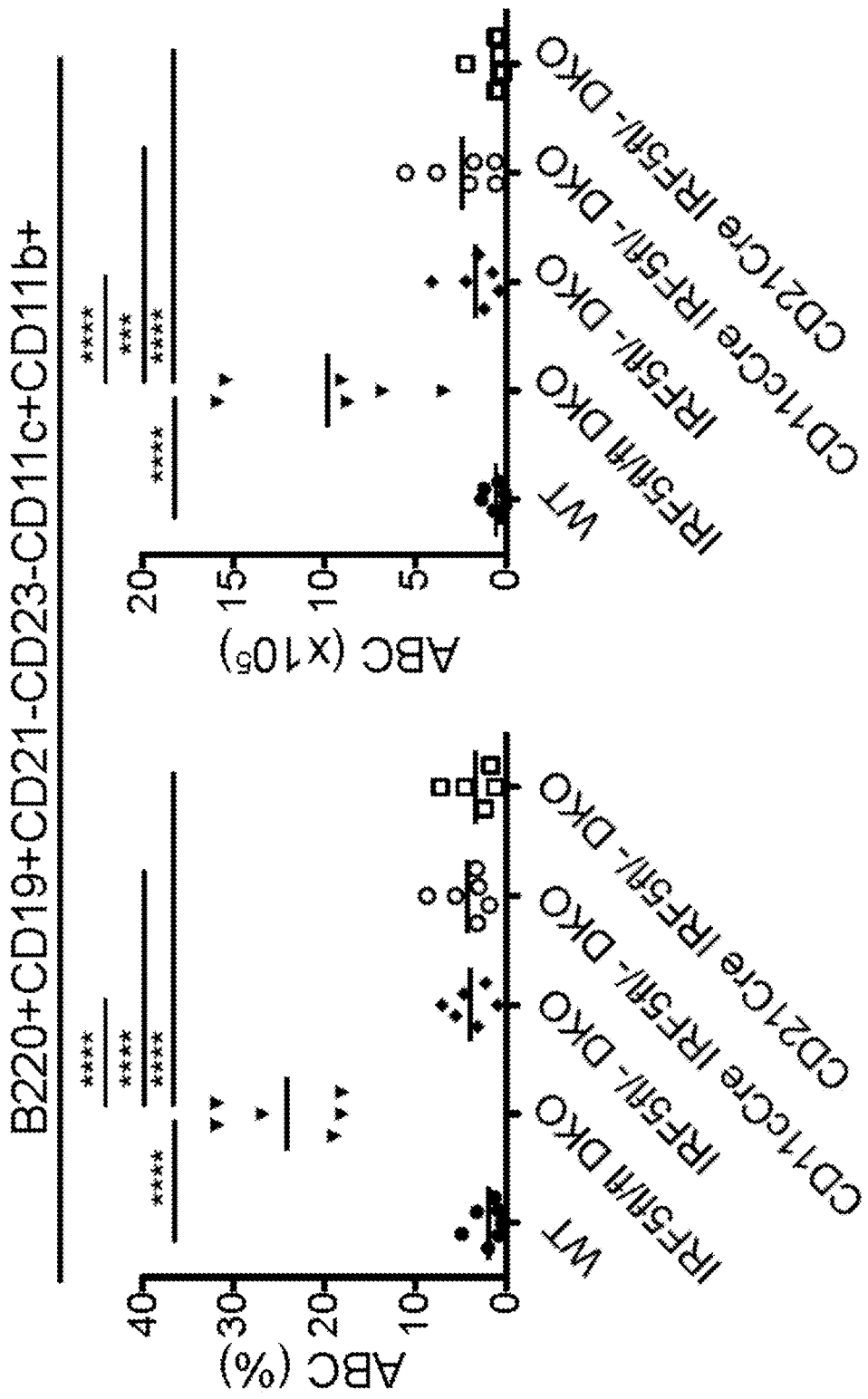
FIG. 7D are graphs of percentages and absolute numbers of B220+CD19+CD21−CD23−CD11c+CD11b+ B cells in the spleens of WT, IRF5$^{fl/fl}$ DKO, IRF5$^{fl/-}$ DKO, CD11cCre IRF5$^{fl/-}$ DKO and CD21Cre IRF5$^{fl/-}$ DKO female mice (>20 weeks-old). Graphs show percentages and numbers in individual mice (n=5-7). *: p≤0.001; ****: p≤0.0001. (One-Way ANOVA).
Figure 7E:
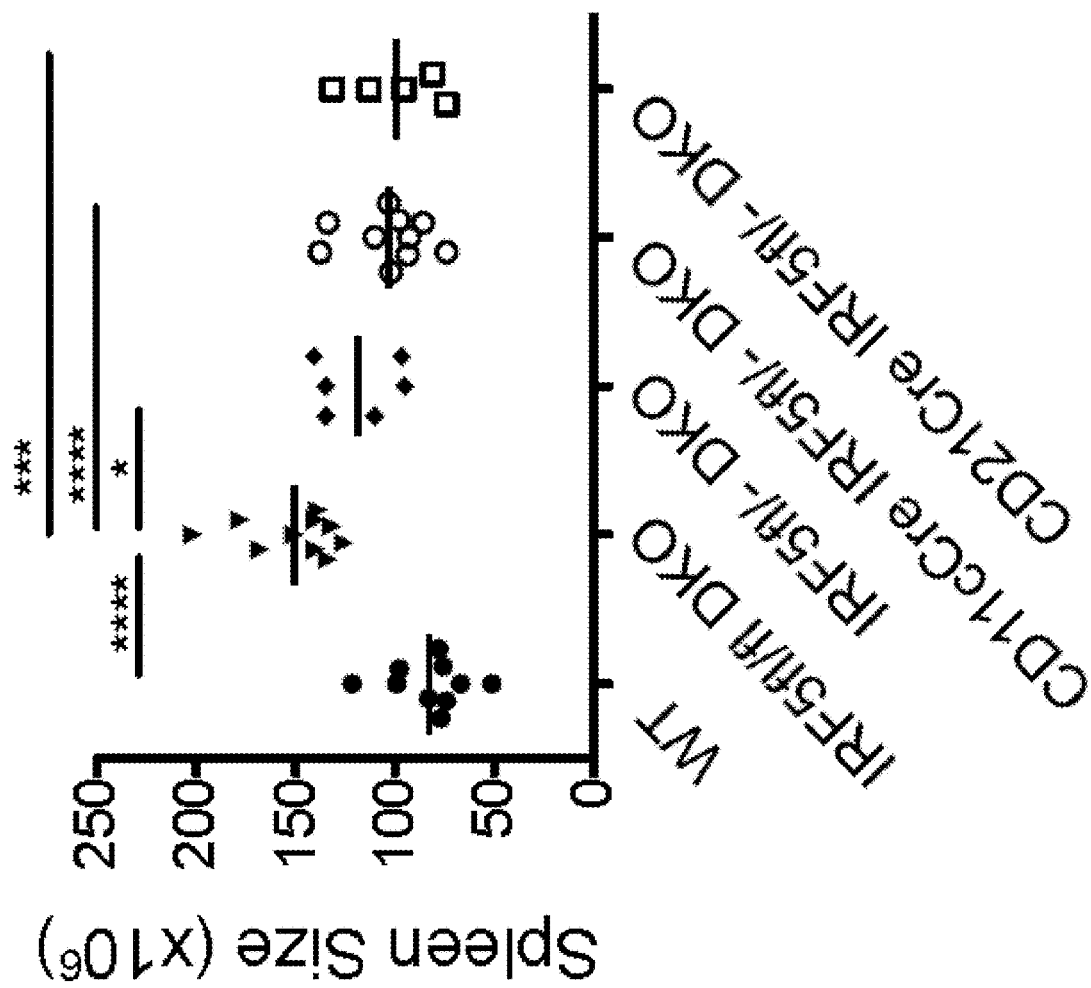
FIG. 7E are graph shows percentages and absolute numbers of total splenocytes in WT, IRF5$^{fl/fl}$ DKO, IRF5$^{fl/-}$ DKO, CD11cCre IRF5$^{fl/-}$ DKO and CD21Cre IRF5$^{fl/-}$ DKO mice (>20 weeks of age) (n=5-10 mice). *: p≤0.05; *: p≤0.001, : p≤0.0001. (One-way ANOVA).
Figure 7F:
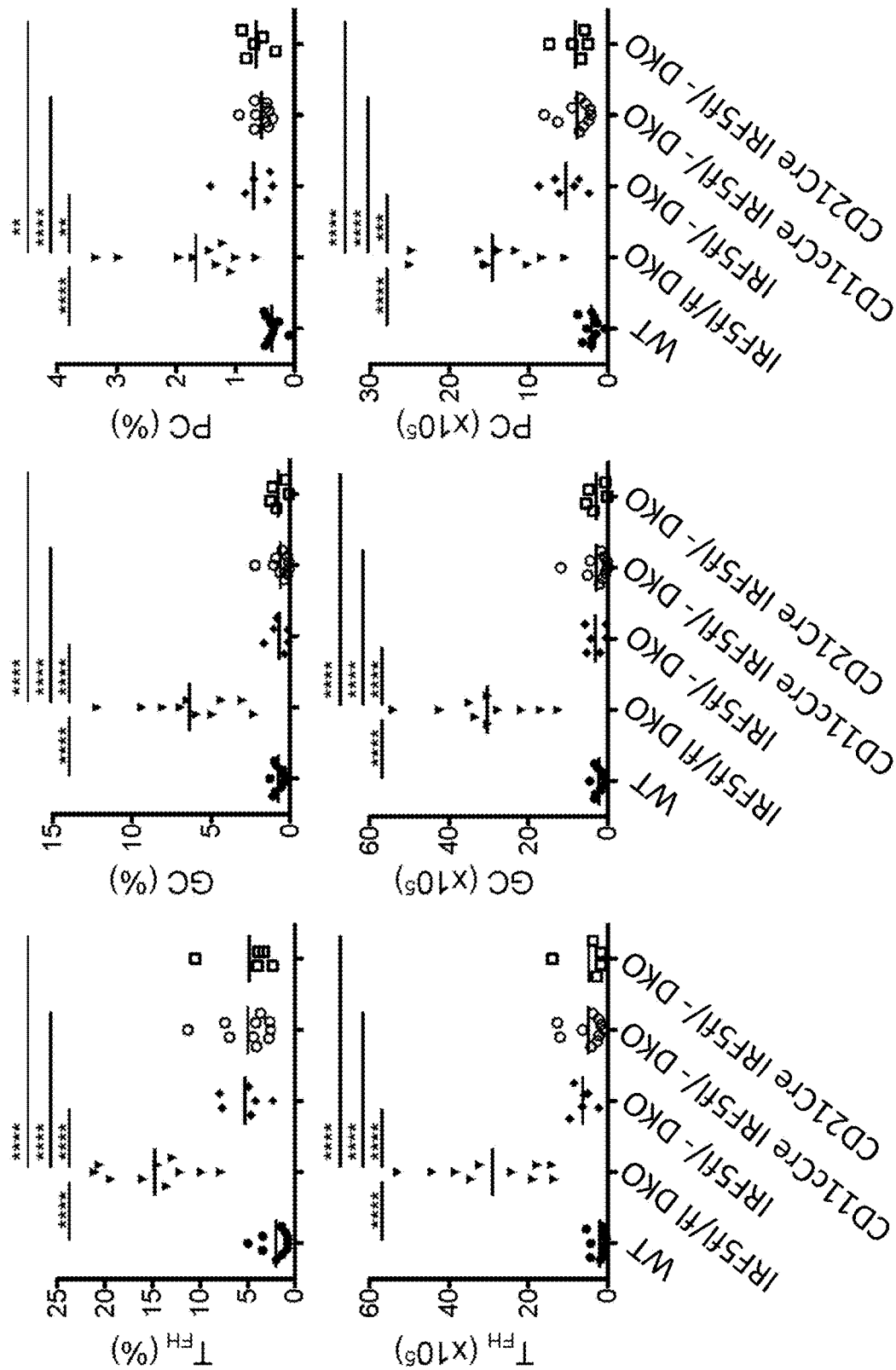
FIG. 7F are graphs quantifying flow cytometric analysis of $T_{FH}$ (CD4+CXCR5+PD1+Foxp3−), germinal center (GC) B cells (B220+FAS+GL-7+), and plasma cells (PC) (B220$^{int}$CD138+) in spleens of WT, IRF5$^{fl/fl}$ DKO, IRF5$^{fl/-}$ DKO, CD11cCre IRF5$^{fl/-}$ DKO and CD21Cre IRF5$^{fl/-}$ DKO mice (>20 weeks). Graphs show percentages and numbers of specific cells types in individual mice (n=5-10). : p≤0.01; *: p≤0.001; : p≤0.0001. (One-way ANOVA).
Figure 7G:
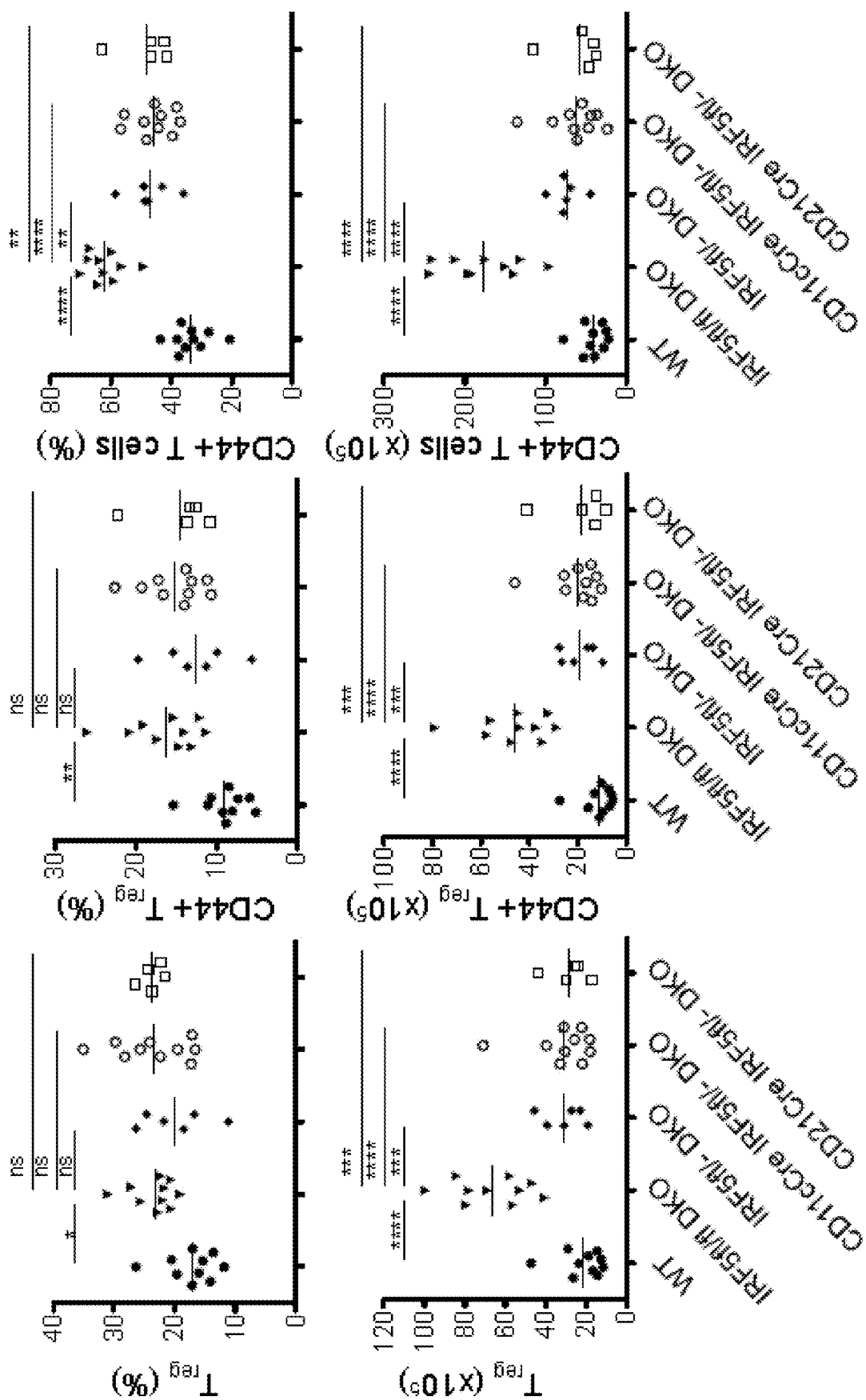
FIG. 7G are graphs quantifying flow cytometric analysis of Treg (CD4+Foxp3+), activated Treg (CD4+Foxp3+CD44+), and activated T cells (CD4+Foxp3−CD44+) in spleens of WT, IRF5$^{fl/fl}$ DKO, IRF5$^{fl/-}$ DKO, CD11cCre IRF5$^{fl/-}$ DKO and CD21Cre IRF5$^{fl/-}$ DKO mice ((>20 weeks). Graphs show frequencies and numbers of individual mice and mean value of 10 independent experiments (n=5-10). : p≤0.01; *: p≤0.001; **: p≤0.0001. (One-way ANOVA).

Monoallelic Deletion of IRF5 Abolishes Accumulation of ABCs and Lupus Development in DKO Mice To further evaluate the role of IRF5 in the generation of ABC cells the effects of manipulating IRF5 levels on the in vivo expansion of ABCs in DKO mice was examined. Remarkably mice with monoallelic expression of IRF5 (IRF5$^{fl/-}$ DKO) exhibited an almost complete loss of ABC cells, irrespective of the markers used to identify the population (FIGS. 7A-7D). Loss of ABCs was accompanied by marked decreases in splenomegaly, $T_{FH}$ cells, GC B cells and PC cells (FIGS. 7E-7G). Further deletion of IRF5 using CD21Cre or CD11cCre to target B cells or CD11c+ cells did not result in additional decreases in the ABC compartment (FIGS. 7A and 7B).

Figure 7H:
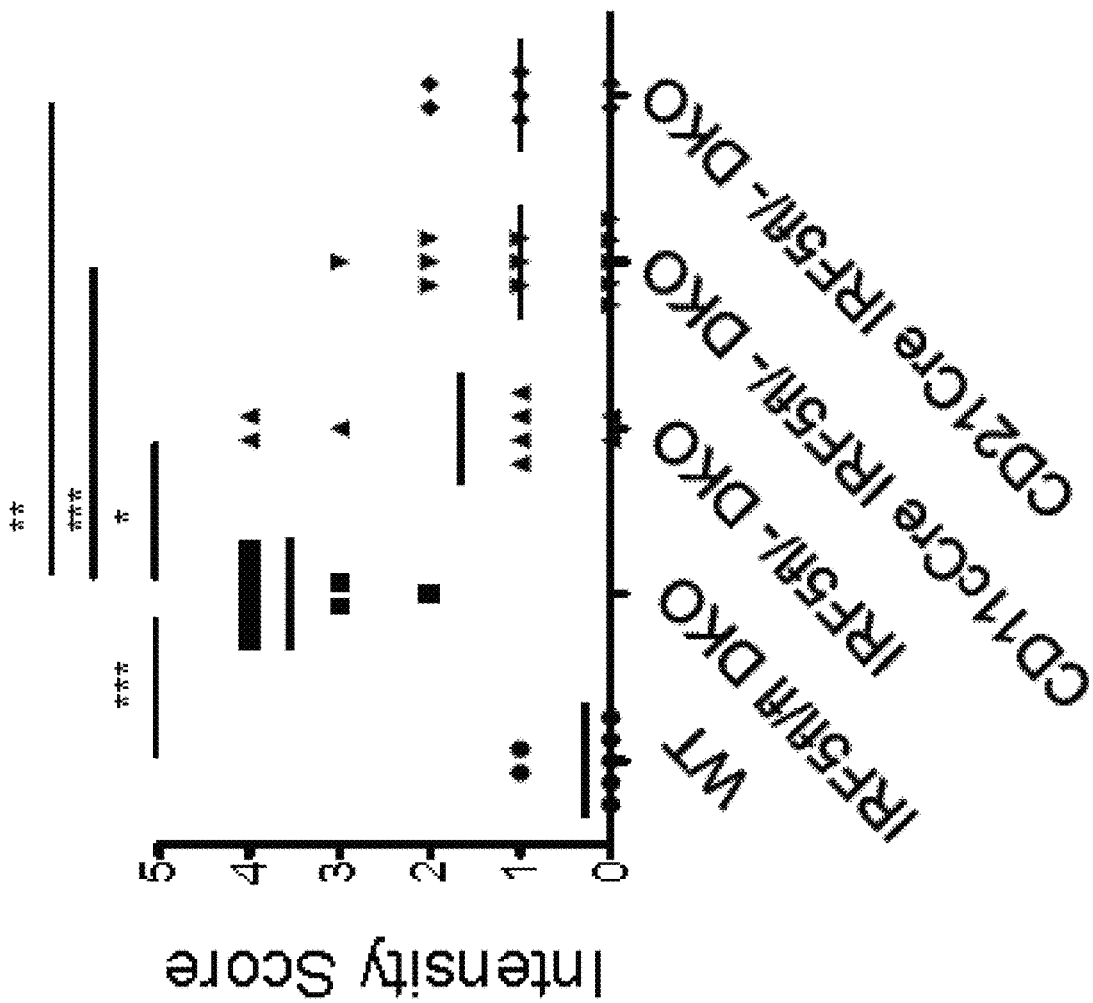
FIG. 7H show graphs of the intensity score of stained cells to determine anti-nuclear antibodies (ANAs) in sera (1:200) from WT, IRF5$^{fl/fl}$ DKO, IRF5$^{fl/-}$ DKO, CD11cCre IRF5$^{fl/-}$ DKO and CD21Cre IRF5$^{fl/-}$ DKO mice (>20 weeks old). Graph shows score of individual mice and mean value of 10 independent experiments (n=7-12). *: p≤0.05, : p≤0.01 *: p≤0.001 (Mann-Whitney test).
Figure 7I:
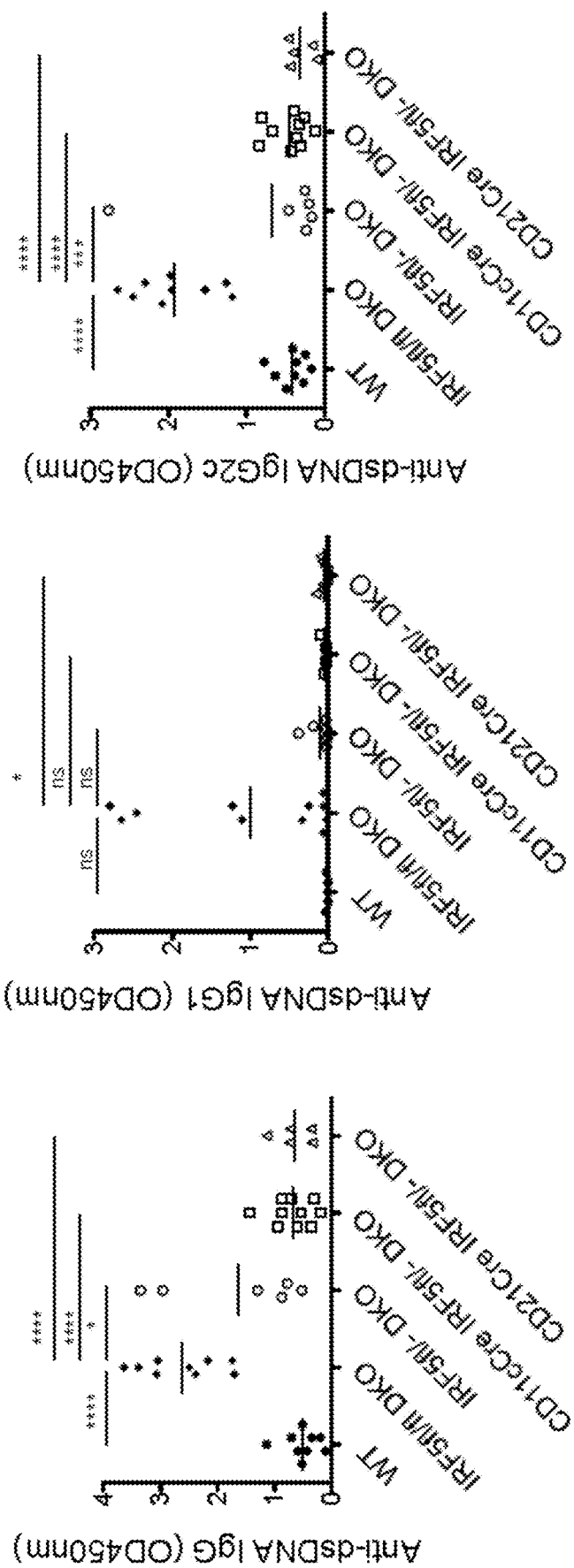
FIG. 7I are graphs of the levels of anti-dsDNA IgG, IgG1, or IgG2c antibodies in the sera of WT, IRF5$^{fl/fl}$ DKO, IRF5$^{fl/-}$ DKO, CD11cCre IRF5$^{fl/-}$ DKO and CD21Cre IRF5$^{fl/-}$ DKO female mice (>20 weeks old) analyzed by ELISA (n=4-11). *: p≤0.05; *: p≤0.001; **: p≤0.0001. (One-way ANOVA).
Figure 7J:
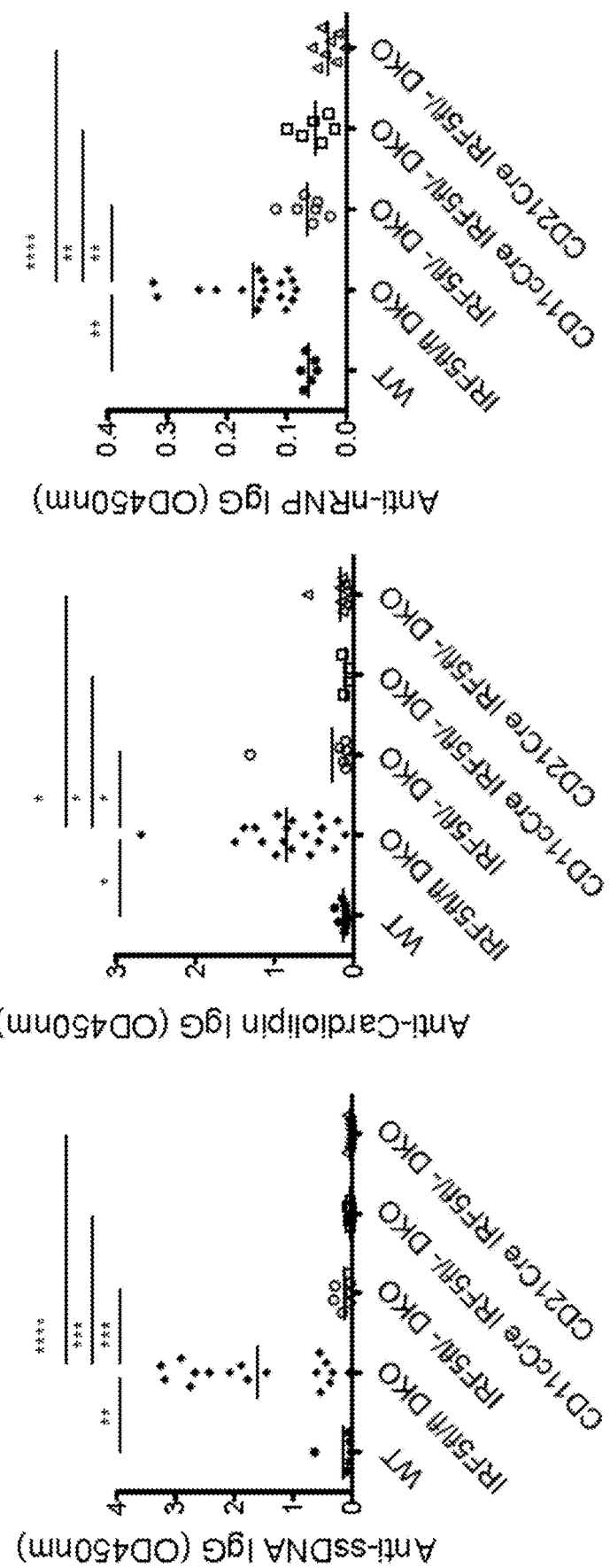
FIG. 7J are graphs of the levels of anti-ssDNA, cardiolipin and nRNP IgG antibodies in the sera of WT, IRF5$^{fl/fl}$ DKO, IRF5$^{fl/-}$ DKO, CD11cCre IRF5$^{fl/-}$ DKO and CD21Cre IRF5$^{fl/-}$ DKO female mice (>20 weeks old) analyzed by ELISA (n=4-19). *: p≤0.05; : p≤0.01; *: p≤0.001; ****: p≤0.0001. (One-way ANOVA).
Figure 7K:
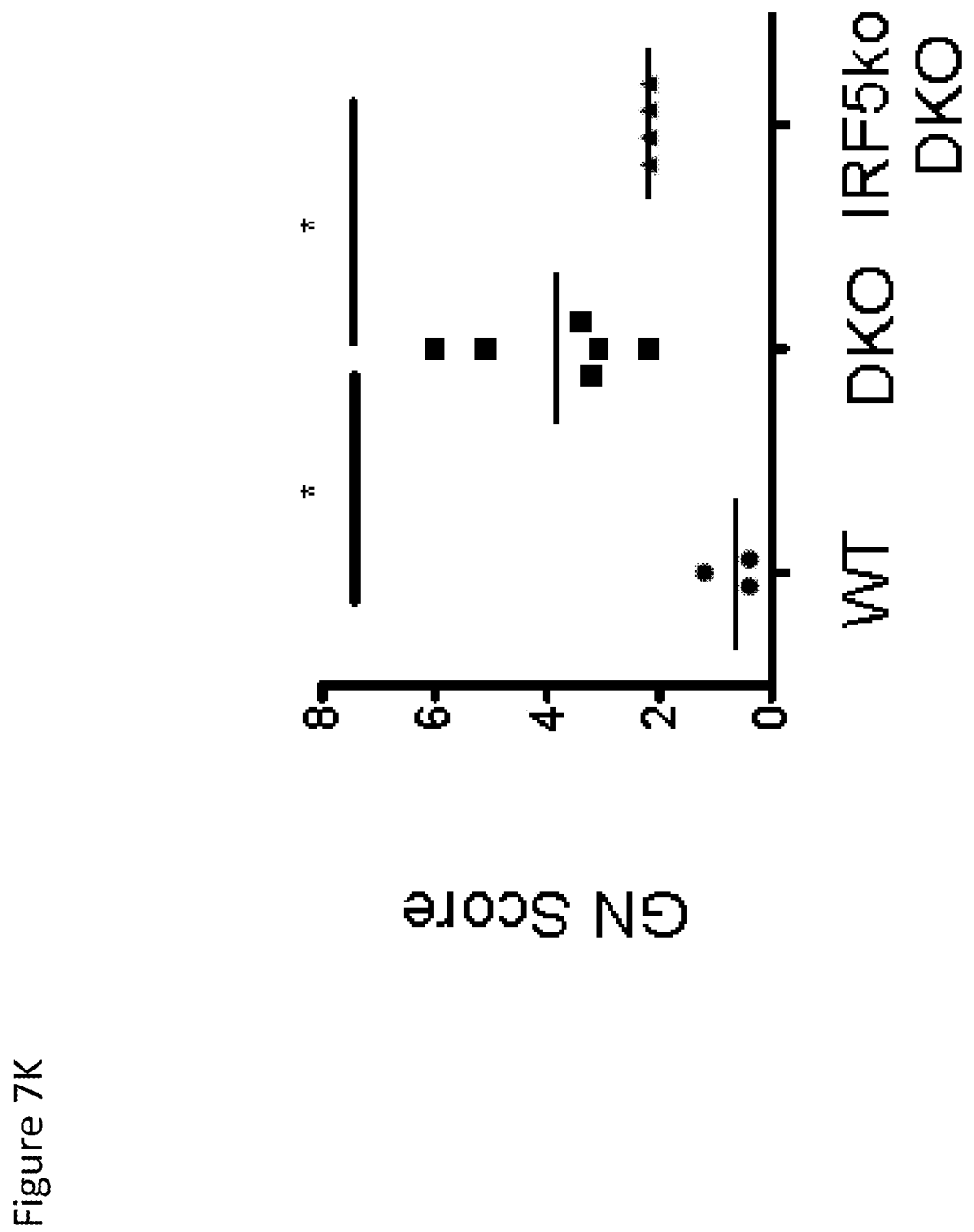
FIG. 7K show a graph of the glomerulonephritis score of WT, DKO and IRF5ko DKO mice (which include CD11cCre IRF5fl/− DKO and CD21Cre IRF5fl/− DKO mice) (n=3-6 mice/group). The graphs are quantification of PAS staining of 3 independent experiments.
Figure 7L:
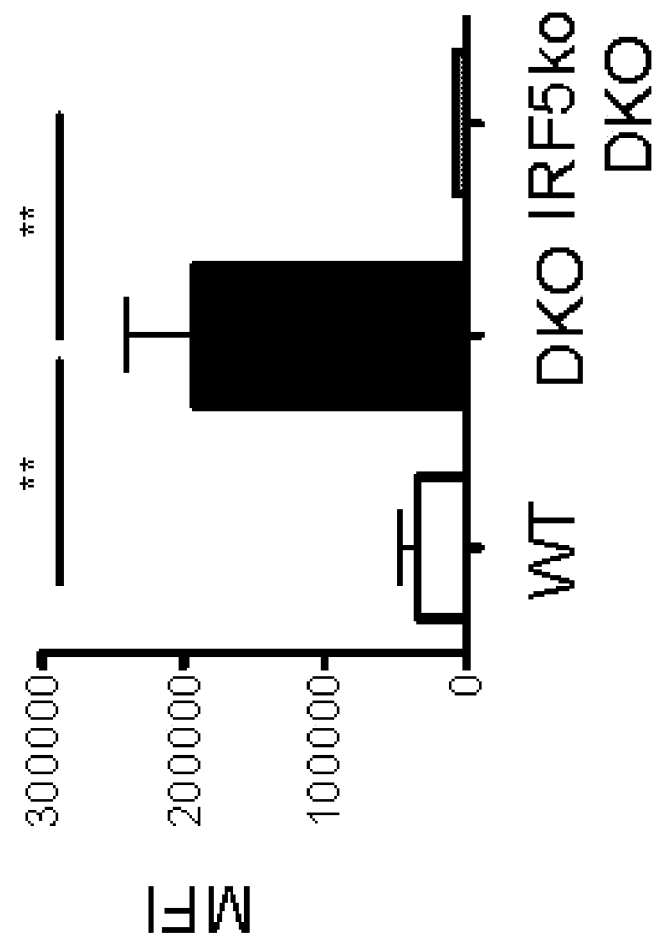
FIG. 7L is a graph showing the MFI quantification of IgG deposition from 3 independent experiments. (n=3-6 mice/group).

Monoallelic expression of IRF5 in DKO female mice also resulted in a profound decrease in autoantibody production as evidence by both anti-antibody (ANA) staining (FIG. 7H) and anti-dsDNA titers (FIG. 7I). Reduction in anti-dsDNA titers primarily reflected decreases in the production of pathogenic IgG2c anti-dsDNA Abs rather than IgG1 anti-dsDNA Abs (FIG. 7I). Production of other autoantibodies like anti-ssDNA, anti-Cardiolipin, and anti-nRNP Abs was also markedly affected by the loss of IRF5 (FIG. 7J). Consistent with these results, manipulating IRF5 expression also ameliorated several parameters of renal injury observed in DKO mice including the expansion of mesangial matrix, the presence of hyaline deposits, the decrease in capillary loops, and the deposition of immune complexes (FIGS. 7K and 7L). Thus, the aberrant expansion of pathogenic ABCs in DKO female mice observed in vivo was dependent on IRF5 and alterations in IRF5 levels exerted profound effects on the spontaneous development of lupus in DKO female mice.

Example 9

DKO B Cells Upregulates Blimp1, IRF4 and CD138

Figure 8A:
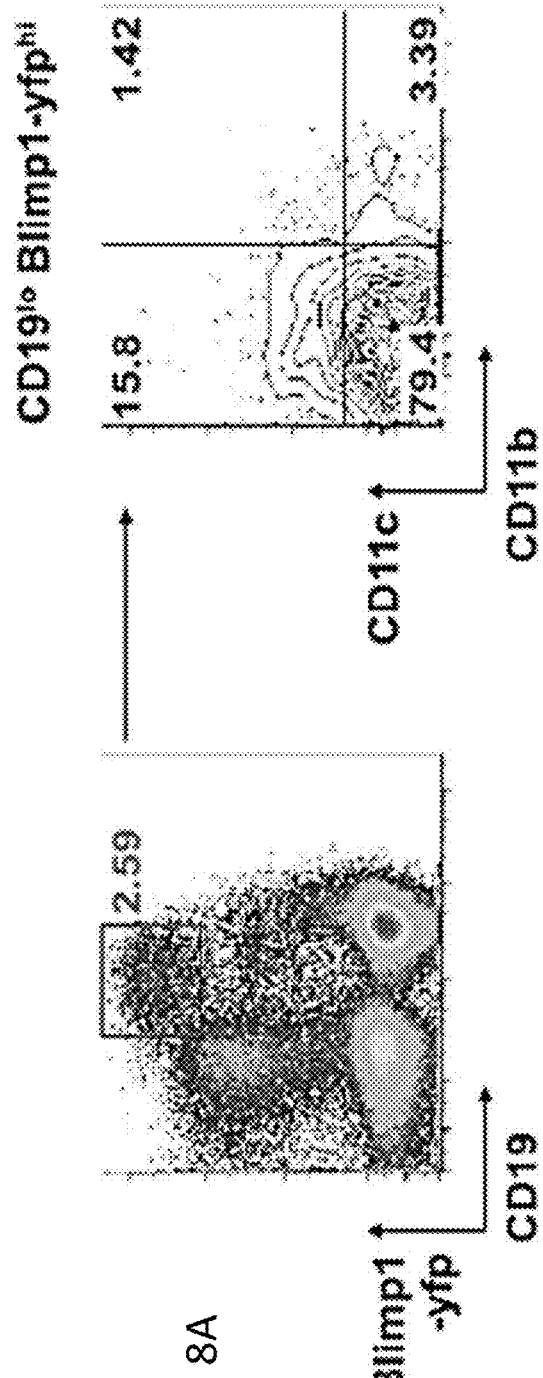
FIG. 8A is a representative FACS plot for CD11c and CD11b expression gated on CD19 Blimp1-yfphi cells from spleens of aging Blimp1-yfp.DKO female mice.
Figure 8B:
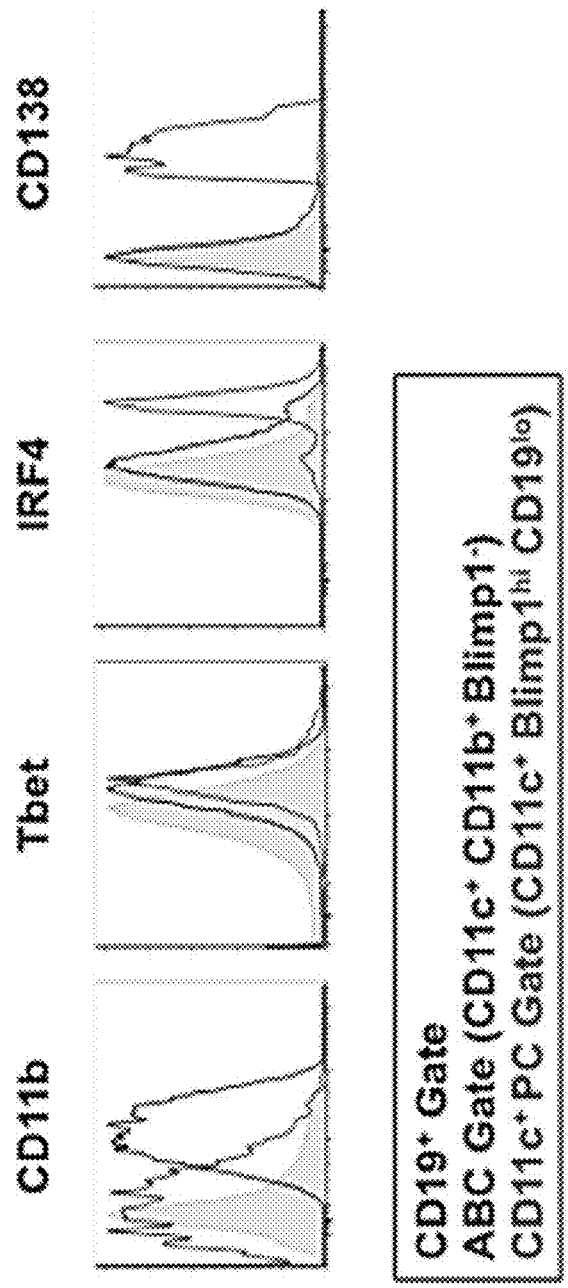
FIG. 8B are histograms showing the relative expression of the indicated marker on CD11c+ PCs (CD11c+ Blimp1hi CD19lo=red), ABCs (CD11c+CD11b+CD19+Blimp1−=blue), and total B cells (CD19+=shaded gray) from aging Blimp1-yfp.DKO female mice.

While ABCs classically express IgM, the ability of ABCs to produce anti-dsDNAIgG2c upon stimulation in vitro prompted the investigation as to whether the ABCs can undergo class switching and differentiate into plasmablasts/plasma cells (PB/PCs). Using the Blimp1-reporter DKO mice and other materials and methods described in Example 1, a population of CD11c+ B cells that expressed high levels of Blimp1, IRF4, and CD138 (FIG. 8) suggesting that ABCs further differentiate into CD11c+ PB/PCs.

Example 10

DKO ABCs Exhibit Sex-Specific Differences in Auto-Ab Production

One of the striking features of the lupus syndrome that develops in DKO mice is the finding that, as observed for human SLE, this disorder preferentially affects females (Biswas et al. 2010).

Cells were sorted from aging DKO female, DKO male and Yaa-DKO male mice using the materials and methods described in Example 1. qPCR was also performed as described in Example 1.

Figure 9A:
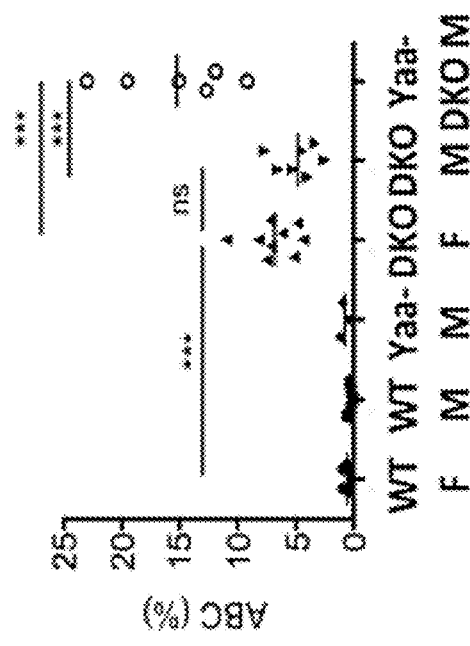
FIG. 9A is a scatter plot showing frequencies of ABCs of individual mice as indicated.

Interestingly ABCs also accumulated in DKO male mice albeit to a slightly lesser extent than DKO female mice (FIG. 9A). Studies demonstrated no differences in BCR repertoire and SHM between female and male DKO ABCs using next-gen sequencing (not shown). Unlike ABCs from DKO male mice, however, ABCs from DKO female mice readily secreted anti-dsDNA IgG2c antibodies upon TLR7 stimulation (FIG. 9B) suggesting that the pathogenic potential of DKO ABCs differs in female and male mice.

Figure 9C:
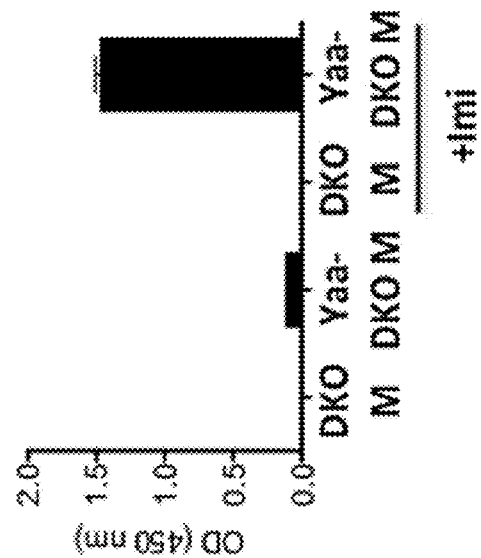
FIG. 9C is a graph of the results of ABCs sorted from spleens of aging DKO male or Yaa-DKO male mice cultured in vitro±1 μg/ml of Imiquimod, assayed by ELISA on day 7.
Figure 9B:
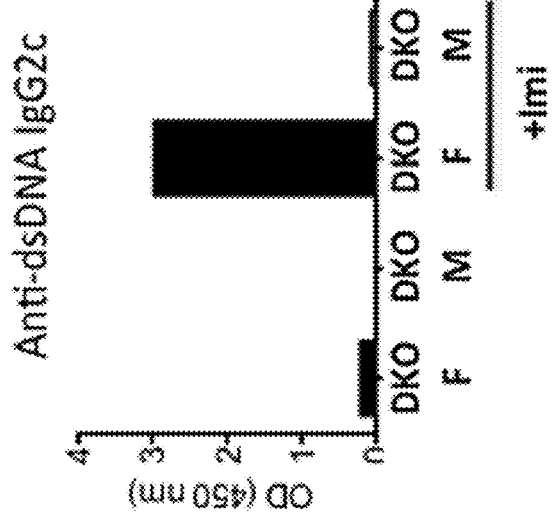
FIG. 9B is a graph of the results of ABCs sorted from spleens of aging DKO female or DKO male mice cultured in vitro±1 μg/ml of Imiquimod, assayed by ELISA on day 7.

Yaa-DKO male mice had an increased expansion of ABCs as compared to male DKO mice and enables them to produce anti-dsDNA IgG2a/c upon stimulation (FIGS. 9A and 9C).

Figure 9D:
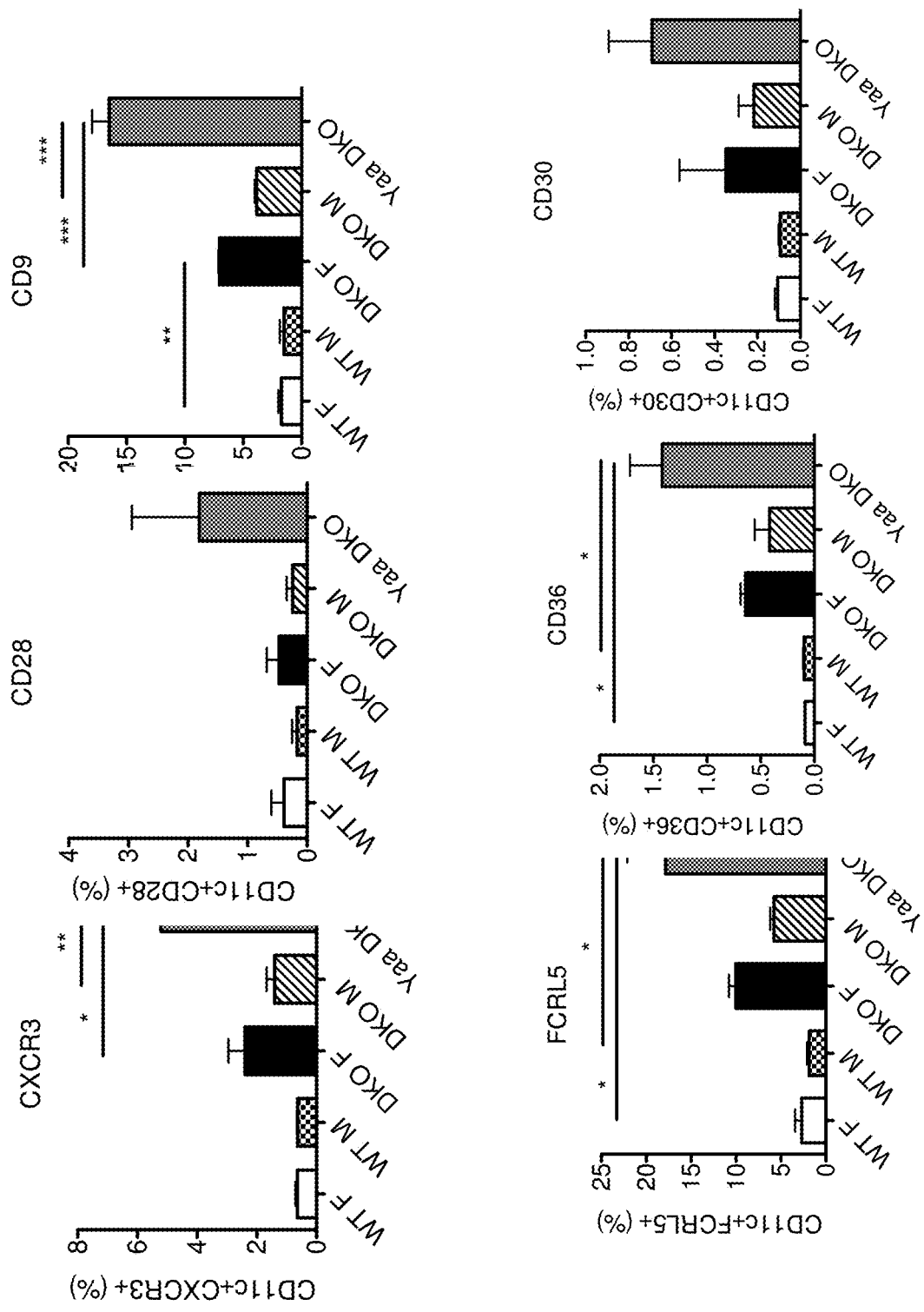
FIG. 9D show graphs of frequencies of ABC expressing the indicated markers using flow cytometric analysis of B220+ B cells in the spleens of WT and DKO female and male mice and Yaa-DKO male mice (>20 weeks-old).
Figure 9D:
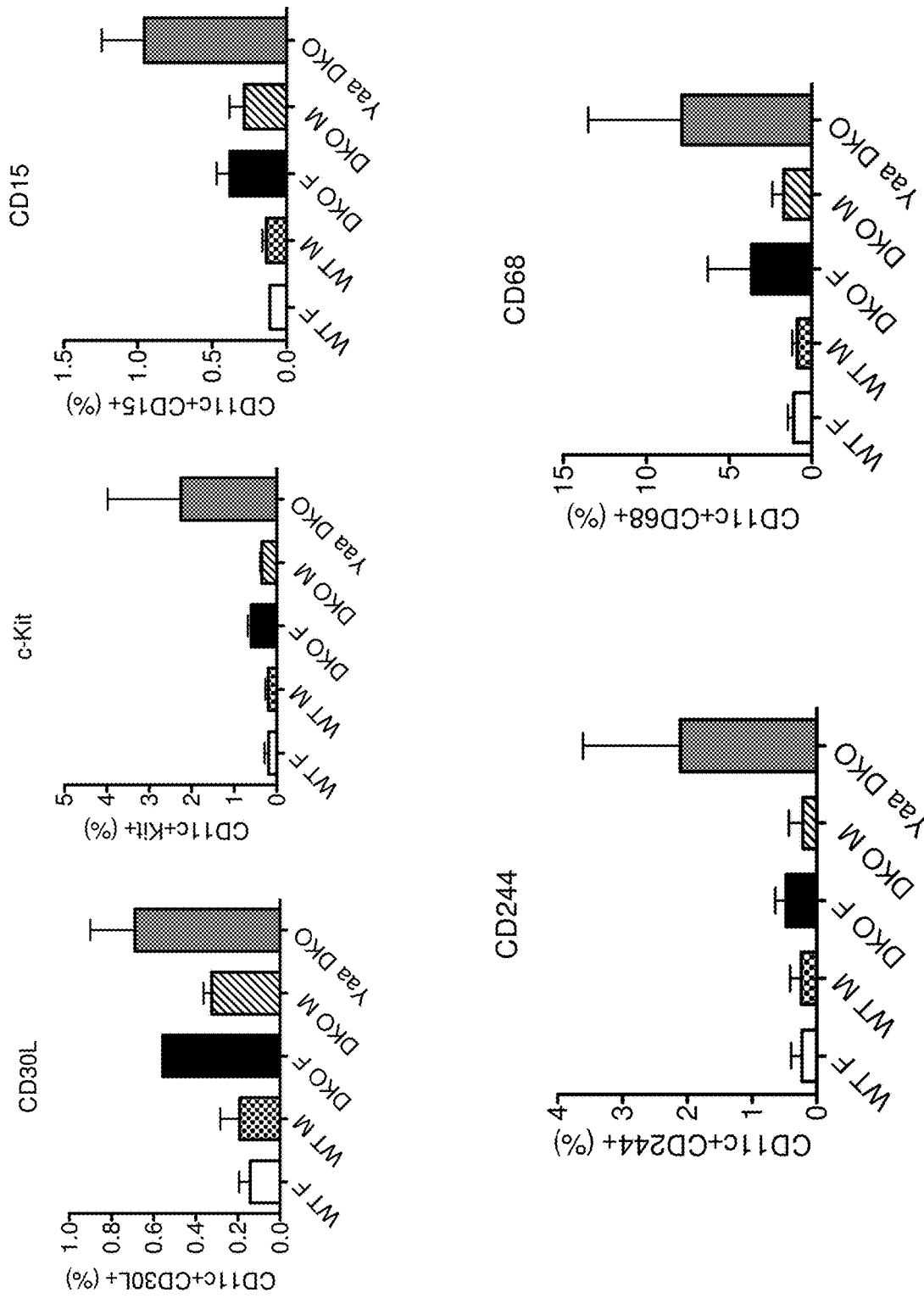
Figure 9E:
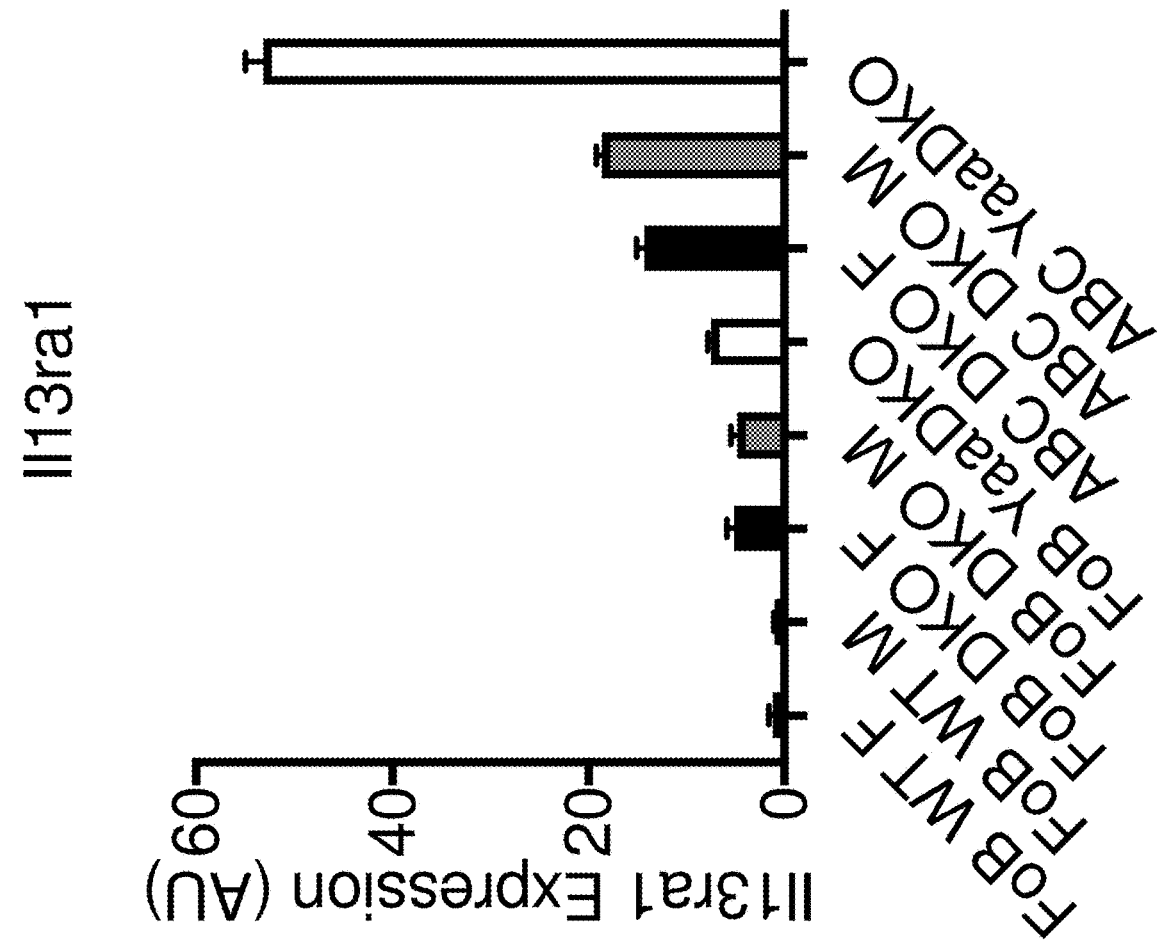
FIG. 9E is a graph showing the qPCR expression analysis of IL13Ra1 in FACS-sorted FoB (B220+CD19+CD11c−CD11b−CD23+) cells and ABC (B220+CD19+CD11c+CD11b+) cells from WT and DKO female and male mice and Yaa-DKO male mice (>20 weeks old). The data were normalized relative to ppia mRNA expression.

Additionally, expression of cell markers on the ABCs in both DKO female and Yaa-DKO male mice were similar and included CXCR3, CD28, CD9, FCRL5, CD36, CD30, CD30L, c-kit, CD15, CD244, and CD68 (FIG. 9D). Expression of Il13ra1 was also increased in ABCs from DKO female, DKO male, and Yaa-DKO mice (FIG. 9E).

Taken together these results suggest that sex-specific factors regulate the pathogenic potential of ABCs.

Example 11

Pathogenic ABCs Express Active Rho-Kinases (ROCK) 1 and 2

FoB cells from WT male and Yaa DKO male mice and ABCs from male Yaa DKO mice as well as CD11c+ plasmablasts and CD11c− plasmablasts (PBs) from Yaa DKO mice were sorted as described in Example 1 and subjected to a ROCK1 or ROCK2 in vitro kinase assay (Biswas et al. 2012).

Increased ROCK2 activity was observed in ABCs and CD11c− plasmablasts (FIG. 10A). Consistent with these results, phosphorylation of IRF4, a ROCK2 target, was observed in CD11c− but not in CD11c+ plasmablasts (FIG. 10B). However, in contrast to the findings for ROCK2, the same populations demonstrated that ROCK1 is activated at higher levels in ABCs and CD11c+ PBs but not in CD11c− PBs (FIG. 10C).

Example 12

The Transcriptional and Epigenetic Profiles of CD11c+ PCs

While ABCs express both CD11c and CD11b, CD11c+ PCs downregulate CD11b expression (FIG. 8) suggesting that as DKO ABCs undergo terminal differentiation they acquire unique characteristics. Using the material and methods described in Example 1, a genome-wide approach is used to test the hypothesis that the transcriptional and epigenetic landscape of CD11c+ PCs is distinct from those of ABCs and of "classical" (CD11c−) PCs.

With the aid of the Blimp-YFP reporter, ABCs (CD11c+ CD11b+CD19hiCD23−Blimp1−CD138−), CD11c+PCs (CD11c+CD11b−CD19loBlimp1hiCD138hi), and "classical" PCs (CD11c−CD11b− B220loCD19loBlimp1hiCD138hi) from aging DKO female mice are sorted. As control "classical" PCs are obtained by immunizing wt Blimp1-YFP reporter mice with NP-CGG as described (Jones et al. 2016).

The different sorted populations are analyzed using will be subjected to RNA-seq and ATAC-seq as described in Example 1. These data are compared with previously performed genome-wide analyses (Shi et al. 2015). A selected number of targets are validated by QPCR, Western blotting, and/or FACS.

Given that CD11c+ PCs express both IRF4 and IRF5 and that both IRF4 and IRF5 have been reported to regulate the expression of Blimp1 (Kwon et al. 2009), the hypothesis that IRF4 cooperates with IRF5 in regulating the differentiation/function of CD11c+ PCs is also tested using the materials and methods of Example 1.

The IRF4$^{fl/fl}$ DKO mice, described in Example 1 are crossed to T-bet-Zsgreen-T2ACreERT2 DKO mice. This strategy minimizes the known impact of IRF4 deletion on other cellular compartments like DCs (which would be affected by using the CD11cCre line) and "classical" B cell compartments (which would be affected by using CD23Cre mice). While DKO mice do exhibit an accumulation of TFH cells that produce IFNγ, as mentioned above, these cells do not express T-bet and thus should not be impacted by the removal of IRF4. All relevant control genotypes are also included.

Once these mice have been generated, IRF4 deletion is induced by tamoxifen administration (and verified by QPCR and or IC FACS) and the effects of removing IRF4 versus IRF5 (using the T-bet-Zsgreen-T2A-CreERT2IRF5$^{fl/fl}$ DKO mice) are evaluated by performing a series of experiments which will include: i) a baseline FACS and serum Ig analysis of 8-12 week old mice, ii) a series of studies to assess PC differentiation in vitro upon exposure to different combinations of ABC-promoting stimuli, and iii) an evaluation of the development of lupus-like disease in aged groups of female mice as described in the previous examples. If warranted, additional genetic manipulations will also be investigated (e.g., IRF4fl/+IRF5fl/+).

A series of mixed bone marrow chimeras are also performed, which will take advantage of the μMTDKO mice. Briefly lethally irradiated μMTDKO recipient mice will be reconstituted with mixtures of 80% μMTDKO BM+20% of CD11c−Cre+IRF4fl/flDKO BM so that only CD11-c expressing DKO B cells will lack IRF4. Once appropriately reconstituted, a full analysis of young and aged mice is performed as described in detail above.

These experiments show a unique transcriptional and epigenetic profile of the CD11c+ PC cells from DKO mice. They also show that both IRF4 and IRF5 regulate the differentiation of these cells from ABCs as well as their function. IRF4 and IRF5 co-regulate a common set of targets in addition to each of them controlling separate targets.

Example 13

Sex-Specific Mechanisms Controlling ABCs

A number of observations have implicated sex-specific pathways in the regulation of ABCs. As shown in Example 10, there is a striking sex-specific differences in the ability of ABCs to produce autoantibodies. Also, while ABCs accumulate in both DKO female and male mice, only ABCs from DKO female mice readily secreted anti-dsDNA IgG2c antibodies upon TLR7 stimulation (Example 10), suggesting that the ABCs from DKO females are functionally distinct from those obtained from DKO males. Dysregulation of TLR7 expression in DKO male mice, i.e., Yaa-DKO mice, rescued their ability to produce anti-dsDNA IgG2c (Example 10). Using the materials and methods described in Example 1, using both targeted and genome-wide approaches, the hypothesis that sex-specific pathways regulate not only the expansion but also the function and differentiation of ABCs is tested.

To gain new insights into additional sex-specific pathways that might control the function/differentiation of ABCs, RNA-seq and ATAC-seq is performed on ABC cells sorted from DKO male and Yaa-DKO male mice (and sex-matched control mice). These profiles are compared to those obtained in ABCs from DKO female mice (Examples 4-6). A motif analysis is performed to determine whether functionally relevant differences map to motifs of specific transcription factors.

These studies are complemented by experiments in primary B cells purified from young female DKO, male DKO, and Yaa-DKO male mice (and appropriately sex-matched wt controls), which are cultured in vitro±ABC-promoting stimuli (which include IL-21, IFNγ, and TLR7 added in various combinations to αIgM+αCD40) followed by evaluations of ABC formation/function/differentiation by FACS and QPCR/Western of selected targets as well as additional assays like ChIP-QPCR and ONPs as described in Example 1.

The transcriptome of ABCs from DKO male and female mice show some similarities (since aberrant expansion of these cells is observed in both female and male DKOs). The ABCS from DKO males and DKO females have crucial transcriptional differences that is revealed by a GSEA analysis and these distinctions reflect the differential expression of a selected group of pathways, and that the ATAC-seq demonstrates that these transcriptional differences are accompanied by differences in the chromatin landscape surrounding these genes.

REFERENCES

Biswas et al. IRF4 and its regulators: evolving insights into the pathogenesis of inflammatory arthritis? *Immunological Reviews* 2010, 233(1):79-96.

Biswas et al. Dual regulation of IRF4 function in T and B cells is required for the coordination of T-B cell interactions and the prevention of autoimmunity. *Journal of Experimental Medicine* 2012, 209:581-596.

Buenrostro et al. ATAC-seq: A Method for Assaying Chromatin Accessibility Genome-Wide. *Curr. Protoc. Mol. Biol.* 2015, 109:21 29 21-29.

Buenrostro et al. Single-cell chromatin accessibility reveals principles of regulatory variation. *Nature* 2015a, 523:486-490.

Cham et al. Interferon regulatory factor 5 in the pathogenesis of systemic lupus erythematosus. *Clinical and Developmental Immunology* 2012, 780436.

Chandrasekaran et al. Regulation of Effector Treg Cells in Murine Lupus. *Arthritis and Rheumatology* 2016, 68(6): 1454-1466.

Cohen-Solal and Diamond Lessons from an anti-DNA autoantibody. *Molecular Immunology* 2011, 48(11):1328-1331.

Deane et al. Control of toll-like receptor 7 expression is essential to restrict autoimmunity and dendritic cell proliferation. *Immunity* 2007 Nov., 7(5):801-10.

Eames et al. Interferon regulatory factor 5 in human autoimmunity and murine models of autoimmune disease. *Translational research: Journal of Laboratory and Clinical Medicine* 2016, 167(1):167-182.

Eisenberg Mechanisms of autoimmunity. *Immunologic research* 2003, 27(2-3):203-218.

Fan et al. Keap1 facilitates p62-mediated ubiquitin aggregate clearance via autophagy. *Autophagy* 2010, 6(5):614-621.

Fang et al. Unique contribution of IRF-5-Ikaros axis to the B-cell IgG2a response. *Genes Immun.* 2012, 13:421-430.

Gupta et al. Molecular cloning of IBP, a SWAP-70 homologous GEF, which is highly expressed in the immune system. *Human Immunology* 2003, 64:389-401.

Hao et al. A B-cell subset uniquely responsive to innate stimuli accumulates in aged mice. *Blood* 2011, 118:1294-1304.

Jones et al. mTOR has distinct functions in generating versus sustaining humoral immunity. *J. Clin. Invest.* 2016, 126:4250-4261.

Kwon et al. Analysis of interleukin-21-induced Prdm1 gene regulation reveals functional cooperation of STAT3 and IRF4 transcription factors. *Immunity* 2009, 31: 941-952.

Lazzari and Jefferies IRF5-mediated signaling and implications for SLE. *Clin. Immunol.* 2014, 153:343-352.

Manni et al. IRF4-Dependent and IRF4-Independent Pathways Contribute to DC Dysfunction in Lupus. *PloS one* 2015, 10(11):e0141927.

Maynard et al.: Regulatory T cells expressing interleukin 10 develop from Foxp3+ and Foxp3– precursor cells in the absence of interleukin 10. *Nature Immunology* 2007, 8(9):931-941.

Minnich et al. Multifunctional role of the transcription factor Blimp-1 in coordinating plasma cell differentiation. *Nature Immunology* 2016, 17:331-343.

Naradikian et al. Cutting Edge: IL-4, IL-21, and IFN-gamma Interact To Govern T-bet and CD11c Expression in TLR-Activated B Cells. *Journal of Immunology* 2016a, 197(4): 1023-1028.

Naradikian et al. Age-associated B cells: key mediators of both protective and autoreactive humoral responses. *Immunological Reviews* 2016, 269(1):118-129.

Parish et al: Chronic viral infection promotes sustained Th1-derived immunoregulatory IL-10 via BLIMP-1. *J. Clin. Invest.* 2014, 124(8):3455-3468.

Ripich et al. SWEF Proteins Distinctly Control Maintenance and Differentiation of Hematopoietic Stem Cells. *PloS one* 2016, 11(8):e0161060.

Rubtsova et al. Age-Associated B Cells: A T-bet-Dependent Effector with Roles in Protective and Pathogenic Immunity. *Journal of Immunology* 2015, 195(5):1933-1937.

Rubtsova et al. B cells expressing the transcription factor T-bet drive lupus-like autoimmunity. *J Clin. Invest.* 2017, 127:1392-1404.

Rogatsky et al. Epigenetics and the IRFs: a complex interplay in the control of immunity and autoimmunity. *Autoimmunity* 2014, 47:242-255.

Sarra et al. Interleukin-21 in chronic inflammatory diseases. Biofactors 2013, 39:368-373.

Shi et al. Transcriptional profiling of mouse B cell terminal differentiation defines a signature for antibody-secreting plasma cells. *Nature Immunology* 2015, 16:663-673.

Sun et al. High-density genotyping of immune-related loci identifies new SLE risk variants in individuals with Asian ancestry. *Nature Genetics* 2016, 48(3):323-330.

Tanaka et al. SWAP-70-like adapter of T cells, an adapter protein that regulates early TCR-initiated signaling in Th2 lineage cells. *Immunity* 2003, 18:403-414.

---

The invention claimed is:

1. A method of treating systemic lupus erythematosus in a subject in need thereof, comprising the administration of a therapeutically effective amount of a nucleic acid which encodes human DEF6 protein and a nucleic acid which encodes human SWAP-70 protein, wherein the administration of the nucleic acid which encodes human DEF6 protein and the nucleic acid which encodes human SWAP-70 protein abolishes or decreases pathogenic age-associated B cells, and wherein the pathogenic age-associated B cells are CD11c+ and secrete anti-dsDNA IgG.

2. The method of claim 1, wherein the nucleic acids are delivered directly to the pathogenic age-associated B cells in the subject.

* * * * *